United States Patent
Fenton et al.

(10) Patent No.: US 9,840,479 B2
(45) Date of Patent: Dec. 12, 2017

(54) POLYAMINE-FATTY ACID DERIVED LIPIDOIDS AND USES THEREOF

(71) Applicant: Massachusetts Institute of Technology, Cambridge, MA (US)

(72) Inventors: Owen Shea Fenton, Cambridge, MA (US); Joseph Robert Dorkin, Somerville, MA (US); Daniel Griffith Anderson, Framingham, MA (US); Rebecca L. McClellan, Westwood, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 14/789,227

(22) Filed: Jul. 1, 2015

(65) Prior Publication Data

US 2016/0002178 A1   Jan. 7, 2016

Related U.S. Application Data

(60) Provisional application No. 62/020,114, filed on Jul. 2, 2014.

(51) Int. Cl.
| | |
|---|---|
| A61K 31/495 | (2006.01) |
| C07D 241/08 | (2006.01) |
| C07C 219/06 | (2006.01) |
| C07C 219/08 | (2006.01) |
| C07D 295/088 | (2006.01) |

(52) U.S. Cl.
CPC .......... *C07D 241/08* (2013.01); *C07C 219/06* (2013.01); *C07C 219/08* (2013.01); *C07D 295/088* (2013.01)

(58) Field of Classification Search
CPC .................................................. C07D 241/08
See application file for complete search history.

(56) References Cited

U.S. PATENT DOCUMENTS

| | | | |
|---|---|---|---|
| 2,580,922 | A | 1/1952 | Jacoby |
| 2,647,121 | A | 7/1953 | Jacoby |
| 2,717,909 | A | 9/1955 | Kosmin |
| 2,819,718 | A | 1/1958 | Goldman |
| 2,844,629 | A | 7/1958 | William et al. |
| 3,096,560 | A | 7/1963 | Liebig |
| 3,170,953 | A | 2/1965 | Lashua |
| 3,268,576 | A | 8/1966 | Wilkinson et al. |
| 3,350,325 | A | 10/1967 | Ashby et al. |
| 3,535,289 | A | 10/1970 | Yoshihara et al. |
| 3,614,954 | A | 10/1971 | Mirowski et al. |
| 3,614,955 | A | 10/1971 | Mirowski |
| 3,656,185 | A | 4/1972 | Carpentier |
| 3,682,980 | A | 8/1972 | Braid et al. |
| 3,805,301 | A | 4/1974 | Liebig |
| 3,945,052 | A | 3/1976 | Liebig |
| 3,956,502 | A | 5/1976 | Slovinsky et al. |

(Continued)

FOREIGN PATENT DOCUMENTS

| | | |
|---|---|---|
| CA | 2518132 A1 | 3/2006 |
| CA | 2 769 408 A1 | 2/2011 |
| CN | 1433478 A | 7/2003 |
| CN | 101506196 A | 8/2009 |
| CN | 100 569 877 C | 12/2009 |
| CN | 101 863 544 B | 9/2011 |
| DE | 1155118 B | 10/1963 |
| DE | 2430998 A1 | 1/1975 |
| DE | 2520814 A1 | 11/1976 |
| DE | 2 530 243 A1 | 1/1977 |

(Continued)

OTHER PUBLICATIONS

STN abstract. Yu et al. Antioxidant nanosphere comprising [1,2]-dithiolane moieties and their preparation. 2009. STN information included only.*

(Continued)

*Primary Examiner* — Brian McDowell
(74) *Attorney, Agent, or Firm* — Wolf, Greenfield & Sacks, P.C.

(57) ABSTRACT

The present disclosure provides polyamine-fatty acid derived lipidoids (e.g., compounds of Formula (I) or (II)) and methods of preparing the lipidoids. A described lipidoid includes R—C(=O)—O— moieties (where R is a lipid moiety), which may be hydrolyzed into non-toxic fatty acids. Also provided are compositions including a described lipidoid and an agent (e.g., polynucleotide, small molecule, peptide, or protein). The present disclosure also provides methods, kits, and uses that involve the lipidoids or compositions for delivering an agent to a subject, tissue, or cell and/or for treating and/or preventing a range of diseases, such as genetic diseases, proliferative diseases, hematological diseases, neurological diseases, immunological diseases, gastrointestinal diseases, respiratory diseases, painful conditions, psychiatric disorders, and metabolic disorders.

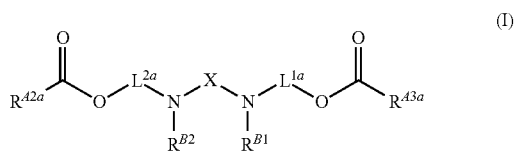

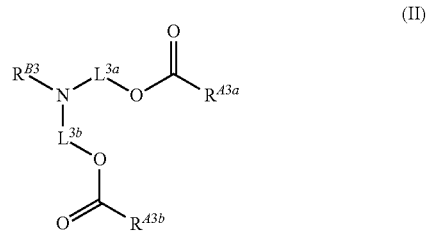

29 Claims, 22 Drawing Sheets

(56) References Cited

U.S. PATENT DOCUMENTS

| | | |
|---|---|---|
| 3,995,623 A | 12/1976 | Blake et al. |
| 4,013,507 A | 3/1977 | Rembaum |
| 4,022,833 A | 5/1977 | Diana et al. |
| 4,072,146 A | 2/1978 | Howes |
| 4,096,860 A | 6/1978 | McLaughlin |
| 4,099,528 A | 7/1978 | Sorenson et al. |
| 4,106,129 A | 8/1978 | Carpentier et al. |
| 4,134,402 A | 1/1979 | Mahurkar |
| 4,140,126 A | 2/1979 | Choudhury |
| 4,180,068 A | 12/1979 | Jacobsen et al. |
| 4,182,833 A | 1/1980 | Hicks |
| 4,227,533 A | 10/1980 | Godfrey |
| 4,284,459 A | 8/1981 | Patel et al. |
| 4,308,085 A | 12/1981 | Horhold et al. |
| 4,323,525 A | 4/1982 | Bornat |
| 4,335,723 A | 6/1982 | Patel |
| 4,339,369 A | 7/1982 | Hicks et al. |
| 4,355,426 A | 10/1982 | MacGregor |
| 4,375,817 A | 3/1983 | Engle et al. |
| 4,385,631 A | 5/1983 | Uthmann |
| 4,401,472 A | 8/1983 | Gerber |
| 4,406,656 A | 9/1983 | Hattler et al. |
| 4,475,972 A | 10/1984 | Wong |
| 4,530,113 A | 7/1985 | Matterson |
| 4,550,447 A | 11/1985 | Seiler, Jr. et al. |
| 4,562,596 A | 1/1986 | Kornberg |
| 4,568,329 A | 2/1986 | Mahurkar |
| 4,571,241 A | 2/1986 | Christopher |
| 4,601,718 A | 7/1986 | Possis et al. |
| 4,647,416 A | 3/1987 | Seiler, Jr. et al. |
| 4,662,382 A | 5/1987 | Sluetz et al. |
| 4,701,162 A | 10/1987 | Rosenberg |
| 4,710,169 A | 12/1987 | Christopher |
| 4,720,517 A | 1/1988 | Ravichandran et al. |
| 4,762,915 A | 8/1988 | Kung et al. |
| 4,782,836 A | 11/1988 | Alt |
| 4,856,521 A | 8/1989 | Irnich |
| 4,860,751 A | 8/1989 | Callaghan |
| 4,873,370 A | 10/1989 | Chiu |
| 4,878,908 A | 11/1989 | Martin et al. |
| 4,892,540 A | 1/1990 | Vallana |
| 4,897,355 A | 1/1990 | Eppstein et al. |
| 4,946,857 A | 8/1990 | Kanehira et al. |
| 4,960,409 A | 10/1990 | Catalano |
| 4,966,945 A | 10/1990 | Drawert et al. |
| 5,024,671 A | 6/1991 | Tu et al. |
| 5,025,005 A | 6/1991 | Nomura et al. |
| 5,047,540 A | 9/1991 | Kamata et al. |
| 5,101,824 A | 4/1992 | Lekholm |
| 5,104,399 A | 4/1992 | Lazarus |
| 5,116,360 A | 5/1992 | Pinchuk et al. |
| 5,138,067 A | 8/1992 | Kamata et al. |
| 5,151,105 A | 9/1992 | Kwan-Gett |
| 5,171,678 A | 12/1992 | Behr et al. |
| 5,176,661 A | 1/1993 | Evard et al. |
| 5,197,977 A | 3/1993 | Hoffman, Jr. et al. |
| 5,200,395 A | 4/1993 | Eto et al. |
| 5,201,998 A | 4/1993 | Topfl et al. |
| 5,261,419 A | 11/1993 | Osypka |
| 5,282,824 A | 2/1994 | Gianturco |
| 5,284,491 A | 2/1994 | Sutton et al. |
| 5,300,022 A | 4/1994 | Klapper et al. |
| 5,314,430 A | 5/1994 | Bardy |
| 5,330,768 A | 7/1994 | Park et al. |
| 5,330,888 A | 7/1994 | Morigaki et al. |
| 5,334,761 A | 8/1994 | Gebeyehu et al. |
| 5,352,461 A | 10/1994 | Feldstein et al. |
| 5,395,619 A | 3/1995 | Zalipsky et al. |
| 5,405,363 A | 4/1995 | Kroll et al. |
| 5,405,379 A | 4/1995 | Lane |
| 5,455,352 A | 10/1995 | Huellmann et al. |
| 5,464,924 A | 11/1995 | Silvis et al. |
| 5,503,852 A | 4/1996 | Steiner et al. |
| 5,528,023 A | 6/1996 | Butturini et al. |
| 5,607,385 A | 3/1997 | Francischelli et al. |
| 5,609,624 A | 3/1997 | Kalis |
| 5,614,548 A | 3/1997 | Piantadosi et al. |
| 5,626,869 A | 5/1997 | Nyqvist et al. |
| 5,631,018 A | 5/1997 | Zalipsky et al. |
| 5,693,088 A | 12/1997 | Lazarus |
| 5,697,953 A | 12/1997 | Kroll et al. |
| 5,700,437 A | 12/1997 | Fujii et al. |
| 5,705,188 A | 1/1998 | Junichi et al. |
| 5,736,573 A | 4/1998 | Galat |
| 5,772,694 A | 6/1998 | Bokros et al. |
| 5,776,165 A | 7/1998 | Ripart |
| 5,776,747 A | 7/1998 | Schinstine et al. |
| 5,817,873 A | 10/1998 | Meyer et al. |
| 5,874,105 A | 2/1999 | Watkins et al. |
| 5,885,613 A | 3/1999 | Holland et al. |
| 5,910,168 A | 6/1999 | Myers et al. |
| 5,916,208 A | 6/1999 | Luther et al. |
| 5,958,894 A | 9/1999 | Heath et al. |
| 5,976,569 A | 11/1999 | Milstein |
| 6,013,429 A | 1/2000 | Franke et al. |
| 6,034,056 A | 3/2000 | Dutta |
| 6,055,454 A | 4/2000 | Heemels |
| 6,067,471 A | 5/2000 | Warren |
| 6,090,384 A | 7/2000 | Ra et al. |
| 6,096,070 A | 8/2000 | Ragheb et al. |
| 6,096,075 A | 8/2000 | Bokros et al. |
| 6,120,799 A | 9/2000 | McDonald et al. |
| 6,152,955 A | 11/2000 | KenKnight et al. |
| 6,169,923 B1 | 1/2001 | Kroll |
| 6,171,612 B1 | 1/2001 | Byk et al. |
| 6,176,877 B1 | 1/2001 | Buchanan et al. |
| 6,204,297 B1 | 3/2001 | Tracy et al. |
| 6,271,209 B1 | 8/2001 | Smith et al. |
| 6,299,604 B1 | 10/2001 | Ragheb et al. |
| 6,331,318 B1 | 12/2001 | Milstein |
| 6,335,199 B1 | 1/2002 | Bischoff et al. |
| 6,358,278 B1 | 3/2002 | Brendzel et al. |
| 6,370,434 B1 | 4/2002 | Zhang et al. |
| 6,371,983 B1 | 4/2002 | Lane |
| 6,372,903 B1 | 4/2002 | Mehdi et al. |
| 6,398,808 B1 | 6/2002 | Palasis |
| 6,696,424 B1 | 2/2004 | Wheeler |
| 6,756,055 B2 | 6/2004 | McDonald et al. |
| 6,821,530 B2 | 11/2004 | Koob et al. |
| 6,887,665 B2 | 5/2005 | Trulson et al. |
| 6,998,115 B2 | 2/2006 | Langer et al. |
| 7,022,214 B2 | 4/2006 | Olech |
| 7,084,303 B2 | 8/2006 | Watanabe et al. |
| 7,427,394 B2 | 9/2008 | Anderson et al. |
| 7,507,859 B2 | 3/2009 | Grinstaff et al. |
| 7,556,684 B2 | 7/2009 | Bury et al. |
| 7,972,435 B2 | 7/2011 | Bury et al. |
| 7,977,452 B2 | 7/2011 | Tomalia et al. |
| 8,071,082 B2 | 12/2011 | Zugates et al. |
| RE43,612 E | 8/2012 | Anderson et al. |
| 8,287,849 B2 | 10/2012 | Langer et al. |
| 8,361,555 B2 | 1/2013 | Paquet, Jr. |
| 8,450,298 B2 | 5/2013 | Mahon et al. |
| 8,557,231 B2 | 10/2013 | Langer et al. |
| 8,562,966 B2 | 10/2013 | Zugates et al. |
| 8,808,681 B2 | 8/2014 | Anderson et al. |
| 8,969,353 B2 | 3/2015 | Mahon et al. |
| 9,006,487 B2 | 4/2015 | Anderson et al. |
| 9,193,827 B2 | 11/2015 | Ma et al. |
| 9,227,917 B2 | 1/2016 | Anderson et al. |
| 9,238,716 B2 | 1/2016 | Dahlman et al. |
| 9,315,472 B2 | 4/2016 | Dong et al. |
| 9,439,968 B2 | 9/2016 | Anderson et al. |
| 9,512,073 B2 | 12/2016 | Dong et al. |
| 9,556,110 B2 | 1/2017 | Mahon et al. |
| 2002/0022721 A1 | 2/2002 | Trulson et al. |
| 2002/0094528 A1 | 7/2002 | Salafsky |
| 2002/0131951 A1 | 9/2002 | Langer et al. |
| 2002/0192721 A1 | 12/2002 | Rizzuto et al. |
| 2002/0193622 A1 | 12/2002 | Watanabe et al. |
| 2003/0215395 A1 | 11/2003 | Yu et al. |
| 2004/0181077 A1 | 9/2004 | Raymond et al. |
| 2004/0235982 A1 | 11/2004 | Rabasco et al. |
| 2005/0059005 A1 | 3/2005 | Tuschl et al. |

(56) References Cited

U.S. PATENT DOCUMENTS

| | | |
|---|---|---|
| 2005/0069590 A1 | 3/2005 | Buehler et al. |
| 2005/0123596 A1 | 6/2005 | Kohane et al. |
| 2005/0143332 A1 | 6/2005 | Monahan et al. |
| 2005/0148786 A1 | 7/2005 | Ikeda et al. |
| 2005/0244961 A1 | 11/2005 | Short et al. |
| 2006/0223939 A1 | 10/2006 | Lange et al. |
| 2006/0228404 A1 | 10/2006 | Anderson et al. |
| 2007/0185128 A1 | 8/2007 | Conde-Frieboes et al. |
| 2007/0275923 A1 | 11/2007 | Chen et al. |
| 2008/0145338 A1 | 6/2008 | Anderson et al. |
| 2008/0242626 A1 | 10/2008 | Zugates et al. |
| 2009/0023673 A1 | 1/2009 | Manoharan et al. |
| 2009/0221684 A1 | 9/2009 | Grinstaff et al. |
| 2010/0036084 A1 | 2/2010 | Langer et al. |
| 2010/0178699 A1 | 7/2010 | Gao et al. |
| 2010/0240072 A1 | 9/2010 | Wester et al. |
| 2010/0331234 A2 | 12/2010 | Mahon et al. |
| 2011/0009641 A1 | 1/2011 | Anderson et al. |
| 2011/0158935 A1 | 6/2011 | Kraft |
| 2011/0293703 A1 | 12/2011 | Mahon et al. |
| 2012/0009222 A1 | 1/2012 | Nguyen et al. |
| 2012/0065358 A1 | 3/2012 | Langer et al. |
| 2012/0128760 A1 | 5/2012 | Manoharan et al. |
| 2012/0196923 A1 | 8/2012 | Rege et al. |
| 2012/0251560 A1 | 10/2012 | Dahlman et al. |
| 2013/0158021 A1 | 6/2013 | Dong et al. |
| 2013/0302401 A1 | 11/2013 | Ma et al. |
| 2014/0094399 A1 | 4/2014 | Langer et al. |
| 2014/0161830 A1 | 6/2014 | Anderson et al. |
| 2014/0329884 A1 | 11/2014 | Dong et al. |
| 2015/0203439 A1 | 7/2015 | Mahon et al. |
| 2016/0009657 A1 | 1/2016 | Anderson et al. |
| 2016/0114042 A1 | 4/2016 | Anderson et al. |
| 2016/0137785 A1 | 5/2016 | Ma et al. |
| 2016/0158363 A1 | 6/2016 | Alabi et al. |
| 2016/0206740 A1 | 7/2016 | Dahlman et al. |
| 2016/0367686 A1 | 12/2016 | Anderson et al. |
| 2017/0152213 A1 | 6/2017 | Anderson et al. |

FOREIGN PATENT DOCUMENTS

| | | |
|---|---|---|
| DE | 2 903 979 A1 | 8/1980 |
| EP | 0 211 305 A2 | 2/1987 |
| EP | 0545305 A1 | 6/1993 |
| EP | 0 673 637 A1 | 9/1995 |
| EP | 0 959 092 A1 | 11/1999 |
| EP | 1 277 829 A2 | 1/2003 |
| EP | 1 912 679 A2 | 4/2008 |
| EP | 2 045 251 A1 | 4/2009 |
| EP | 2 476 756 A1 | 7/2012 |
| EP | 2 532 649 | 12/2012 |
| FR | 1 378 382 | 11/1964 |
| FR | 2235112 A1 | 1/1975 |
| GB | 866 408 A | 4/1961 |
| GB | 1072118 A | 6/1967 |
| GB | 137749 A | 12/1974 |
| GB | 1 602 085 A | 11/1981 |
| JP | S48-022365 A | 3/1973 |
| JP | S49-127908 A | 12/1974 |
| JP | 50-24216 A | 3/1975 |
| JP | S51-023537 A | 2/1976 |
| JP | 51-125144 | 11/1976 |
| JP | S52-010847 A | 1/1977 |
| JP | 52078924 | 7/1977 |
| JP | 63-125144 A | 5/1988 |
| JP | 63-154788 A | 6/1988 |
| JP | 1099679 | 4/1989 |
| JP | 4-108173 A | 4/1992 |
| JP | H06-200073 A | 7/1994 |
| JP | H06-211978 A | 8/1994 |
| JP | H07-053535 A | 2/1995 |
| JP | H098-505593 A | 6/1997 |
| JP | H10-197978 A | 7/1998 |
| JP | 11-005786 A | 1/1999 |
| JP | 11-080142 A | 3/1999 |
| JP | 2000-501383 A | 2/2000 |
| JP | 2001-523215 A | 11/2001 |
| JP | 2002-167368 A | 6/2002 |
| JP | 2003-519199 A | 6/2003 |
| JP | 2008-202015 A | 9/2008 |
| JP | 2008-247749 A | 10/2008 |
| JP | 2012197433 A | 10/2012 |
| JP | 2014172827 A | 9/2014 |
| JP | 5777846 B2 | 9/2015 |
| WO | WO 93/18229 A1 | 9/1993 |
| WO | WO 93/18754 A1 | 9/1993 |
| WO | WO 95/11004 A1 | 4/1995 |
| WO | WO 95/14651 A1 | 6/1995 |
| WO | WO 95/18863 A1 | 7/1995 |
| WO | WO 96/25508 A1 | 8/1996 |
| WO | WO 96/26179 A1 | 8/1996 |
| WO | WO 96/36314 A2 | 11/1996 |
| WO | WO 97/23457 A1 | 7/1997 |
| WO | WO 98/16202 A1 | 4/1998 |
| WO | WO 00/03044 A1 | 1/2000 |
| WO | WO 01/15726 A2 | 3/2001 |
| WO | WO 01/49324 A2 | 7/2001 |
| WO | WO 02/22709 A1 | 3/2002 |
| WO | WO 02/31025 A2 | 4/2002 |
| WO | WO 02/097068 A2 | 12/2002 |
| WO | WO 03/040288 A2 | 5/2003 |
| WO | WO 03/070735 A2 | 8/2003 |
| WO | WO 2004/043588 A2 | 5/2004 |
| WO | WO 2004/048345 A2 | 6/2004 |
| WO | WO 2004/106411 A2 | 12/2004 |
| WO | WO 2005/028619 A2 | 3/2005 |
| WO | WO 2005/055979 A2 | 6/2005 |
| WO | WO 2005/121348 A1 | 12/2005 |
| WO | WO 2006/065266 A2 | 6/2006 |
| WO | WO 2006/082088 A1 | 8/2006 |
| WO | WO 2006/105043 A2 | 10/2006 |
| WO | WO 2006/138380 A2 | 12/2006 |
| WO | WO 2007/096662 A2 | 8/2007 |
| WO | WO 2007/143659 A2 | 12/2007 |
| WO | WO 2008/011561 A2 | 1/2008 |
| WO | WO 2008/036168 A2 | 3/2008 |
| WO | WO 2008/113364 A2 | 9/2008 |
| WO | WO 2008/119741 A2 | 10/2008 |
| WO | WO 2009/046220 A2 | 4/2009 |
| WO | WO 2009/086547 A1 | 7/2009 |
| WO | WO 2010/042877 A1 | 4/2010 |
| WO | WO 2010/045512 A2 | 4/2010 |
| WO | WO 2010/053572 A2 | 5/2010 |
| WO | WO 2010/078373 A1 | 7/2010 |
| WO | WO 2010/099387 A1 | 9/2010 |
| WO | WO 2010/114789 A1 | 10/2010 |
| WO | WO 2010/129709 A1 | 11/2010 |
| WO | WO 2010/144789 A2 | 12/2010 |
| WO | WO 2011/012746 A2 | 2/2011 |
| WO | WO 2011/068810 A1 | 6/2011 |
| WO | WO 2012/027675 A2 | 3/2012 |
| WO | WO 2012/133737 A1 | 10/2012 |
| WO | WO 2012/135025 A2 | 10/2012 |
| WO | WO 2012/170889 A1 | 12/2012 |
| WO | WO 2012/170930 A1 | 12/2012 |
| WO | WO 2013/063468 A | 5/2013 |
| WO | WO 2013/063468 A1 | 5/2013 |
| WO | WO 2014/028487 A1 | 2/2014 |
| WO | WO 2014/179562 A1 | 11/2014 |
| WO | WO 2014/210356 A1 | 12/2014 |
| WO | WO 2015/061467 A1 | 4/2015 |

OTHER PUBLICATIONS

Invitation to Pay Additional Fees for PCT/US2015/038827, dated Sep. 24, 2015.
International Search Report and Written Opinion for PCT/US2015/038827, dated Dec. 8, 2015.
Chiavarelli et al., Esteri de acidi carbossilici della N,N'-Di-(2-Idrossietil)-piperazina. Nota I. Annali di Chimica. Jan. 1, 1973;63:607-611.
Niyomtham et al., Synergistic effect of cationic lipids with different polarheads, central core structures and hydrophobic tails on gene

(56) References Cited

OTHER PUBLICATIONS transfection efficiency. Biol Pharm Bull. 2014;37(9):1534-42.
Saab-Ismail et al., Synthesis and in vivo evaluation of new contrast agents for cardiac MRI. J Med Chem. Jul. 29, 1999;42(15):2852-61.
Webb et al., Pyromellitamide aggregates and their response to anion stimuli. J Am Chem Soc. Jun. 6, 2007;129(22):7155-62. Epub May 11, 2007.
Akhtar et al., Toxicogenomics of non-viral drug delivery systems for RNAi: potential impact on siRNA-mediated gene silencing activity and specificity. Adv Drug Deliv Rev. Mar. 30, 2007;59(2-3):164-82.
Akinc et al., Targeted delivery of RNAi therapeutics with endogenous and exogenous ligand-based mechanisms. Mol Ther. Jul. 2010;18(7):1357-64.
Berge et al., Pharmaceutical salts. J Pharm Sci. Jan. 1977;66(1):1-19.
Byk et al., Synthesis, activity, and structure—activity relationship studies of novel cationic lipids for DNA transfer. J Med Chem. Jan. 15, 1998;41(2):229-35.
Chen et al., Rapid discovery of potent siRNA-containing lipid nanoparticles enabled by controlled microfluidic formulation. J Am Chem Soc. Apr. 25, 2012;134(16):6948-51.
Chen et al., Tumor-targeted delivery of siRNA by non-viral vector: safe and effective cancer therapy. Expert Opin Drug Deliv. Dec. 2008;5(12):1301-11.
Damen et al., Delivery of DNA and siRNA by novel gemini-like amphiphilic peptides. J Control Release. Jul. 1, 2010;145(1):33-9.
Davis et al., Evidence of RNAi in humans from systemically administered siRNA via targeted nanoparticles. Nature. Apr. 15, 2010;464(7291):1067-70.
Davis, The first targeted delivery of siRNA in humans via a self-assembling, cyclodextrin polymer-based nanoparticle: from concept to clinic. Mol Pharm. May-Jun. 2009;6(3):659-68.
Fenske et al., Liposomal nanomedicines. Expert Opin Drug Deliv. Jan. 2008;5(1):25-44.
Giuliani et al., Beyond natural antimicrobial peptides: multimeric peptides and other peptidomimetic approaches. Cell Mol Life Sci. Jul. 2011;68(13):2255-66.
Hofland et al., Formation of stable cationic lipid/DNA complexes for gene transfer. Proc Natl Acad Sci U S A. Jul. 9, 1996;93(14):7305-9.
Incani et al., Lipid and hydrophobic modification of cationic carriers on route to superior gene vectors. Soft Matter, Feb. 2010;6(10):2124-38.
Lukyanov et al., Micelles from lipid derivatives of water-soluble polymers as delivery systems for poorly soluble drugs. Adv Drug Deliv Rev. May 7, 2004;56(9):1273-89.
Lv et al., Toxicity of cationic lipids and cationic polymers in gene delivery. J Control Release. Aug. 10, 2006;114(1):100-9.
Ma et al., Cationic lipids enhance siRNA-mediated interferon response in mice. Biochem Biophys Res Commun. May 13, 2005;330(3):755-9.
Mathiowitz et al., Novel microcapsules for delivery systems. React Poly Ion Exchang Sorb. Oct. 1987;6(2):275-83.
Mathiowitz et al., Polyanhydride microspheres as drug carriers I. Hot-melt microencapsulation. J Cont Release. Jun. 1987;5(1):13-22.
Mathiowitz et al., Polyanhydride microspheres as drug carriers. II. Microencapsulation by solvent removal. J App Poly Sci. Feb. 1988;35(3):755-74.
Morris et al., Lentiviral-mediated delivery of siRNAs for antiviral therapy. Gene Ther. Mar. 2006;13(6):553-8.
Narang et al., Cationic lipids with increased DNA binding affinity for nonviral gene transfer in dividing and nondividing cells. Bioconjug Chem. Jan.-Feb. 2005;16(1):156-68.
Neises et al., Simple Method for the Esterification of Carboxylic Acids. Angew Chem Int Ed. Jul. 1978;17(7):522-24.
Peer et al., Nanocarriers as an emerging platform for cancer therapy. Nat Nanotechnol. Dec. 2007;2(12):751-60.
Sen., Surfactin: biosynthesis, genetics and potential applications. Adv Exp Med Biol. 2010;672:316-23.
Szoka et al., Comparative properties and methods of preparation of lipid vesicles (liposomes). Annu Rev Biophys Bioeng. 1980;9:467-508.
Tan et al., Engineering nanocarriers for siRNA delivery. Small. Apr. 4, 2011;7(7):841-56.
Tranchant et al., Physicochemical optimisation of plasmid delivery by cationic lipids. J Gene Med. Feb. 2004;6 Suppl 1:S24-35.
Van Balen et al., Liposome/water lipophilicity: methods, information content, and pharmaceutical applications. Med Res Rev. May 2004;24(3):299-324.
Wu et al., Cationic lipid polymerization as a novel approach for constructing new DNA delivery agents. Bioconjug Chem. Mar.-Apr. 2001;12(2):251-7.
Invitation to Pay Additional Fees for PCT/US2012/062222 dated Dec. 14, 2012.
International Search Report and Written Opinion for PCT/US2012/062222 dated Mar. 27, 2013.
International Preliminary Report on Patentability for PCT/US2012/062222, dated May 8, 2014.
Extended European Search Report for European Application No. 06784878.8 dated Jun. 29, 2009.
Extended European Search Report for European Application No. 11186795.8, dated Jun. 19, 2012.
International Search Report and Written Opinion for PCT/US2006/023171 dated May 29, 2008.
International Preliminary Report on Patentability for PCT/US2006/023171 dated Jul. 3, 2008.
Extended European Search Report, dated Jan. 28, 2008, for EP 07013193.3.
Invitation to Pay Additional Fees for PCT/US2004/016521 dated Sep. 29, 2004.
International Search Report and Written Opinion for PCT/US2004/016521 dated Dec. 8, 2004.
International Preliminary Report on Patentability for PCT/US2004/016521 dated Dec. 15, 2005.
International Search Report for PCT/US2001/031270 dated May 22, 2002.
Written Opinion for PCT/US2001/031270 dated Jan. 2, 2003.
International Preliminary Examination Report for PCT/US2001/031270 dated Aug. 19, 2003.
Extended European Search Report, dated Oct. 5, 2009, for EP 07813156.2.
International Search Report and Written Opinion for PCT/US2007/073976 dated Sep. 29, 2008.
International Preliminary Report on Patentability for PCT/US2007/073976 dated Feb. 5, 2009.
Extended European Search Report for EP 07798132.2 dated Jul. 18, 2011.
International Search Report and Written Opinion for PCT/US2007/070430 dated Dec. 13, 2007.
International Preliminary Report on Patentability for PCT/US2007/070430 dated Dec. 24, 2008.
Extended European Search Report for European Application No. 09825132.5 dated Jul. 16, 2013.
International Search Report and Written Opinion for PCT/US2009/006018 dated May 25, 2010.
International Preliminary Report on Patentability for PCT/US2009/006018 dated May 19, 2011.
International Search Report and Written Opinion for PCT/US2009/005810 dated Jun. 16, 2010.
International Preliminary Report on Patentability for PCT/US2009/005810 dated May 12, 2011.
International Search Report and Written Opinion for PCT/US2011/049360 dated Mar. 20, 2012.
International Preliminary Report on Patentability for PCT/US2011/049360 dated Mar. 7, 2013.
Partial Supplementary European Search Report for European Application No. 11820727.3, dated Nov. 26, 2014.
Extended European Search Report for European Application No. 11820727.3, dated Apr. 22, 2015.

(56) References Cited

OTHER PUBLICATIONS

Invitation to Pay Additional Fees for PCT/US2012/030349, dated Jul. 24, 2012.
International Search Report and Written Opinion for PCT/US2012/030349 dated Oct. 5, 2012.
International Preliminary Report on Patentability for PCT/US2012/030349 dated Oct. 10, 2013.
Invitation to Pay Additional Fees for PCT/US2013/054726, dated Oct. 31, 2013.
International Search Report and Written Opinion for PCT/US2013/054726, dated Jan. 7, 2014.
International Preliminary Report on Patentability for PCT/US2013/054726, dated Feb. 26, 2015.
International Search Report and Written Opinion for PCT/US2014/036355, dated Aug. 5, 2014.
International Preliminary Report on Patentability for PCT/US2014/036355, dated Nov. 12, 2015.
International Search Report and Written Opinion for PCT/US2014/044408, dated Oct. 24, 2014.
International Preliminary Report on Patentability for PCT/US2014/044408, dated Jan. 7, 2016.
Invitation to Pay Additional Fees for PCT/US2016/038141, dated Sep. 20, 2016.
Adami et al., An amino acid-based amphoteric liposomal delivery system for systemic administration of siRNA. Mol Ther. Jun. 2011;19(6):1141-51.
Akinc et al., A combinatorial library of lipid-like materials for delivery of RNAi therapeutics. Nat Biotech. 2008;26(5):561-69.
Akinc et al., Development of lipidoid-siRNA formulations for systemic delivery to the liver. Mol Ther. May 2009;17(5):872-9. doi: 10.1038/mt.2009.36. Epub Mar. 3, 2009.
Akinc et al., Exploring polyethylenimine-mediated DNA transfection and the proton sponge hypothesis. J Gene Med. May 2005;7(5):657-63.
Akira et al., Functions of toll-like receptors: lessons from KO mice. C R Biol. Jun. 2004;327(6):581-9.
Ali et al., Derivation of type II alveolar epithelial cells from murine embryonic stem cells. Tissue Eng. Aug. 2002;8(4):541-50.
Allison, the mode of action of immunological adjuvants. Dev Biol Stand. 1998;92:3-11. Review.
Alshamsan et al., The induction of tumor apoptosis in B16 melanoma following STAT3 siRNA delivery with a lipid-substituted polyethylenimine. Biomaterials. Feb. 2010;31(6):1420-8. Epub Nov. 13, 2009.
Anderson et al., Nanoliter-scale synthesis of arrayed biomaterials and application to human embryonic stem cells. Nat. Biotechnol. Jul. 2004;22(7):863-6. Epub Jun. 13, 2004.
Anderson et al., Structure/property studies of polymeric gene delivery using a library of poly(beta-amino esters). Mol Ther. Mar. 2005;11(3):426-34.
Anderson, Biological Responses to Materials. Annu Rev Mater Res. 2001;31:81-110.
Anderson, Chapter 4. Mechanisms of Inflammation and Infection With Implanted Devices. Cardiovasc Pathol. 1993;2:33S-41S.
Anderson, Human gene therapy. Nature. Apr. 30, 1998;392(6679 Suppl):25-30. Review.
Asokan et al., Cytosolic delivery of macromolecules. 3. Synthesis and characterization of acid-sensitive bis-detergents. Bioconjug Chem. Nov.-Dec. 2004;15(6):1166-73.
Astle et al., A VEGFR2 Antagonist and Other Peptoids Evade Immune Recognition. Int J Pept Res Ther. 2008;14(3):223-227.
Bajaj et al., Synthesis and gene transfection efficacies of Pei-cholesterol-based lipopolymers. Bioconjug Chem. Aug. 2008;19(8):1640-51. Epub Jul. 11, 2008.
Ballermann et al., Shear stress and the endothelium. Kidney Int Suppl. Sep. 1998;67:S100-8.
Bartel, MicroRNAs: Genomics, Biogenesis, Mechanism, and Function. Cell. 2004;116:281-97.
Behr et al., Efficient gene transfer into mammalian primary endocrine cells with lipopolyamine-coated DNA. Proc Natl Acad Sci U S A. Sep. 1989;86(18):6982-6.
Behr, Synthetic gene-transfer vectors. Acc Chem Res. 1993;26:274-278.
Bossle et al., Synthesis and biological activity of new 2-substituted analogs of fluphenazine. J Med Chem. Mar. 1, 1976;19(3):370-3.
Boudou et al., Multiple functionalities of polyelectrolyte multilayer films: new biomedical applications. Adv Mater. Jan. 26, 2010;22(4):441-67.
Boussif et al., A versatile vector for gene and oligonucleotide transfer into cells in culture and in vivo: polyethylenimine. Proc Natl Acad Sci U S A. Aug. 1, 1995;92(16):7297-301.
Bratlie et al., Rapid biocompatibility analysis of materials via in vivo fluorescence imaging of mouse models. PLoS One. Apr. 6, 2010;5(4):e10032.
Braun et al., Structure/function relationships of polyamidoamine/DNA dendrimers as gene delivery vehicles. J Pharm Sci. Feb. 2005;94(2):423-36.
Breunig et al., Breaking up the correlation between efficacy and toxicity for nonviral gene delivery. Proc Natl Acad Sci U S A. Sep. 4, 2007;104(36):14454-9. Epub Aug. 28, 2007.
Breunig et al., Mechanistic investigation of poly(ethylene imine)-based siRNA delivery: disulfide bonds boost intracellular release of the cargo. J Control Release. Aug. 25, 2008;130(1):5763. Epub May 24, 2008.
Brey et al., Controlling poly(beta-amino ester) network properties through macromer branching. Acta Biomater. Mar. 2008;4(2):207-17. Epub Oct. 22, 2007.
Brey et al., Influence of macromer molecular weight and chemistry on poly(beta-amino ester) network properties and initial cell interactions. J Biomed Mater Res A. Jun. 1, 2008;85(3):731-41.
Brodbeck et al., Biomaterial surface chemistry dictates adherent monocyte/macrophage cytokine expression in vitro. Cytokine. Jun. 21, 2002;18(6):311-9.
Burnett et al., Current progress of siRNA/shRNA therapeutics in clinical trials. Biotechnol J. Sep. 2011;6(9):1130-46. doi: 10.1002/biot.201100054. Epub Jul. 11, 2011.
Campbell et al., Application of cytokeratin 7 and 20 immunohistochemistry to diagnostic pathology. Current Diagnostic Pathology. 2001;7:113-22.
Carter et al., Mechanobiology of skeletal regeneration. Clin Orthop Relat Res. Oct. 1998;(355 Suppl):S41-55.
Castanotto et al.,. The promises and pitfalls of RNA-interference-based therapeutics. Nature. Jan. 22, 2009;457(7228):426-33. doi: 10.1038/nature07758.
Chakraborty, Potentiality of Small Interfering RNAs (siRNA) as Recent Therapeutic Targets for Gene-Silencing. Curr Drug Targets. 2007;8:469-82.
Chan et al., Triplex DNA: fundamentals, advances, and potential applications for gene therapy. J Mol Med. Apr. 1997;75(4):267-82. Review.
Chang, Therapeutic applications of polymeric artificial cells. Nat Rev Drug Discov. Mar. 2005;4(3):221-35.
Chen et al., Polymeric growth factor delivery strategies for tissue engineering. Pharm Res. Aug. 2003;20(8):1103-12.
Chiang et al., Synthesis, characterization and properties of novel self-extinguishing organic-inorganic nanocomposites containing nitrogen, silicon and phosphorus via sol-gel method. Composite Science and Technology. 2008;68(14):2849-57.
Chu et al., Cytokeratin 7 and cytokeratin 20 expression in epithelial neoplasms: a survey of 435 cases. Mod Pathol. Sep. 2000;13(9):962-72.
Conley et al., Derivation, propagation and differentiation of human embryonic stem cells. Int J Biochem Cell Biol. Apr. 2004;36(4):555-67.
Conte et al., Regioselective ring opening of [(perfluoroalkyl)methyl] oxiranes with N-nucleophiles. J Fluorine Chem. 2005;126(9-10):1274-80.
Cotten et al., Receptor-mediated transport of DNA into eukaryotic cells. Methods Enzymol. 1993;217:618-44.

(56) References Cited

OTHER PUBLICATIONS

Creusat et al., Proton sponge trick for pH-sensitive disassembly of polyethylenimine-based siRNA delivery systems. Bioconjug Chem. May 19, 2010;21(5):994-1002.
Cristofaro et al., Role of Toll-like receptors in infection and immunity: clinical implications. Drugs. 2006;66(1):15-29.
Crooke, Evaluating the mechanism of action of antiproliferative antisense drugs. Antisense Nucleic Acid Drug Dev. Apr. 2000;10(2):123-6.
Crooke, Molecular mechanisms of action of antisense drugs. Biochim Biophys Acta. Dec. 10, 1999;1489(1):31-44. Review.
Crystal, Transfer of genes to humans: early lessons and obstacles to success. Science. Oct. 20, 1995;270(5235):404-10. Review.
Decher, Fuzzy Nanoassemblies: Toward Layered Polymeric Multicomposites. Science. 1997;277;1232-37.
Dern et al., Toxicity studies of pyrimethamine (daraprim). Am J Trop Med Hyg. Mar. 1955;4(2):217-20.
Deshmukh et al., Liposome and polylysine mediated gene therapy. New J Chem. 1997;21:113-124.
Diebold et al., Innate antiviral responses by means of TLR7-mediated recognition of single-stranded RNA. Science. Mar. 5, 2004;303(5663):1529-31. Epub Feb. 19, 2004.
Discher et al., Polymer vesicles. Science. Aug. 9, 2002;297(5583):967-73. Review.
Discher et al., Polymersomes: tough vesicles made from diblock copolymers. Science. May 14, 1999;284(5417):1143-6.
Dong et al., Lipopeptide nanoparticles for potent and selective siRNA delivery in rodents and nonhuman primates. Proc Natl Acad Sci U S A. Mar. 18, 2014;111(11):3955-60. doi: 10.1073/pnas.1322937111. Epub Feb. 10, 2014.
Dushnik-Levinson et al., Embryogenesis in vitro: study of differentiation of embryonic stem cells. Biol Neonate. 1995;67(2):77-83.
Eberle et al., Modifications in small interfering RNA that separate immunostimulation from RNA interference. J Immunol. Mar. 1, 2008;180(5):3229-37.
Elbashir et al., Duplexes of 21-nucleotide RNAs mediate RNA interference in cultured mammalian cells. Nature. May 24, 2001;411(6836):494-8.
Elbashir et al., RNA interference is mediated by 21- and 22-nucleotide RNAs. Genes Dev. 2001;15:188-200.
Ewert et al., Cationic lipid-DNA complexes for gene therapy: understanding the relationship between complex structure and gene delivery pathways at the molecular level. Curr Med Chem. Jan. 2004;11(2):133-49.
Felgner et al., Lipofection: a highly efficient, lipid-mediated DNA-transfection procedure. Proc Natl Acad Sci U S A. Nov. 1987;84(21):7413-7.
Fenton et al., Bioinspired Alkenyl Amino Alcohol Ionizable Lipid Materials for Highly Potent in Vivo mRNA Delivery. Adv Mater. Apr. 20, 2016;28(15):2939-43. doi: 10.1002/adma.201505822. Epub Feb. 18, 2016.
Ferruti et al., A novel modification of poly(1-lysine) leading to a soluble cationic polymer with reduced toxicity and with potential as a transfection agent. Macromol Chem Phys 1998;199:2565-75.
Ferruti et al., Linear amino polymers: Synthesis, protonation and complex formation. Advances in Polymer Science. 1984;58:55-92.
Fire et al., Potent and specific genetic interference by double-stranded RNA in Caenorhabditis elegans. Nature. Feb. 19, 1998;391(6669):806-11.
Fisher et al., Photoinitiated Polymerization of Biomaterials. Annu Rev Mater Res. 2001;31:171-81.
Forsbach et al., Identification of RNA sequence motifs stimulating sequence-specific TLR8-dependent immune responses. J Immunol. Mar. 15, 2008;180(6):3729-38.
Fourneau et al., Two new series of local anesthetics derived from piperazine. Bulletin de la Societe Chimique de France. 1930;47:1003-16. French.
Frank-Kamenetsky et al., Therapeutic RNAi targeting PCSK9 acutely lowers plasma cholesterol in rodents and LDL cholesterol in nonhuman primates. Proc Natl Acad Sci U S A. Aug. 19, 2008;105(33):11915-20. doi: 10.1073/pnas.0805434105. Epub Aug. 11, 2008.
Friedmann, Human gene therapy—an immature genie, but certainly out of the bottle. Nat Med. Feb. 1996;2(2):144-7.
Furgeson et al., Modified linear polyethylenimine-cholesterol conjugates for DNA complexation. Bioconjug Chem. Jul.-Aug. 2003;14(4):840-7.
Furgeson et al., Novel water insoluble lipoparticulates for gene delivery. Pharm Res. Apr. 2002;19(4):382-90.
Gademann et al., the fourth helical secondary structure of beta-peptides: the (P)-28-helix of a beta-hexapeptide consisting of (2R,3S)-3-amino-2-hydroxy acid residues. Angew Chem Int Ed Engl. Apr. 4, 2003;42(13):1534-7.
Gardner, Stem cells and regenerative medicine: principles, prospects and problems. C R Biol. Jun.-Jul. 2007;330(6-7):465-73. Epub Feb. 15, 2007.
Geisbert et al., Postexposure protection of non-human primates against a lethal Ebola virus challenge with RNA interference: a proof-of-concept study. Lancet. May 29, 2010;375(9729):1896905. doi:10.1016/S0140-6736(10)60357-1.
Geissmann et al., Development of monocytes, macrophages, and dendritic cells. Science. Feb. 5, 2010;327(5966):656-61. doi: 10.1126/science.1178331.
Geng et al., Hydrolytic degradation of poly(ethylene oxide)-block-polycaprolactone worm micelles. J Am Chem Soc. Sep. 21, 2005;127(37):12780-1.
Ghosh et al., Toll-like receptor (TLR) 2-9 agonists-induced cytokines and chemokines: I. Comparison with T cell receptor-induced responses. Cell Immunol. Sep. 2006;243(1):48-57. Epub Jan. 23, 2007.
Godbey et al., Size matters: molecular weight affects the efficiency of poly(ethylenimine) as a gene delivery vehicle. J Biomed Mater Res. Jun. 5, 1999;45(3):268-75.
Gonzalez et al., New class of polymers for the delivery of macromolecular therapeutics. Bioconjug Chem. Nov.-Dec. 1999;10(6):1068-74.
Grayson et al., Biophysical and structural characterization of polyethylenimine-mediated siRNA delivery in vitro. Pharm Res. Aug. 2006;23(8):1868-76.
Grivennikov et al., Immunity, inflammation, and cancer. Cell. Mar. 19, 2010;140(6):883-99. doi: 10.1016/j.ce11.2010.01.025.
Gross et al., Bioluminescence imaging of myeloperoxidase activity in vivo. Nat Med. Apr. 2009;15(4):455-61. Epub Mar. 22, 2009.
Grunlan et al., Synthesis of 1,9-bis[glycidyloxypropyl]penta(1'H, 1'H, 2'H, 2'H-perfluoroalkylmethylsiloxane)s and copolymerization with piperazine. Polymer. 2004;45:2517-23.
Grzelinski et al., RNA interference-mediated gene silencing of pleiotrophin through polyethylenimine-complexed small interfering RNAs in vivo exerts antitumoral effects in glioblastoma xenografts. Hum Gene Ther. Jul. 2006;17(7):751-66.
Guan et al., Embryonic stem cell-derived neurogenesis. Retinoic acid induction and lineage selection of neuronal cells. Cell Tissue Res. Aug. 2001;305(2):171-6.
Guan et al., Surface photo-grafting of polyurethane with 2-hydroxyethyl acrylate for promotion of human endothelial cell adhesion and growth. J Biomater Sci Polym Ed. 2000;11(5):523-36.
Gunatillake et al., Recent developments in biodegradable synthetic polymers. Biotechnol Annu Rev. 2006;12:301-47.
Gupta et al., A review of in vitro-in vivo investigations on dendrimers: the novel nanoscopic drug carriers. Nanomedicine. Jun. 2006;2(2):66-73.
Haensler et al., Polyamidoamine cascade polymers mediate efficient transfection of cells in culture. Bioconjug Chem. Sep.-Oct. 1993;4(5):372-9.
Hammond et al., An RNA-directed nuclease mediates post-transcriptional gene silencing in *Drosophila* cells. Nature. 2000;404:293-96.
Harder et al., Molecular Conformation in Oligo(ethylene glycol)-Terminated Self-Assembled Monolayers on Gold and Silver Surfaces Determines Their Ability to Resist Protein Adsorpotion. J Phys Chem B. 1998;102:426-36.

(56) References Cited

OTHER PUBLICATIONS

Hasan et al., Identification of cytokeratin 1 as a binding protein and presentation receptor for kininogens on endothelial cells. Proc Natl Acad Sci U S A. Mar. 31, 1998;95(7):3615-20.
Heil et al., Species-specific recognition of single-stranded RNA via toll-like receptor 7 and 8. Science. Mar. 5, 2004;303(5663):1526-9. Epub Feb. 19, 2004.
Hemmi et al., Small anti-viral compounds activate immune cells via the TLR7 MyD88-dependent signaling pathway. Nat Immunol. Feb. 2002;3(2):196-200. Epub Jan. 22, 2002.
Heyes et al., Cationic lipid saturation influences intracellular delivery of encapsulated nucleic acids. J Control Release. Oct. 3, 2005;107(2):276-87.
Hill et al., Enantioselective Epoxidation of Allylic Alcohols: (2S,3S)-3-Propyloxiranemethanol. Org Syn. 1990;7:461.
Hill et al., In vitro cytotoxicity of poly(amidoamine)s: relevance to DNA delivery. Biochim Biophys Acta. Apr. 19, 1999;1427(2):161-74.
Hoekenga, The treatment of malaria with hydroxychloroquine. Am J Trop Med Hyg. Mar. 1955;4(2):221-3.
Holmlin et al., Zwitterionic SAMs that Resist Nonspecific Adsorption of Protein from Aqueous Buffer. Langmuir. 2001;17:2841-50.
Hope et al., Cationic Lipids, Phosphatidylethanolamine and the Intracellular Delivery of Polymeric, Nucleic Acid-Based Drugs. Molecular Membrane Technology. 1998;15:1-14.
Hornung et al., Quantitative expression of toll-like receptor 1-10 mRNA in cellular subsets of human peripheral blood mononuclear cells and sensitivity to CpG oligodeoxynucleotides. J Immunol. May 1, 2002;168(9):4531-7.
Hornung et al., Sequence-specific potent induction of IFN-alpha by short interfering RNA in plasmacytoid dendritic cells through TLR7. Nat Med. Mar. 2005;11(3):263-70. Epub Feb. 20, 2005.
Howard, Delivery of RNA interference therapeutics using polycation-based nanoparticles. Adv Drug Deliv Rev. Jul. 25, 2009;61(9):710-20. Epub Apr. 5, 2009.
Hsu et al., Diethanolamine (DEA) degradation under gas-treating conditions. Industrial and Engineering Chemistry Product Research and Development. 1985;24(4):630-35.
Huang et al., Claudin-3 gene silencing with siRNA suppresses ovarian tumor growth and metastasis. Proc Natl Acad Sci U S A. Mar. 3, 2009;106(9):3426-30. doi: 10.1073/pnas.0813348106. Epub Feb. 10, 2009.
Hunt et al., Effect of biomaterial surface charge on the inflammatory response: evaluation of cellular infiltration and TNF alpha production. J Biomed Mater Res. May 1996;31(1):139-44.
Ichimaru et al., Synthesis and characterization of new piperazine-type inhibitors for mitochondrial NADH-ubiquinone oxidoreductase (complex I). Biochemistry. Oct. 7, 2008;47(40):10816-26. Epub Sep. 10, 2008.
Ikeda et al., Role of micafungin in the antifungal armamentarium. Curr Med Chem. 2007;14(11):1263-75.
Ingber et al., Mechanochemical switching between growth and differentiation during fibroblast growth factor-stimulated angiogenesis in vitro: role of extracellular matrix. J Cell Biol. Jul. 1989;109(1):317-30.
Irwin et al., Modulus-dependent macrophage adhesion and behavior. J Biomater Sci Polym Ed. 2008;19(10):1363-82.
Ito, Surface micropatterning to regulate cell functions. Biomaterials. Dec. 1999;20(23-24):2333-42.
Itskovitz-Eldor et al., Differentiation of human embryonic stem cells into embryoid bodies compromising the three embryonic germ layers. Mol Med. Feb. 2000;6(2):88-95.
Iwasaki et al., Toll-like receptor control of the adaptive immune responses. Nat Immunol. Oct. 2004;5(10):987-95.
Jarrossay et al., Specialization and complementarity in microbial molecule recognition by human myeloid and plasmacytoid dendritic cells. Eur J Immunol. Nov. 2001;31(11):3388-93.

Jayaraman et al., Maximizing the potency of siRNA lipid nanoparticles for hepatic gene silencing in vivo. Angew Chem Int Ed Engl. Aug. 20, 2012;51(34):8529-33. doi: 10.1002/anie.201203263. Epub Jul. 10, 2012.
Jia et al., Demonstration of two novel methods for predicting functional siRNA efficiency. BMC Bioinformatics. 2006;7:271.
Jiang et al., Electrochemically controlled release of lipid/DNA complexes: a new tool for synthetic gene delivery system. Electrochem Commun. 2004;6:576-82.
Jiang et al., Hyaluronic acid-polyethyleneimine conjugate for target specific intracellular delivery of siRNA. Biopolymers. Jul. 2008;89(7):635-42.
Jiang et al., Ultralow-fouling, functionalizable, and hydrolyzable zwitterionic materials and their derivatives for biological applications. Adv Mater. Mar. 5, 2010;22(9):920-32.
Johansson et al., Evidence for involvement of activin A and bone morphogenetic protein 4 in mammalian mesoderm and hematopoietic development. Mol Cell Biol. Jan. 1995;15(1):141-51.
John et al. Effective RNAi-mediated gene silencing without interruption of the endogenous microRNA pathway. Nature. Oct. 11, 207;449(7163):745-7. Epub Sep. 26, 2007.
Jolck et al., Solid-phase synthesis of PEGylated lipopeptides using click chemistry. Bioconjug Chem. May 19, 2010;21(5):807-10.
Jon et al., Degradable poly(amino alcohol esters) as potential DNA vectors with low cytotoxicity. Biomacromolecules. Nov.-Dec. 2003;4(6):1759-62.
Judge et al., Design of noninflammatory synthetic siRNA mediating potent gene silencing in vivo. Mol Ther. Mar. 2006;13(3):494-505. Epub Dec. 15, 2005.
Juliano et al., Biological barriers to therapy with antisense and siRNA oligonucleotides. Mol Pharm. May-Jun. 2009;6(3):686-95. doi:10.1021/mp900093r.
Kabanov et al., DNA complexes with polycations for the delivery of genetic material into cells. Bioconjug Chem. Jan.-Feb. 1995;6(1):7-20.
Kamath et al., Surface chemistry influences implant-mediated host tissue responses. J Biomed Mater Res A. Sep. 2008;86(3):617-26.
Kanetani et al., Synthesis, and physicochemical and antimicrobial properties of 3-(3-alkyl-1-piperazinyl)-1-propanesulfonic acids and some related compounds. Nippon Kagaku Kaishi. 1983(12):1783-91.
Katsuki et al., Chapter 1. Asymmetric Epoxidation of Allylic Alcohols: The Katsuki-Sharpless Epoxidation Reaction. Org React 1996;48:1-299.
Katsuki et al., The First Practical Method for Asymmetric Epoxidation. J Am Chem Soc. 1980:102;5974-76.
Kaufman et al., Hematopoietic colony-forming cells derived from human embryonic stem cells. Proc Natl Acad Sci U S A. Sep. 11, 2001;98(19):10716-21. Epub Sep. 4, 2001.
Kaur et al., A delineation of diketopiperazine self-assembly processes: understanding the molecular events involved in Nepsilon-(fumaroyl)diketopiperazine of L-Lys (FDKP) interactions. Mol Pharm. Mar.-Apr. 2008;5(2):294-315.
Kim et al., Comparative evaluation of target-specific GFP gene silencing efficiencies for antisense ODN, synthetic siRNA, and siRNA plasmid complexed with PEI-PEG-FOL conjugate. Bioconjug Chem. Jan.-Feb. 2006;17(1):241-4.
Kim et al., Efficient siRNA delivery using water soluble lipopolymer for anti-angiogenic gene therapy. J Control Release. Apr. 23, 2007;118(3):357-63. Epub Jan. 9, 2007.
Kim et al., Local and systemic delivery of Vegf siRNA using polyelectrolyte complex micelles for effective treatment of cancer. J Control Release. Jul. 14, 2008;129(2):107-16. Epub Mar. 14, 2008.
Kim et al., Synthesis of biodegradable cross-linked poly(beta-amino ester) for gene delivery and its modification, inducing enhanced transfection efficiency and stepwise degradation. Bioconjug Chem. Sep.-Oct. 2005;16(5):1140-8.
Kleinman et al., Sequence- and target-independent angiogenesis suppression by siRNA via TLR3. Nature. Apr. 3, 2008;452(7187):591-7. Epub Mar. 26, 2008.

(56) References Cited

OTHER PUBLICATIONS

Klibanov et al., Amphipathic polyethyleneglycols effectively prolong the circulation time of liposomes. FEBS Lett. Jul. 30, 1990;268(1):235-7.
Krieg et al., CpG motifs in bacterial DNA trigger direct B-cell activation. Nature. Apr. 6, 1995;374(6522):546-9.
Krieg et al., Toll-like receptors 7, 8, and 9: linking innate immunity to autoimmunity Immunol. Rev. Dec. 2007;220:251-69.
Krieg, The toll of too much TLR7. Immunity. Nov. 2007;27(5):695-7.
Kukowska-Latallo et al., Efficient transfer of genetic material into mammalian cells using Starburst polyamidoamine dendrimers. Proc Natl Acad Sci USA. May 14, 1996;93(10):4897-902.
Kwon et al., Application of an HIV gp41-derived peptide for enhanced intracellular trafficking of synthetic gene and siRNA delivery vehicles. Bioconjug Chem. Apr. 2008;19(4):920-7. Epub Apr. 1, 2008.
Lan et al., Stabilized immune modulatory RNA compounds as agonists of Toll-like receptors 7 and 8. Proc Natl Acad Sci U S A. Aug. 21, 2007;104(34):13750-5. Epub Aug. 14, 2007.
Langer, Perspectives and challenges in tissue engineering and regenerative medicine. Adv Mater. Sep. 4, 2009;21(32-33):3235-6.
Lee et al., Rapid pharmacokinetic and biodistribution studies using cholorotoxin-conjugated iron oxide nanoparticles: a novel non-radioactive method. PLoS One. Mar. 4, 2010;5(3):e9536. doi: 10.1371/journal.pone.0009536.
Lee et al., Stability and cellular uptake of polymerized siRNA (poly-siRNA)/polyethylenimine (PEI) complexes for efficient gene silencing. J Control Release. Feb. 15, 2010;141(3):339-46. Epub Oct. 14, 2009.
Leuschner et al., Therapeutic siRNA silencing in inflammatory monocytes in mice. Nat Biotechnol. Oct. 9, 2011;29(11):1005-10. doi: 10.1038/nbt.1989.
Levenberg et al., Differentiation of human embryonic stem cells on three-dimensional polymer scaffolds. Proc Natl Acad Sci U S A. Oct. 28, 2003;100(22):12741-6. Epub Oct. 15, 2003.
Li et al., Defining the optimal parameters for hairpin-based knockdown constructs. RNA. 2007;13:1765-74.
Li et al., Plasticity of the urothelial phenotype: effects of gastrointestinal mesenchyme/stroma and implications for urinary tract reconstruction. Differentiation. Oct. 2000;66(2-3):126-35.
Li et al., Reverse Atom Transfer Radical Polymerization in Miniemulsion. Macromolecules. 2003;36(16):6028-6035.
Lim, et al., A self-destroying polycationic polymer: biodegradable poly(4-hydroxy-l-proline ester. J. Am. Chem. Soc. 1999;121:5633-5639.
Love et al., Lipid-like materials for low-dose, in vivo gene silencing. Proc Natl Acad Sci U S A. Feb. 2, 2010;107(5):1864-9. Epub Jan. 11, 2010.
Luo et al., Synthetic DNA delivery systems. Nat Biotechnol. Jan. 2000;18(1):33-7. Review.
Lyle et al., Cytokeratin 15 (K15) as an Epithelial Stem Cell Marker: Implications for Aging and Carcinogenesis. J Invest Derma. 1999;112(4):623. Abstract #606.
Lynn et al., Accelerated discovery of synthetic transfection vectors: parallel synthesis and screening of a degradable polymer library. J Am Chem Soc. Aug. 22, 2001;123(33):8155-6.
Lynn et al., Degradable Poly((3-amino esters): Synthesis, Characterization, and Self-Assembly with Plasmid DNA. J. Am. Chem. Soc. 2000;122 (44): 10761-8.
Lynn et al., pH-Responsive Polymer Microspheres: Rapid Release of Encapsulated Material within the Range of Intracellular pH. Angew Chem Int Ed Engl. May 4, 2001;40(9):1707-10.
Ma et al., Development of Cationic Polymer Coatings to Regulate Foreign Body Responses. Adv Mater. 2011;23:H189-94.
Margus et al., Cell-penetrating peptides as versatile vehicles for oligonucleotide delivery. Mol Ther. Mar. 2012;20(3):525-33. doi: 10.1038/mt.2011.284. Epub Jan. 10, 2012.
Marques et al., Activation of the mammalian immune system by siRNAs. Nat Biotechnol. Nov. 2005;23(11):1399-405.
Marshak-Rothstein, Toll-like receptors in systemic autoimmune disease. Nat Rev Immunol. Nov. 2006;6(11):823-35.
Martell et al., The Preparation and the Properties of Some N,N'-Disubstituted-ethylenediaminedipropionic Acids. J Am Chem Soc. 1950;72:5357-61.
Mathias et al., Synthesis of New Hydroxylated Monomers Based on Methacrylate, Dimethacrylate, and Tetramethacrylate Michael Adducts and Photopolymerization Kinetics of Bulk Cross-Linkers. Macromolecules. 2004;37(9):32313-38.
Mattey et al., Demonstration of cytokeratin in endothelial cells of the synovial microvasculature in situ and in vitro. Br J Rheumatol. Aug. 1993;32(8):676-82.
Mendelsohn et al., Rational design of cytophilic and cytophobic polyelectrolyte multilayer thin films. Biomacromolecules. Jan.-Feb. 2003;4(1):96-106.
Miller, Cationic Liposomes for Gene Therapy. Angew. Chem. Int. Ed. 1998;37:1769-1785.
Mintzer et al., Nonviral vectors for gene delivery. Chem Rev. Feb. 2009;109(2):259-302.
Moll et al., The human keratins: biology and pathology. Histochem Cell Biol. Jun. 2008;129(6):705-33. Epub May 7, 2008.
Moll, [Cytokeratins as markers of differentiation. Expression profiles in epithelia and epithelial tumors] Veroff Pathol. 1993;142:1-197. German.
Morrissey et al., Potent and persistent in vivo anti-HBV activity of chemically modified siRNAs. Nat Biotechnol. Aug. 2005;23(8):1002-7. Epub Jul. 24, 2005.
Moure et al. Chemical modulation of peptoids: synthesis and conformational studies on partially constrained derivatives. Chemistry. Jul. 4, 2011;17(28):7927-39. doi: 10.1002/chem.201100216. Epub May 24, 2011.
Mulligan, The basic science of gene therapy. Science. May 14, 1993;260(5110):926-32. Review.
Nahrendorf et al., Dual channel optical tomographic imaging of leukocyte recruitment and protease activity in the healing myocardial infarct. Circ Res. Apr. 27, 2007;100(8):1218-25. Epub Mar. 22, 2007.
Naito et al., siVirus: web-based antiviral siRNA design software for highly divergent viral sequences. Nucleic Acids Res. 2006;34:W448-450.
Navarro et al., Phospholipid—polyethylenimine conjugate-based micelle-like nanoparticles for siRNA delivery. Drug Deliv and Trans Res. 2011; 25-33.
Neamnark et al., Aliphatic lipid substitution on 2 kDa polyethylenimine improves plasmid delivery and transgene expression. Mol Pharm. Nov.-Dec. 2009;6(6):1798-815.
Nguyen et al., A novel high-throughput cell-based method for integrated quantification of type I interferons and in vitro screening of immunostimulatory RNA drug delivery. Biotechnol Bioeng. Jul. 1, 2009;103(4):664-75.
Nguyen et al., Drug delivery-mediated control of RNA immunostimulation. Mol Ther. Sep. 2009;17(9):1555-62. Epub Jul. 7, 2009.
Nolan et al., Quantification of mRNA using real-time RT-PCR. Nat Protoc. 2006;1(3):1559-82.
Novak et al., Biomimetic strategies based on viruses and bacteria for the development of immune evasive biomaterials. Biomaterials. Apr. 2009;30(11):1989-2005. Epub Jan. 29, 2009.
Novina et al., The RNAi revolution. Nature. 2004;430:161-64.
Novobrantseva et al., Systemic RNAi-mediated Gene Silencing in Nonhuman Primate and Rodent Myeloid Cells. Mol Ther Nucleic Acids. Jan. 24, 2012;1:e4. doi: 10.1038/mtna.2011.3.
Odorico et al., Multilineage differentiation from human embryonic stem cell lines. Stem Cells. 2001;19(3):193-204.
Onuki et al., A review of the biocompatibility of implantable devices: current challenges to overcome foreign body response. J Diabetes Sci Technol. Nov. 2008;2(6):1003-15.
Orive et al., Cell encapsulation: promise and progress. Nat Med. Jan. 2003;9(1):104-7.
Ostuni et al., A Survey of Structure-Property Relationships of Surfaces that Resist the Adsorption of Protein . Langmuir. 2001;17:5605-20.

(56) References Cited

OTHER PUBLICATIONS

Parrish et al., Five- and six-membered ring opening of pyroglutamic diketopiperazine. J Org Chem. Mar. 22, 2002;67(6):1820-6.
Pashine et al., Targeting the innate immune response with improved vaccine adjuvants. Nat Med. Apr. 2005;11(4 Suppl):S63-8.
Paul et al., Topographical control of human macrophages by a regularly microstructured polyvinylidene fluoride surface. Biomaterials. Oct. 2008;29(30):4056-64. Epub Jul. 29, 2008.
Peppas et al., Hydrogels in Biology and Medicine: From Molecular Principles to Bionanotechnology. Mater. 2006;18:1345-60.
Pera et al., Human embryonic stem cells. J Cell Sci. Jan. 2000;113 ( Pt 1):5-10.
Philipp et al., Hydrophobically modified oligoethylenimines as highly efficient transfection agents for siRNA delivery. Bioconjug Chem. Nov. 2009;20(11):2055-61.
Phillips et al., Enhanced antibody response to liposome-associated protein antigens: preferential stimulation of IgG2a/b production. Vaccine. 1992;10(3):151-8.
Pollard et al., Ether amino alcohols. II. J Org Chem. 1952;17:1-3.
Prata et al., Lipophilic peptides for gene delivery. Bioconjug Chem. Feb. 2008;19(2):418-20.
Putnam et al., Poly(4-hydroxy-l-proline ester): Low-Temperature Polycondensation and Plasmid DNA Complexation. Macromolecules 1999;32:3658-62.
Putnam, Polymers for gene delivery across length scales. Nat Mater. Jun. 2006;5(6):439-51.
Ratner et al., Biomaterials: where we have been and where we are going. Annu Rev Biomed Eng. 2004;6:41-75.
Refai et al., Effect of titanium surface topography on macrophage activation and secretion of proinflammatory cytokines and chemokines. J Biomed Mater Res A. Aug. 1, 2004;70(2):194-205.
Reynolds et al., Rational siRNA design for RNA interference. Nat Biotechnol. 2004;22(3):326-30.
Robbins et al., 2'-0-methyl-modified RNAs act as TLR7 antagonists. Mol Ther. Sep. 2007;15(9):1663-9. Epub Jun. 19, 2007.
Robbins et al., siRNA and innate immunity. Oligonucleotides. Jun. 2009;19(2):89-102.
Rogers et al., Synthetic Experiments in the Ferrichrome Series. Biochemistry. Dec. 1964;3:1850-5.
Ryng et al., Synthesis and Structure Elucidation of 5-Aminomethinimino-3-methyl-4-isoxazolecarboxylic Acid Phenylamides and Their Immunological Activity. Archiv der Pharmazie. Jan. 1, 1997;330(11):319-26.
Sahay et al., Endocytosis of nanomedicines. J Control Release. Aug. 3, 2010;145(3):182-95. Epub Mar. 10, 2010.
Sakiyama-Elbert et al., Functional Biomaterials: Design of Novel Biomaterials. Ann Rev Mater Res. 2001;31:183-201.
Saltzman, Chapter 19. Cell Interactions with Polymers. In: Principles of Tissue Engineering, 2d ed., 2000:221-35.
Sanford, The biolistic process. Trends Biotechnol. 1988;6:299-302.
Sato et al., Resolution of liver cirrhosis using vitamin A-coupled liposomes to deliver siRNA against a collagen-specific chaperone. Nat Biotechnol. Apr. 2008;26(4):431-42. doi: 10.1038/nbt1396. Epub Mar. 30, 2008.
Sawaf et al., [Cytokeratins, markers of epithelial cell differentiation: expression in normal epithelia.] Pathol Biol (Paris). 1992;40:655-65. French.
Schaus et al., Highly Selective Hydrolytic Kinetic Resolution of Terminal Epoxides Catalyzed by Chiral (salen)CoIII Complexes. Practical Synthesis of Enantioenriched Terminal Epoxides and 1,2-Biols. J Am Chem Soc. 2002;124(7):1307-15.
Scheel et al., Therapeutic anti-tumor immunity triggered by injections of immunostimulating single-stranded RNA. Eur J Immunol. Oct. 2006;36(10):2807-16.
Schena et al., Quantitative monitoring of gene expression patterns with a complementary DNA microarray. Science. Oct. 20, 1995;270(5235):467-70.
Schön et al., TLR7 and TLR8 as targets in cancer therapy. Oncogene. Jan. 7, 2008;27(2):190-9.
Schuldiner et al., Effects of eight growth factors on the differentiation of cells derived from human embryonic stem cells. Proc Natl Acad Sci U S A. Oct. 10, 2000;97(21):11307-12.
Schutte et al., Cytokine profiling using monocytes/macrophages cultured on common biomaterials with a range of surface chemistries. J Biomed Mater Res A. Jan. 2009;88(1):128-39.
Schweizer et al., Synthetic Studies towards the Total Synthesis of Providencin. Synthesis. 2007;24:3807-14.
Semple et al., Rational design of cationic lipids for siRNA delivery. Nat Biotechnol. Feb. 2010;28(2):172-6. doi:10.1038/nbt.1602. Epub Jan. 17, 2010.
Shchori, Poly(secondary Amine)s from Diacrylates and Diamines. J Polym Sci Polymer. Jun. 1983;21(6):413-15.
Shemper et al., Synthetic clay nanocomposite-based coatings prepared by UV-Cure photopolymerization. J Appl Polymer Sci. 2004;93:1252-63.
Siegwart et al., Combinatorial synthesis of chemically diverse core-shell nanoparticles for intracellular delivery. Proc Natl Acad Sci U S A. Aug. 9, 2011;108(32):12996-3001. doi: 10.1073/pnas.1106379108. Epub Jul. 22, 2011.
Sioud, Induction of inflammatory cytokines and interferon responses by double-stranded and single-stranded siRNAs is sequence-dependent and requires endosomal localization. J Mol Biol. May 20, 2005;348(5):1079-90. Epub Mar. 22, 2005.
Sioud, Innate sensing of self and non-self RNAs by Toll-like receptors. Trends Mol Med. Apr. 2006;12(4):167-76. Epub Mar. 10, 2006.
Sioud, Single-stranded small interfering RNA are more immunostimulatory than their double-stranded counterparts: a central role for 2'-hydroxyl uridines in immune responses. Eur J Immunol. May 2006;36(5):1222-30.
Spradling et al., Stem cells find their niche. Nature. Nov. 1, 2001;414(6859):98-104.
Staubli et al., Hydrolytically degradable amino acid containing polymers. J Am Chem Soc. 1990;45:4419-24.
Steinman et al., Taking dendritic cells into medicine. Nature. Sep. 27, 2007;449(7161):419-26.
STN-CAS database Registry No. 1016794-08-3. Entered STN-CAS database on Apr. 23, 2008.
STN-CAS database Registry No. 1030297-07-4. Entered STN-CAS database on Jun. 24, 2008.
STN-CAS database Registry No. 1030297-42-7. Entered STN-CAS database on Jun. 24, 2008.
STN-CAS database Registry No. 1030297-62-1. Entered STN-CAS database on Jun. 24, 2008. With chemical structure.
STN-CAS database Registry No. 1030297-62-1. Entered STN-CAS database on Jun. 24, 2008.
STN-CAS database Registry No. 1043632-07-0. Entered STN-CAS database on Aug. 26, 2008.
STN-CAS database Registry No. 1044533-56-3. Entered STN-CAS database on Aug. 28, 2008.
STN-CAS database Registry No. 104538-56-9. Entered STN-CAS database on Oct. 4, 1986.
STN-CAS database Registry No. 105317-96-2. Entered STN-CAS database on Nov. 22, 1986.
STN-CAS database Registry No. 1056016-23-9. Entered STN-CAS database on Oct. 1, 2008.
STN-CAS database Registry No. 1067642-37-8. Entered STN-CAS database on Oct. 29, 2008.
STN-CAS database Registry No. 1071084-05-3. Entered STN-CAS database on Nov. 6, 2008.
STN-CAS database Registry No. 116071-63-7. Entered STN-CAS database on Aug. 27, 1988.
STN-CAS database Registry No. 136581-83-4. Entered STN-CAS database on Oct. 4, 1991.
STN-CAS database Registry No. 295781-15-6. Entered STN-CAS database on Oct. 19, 2000.
STN-CAS database Registry No. 302899-57-6. Entered STN-CAS database on Nov. 15, 2000.
STN-CAS database Registry No. 42381-51-1. Entered STN-CAS database on Nov. 16, 1984.
STN-CAS database Registry No. 488783-17-1. Entered STN-CAS database on Feb. 12, 2003.

(56) References Cited

OTHER PUBLICATIONS

STN-CAS database Registry No. 490035-26-2. Entered STN-CAS database on Feb. 14, 2003.
STN-CAS database Registry No. 51750-80-2. Entered STN-CAS database on Nov. 16, 1984.
STN-CAS database Registry No. 56619-89-7. Entered STN-CAS database on Nov. 16, 1984.
STN-CAS database Registry No. 60068-43-1. Entered STN-CAS database on Nov. 16, 1984.
STN-CAS database Registry No. 60068-44-2. Entered STN-CAS database on Nov. 16, 1984.
STN-CAS database Registry No. 63888-68-6. Entered STN-CAS database on Nov. 16, 1984.
STN-CAS database Registry No. 63888-69-7. Entered STN-CAS database on Nov. 16, 1984.
STN-CAS database Registry No. 63888-70-0. Entered STN-CAS database on Nov. 16, 1984.
STN-CAS database Registry No. 63888-73-3. Entered STN-CAS database on Nov. 16, 1984.
STN-CAS database Registry No. 698698-42-9. Entered STN-CAS database on Jun. 24, 2004.
STN-CAS database Registry No. 757226-26-9. Entered STN-CAS database on Oct. 6, 2004.
STN-CAS database Registry No. 85438-36-4. Entered STN-CAS database on Nov. 16, 1984.
STN-CAS database Registry No. 90018-95-4. Entered STN-CAS database on Nov. 16, 1984.
STN-CAS database Registry No. 909783-96-6. Entered STN-CAS database on Oct. 6, 2006.
STN-CAS database Registry No. 909784-08-3. Entered STN-CAS database on Oct. 6, 2006.
STN-CAS database Registry No. 909784-14-1. Entered STN-CAS database on Oct. 6, 2006.
STN-CAS database Registry No. 94159-80-5. Entered STN-CAS database on Sep. 8, 1985.
Stocum, Stem cells in regenerative biology and medicine. Wound Repair Regen. Nov.-Dec. 2001;9(6):429-42.
Streuli, Extracellular matrix remodeling and cellular differentiation. Curr Opin Cell Biol. 1999;11:634-40.
Suh et al., Ionization of Poly(ethylenimine) and Poly(allylamine) at Various PHS. Bioorg Chem. 1994;22:318-27.
Swali et al., Solid-Phase Dendrimer Synthesis and the Generation of Super-High-Loading Resin Beads for Combinatorial Chemistry. J Org Chem Am Chem Soc. 1997;62:4902-03.
Tabara et al., The rde-1 Gene, RNA Interference, and Transposon Silencing in C. elegans. Cell. 1999;99:123-32.
Tang et al., in vitro gene delivery by degraded polyamidoamine dendrimers. Bioconjug Chem. Nov.-Dec. 1996;7(6):703-14.
Tarcha et al., Synthesis and characterization of chemically condensed oligoethylenimine containing beta-aminopropionamide linkages for siRNA delivery. Biomaterials. Sep. 2007;28(25):3731-40. Epub May 3, 2007.
Thiel et al., Therapeutic applications of DNA and RNA aptamers. Oligonucleotides. Sep. 2009;19(3):209-22. doi: 10.1089/oli.2009.0199.
Thompson et al., Antiamebic action of 5-chloro-7-diethylaminomethyl-8-quinolinol and of other substituted 8-quinolinols in vitro and in experimental animals. Am J Trop Med Hyg. Mar. 1955;4(2):224-48.
Thomson et al., Embryonic stem cell lines derived from human blastocysts. Science. Nov. 6, 1998;282(5391):1145-7.
Toom et al., Synthesis of amphiphilic amino alcohols. Synthetic Communication. 2008;38(23):4295-4313.
Tsvetkov et al., [Neoglycoconjugates based on dendrimeric poly(aminoamides)]. Bioorg Khim. Nov.-Dec. 2002;28(6):518-34. Russian. Published in English in Russian Journal of Bioorganic Chemistry, 2002:28(6):470-86.
Unkeless et al., Structure and function of human and murine receptors for IgG. Annu Rev Immunol. 1988;6:251-81.

Urban-Klein et al., RNAi-mediated gene-targeting through systemic application of polyethylenimine (PEI)-complexed siRNA in vivo. Gene Ther. Mar. 2005;12(5):461-6.
Van De Wetering et al., Structure-activity relationships of water-soluble cationic methacrylate/methacrylamide polymers for nonviral gene delivery. Bioconjug Chem. Jul.-Aug. 1999;10(4):589-97.
Van Dijkhuizen-Radersma et al., Biocompatibility and degradation of poly(ether-ester) microspheres: in vitro and in vivo evaluation. Biomaterials. Dec. 2002;23(24):4719-29.
Vandenbroucke et al., Prolonged gene silencing in hepatoma cells and primary hepatocytes after small interfering RNA delivery with biodegradable poly(beta-amino esters). J Gene Med. Jul. 2008;10(7):783-94.
Von Harpe et al., Characterization of commercially available and synthesized polyethylenimines for gene delivery. J Control Release. Nov. 3, 2000;69(2):309-22.
Walde et al., Preparation of Vesicles (Liposomes). In: Encyclopedia of Nanoscience and Nanotechnology. Nalwa, ed. American Scientific Publishers: Los Angeles. 2004;9:43-79.
Wang et al, The functions of microRNAs in plants. Front Biosci. 2007;12:3975-82.
Ward, A Review of the Foreign-body Response to Subcutaneously-implanted Devices: The Role of Macrophages and Cytokines in Biofouling and Fibrosis. J Diabetes Sci Technol. 2008;2:768-77.
Weinstein et al., RNAi nanomedicines: challenges and opportunities within the immune system. Nanotechnology. Jun. 11, 2010;21(23):232001. doi: 10.1088/0957-4484/21/23/232001. Epub May 13, 2010.
Werth et al., A low molecular weight fraction of polyethylenimine (PEI) displays increased transfection efficiency of DNA and siRNA in fresh or lyophilized complexes. J Control Release. May 15, 2006;112(2):257-70. Epub Mar. 6, 2006.
White et al., Poly(hydroxyaminoethers): A New Family of Epoxy-Based Thermoplastics. Adv Mater. 2000;12:1791-1800.
White et al., Step-growth polymerization of 10,11-epoxyundecanoic acid. Synthesis and properties of a new hydroxy-functionalized thermopastic polyester. Adv Mater. 2007;48:3990-98.
Whitehead et al., In vitro-in vivo translation of lipid nanoparticles for hepatocellular siRNA delivery. Acs Nano. Aug. 28, 2012;6(8):6922-9. doi: 10.1021/nn301922x. Epub Jul. 6, 2012.
Whitehead et al., Knocking down barriers: advances in siRNA delivery. Nat Rev Drug Discov. Feb. 2009;8(2):129-38.
Wilen et al., Strategies in Optical Resolutions. Tetrahedron. 1977;33:2725-36.
Williams, On the mechanisms of biocompatibility. Biomaterials. Jul. 2008;29(20):2941-53. Epub Apr. 28, 2008.
Winter et al., Transforming terpene-derived aldehydes into 1,2-epoxides via asymmetric α-chlorination: subsequent epoxide opening with carbon nucleophiles. Chem Commun (Camb). Nov. 28, 2011;47(44):12200-2. doi: 10.1039/c1cc15173h. Epub Oct. 10, 2011.
Wintermantel et al., Blocked polyurethane prepolymers as component A in reactive adhesives. STN International HCAPLUS Database. 2006. Accession No. 2006:215601.
Wobus, Potential of embryonic stem cells. Mol Aspects Med. Jun. 2001;22(3):149-64.
Yaffee et al., Serial passaging and differentiation of myogenic cells isolated from dystrophic mouse muscle. Nature. 1977;270:725-27.
Yiu et al., Filtering of Ineffective siRNAs and Improved siRNA Design Tool. Bioinformatics. 2005;21(2):144-51.
Yoshioka et al., Epoxy-based Electroactive Polymer Gels. Experimental Mechanics. 2002;42:404-08.
Zagridullin et al., Monobasic amines. II. Cycloalkylation and hydroxyalkylation of cyclic and acyclic di- and polyamines.. Zhurnal Organicheskoi Khimii. 1990;26(1):184-88. Russian.
Zamora et al., RNA interference therapy in lung transplant patients infected with respiratory syncytial virus. Am J Respir Crit Care Med. Feb. 15, 2011;183(4):531-8. doi: 10.1164/rccm.201003-0422OC. Epub Sep. 17, 2010.
Zamore et al., RNAi: Double-Stranded RNA Directs the ATP-Dependent Cleavage of mRNA at 21 to 23 Nucleotide Intervals. Cell. 2000;101:25-33.

(56) References Cited

OTHER PUBLICATIONS

Zaugg et al., 3-Carboxy-2,5-piperazinedione and Derivatives. J Amer Chem Soc. Jun. 5, 1956;78(11):2626-2631.
Zauner et al., Polylysine-based transfection systems utilizing receptor-mediated delivery. Adv Drug Deliv Rev. Mar. 2, 1998;30(1-3):97-113.
Zhang et al., Human Toll-like receptor-dependent induction of interferons in protective immunity to viruses. Immunol Rev. Dec. 2007;220:225-36.
Zhang et al., Ionization behavior of amino lipids for siRNA delivery: determination of ionization constants, SAR, and the impact of lipid pKa on cationic lipid-biomembrane interactions. Langmuir. Mar. 1, 2011;27(5):1907-14. doi: 10.1021/Ia104590k. Epub Jan. 20, 2011.
Zhao et al., A developmental view of microRNA function. Trends Biochem. 2007;32(4):189-97.
Zintchenko et al., Simple modifications of branched PEI lead to highly efficient siRNA carriers with low toxicity. Bioconjug Chem. Jul. 2008;19(7):1448-55. Epub Jun. 14, 2008.
U.S. Appl. No. 11/453,222, filed Jul. 14, 2006, Anderson et al.
U.S. Appl. No. 14/643,845, filed Mar. 10, 2015, Anderson et al.
U.S. Appl. No. 12/613,968, filed Nov. 6, 2009, Mahon et al.
U.S. Appl. No. 12/716,732, filed Mar. 3, 2010, Mahon et al.
U.S. Appl. No. 13/128,020, filed Aug. 16, 2011, Mahon et al.
U.S. Appl. No. 14/599,004, filed Jan. 16, 2015, Mahon et al.
U.S. Appl. No. 13/126,260, filed Apr. 27, 2011, Nguyen et al.
U.S. Appl. No. 13/819,280, filed Feb. 26, 2013, Ma et al.
U.S. Appl. No. 14/941,684, filed Nov. 13, 2015, Ma et al.
U.S. Appl. No. 13/428,695, filed Mar. 23, 2012, Dahlman et al.
U.S. Appl. No. 14/995,842, filed Jan. 14, 2016, Dahlman et al.
U.S. Appl. No. 14/089,603, filed Aug. 13, 2013, Anderson et al.
U.S. Appl. No. 14/089,603, filed Nov. 25, 2013, Anderson et al.
U.S. Appl. No. 14/987,717, filed Jan. 4, 2016, Anderson et al.
U.S. Appl. No. 15/264,315, filed Sep. 13, 2016, Anderson et al.
U.S. Appl. No. 14/267,530, filed May 1, 2014, Dong et al.
U.S. Appl. No. 14/900,869, filed Dec. 22, 2015, Alibi et al.
International Preliminary Report on Patentability for PCT/US2015/038827, dated Jan. 12, 2017.
Bourque et al., Hydroformylation Reactions Using Recyclable Rhodium-Complexed Dendrimers on Silica. J Am Chem Soc. 2000;122(5):956-957.
Kusumoto et al., Gene transfer effects on various cationic amphiphiles in CHO cells. Cytotechnology. Jun. 2006;51(2):57-66. doi: 10.1007/s10616-006-9014-7. Epub Sep. 7, 2006.
Li et al., [Analysis of HLA matching probability in Guangzhou Cord Blood Bank]. Zhongguo Shi Yan Xue Ye Xue Za Zhi. Aug. 2003;11(4):424-8.
Reichmutch et al., mRNA vaccine delivery using lipid nanoparticles. Ther Deilv. 2016;7(5):319-34. doi: 10.4155/tde-2016-0006.
Shen et al., Synthesis of Novel Amphiphilic Poly (ester-amine) Dendrimers and Their Recognition of Hg2+ at the Air/Water Interface. Chin. J. Chem. Oct. 2003;21(8):1011-14.
Winter et al., Transforming terpene-derived aldehydes into 1,2-epoxides via asymmetric α-chlorination: subsequent epoxide opening with carbon nucleophiles. Chem Commun (Camb). Nov. 28, 2011;47(44):12200-2. doi: 10.1039/c1cc15173h. Epub Oct. 10, 2011.
U.S. Appl. No. 15/417,530, filed Jan. 27, 2017, Mahon et al.

\* cited by examiner

US 9,840,479 B2

POLYAMINE-FATTY ACID DERIVED LIPIDOIDS AND USES THEREOF

RELATED APPLICATIONS

The present application claims priority under 35 U.S.C. §119(e) to U.S. provisional application, U.S. Ser. No. 62/020,114, filed Jul. 2, 2014, which is incorporated herein by reference.

GOVERNMENT SUPPORT

This invention was made with Government support under Grant No. R01 HL107550 awarded by the National Institutes of Health. The Government has certain rights in the invention.

BACKGROUND OF THE INVENTION

The ability to silence genes via RNA interference (RNAi) was reported by Mello and Fire in 1998. See Fire et al., *Nature* (1998) 391:806-811. Since then, scientists have rushed to take advantage of the enormous therapeutic potential driven by targeted gene knockdown. This is evidenced by the fact that the first report of small interfering RNA (siRNA) mediated RNAi in human beings was reported only twelve years after the phenomenon was described in *Caenorhabditis elegans*. See Davis et al., *Nature* (2010) 464: 1067-1070. The advantages of siRNA therapeutics include high target selectivity and specificity, and the potential to target pathways currently believed to be "undruggable" for the treatment of genetic diseases without effective therapy. siRNA therapeutics has shown promising results for the treatment of various diseases, such as hepatic carcinoma, hypercholesterolemia, refractory anemia, and familial amyloid neuropathy.

However, the efficient delivery of siRNA is still a challenge in the development of siRNA therapeutics. Due to issues associated with delivery efficiency and toxicity, the clinical use of siRNA requires safer and more effective delivery systems. It is understood that the development of genetic drugs is slowed by the inability to deliver nucleic acids effectively in vivo. When unprotected, genetic materials injected into the bloodstream can be degraded by deoxyribonucleases (DNAases) and ribonucleases (RNAases), or, if not degraded, the genetic materials can stimulate an immune response. See, e.g., Whitehead et al., *Nature Reviews Drug Discovery* (2009) 8:129-138; Robbins et al., *Oligonucleotides* (2009) 19:89-102. Intact siRNA must then enter the cytosol, where the antisense strand is incorporated into the RNA-induced silencing complex (RISC) (Whitehead et al., supra). The RISC associates with and degrades complementary mRNA sequences, thereby preventing translation of the target mRNA into protein, i.e., "silencing" the gene.

To overcome difficulties in the delivery of polynucleotides, polynucleotides have been complexed with a wide variety of delivery systems, including polymers, lipids, inorganic nanoparticles, and viruses. See, e.g., Peer et al., *Nature Nanotechnology*, (2007) 2:751-760. However, despite promising data from ongoing clinical trials for the treatment of respiratory syncytial virus infection and liver cancers (see, e.g., Zamora et al., *Am. J. Respir. Crit. Care Med*. (2011) 183:531-538), the clinical use of siRNA continues to require development of safer and more effective delivery systems. Toward this end, numerous lipid-like molecules have been developed including poly β-amino esters and amino alcohol lipids. See, e.g., International PCT Patent Application Publications, WO 2002/031025, WO 2004/106411, WO 2008/011561, WO 2007/143659, WO 2006/138380, WO 2010/053572, and WO 2013/063468. Amino acid, peptide, and polypeptide-derived lipids have also been studied for a variety of applications, including use as therapeutics, biosurfactants, and nucleotide delivery systems. See, e.g., Giuliani et al., *Cellular and Molecular Life Sciences* (2011) 68:2255-2266; Ikeda et al., *Current Medicinal Chemistry* (2007) 14: 111263-1275; Sen, *Advances in Experimental Medicine and Biology* (2010) 672:316-323; and Damen et al., *Journal of Controlled Release* (2010) 145:33-39.

Therefore, there remains the need for new materials and systems for the delivery of siRNAs, other nucleic acids, and other agents to cells.

SUMMARY OF THE INVENTION

The present disclosure provides lipidoids (e.g., compounds of Formula (I) or (II)) and methods of preparing the compounds. The compounds described herein are polyamine-fatty acid derived lipidoids. The compounds described herein may be useful in delivering an agent (e.g., a polynucleotide (e.g., an RNA (e.g., siRNA or mRNA), DNA), small molecule, peptide, or protein) to a subject, tissue (e.g., liver, spleen, or lung), or cell. A compound described herein includes one or more amino moieties and one or more lipid moieties ("lipid tails") (e.g., substituted or unsubstituted, $C_{4-30}$ alkyl, and substituted or unsubstituted, $C_{4-30}$ alkenyl) (e.g., $R^{A1a}$, $R^{A1b}$, $R^{A2a}$, $R^{A2b}$, $R^{A3a}$, $R^{A3b}$, $R^{A3c}$, and $R^{X1}$ moieties of a compound described herein). The amino moieties of a described compound may be protonated to form positively charged ammonium cations that may bind to an agent that includes negatively charged moieties, such as a polynucleotide. The lipid moieties of a described compound are typically hydrophobic and may assist the described compound and/or a complex of the described compound and the agent to pass through cell membranes or be taken up by cells. The compounds may also be able to form lipid nanoparticles (LNPs), microparticles, micelles, liposomes, lipoplexes, and other forms.

A compound described herein includes "internal" ester moieties R—C(=O)—O— (where R is a lipid moiety), which may be hydrolyzed under physiological conditions to form carboxylic acids (RC(=O)OH, e.g., fatty acids), which are typically non-toxic. Therefore, in certain embodiments, the compounds described herein may be biodegradable and/or non-toxic. The compounds described herein are thus advantageous over reported lipidoids, such as polyamine-acrylamide derived lipidoids, which do not readily hydrolyze under physiological conditions due to the amide moieties, and polyamine-acrylate derived lipidoids that include "external" ester moieties R—O—C(=O)— (where R is a lipid moiety), which may hydrolyze to form aliphatic alcohols (ROH) due to the "external" orientation of the ester moieties, and the resulting aliphatic alcohols are often toxic.

Also described herein are compositions (e.g., pharmaceutical compositions) including a compound described herein and optionally an agent. The present disclosure also provides methods and kits using the compounds or compositions for delivering an agent to a subject, tissue, or cell and for treating and/or preventing a range of diseases, such as genetic diseases, proliferative diseases, hematological diseases, neurological diseases, immunological diseases, gastrointestinal diseases (e.g., liver diseases), immunological diseases (e.g., autoimmune diseases), spleen diseases, respiratory diseases (e.g., lung diseases), painful conditions, psychiatric disorders, and metabolic disorders.

In one aspect, the present disclosure provides compounds of Formula (I):

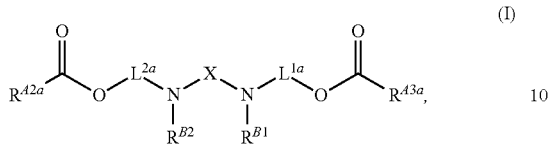

and salts thereof, wherein X, $L^{1a}$, $L^{2a}$, $R^{A1a}$, $R^{A2a}$, $R^{B1}$, and $R^{B2}$ are as described herein.

Exemplary compounds of Formula (I) include, but are not limited to:

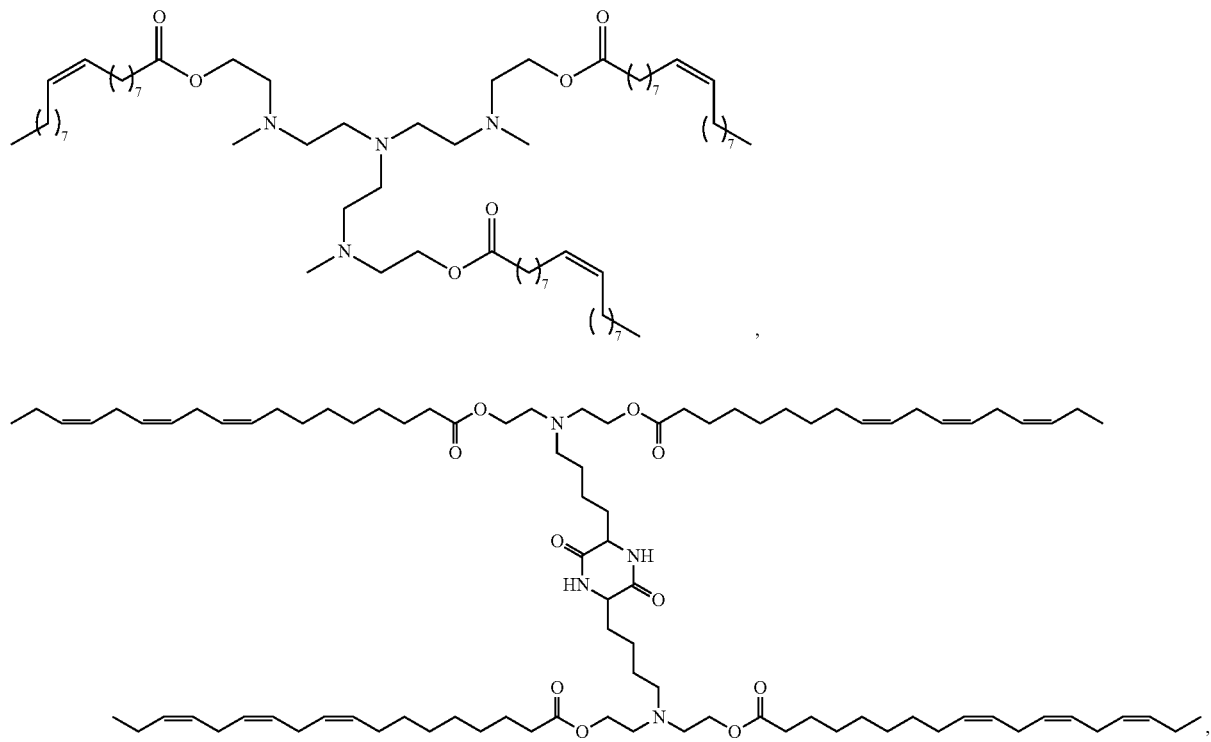

and salts thereof.

In another aspect, the present disclosure provides compounds of Formula (II):

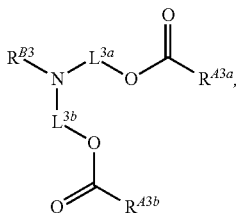

and salts thereof, wherein $L^{3a}$, $L^{3b}$, $R^{A3a}$, $R^{A3b}$, and $R^{B3}$ as described herein.

Exemplary compounds of Formula (II) include, but are not limited to:

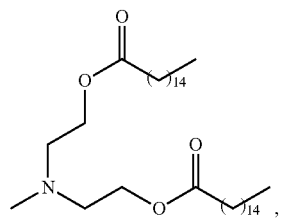

-continued

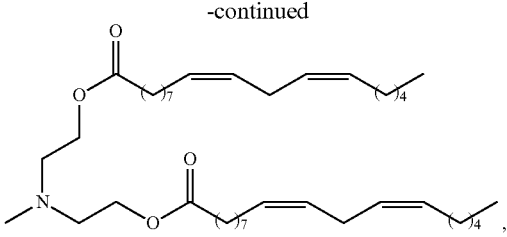

and salts thereof.

Another aspect of the present disclosure relates to methods of preparing compounds of Formula (I), and salts thereof, the methods including esterifying an alcohol of Formula (A), or a salt thereof, with a carboxylic acid of Formula (B), or a salt thereof:

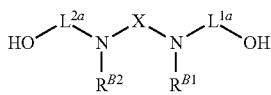
(A)

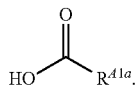
(B)

Another aspect of the present disclosure relates to methods of preparing the compounds of Formula (I), and salts thereof, the methods including alkylating an amine of Formula (C), or a salt thereof, with a compound of Formula (D), or a salt thereof:

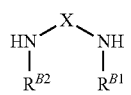
(C)

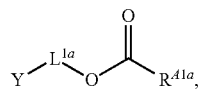
(D)

wherein Y is as described herein.

Another aspect of the present disclosure relates to methods of preparing the compounds of Formula (I), and salts thereof, the methods including reacting an amine of Formula (C), or a salt thereof, with an aldehyde of Formula (K), or a salt thereof, in the presence of a reductant:

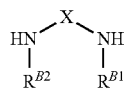
(C)

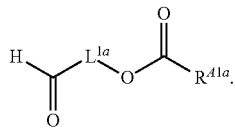
(K)

Another aspect of the present disclosure relates to methods of preparing the compounds of Formula (II), and salts thereof, the methods including esterifying an alcohol of Formula (E), or a salt thereof, with a carboxylic acid of Formula (F), or a salt thereof:

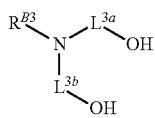
(E)

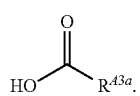
(F)

Another aspect of the present disclosure relates to methods of preparing the compounds of Formula (II), and salts thereof, the methods including alkylating an amine of Formula (G), or a salt thereof, with a compound of Formula (H), or a salt thereof:

(G)

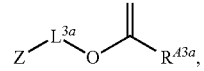
(H)

wherein Z is as described herein.

Another aspect of the present disclosure relates to methods of preparing the compounds of Formula (II), and salts thereof, the methods including reacting an amine of Formula (G), or a salt thereof, with an aldehyde of Formula (J), or a salt thereof, in the presence of a reductant:

(G)

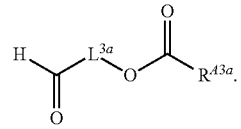
(J)

In yet another aspect, the present disclosure provides compositions (e.g., pharmaceutical compositions) comprising a compound described herein and optionally an excipient (e.g., a pharmaceutically acceptable excipient). The described compositions are thought to be useful for delivering an agent to a subject, tissue, or cell. A described composition including a compound described herein may be in the form of particles (e.g., nanoparticles, microparticles, micelles, or liposomes). In certain embodiments, the lipid moieties of a compound described herein are substantially on or outside the outer portion of a particle described herein. In certain embodiments, the amine moieties of a compound described herein are substantially within the inner portion of a particle described herein. An agent may be encapsulated within the inner portion of the particle described herein and may get transported through the cell membranes (e.g., into or out of a cell). The particle may dissociate and release the agent to a cell (e.g., a target cell) or tissue (e.g., a target tissue).

The compositions described herein (e.g., pharmaceutical compositions) may also be useful in treating a range of diseases (e.g., genetic diseases, proliferative diseases, hematological diseases, neurological diseases, immunological diseases, gastrointestinal diseases (e.g., liver diseases), spleen diseases, respiratory diseases (e.g., lung diseases)), painful conditions, psychiatric disorders, and metabolic disorders in a subject in need thereof. In certain embodiments, a composition described herein includes a therapeutically effective amount of the agent.

The compositions described herein (e.g., pharmaceutical compositions) may also be useful in preventing a range of diseases (e.g., genetic diseases, proliferative diseases, hematological diseases, neurological diseases, immunological diseases, gastrointestinal diseases (e.g., liver diseases), spleen diseases, respiratory diseases (e.g., lung diseases)), painful conditions, psychiatric disorders, and metabolic disorders in a subject in need thereof. In certain embodiments, a composition described herein includes a prophylactically effective amount of the agent.

Another aspect of the present disclosure relates to methods of delivering an agent to a subject. In certain embodiments, the method of delivering an agent comprises administering to a subject (e.g., a human) a compound or composition described herein.

Another aspect of the present disclosure relates to methods of delivering an agent to a tissue. In certain embodiments, the method of delivering an agent comprises contacting a tissue (e.g., a liver, spleen, or lung) with a compound or composition described herein. In certain embodiments, the agent is selectively delivered to a target tissue, compared to the delivery of the agent to a non-target tissue.

Another aspect of the present disclosure relates to methods of delivering an agent to a cell. In certain embodiments, the method of delivering an agent comprises contacting a cell with a compound or composition described herein. The cell may be in vitro or in vivo. In certain embodiments, the agent is selectively delivered to a target cell, compared to the delivery of the agent to a non-target cell.

Another aspect of the disclosure relates to methods of increasing the exposure or concentration of an agent in a subject, tissue, or cell.

In another aspect, the present disclosure provides methods of treating a disease in a subject in need thereof. In certain embodiments, the methods of treating a disease comprise administering to the subject a therapeutically effective amount of a compound or composition described herein.

In still another aspect, the present disclosure provides methods of preventing a disease in a subject in need thereof. In certain embodiments, the methods of treating a disease comprise administering to the subject a prophylactically effective amount of a compound or composition described herein.

In certain embodiments, the disease that is treated or prevented by a described method is a genetic disease, a proliferative disease, a hematological disease, a neurological disease, an immunological disease, a gastrointestinal disease (e.g., a liver disease), a spleen disease, a respiratory disease (e.g., a lung disease), a painful condition, a psychiatric disorder, or a metabolic disorder. In certain embodiments, the disease is hepatic carcinoma, hypercholesterolemia, refractory anemia, or familial amyloid neuropathy.

Another aspect of the disclosure relates to methods of screening a library of compounds described herein to identify a compound that is useful in a method described herein (e.g., a compound useful for delivering a polynucleotide to a subject, tissue, or cell).

In yet another aspect, the present disclosure provides compounds and compositions described herein for use in a method of the present disclosure.

Another aspect of the present disclosure relates to kits comprising a container with a compound or composition described herein. The kits may include a single dose or multiple doses of the compound or composition. The kits may be useful in a method described herein. In certain embodiments, a kit of the disclosure further includes instructions for using the kit (e.g., for administering the compound or composition to a subject (e.g., as required by a regulatory agency)).

The details of one or more embodiments of the disclosure are set forth herein. Other features, objects, and advantages of the disclosure will be apparent from the Detailed Description, the Figures, the Examples, and the Claims.

Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, *Tables of Resolving Agents and Optical Resolutions* p. 268 (E. L. Eliel, Ed., Univ. of Notre Dame Press, Notre Dame, Ind. 1972). The invention additionally encompasses compounds described herein as individual isomers substantially free of other isomers, and alternatively, as mixtures of various isomers.

When a range of values is listed, it is intended to encompass each value and sub-range within the range. For example "$C_{1-6}$" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

The term "aliphatic" refers to alkyl, alkenyl, alkynyl, and carbocyclic groups. Likewise, the term "heteroaliphatic" refers to heteroalkyl, heteroalkenyl, heteroalkynyl, and heterocyclic groups.

"Alkyl" refers to a radical of a straight-chain or branched saturated hydrocarbon group having from 1 to 20 carbon atoms ("$C_{1-20}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-4}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently optionally substituted, i.e., unsubstituted (an "unsubstituted alkyl") or substituted (a "substituted alkyl") with one or more substituents. In certain embodiments, the alkyl group is unsubstituted $C_{1-10}$ alkyl (e.g., —$CH_3$). In certain embodiments, the alkyl group is substituted $C_{1-10}$ alkyl.

"Alkenyl" refers to a radical of a straight-chain or branched hydrocarbon group having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_2$4 alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl. In an alkenyl group, a C=C double bond for which the stereochemistry is unspecified (e.g., —CH=$CHCH_3$ or

)

may be an (E)- or (Z)-double bond.

"Alkynyl" refers to a radical of a straight-chain or branched hydrocarbon group having from 2 to 20 carbon atoms, one or more carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

The term "heteroatom" refers to an atom that is not hydrogen or carbon. In certain embodiments, the heteroatom is nitrogen. In certain embodiments, the heteroatom is oxygen. In certain embodiments, the heteroatom is sulfur.

The term "carbocyclyl" or "carbocyclic" refers to a radical of a non-aromatic cyclic hydrocarbon group having from 3 to 14 ring carbon atoms ("$C_{3-14}$ carbocyclyl") and zero heteroatoms in the non-aromatic ring system. In some embodiments, a carbocyclyl group has 3 to 10 ring carbon atoms ("$C_{3-10}$ carbocyclyl"). In some embodiments, a carbocyclyl group has 3 to 8 ring carbon atoms ("$C_{3-8}$ carbocyclyl"). In some embodiments, a carbocyclyl group has 3 to 7 ring carbon atoms ("$C_{3-7}$ carbocyclyl"). In some embodiments, a carbocyclyl group has 3 to 6 ring carbon atoms ("$C_{3-6}$ carbocyclyl"). In some embodiments, a carbocyclyl group has 4 to 6 ring carbon atoms ("$C_{4-6}$ carbocyclyl"). In some embodiments, a carbocyclyl group has 5 to 6 ring carbon atoms ("$C_{5-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-$^1$H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted $C_{3-14}$ carbocyclyl. In certain embodiments, the carbocyclyl group is a substituted $C_{3-14}$ carbocyclyl.

In some embodiments, "carbocyclyl" is a monocyclic, saturated carbocyclyl group having from 3 to 14 ring carbon atoms ("$C_{3-14}$ cycloalkyl"). In some embodiments, a cycloalkyl group has 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 4 to 6 ring carbon atoms ("$C_{4-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-14}$ cycloalkyl. In certain embodiments, the cycloalkyl group is a substituted $C_{3-14}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclic ring, as defined above, is fused with one or more carbocyclyl groups wherein the point of attachment is either on the carbocyclyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, and thiiranyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, and dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4 n+2 aromatic ring system (e.g., having 6, 10, or 14 p electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{1-4}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Aralkyl" is a subset of alkyl and aryl and refers to an optionally substituted alkyl group substituted by an optionally substituted aryl group. In certain embodiments, the aralkyl is optionally substituted benzyl. In certain embodiments, the aralkyl is benzyl. In certain embodiments, the aralkyl is optionally substituted phenethyl. In certain embodiments, the aralkyl is phenethyl.

"Heteroaryl" refers to a radical of a 5-10 membered monocyclic or bicyclic 4 n+2 aromatic ring system (e.g., having 6 or 10 p electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl, and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Heteroaralkyl" is a subset of alkyl and heteroaryl and refers to an optionally substituted alkyl group substituted by an optionally substituted heteroaryl group.

"Unsaturated" or "partially unsaturated" refers to a group that includes at least one double or triple bond. A "partially unsaturated" ring system is further intended to encompass rings having multiple sites of unsaturation, but is not intended to include aromatic groups (e.g., aryl or heteroaryl groups) as herein defined. Likewise, "saturated" refers to a group that does not contain a double or triple bond, i.e., contains all single bonds.

Alkyl, alkenyl, alkynyl, carbocyclyl, heterocyclyl, aryl, and heteroaryl groups, which are divalent bridging groups are further referred to using the suffix -ene, e.g., alkylene, alkenylene, alkynylene, carbocyclylene, heterocyclylene, arylene, and heteroarylene.

The term "optionally substituted" refers to substituted or unsubstituted.

Alkyl, alkenyl, alkynyl, carbocyclyl, heterocyclyl, aryl, and heteroaryl groups are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group) if not otherwise provided explicitly. In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound.

The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3^+$X$^-$, —N(OR$^{cc}$)R$^{bb}$, —C(=O)R$^{aa}$, —CO$_2$H, —CHO, —C(OR$^{cc}$)$_2$, —CO$_2$R, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{a}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3^+$X$^-$, —N(OR$^{ee}$)R$^{ff}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-6}$ alkyl, C$_{1-4}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl and 5-10 membered heteroaryl, or two R$^{ff}$ groups are joined to form a 3-10 membered heterocyclyl or 5-10 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3^+$X$^-$, —NH(C$_{1-5}$ alkyl)$_2^+$X$^-$, —NH$_2$(C$_{1-6}$ alkyl)$^+$X$^-$, —NH$_3^+$X$^-$, —N(OC$_{1-6}$ alkyl)(C$_{1-6}$ alkyl), —N(OH)(C$_{1-6}$ alkyl), —NH(OH), —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_6$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, 5-10 membered heteroaryl; or two geminal R$^{gg}$ substituents can be joined to form =O or =S; wherein X is a counterion.

"Halo" or "halogen" refers to fluorine (fluoro, —F), chlorine (chloro, —Cl), bromine (bromo, —Br), or iodine (iodo, —I).

"Acyl" refers to a moiety selected from the group consisting of —C(=O)R$^{aa}$, —CHO, —CO$_2$R$^{aa}$, —C(=O)N ($R^{bb}$)$_2$, —C(=N$R^{bb}$)$R^{aa}$, —C(=N$R^{bb}$)O$R^{aa}$, —C(=N$R^{bb}$)N($R^{bb}$)$_2$, —C(=O)N$R^{bb}$SO$_2$$R^{aa}$, —C(=S)N($R^{bb}$)$_2$, —C(=O)S$R^{aa}$, or —C(=S)S$R^{aa}$, wherein $R^{aa}$ and $R^{bb}$ are as defined herein.

Nitrogen atoms can be substituted or unsubstituted as valency permits, and include primary, secondary, tertiary, and quarternary nitrogen atoms. Exemplary nitrogen atom substituents include, but are not limited to, hydrogen, —OH, —O$R^{aa}$, —N($R^{cc}$)$_2$, —CN, —C(=O)$R^{aa}$, —C(=O)N($R^{cc}$)$_2$, —CO$_2$$R^{aa}$, —SO$_2$$R^{aa}$, —C(=N$R^{bb}$)$R^{aa}$, —C(=N$R^{cc}$)O$R^{aa}$, —C(=N$R^{cc}$)N($R^{cc}$)$_2$, —SO$_2$N($R^{cc}$)$_2$, —SO$_2$$R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, —P(=O)$_2$$R^{aa}$, —P(=O)($R^{aa}$)$_2$, —P(=O)$_2$N($R^{cc}$)$_2$, —P(=O)(N$R^{cc}$)$_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$, and $R^{dd}$ are as defined above.

In certain embodiments, the substituent present on a nitrogen atom is a nitrogen protecting group (also referred to as an amino protecting group). Nitrogen protecting groups include, but are not limited to, —OH, —O$R^{aa}$, —N($R^{cc}$)$_2$, —C(=O)$R^{aa}$, —C(=O)N($R^{cc}$)$_2$, —CO$_2$$R^{aa}$, —SO$_2$$R^{aa}$, —C(=N$R^{cc}$)$R^{aa}$, —C(=N$R^{cc}$)O$R^{aa}$, —C(=N$R^{cc}$)N($R^{cc}$)$_2$, —SO$_2$N($R^{cc}$)$_2$, —SO$_2$$R^{cc}$, —SO$_2$O$R^{cc}$, SO$R^{aa}$, —C(=S)N($R^{cc}$)$_2$, —C(=O)S$R^{cc}$, —C(=S)S$R^{cc}$, $C_{1-10}$ alkyl (e.g., aralkyl, heteroaralkyl), $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)$R^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, and o-(benzoyloxymethyl)benzamide.

Nitrogen protecting groups such as carbamate groups (e.g., —C(=O)O$R^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo) benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$$R^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to as a hydroxyl protecting group). Oxygen protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3$, —$P(=O)_2R^{aa}$, —$P(=O)(R^{aa})_2$, —$P(=O)(OR^{cc})_2$, —$P(=O)_2N(R^{bb})_2$, and —$P(=O)(NR^{bb})_2$, wherein $R^{aa}$, $R^{bb}$, and $R^{cc}$ are as defined herein. Oxygen protecting groups are well known in the art and include those described in detail in *Protecting Groups in Organic Synthesis*, T. W. Greene and P. G. M. Wuts, 3rd edition, John Wiley & Sons, 1999, incorporated herein by reference.

Exemplary oxygen protecting groups include, but are not limited to, methyl, methoxylmethyl (MOM), tert-butoxycarbonyl, methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxide, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl)ethyl carbonate (Psec), 2-(triphenylphosphonio)ethyl carbonate (Peoc), alkyl isobutyl carbonate, alkyl vinyl carbonate, alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

The term "leaving group" is given its ordinary meaning in the art of synthetic organic chemistry and refers to an atom or a group capable of being displaced by a nucleophile. Examples of suitable leaving groups include, but are not limited to, halogen (such as F, Cl, Br, or I (iodine)), alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, N,O-dimethylhydroxylamino, pixyl, and haloformates. In some cases, the leaving group is a sulfonic acid ester, such as toluenesulfonate (tosylate, —OTs), methanesulfonate (mesylate, —OMs), p-bromobenzenesulfonyloxy (brosylate, —OBs), or trifluoromethanesulfonate (triflate, —OTf). In some cases, the leaving group is a brosylate, such as p-bromobenzenesulfonyloxy. In some cases, the leaving group is a nosylate, such as 2-nitrobenzenesulfonyloxy. In some embodiments, the leaving group is a sulfonate-containing group. In some embodiments, the leaving group is a tosylate group. The leaving group may also be a phosphineoxide (e.g., formed during a Mitsunobu reaction) or an internal leaving group such as an epoxide or cyclic sulfate. Other non-limiting examples of leaving groups are water, ammonia, alcohols, ether moieties, thioether moieties, zinc halides, magnesium moieties, diazonium salts, and copper moieties.

The term "salt" refers to ionic compounds that result from the neutralization reaction of an acid and a base. A salt is composed of one or more cations (positively charged ions) and one or more anions (negative ions) so that the salt is electrically neutral (without a net charge). Salts of the compounds of this invention include those derived from inorganic and organic acids and bases. Examples of acid addition salts are salts of an amino group formed with inorganic acids such as hydrochloric acid, hydrobromic acid, phosphoric acid, sulfuric acid, and perchloric acid, or with organic acids such as acetic acid, oxalic acid, maleic acid, tartaric acid, citric acid, succinic acid, or malonic acid or by using other methods known in the art such as ion exchange. Other salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}\text{ alkyl})_4$ salts. Representative alkali or alkaline earth metal salts include sodium, lithium, potassium, calcium, magnesium, and the like. Further salts include ammonium, quaternary ammonium, and amine cations formed using counterions such as halide, hydroxide, carboxylate, sulfate, phosphate, nitrate, lower alkyl sulfonate, and aryl sulfonate.

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences*, 1977, 66, 1-19, incorporated herein by reference. Pharmaceutically acceptable salts of the compounds of this disclosure include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}\text{ alkyl})_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound that are associated with a solvent, usually by a solvolysis reaction. This physical association may include hydrogen bonding. Conventional solvents include water, methanol, ethanol, acetic acid, DMSO, THF, diethyl ether, and the like. The compounds of Formula (I) or (II) may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula $R.xH_2O$, wherein R is the compound and wherein x is a number greater than 0. A given compound may form more than one type of hydrates, including, e.g., monohydrates (x is 1), lower hydrates (x is a number greater than 0 and smaller than 1, e.g., hemihydrates ($R.0.5H_2O$)), and polyhydrates (x is a number greater than 1, e.g., dihydrates ($R.2H_2O$) and hexahydrates ($R.6H_2O$)).

The term "tautomers" refer to compounds that are interchangeable forms of a particular compound structure, and that vary in the displacement of hydrogen atoms and electrons. Thus, two structures may be in equilibrium through the movement of it electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base.

Tautomeric forms may be relevant to the attainment of the optimal chemical reactivity and biological activity of a compound of interest.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorphs" refers to a crystalline form of a compound (or a salt, hydrate, or solvate thereof) in a particular crystal packing arrangement. All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "lipophilic" or "hydrophobic" refers to the ability of a compound to dissolve, or the ability of a moiety of a compound to assist the compound in dissolving in fats, oils, lipids, and/or non-polar solvents (e.g., hexane or toluene). Lipophilic moieties include, but are not limited to, substituted or unsubstituted, branched or unbranched alkyl groups having 1 to 50 carbon atoms. In certain embodiments, the lipophilic moiety is an alkyl group including at least 1, at least 6, at least 12, at least 18, at least 24, at least 36, or at least 50 carbon atoms. In certain embodiments, the lipophilic moiety is an alkyl group including at most 50, at most 36, at most 24, at most 18, at most 12, or at most 6 carbon atoms. Combinations of the above-referenced ranges (e.g., at least about 1 and at most about 24 carbon atoms) are also within the scope of the disclosure. In certain embodiments, the lipophilic moiety is unsubstituted alkyl. In certain embodiments, the lipophilic moiety is unsubstituted and unbranched alkyl. In certain embodiments, the lipophilic moiety is unsubstituted and unbranched $C_{1-24}$ alkyl. In certain embodiments, the lipophilic moiety is unsubstituted and unbranched $C_{6-24}$ alkyl. In certain embodiments, the lipophilic moiety is unsubstituted and unbranched $C_{12-24}$ alkyl.

The term "small molecule" refers to molecules, whether naturally-occurring or artificially created (e.g., via chemical synthesis) that have a relatively low molecular weight. Typically, a small molecule is an organic compound (i.e., it contains carbon). The small molecule may contain multiple carbon-carbon bonds, stereocenters, and other functional groups (e.g., amines, hydroxyl, carbonyls, and heterocyclic rings, etc.). In certain embodiments, the molecular weight of a small molecule is at most about 1,000 g/mol, at most about 900 g/mol, at most about 800 g/mol, at most about 700 g/mol, at most about 600 g/mol, at most about 500 g/mol, at most about 400 g/mol, at most about 300 g/mol, at most about 200 g/mol, or at most about 100 g/mol. In certain embodiments, the molecular weight of a small molecule is at least about 100 g/mol, at least about 200 g/mol, at least about 300 g/mol, at least about 400 g/mol, at least about 500 g/mol, at least about 600 g/mol, at least about 700 g/mol, at least about 800 g/mol, or at least about 900 g/mol, or at least about 1,000 g/mol. Combinations of the above ranges (e.g., at least about 200 g/mol and at most about 500 g/mol) are also possible. In certain embodiments, the small molecule is a therapeutically active agent such as a drug (e.g., a molecule approved by the U.S. Food and Drug Administration as provided in the Code of Federal Regulations (C.F.R.)). The small molecule may also be complexed with one or more metal atoms and/or metal ions. In this instance, the small molecule is also referred to as a "small organometallic molecule." Preferred small molecules are biologically active in that they produce a biological effect in animals, preferably mammals, more preferably humans. Small molecules include, but are not limited to, radionuclides and imaging agents. In certain embodiments, the small molecule is a drug. Preferably, though not necessarily, the drug is one that has already been deemed safe and effective for use in humans or animals by the appropriate governmental agency or regulatory body. For example, drugs approved for human use are listed by the FDA under 21 C.F.R. §§330.5, 331 through 361, and 440 through 460, incorporated herein by reference; drugs for veterinary use are listed by the FDA under 21 C.F.R. §§500 through 589, incorporated herein by reference. All listed drugs are considered acceptable for use in accordance with the present disclosure.

A "protein," "peptide," or "polypeptide" comprises a polymer of amino acid residues linked together by peptide bonds. The term refers to proteins, polypeptides, and peptides of any size, structure, or function. Typically, a protein will be at least three amino acids long. A protein may refer to an individual protein or a collection of proteins. The proteins preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in a protein may be modified, for example, by the addition of a chemical entity such as a carbohydrate group, a hydroxyl group, a phosphate group, a farnesyl group, an isofarnesyl group, a fatty acid group, a linker for conjugation or functionalization, or other modification. A protein may also be a single molecule or may be a multi-molecular complex. A protein may be a fragment of a naturally occurring protein or peptide. A protein may be naturally occurring, recombinant, synthetic, or any combination of these.

The term "gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" or "chimeric construct" refers to any gene or a construct, not a native gene, comprising regulatory and coding sequences that are not found together in nature. Accordingly, a chimeric gene or chimeric construct may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but which is introduced into the host organism by gene transfer. Foreign genes can comprise native genes inserted into a non-native organism, or chimeric genes. A "transgene" is a gene that has been introduced into the genome by a transformation procedure.

The terms "polynucleotide", "nucleotide sequence", "nucleic acid", "nucleic acid molecule", "nucleic acid sequence", and "oligonucleotide" refer to a series of nucleotide bases (also called "nucleotides") in DNA and RNA, and mean any chain of two or more nucleotides. The polynucleotides can be chimeric mixtures or derivatives or modified versions thereof, single-stranded or double-stranded. The oligonucleotide can be modified at the base moiety, sugar moiety, or phosphate backbone, for example, to improve stability of the molecule, its hybridization parameters, etc. The antisense oligonuculeotide may comprise a modified base moiety which is selected from the group including, but not limited to, 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid, 5-methyl-2-thiouracil, 3-(3-amino-3-N-2-carboxypropyl) uracil, a thio-guanine, and 2,6-diaminopurine. A nucleotide sequence typically carries genetic information, including the information used by cellular machinery to make proteins and enzymes. These terms include double- or single-stranded genomic and cDNA, RNA, any synthetic and genetically manipulated polynucleotide, and both sense and antisense polynucleotides. This includes single- and double-stranded molecules, i.e., DNA-DNA, DNA-RNA and RNA-RNA hybrids, as well as "protein nucleic acids" (PNAs) formed by conjugating bases to an amino acid backbone. This also includes nucleic acids containing carbohydrate or lipids. Exemplary DNAs include single-stranded DNA (ssDNA), double-stranded DNA (dsDNA), plasmid DNA (pDNA), genomic DNA (gDNA), complementary DNA (cDNA), antisense DNA, chloroplast DNA (ctDNA or cpDNA), microsatellite DNA, mitochondrial DNA (mtDNA or mDNA), kinetoplast DNA (kDNA), provirus, lysogen, repetitive DNA, satellite DNA, and viral DNA. Exemplary RNAs include single-stranded RNA (ssRNA), double-stranded RNA (dsRNA), small interfering RNA (siRNA), messenger RNA (mRNA), precursor messenger RNA (pre-mRNA), small hairpin RNA or short hairpin RNA (shRNA), microRNA (miRNA), guide RNA (gRNA), transfer RNA (tRNA), antisense RNA (asRNA), heterogeneous nuclear RNA (hnRNA), coding RNA, non-coding RNA (ncRNA), long non-coding RNA (long ncRNA or lncRNA), satellite RNA, viral satellite RNA, signal recognition particle RNA, small cytoplasmic RNA, small nuclear RNA (snRNA), ribosomal RNA (rRNA), Piwi-interacting RNA (piRNA), polyinosinic acid, ribozyme, flexizyme, small nucleolar RNA (snoRNA), spliced leader RNA, viral RNA, and viral satellite RNA.

Polynucleotides described herein may be synthesized by standard methods known in the art, e.g., by use of an automated DNA synthesizer (such as those that are commercially available from Biosearch, Applied Biosystems, etc.). As examples, phosphorothioate oligonucleotides may be synthesized by the method of Stein et al., *Nucl. Acids Res.*, 16, 3209, (1988), methylphosphonate oligonucleotides can be prepared by use of controlled pore glass polymer supports (Sarin et al., *Proc. Natl. Acad. Sci. U.S.A.* 85, 7448-7451, (1988)). A number of methods have been developed for delivering antisense DNA or RNA to cells, e.g., antisense molecules can be injected directly into the tissue site, or modified antisense molecules, designed to target the desired cells (antisense linked to peptides or antibodies that specifically bind receptors or antigens expressed on the target cell surface) can be administered systemically. Alternatively, RNA molecules may be generated by in vitro and in vivo transcription of DNA sequences encoding the antisense RNA molecule. Such DNA sequences may be incorporated into a wide variety of vectors that incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines. However, it is often difficult to achieve intracellular concentrations of the antisense sufficient to suppress translation of endogenous mRNAs. Therefore a preferred approach utilizes a recombinant DNA construct in which the antisense oligonucleotide is placed under the control of a strong promoter. The use of such a construct to transfect target cells in the subject will result in the transcription of sufficient amounts of single stranded RNAs that will form complementary base pairs with the endogenous target gene transcripts and thereby prevent translation of the target gene mRNA. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human, cells. Such promoters can be inducible or constitutive. Such promoters include, but are not limited to: the SV40 early promoter region (Bernoist et al., *Nature*, 290, 304-310, (1981); Yamamoto et al., *Cell*, 22, 787-797, (1980); Wagner et al., *Proc. Natl. Acad. Sci. U.S.A.* 78, 1441-1445, (1981); Brinster et al., *Nature* 296, 39-42, (1982)). Any type of plasmid, cosmid, yeast artificial chromosome or viral vector can be used to prepare the recombinant DNA construct that can be introduced directly into the tissue site. Alternatively, viral vectors can be used which selectively infect the desired tissue, in which case administration may be accomplished by another route (e.g., systemically).

The polynucleotides may be flanked by natural regulatory (expression control) sequences or may be associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like. The nucleic acids may also be modified by many means known in the art. Non-limiting examples of such modifications include methylation, "caps", substitution of one or more of the naturally occurring nucleotides with an analog, and internucleotide modifications, such as, for example, those with uncharged linkages (e.g., methyl phosphonates, phosphotriesters, phosphoroamidates, carbamates, etc.) and with charged linkages (e.g., phosphorothioates, phosphorodithioates, etc.). Polynucleotides may contain one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. The polynucleotides may be derivatized by formation of a methyl or ethyl phosphotriester or an alkyl phosphoramidate linkage. Furthermore, the polynucleotides herein may also be modified with a label capable of providing a detectable signal, either directly or indirectly. Exemplary labels include radioisotopes, fluorescent molecules, biotin, and the like.

A "recombinant nucleic acid molecule" is a nucleic acid molecule that has undergone a molecular biological manipulation, i.e., non-naturally occurring nucleic acid molecule or genetically engineered nucleic acid molecule. Furthermore, the term "recombinant DNA molecule" refers to a nucleic acid sequence which is not naturally occurring, or can be made by the artificial combination of two otherwise separated segments of nucleic acid sequence, i.e., by ligating together pieces of DNA that are not normally continuous. By "recombinantly produced" is meant artificial combination often accomplished by either chemical synthesis means, or by the artificial manipulation of isolated segments of nucleic acids, e.g., by genetic engineering techniques using restriction enzymes, ligases, and similar recombinant techniques as described by, for example, Sambrook et al., *Molecular Cloning*, second edition, Cold Spring Harbor Laboratory, Plainview, N.Y.; (1989), or Ausubel et al., *Current Protocols in Molecular Biology*, Current Protocols (1989), and *DNA Cloning: A Practical Approach*, Volumes I and II (ed. D. N. Glover) IREL Press, Oxford, (1985); each of which is incorporated herein by reference.

Such manipulation may be done to replace a codon with a redundant codon encoding the same or a conservative amino acid, while typically introducing or removing a sequence recognition site. Alternatively, it may be performed to join together nucleic acid segments of desired functions to generate a single genetic entity comprising a desired combination of functions not found in nature. Restriction enzyme recognition sites are often the target of such artificial manipulations, but other site specific targets, e.g., promoters, DNA replication sites, regulation sequences, control sequences, open reading frames, or other useful features may be incorporated by design.

The term "pDNA," "plasmid DNA," or "plasmid" refers to a small DNA molecule that is physically separate from, and can replicate independently of, chromosomal DNA within a cell. Plasmids can be found in all three major domains: Archaea, Bacteria, and Eukarya. In nature, plasmids carry genes that may benefit survival of the subject (e.g., antibiotic resistance) and can frequently be transmitted from one bacterium to another (even of another species) via horizontal gene transfer. Artificial plasmids are widely used as vectors in molecular cloning, serving to drive the replication of recombinant DNA sequences within host subjects. Plasmid sizes may vary from 1 to over 1,000 kbp. Plasmids are considered replicons, capable of replicating autonomously within a suitable host.

"RNA transcript" refers to the product resulting from RNA polymerase-catalyzed transcription of a DNA sequence. When the RNA transcript is a complementary copy of the DNA sequence, it is referred to as the primary transcript, or it may be an RNA sequence derived from post-transcriptional processing of the primary transcript and is referred to as the mature RNA. "Messenger RNA (mRNA)" refers to the RNA that is without introns and can be translated into polypeptides by the cell. "cRNA" refers to complementary RNA, transcribed from a recombinant cDNA template. "cDNA" refers to DNA that is complementary to and derived from an mRNA template. The cDNA can be single-stranded or converted to double-stranded form using, for example, the Klenow fragment of DNA polymerase I.

A sequence "complementary" to a portion of an RNA, refers to a sequence having sufficient complementarity to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

The terms "nucleic acid" or "nucleic acid sequence", "nucleic acid molecule", "nucleic acid fragment" or "polynucleotide" may be used interchangeably with "gene", "mRNA encoded by a gene" and "cDNA".

The term "mRNA" or "mRNA molecule" refers to messenger RNA, or the RNA that serves as a template for protein synthesis in a cell. The sequence of a strand of mRNA is based on the sequence of a complementary strand of DNA comprising a sequence coding for the protein to be synthesized.

The term "siRNA" or "siRNA molecule" refers to small inhibitory RNA duplexes that induce the RNA interference (RNAi) pathway, where the siRNA interferes with the expression of specific genes with a complementary nucleotide sequence. siRNA molecules can vary in length (e.g., between 18-30 or 20-25 basepairs) and contain varying degrees of complementarity to their target mRNA in the antisense strand. Some siRNA have unpaired overhanging bases on the 5' or 3' end of the sense strand and/or the antisense strand. The term siRNA includes duplexes of two separate strands, as well as single strands that can form hairpin structures comprising a duplex region.

The term "gene silencing" refers to an epigenetic process of gene regulation where a gene is "switched off" by a mechanism other than genetic modification. That is, a gene which would be expressed (i.e., "turned on") under normal circumstances is switched off by machinery in the cell. Gene silencing occurs when RNA is unable to make a protein during translation. Genes are regulated at either the transcriptional or post-transcriptional level. Transcriptional gene silencing is the result of histone modifications, creating an environment of heterochromatin around a gene that makes it inaccessible to transcriptional machinery (e.g., RNA polymerase and transcription factors). Post-transcriptional gene silencing is the result of mRNA of a particular gene being destroyed or blocked. The destruction of the mRNA prevents translation and thus the formation of a gene product (e.g., a protein). A common mechanism of post-transcriptional gene silencing is RNAi.

The term "particle" refers to a small object, fragment, or piece of a substance that may be a single element, inorganic material, organic material, or mixture thereof. Examples of particles include polymeric particles, single-emulsion particles, double-emulsion particles, coacervates, liposomes, microparticles, nanoparticles, macroscopic particles, pellets, crystals, aggregates, composites, pulverized, milled or otherwise disrupted matrices, and cross-linked protein or polysaccharide particles, each of which have an average characteristic dimension of about less than about 1 mm and at least 1 nm, where the characteristic dimension, or "critical dimension," of the particle is the smallest cross-sectional dimension of the particle. A particle may be composed of a single substance or multiple substances. In certain embodiments, the particle is not a viral particle. In other embodiments, the particle is not a liposome. In certain embodiments, the particle is not a micelle. In certain embodiments, the particle is substantially solid throughout. In certain embodiments, the particle is a nanoparticle. In certain embodiments, the particle is a microparticle.

The term "nanoparticle" refers to a particle having a characteristic dimension of less than about 1 micrometer and at least about 1 nanometer, where the characteristic dimension of the particle is the smallest cross-sectional dimension of the particle.

The term "microparticle" refers to a particle having a characteristic dimension of less than about 1 millimeter and at least about 1 micrometer, where the characteristic dimension of the particle is the smallest cross-sectional dimension of the particle.

The terms "composition" and "formulation" are used interchangeably.

The term "toxic" refers to a substance showing detrimental, deleterious, harmful, or otherwise negative effects on a subject, tissue, or cell when or after administering the substance to the subject or contacting the tissue or cell with the substance, compared to the subject, tissue, or cell prior to administering the substance to the subject or contacting the tissue or cell with the substance. In certain embodiments, the effect is death or destruction of the subject, tissue, or cell. In certain embodiments, the effect is a detrimental effect on the metabolism of the subject, tissue, or cell. In certain embodiments, a toxic substance is a substance that has a median lethal dose ($LD_{50}$) of not more than 500 milligrams per kilogram of body weight when administered orally to an albino rat weighing between 200 and 300 grams, inclusive. In certain embodiments, a toxic substance is a substance that has an $LD_{50}$ of not more than 1,000 milligrams per kilogram of body weight when administered by continuous contact for 24 hours (or less if death occurs within 24 hours) with the bare skin of an albino rabbit weighing between two and three kilograms, inclusive. In certain embodiments, a toxic substance is a substance that has an $LC_{50}$ in air of not more than 2,000 parts per million by volume of gas or vapor, or not more than 20 milligrams per liter of mist, fume, or dust, when administered by continuous inhalation for one hour (or less if death occurs within one hour) to an albino rat weighing between 200 and 300 grams, inclusive. The term "non-toxic" refers to a substance that is not toxic.

A "subject" to which administration is contemplated includes, but is not limited to, humans (i.e., a male or female of any age group, e.g., a pediatric subject (e.g., infant, child, adolescent) or adult subject (e.g., young adult, middle-aged adult, or senior adult)) and/or other non-human animals, for example, mammals (e.g., primates (e.g., cynomolgus monkeys, rhesus monkeys); commercially relevant mammals such as cattle, pigs, horses, sheep, goats, cats, and/or dogs) and birds (e.g., commercially relevant birds such as chickens, ducks, geese, and/or turkeys). In certain embodiments, the animal is a mammal. The animal may be a male or female at any stage of development. The animal may be a transgenic animal or genetically engineered animal. In certain embodiments, the subject is a non-human animal. In certain embodiments, the animal is a fish or reptile.

The term "target tissue" refers to any biological tissue of a subject (including a group of cells, a body part, or an organ) or a part thereof, including blood and/or lymph vessels, which is the object to which a compound, particle, and/or composition of the disclosure is delivered. A target tissue may be an abnormal or unhealthy tissue, which may need to be treated. A target tissue may also be a normal or healthy tissue that is under a higher than normal risk of becoming abnormal or unhealthy, which may need to be prevented. In certain embodiments, the target tissue is the liver. In certain embodiments, the target tissue is the lung. In certain embodiments, the target tissue is the spleen. A "non-target tissue" is any biological tissue of a subject (including a group of cells, a body part, or an organ) or a part thereof, including blood and/or lymph vessels, which is not a target tissue.

The terms "administer," "administering," or "administration" refers to implanting, absorbing, ingesting, injecting, inhaling, or otherwise introducing a compound described herein, or a composition thereof, in or on a subject.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen). Treatment may also be continued after symptoms have resolved, for example, to delay or prevent recurrence.

The terms "condition," "disease," and "disorder" are used interchangeably.

An "effective amount" of a compound described herein refers to an amount sufficient to elicit the desired biological response, i.e., treating the condition. As will be appreciated by those of ordinary skill in this art, the effective amount of a compound described herein may vary depending on such factors as the desired biological endpoint, the pharmacokinetics of the compound, the condition being treated, the mode of administration, and the age and health of the subject. An effective amount encompasses therapeutic and prophylactic treatment.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent.

A "prophylactically effective amount" of a compound described herein is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

The term "genetic disease" refers to a disease caused by one or more abnormalities in the genome of a subject, such as a disease that is present from birth of the subject. Genetic diseases may be heritable and may be passed down from the parents' genes. A genetic disease may also be caused by mutations or changes of the DNAs and/or RNAs of the subject. In such cases, the genetic disease will be heritable if it occurs in the germline. Exemplary genetic diseases include, but are not limited to, Aarskog-Scott syndrome, Aase syndrome, achondroplasia, acrodysostosis, addiction, adreno-leukodystrophy, albinism, ablepharon-macrostomia syndrome, alagille syndrome, alkaptonuria, alpha-1 antitrypsin deficiency, Alport's syndrome, Alzheimer's disease, asthma, autoimmune polyglandular syndrome, androgen insensitivity syndrome, Angelman syndrome, ataxia, ataxia telangiectasia, atherosclerosis, attention deficit hyperactivity disorder (ADHD), autism, baldness, Batten disease, Beckwith-Wiedemann syndrome, Best disease, bipolar disorder, brachydactyl), breast cancer, Burkitt lymphoma, chronic myeloid leukemia, Charcot-Marie-Tooth disease, Crohn's disease, cleft lip, Cockayne syndrome, Coffin Lowry syndrome, colon cancer, congenital adrenal hyperplasia, Cornelia de Lange syndrome, Costello syndrome, Cowden syndrome, craniofrontonasal dysplasia, Crigler-Najjar syndrome, Creutzfeldt-Jakob disease, cystic fibrosis, deafness, depression, diabetes, diastrophic dysplasia, DiGeorge syndrome, Down's syndrome, dyslexia, Duchenne muscular dystrophy, Dubowitz syndrome, ectodermal dysplasia Ellisvan Creveld syndrome, Ehlers-Danlos, epidermolysis bullosa, epilepsy, essential tremor, familial hypercholesterolemia, familial Mediterranean fever, fragile X syndrome, Friedreich's ataxia, Gaucher disease, glaucoma, glucose galactose malabsorption, glutaricaciduria, gyrate atrophy, Goldberg Shprintzen syndrome (velocardiofacial syndrome), Gorlin syndrome, Hailey-Hailey disease, hemihypertrophy, hemochromatosis, hemophilia, hereditary motor and sensory neuropathy (HMSN), hereditary non polyposis colorectal cancer (HNPCC), Huntington's disease, immunodeficiency with hyper-IgM, juvenile onset diabetes, Klinefelter's syndrome, Kabuki syndrome, Leigh's disease, long QT syndrome, lung cancer, malignant melanoma, manic depression, Marfan syndrome, Menkes syndrome, miscarriage, mucopolysaccharide disease, multiple endocrine neoplasia, multiple sclerosis, muscular dystrophy, myotrophic lateral sclerosis, myotonic dystrophy, neurofibromatosis, Niemann-Pick disease, Noonan syndrome, obesity, ovarian cancer, pancreatic cancer, Parkinson's disease, paroxysmal nocturnal hemoglobinuria, Pendred syndrome, peroneal muscular atrophy, phenylketonuria (PKU), polycystic kidney disease, Prader-Willi syndrome, primary biliary cirrhosis, prostate cancer, REAR syndrome, Refsum disease, retinitis pigmentosa, retinoblastoma, Rett syndrome, Sanfilippo syndrome, schizophrenia, severe combined immunodeficiency, sickle cell anemia, spina bifida, spinal muscular atrophy, spinocerebellar atrophy, sudden adult death syndrome, Tangier disease, Tay-Sachs disease, thrombocytopenia absent radius syndrome, Townes-Brocks syndrome, tuberous sclerosis, Turner syndrome, Usher syndrome, von Hippel-Lindau syndrome, Waardenburg syndrome, Weaver syndrome, Werner syndrome, Williams syndrome, Wilson's disease, xeroderma piginentosum, and Zellweger syndrome.

A "proliferative disease" refers to a disease that occurs due to abnormal growth or extension by the multiplication of cells (Walker, *Cambridge Dictionary of Biology*; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as the matrix metalloproteinases (e.g., collagenases, gelatinases, and elastases); or 4) the pathological angiogenesis as in proliferative retinopathy and tumor metastasis. Exemplary proliferative diseases include cancers (i.e., "malignant neoplasms"), benign neoplasms, angiogenesis, inflammatory diseases, and autoimmune diseases.

The term "angiogenesis" refers to the physiological process through which new blood vessels form from pre-existing vessels. Angiogenesis is distinct from vasculogenesis, which is the de novo formation of endothelial cells from mesoderm cell precursors. The first vessels in a developing embryo form through vasculogenesis, after which angiogenesis is responsible for most blood vessel growth during normal or abnormal development. Angiogenesis is a vital process in growth and development, as well as in wound healing and in the formation of granulation tissue. However, angiogenesis is also a fundamental step in the transition of tumors from a benign state to a malignant one, leading to the use of angiogenesis inhibitors in the treatment of cancer. Angiogenesis may be chemically stimulated by angiogenic proteins, such as growth factors (e.g., VEGF). "Pathological angiogenesis" refers to abnormal (e.g., excessive or insufficient) angiogenesis that amounts to and/or is associated with a disease.

The terms "neoplasm" and "tumor" are used interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites. The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue.

The term "cancer" refers to a malignant neoplasm (*Stedman's Medical Dictionary,* 25th ed.; Hensyl ed.; Williams & Wilkins: Philadelphia, 1990). Exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; ocular cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenstrim's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungiodes, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendocrinetumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

The term "inflammatory disease" refers to a disease caused by, resulting from, or resulting in inflammation. The term "inflammatory disease" may also refer to a dysregulated inflammatory reaction that causes an exaggerated response by macrophages, granulocytes, and/or T-lymphocytes leading to abnormal tissue damage and/or cell death. An inflammatory disease can be either an acute or chronic inflammatory condition and can result from infections or non-infectious causes. Inflammatory diseases include, without limitation, atherosclerosis, arteriosclerosis, autoimmune disorders, multiple sclerosis, systemic lupus erythematosus, polymyalgia rheumatica (PMR), gouty arthritis, degenerative arthritis, tendonitis, bursitis, psoriasis, cystic fibrosis, arthrosteitis, rheumatoid arthritis, inflammatory arthritis, Sjogren's syndrome, giant cell arteritis, progressive systemic sclerosis (scleroderma), ankylosing spondylitis, polymyositis, dermatomyositis, pemphigus, pemphigoid, diabetes (e.g., Type I), myasthenia gravis, Hashimoto's thyroiditis, Graves' disease, Goodpasture's disease, mixed connective tissue disease, sclerosing cholangitis, inflammatory bowel disease, Crohn's disease, ulcerative colitis, pernicious anemia, inflammatory dermatoses, usual interstitial pneumonitis (UIP), asbestosis, silicosis, bronchiectasis, berylliosis, talcosis, pneumoconiosis, sarcoidosis, desquamative interstitial pneumonia, lymphoid interstitial pneumonia, giant cell interstitial pneumonia, cellular interstitial pneumonia, extrinsic allergic alveolitis, Wegener's granulomatosis and related forms of angiitis (temporal arteritis and polyarteritis nodosa), inflammatory dermatoses, hepatitis, delayed-type hypersensitivity reactions (e.g., poison ivy dermatitis), pneumonia, respiratory tract inflammation, Adult Respiratory Distress Syndrome (ARDS), encephalitis, immediate hypersensitivity reactions, asthma, hayfever, allergies, acute anaphylaxis, rheumatic fever, glomerulonephritis, pyelonephritis, cellulitis, cystitis, chronic cholecystitis, ischemia (ischemic injury), reperfusion injury, allograft rejection, host-versus-graft rejection, appendicitis, arteritis, blepharitis, bronchiolitis, bronchitis, cervicitis, cholangitis, chorioamnionitis, conjunctivitis, dacryoadenitis, dermatomyositis, endocarditis, endometritis, enteritis, enterocolitis, epicondylitis, epididymitis, fasciitis, fibrositis, gastritis, gastroenteritis, gingivitis, ileitis, iritis, laryngitis, myelitis, myocarditis, nephritis, omphalitis, oophoritis, orchitis, osteitis, otitis, pancreatitis, parotitis, pericarditis, pharyngitis, pleuritis, phlebitis, pneumonitis, proctitis, prostatitis, rhinitis, salpingitis, sinusitis, stomatitis, synovitis, testitis, tonsillitis, urethritis, urocystitis, uveitis, vaginitis, vasculitis, vulvitis, vulvovaginitis, angitis, chronic bronchitis, osteomyelitis, optic neuritis, temporal arteritis, transverse myelitis, necrotizing fasciitis, and necrotizing enterocolitis. An ocular inflammatory disease includes, but is not limited to, post-surgical inflammation.

An "autoimmune disease" refers to a disease arising from an inappropriate immune response of the body of a subject against substances and tissues normally present in the body. In other words, the immune system mistakes some part of the body as a pathogen and attacks its own cells. This may be restricted to certain organs (e.g., in autoimmune thyroiditis) or involve a particular tissue in different places (e.g., Goodpasture's disease which may affect the basement membrane in both the lung and kidney). The treatment of autoimmune diseases is typically with immunosuppression, e.g., medications which decrease the immune response. Exemplary autoimmune diseases include, but are not limited to, glomerulonephritis, Goodpasture's syndrome, necrotizing vasculitis, lymphadenitis, peri-arteritis nodosa, systemic lupus erythematosis, rheumatoid, arthritis, psoriatic arthritis, systemic lupus erythematosis, psoriasis, ulcerative colitis, systemic sclerosis, dermatomyositis/polymyositis, anti-phospholipid antibody syndrome, scleroderma, pemphigus vulgaris, ANCA-associated vasculitis (e.g., Wegener's granulomatosis, microscopic polyangiitis), uveitis, Sjogren's syndrome, Crohn's disease, Reiter's syndrome, ankylosing spondylitis, Lyme disease, Guillain-Barré syndrome, Hashimoto's thyroiditis, and cardiomyopathy.

The term "liver disease" or "hepatic disease" refers to damage to or a disease of the liver. Non-limiting examples of liver disease include intrahepatic cholestasis (e.g., alagille syndrome, biliary liver cirrhosis), fatty liver (e.g., alcoholic fatty liver, Reye's syndrome), hepatic vein thrombosis, hepatolenticular degeneration (i.e., Wilson's disease), hepatomegaly, liver abscess (e.g., amebic liver abscess), liver cirrhosis (e.g., alcoholic, biliary, and experimental liver cirrhosis), alcoholic liver diseases (e.g., fatty liver, hepatitis, cirrhosis), parasitic liver disease (e.g., hepatic echinococcosis, fascioliasis, amebic liver abscess), jaundice (e.g., hemolytic, hepatocellular, cholestatic jaundice), cholestasis, portal hypertension, liver enlargement, ascites, hepatitis (e.g., alcoholic hepatitis, animal hepatitis, chronic hepatitis (e.g., autoimmune, hepatitis B, hepatitis C, hepatitis D, drug induced chronic hepatitis), toxic hepatitis, viral human hepatitis (e.g., hepatitis A, hepatitis B, hepatitis C, hepatitis D, hepatitis E), granulomatous hepatitis, secondary biliary cirrhosis, hepatic encephalopathy, varices, primary biliary cirrhosis, primary sclerosing cholangitis, hepatocellular adenoma, hemangiomas, bile stones, liver failure (e.g., hepatic encephalopathy, acute liver failure), angiomyolipoma, calcified liver metastases, cystic liver metastases, fibrolamellar hepatocarcinoma, hepatic adenoma, hepatoma, hepatic cysts (e.g., Simple cysts, Polycystic liver disease, hepatobiliary cystadenoma, choledochal cyst), mesenchymal tumors (mesenchymal hamartoma, infantile hemangioendothelioma, hemangioma, peliosis hepatis, lipomas, inflammatory pseudotumor), epithelial tumors (e.g., bile duct hamartoma, bile duct adenoma), focal nodular hyperplasia, nodular regenerative hyperplasia, hepatoblastoma, hepatocellular carcinoma, cholangiocarcinoma, cystadenocarcinoma, tumors of blood vessels, angiosarcoma, Karposi's sarcoma, hemangioendothelioma, embryonal sarcoma, fibrosarcoma, leiomyosarcoma, rhabdomyosarcoma, carcinosarcoma, teratoma, carcinoid, squamous carcinoma, primary lymphoma, peliosis hepatis, erythrohepatic porphyria, hepatic porphyria (e.g., acute intermittent porphyria, porphyria cutanea tarda), and Zellweger syndrome.

The term "spleen disease" refers to a disease of the spleen. Example of spleen diseases include, but are not limited to, splenomegaly, spleen cancer, asplenia, spleen trauma, idiopathic purpura, Felty's syndrome, Hodgkin's disease, and immune-mediated destruction of the spleen.

The term "lung disease" or "pulmonary disease" refers to a disease of the lung. Examples of lung diseases include, but are not limited to, bronchiectasis, bronchitis, bronchopulmonary dysplasia, interstitial lung disease, occupational lung disease, emphysema, cystic fibrosis, acute respiratory distress syndrome (ARDS), severe acute respiratory syndrome (SARS), asthma (e.g., intermittent asthma, mild persistent asthma, moderate persistent asthma, severe persistent asthma), chronic bronchitis, chronic obstructive pulmonary disease (COPD), emphysema, interstitial lung disease, sarcoidosis, asbestosis, aspergilloma, aspergillosis, pneumonia (e.g., lobar pneumonia, multilobar pneumonia, bronchial pneumonia, interstitial pneumonia), pulmonary fibrosis, pulmonary tuberculosis, rheumatoid lung disease, pulmonary embolism, and lung cancer (e.g., non-small-cell lung carcinoma (e.g., adenocarcinoma, squamous-cell lung carcinoma, large-cell lung carcinoma), small-cell lung carcinoma).

A "hematological disease" includes a disease which affects a hematopoietic cell or tissue. Hematological diseases include diseases associated with aberrant hematological content and/or function. Examples of hematological diseases include diseases resulting from bone marrow irradiation or chemotherapy treatments for cancer, diseases such as pernicious anemia, hemorrhagic anemia, hemolytic anemia, aplastic anemia, sickle cell anemia, sideroblastic anemia, anemia associated with chronic infections such as malaria, trypanosomiasis, HIV, hepatitis virus or other viruses, myelophthisic anemias caused by marrow deficiencies, renal failure resulting from anemia, anemia, polycythemia, infectious mononucleosis (EVI), acute non-lymphocytic leukemia (ANLL), acute myeloid leukemia (AML), acute promyelocytic leukemia (APL), acute myelomonocytic leukemia (AMMoL), polycythemia vera, lymphoma, acute lymphocytic leukemia (ALL), chronic lymphocytic leukemia, Wilm's tumor, Ewing's sarcoma, retinoblastoma, hemophilia, disorders associated with an increased risk of thrombosis, herpes, thalassemia, antibody-mediated disorders such as transfusion reactions and erythroblastosis, mechanical trauma to red blood cells such as micro-angiopathic hemolytic anemias, thrombotic thrombocytopenic purpura and disseminated intravascular coagulation, infections by parasites such as *Plasmodium*, chemical injuries from, e.g., lead poisoning, and hypersplenism.

The term "neurological disease" refers to any disease of the nervous system, including diseases that involve the central nervous system (brain, brainstem and cerebellum), the peripheral nervous system (including cranial nerves), and the autonomic nervous system (parts of which are located in both central and peripheral nervous system). Neurodegenerative diseases refer to a type of neurological disease marked by the loss of nerve cells, including, but not limited to, Alzheimer's disease, Parkinson's disease, amyotrophic lateral sclerosis, tauopathies (including frontotemporal dementia), and Huntington's disease. Examples of neurological diseases include, but are not limited to, headache, stupor and coma, dementia, seizure, sleep disorders, trauma, infections, neoplasms, neuro-ophthalmology, movement disorders, demyelinating diseases, spinal cord disorders, and disorders of peripheral nerves, muscle and neuromuscular junctions. Addiction and mental illness, include, but are not limited to, bipolar disorder and schizophrenia, are also included in the definition of neurological diseases. Further examples of neurological diseases include acquired epileptiform aphasia; acute disseminated encephalomyelitis; adrenoleukodystrophy; agenesis of the corpus callosum; agnosia; Aicardi syndrome; Alexander disease; Alpers' disease; alternating hemiplegia; Alzheimer's disease; amyotrophic lateral sclerosis; anencephaly; Angelman syndrome; angiomatosis; anoxia; aphasia; apraxia; arachnoid cysts; arachnoiditis; Arnold-Chiari malformation; arteriovenous malformation; Asperger syndrome; ataxia telangiectasia; attention deficit hyperactivity disorder; autism; autonomic dysfunction; back pain; Batten disease; Behcet's disease; Bell's palsy; benign essential blepharospasm; benign focal; amyotrophy; benign intracranial hypertension; Binswanger's disease; blepharospasm; Bloch Sulzberger syndrome; brachial plexus injury; brain abscess; bbrain injury; brain tumors (including glioblastoma multiforme); spinal tumor; Brown-Sequard syndrome; Canavan disease; carpal tunnel syndrome (CTS); causalgia; central pain syndrome; central pontine myelinolysis; cephalic disorder; cerebral aneurysm; cerebral arteriosclerosis; cerebral atrophy; cerebral gigantism; cerebral palsy; Charcot-Marie-Tooth disease; chemotherapy-induced neuropathy and neuropathic pain; Chiari malformation; chorea; chronic inflammatory demyelinating polyneuropathy (CIDP); chronic pain; chronic regional pain syndrome; Coffin Lowry syndrome; coma, including persistent vegetative state; congenital facial diplegia; corticobasal degeneration; cranial arteritis; craniosynostosis; Creutzfeldt-Jakob disease; cumulative trauma disorders; Cushing's syndrome; cytomegalic inclusion body disease (CIBD); cytomegalovirus infection; dancing eyes-dancing feet syndrome; Dandy-Walker syndrome; Dawson disease; De Morsier's syndrome; Dejerine-Klumpke palsy; dementia; dermatomyositis; diabetic neuropathy; diffuse sclerosis; dysautonomia; dysgraphia; dyslexia; dystonias; early infantile epileptic encephalopathy; empty sella syndrome; encephalitis; encephaloceles; encephalotrigeminal angiomatosis; epilepsy; Erb's palsy; essential tremor; Fabry's disease; Fahr's syndrome; fainting; familial spastic paralysis; febrile seizures; Fisher syndrome; Friedreich's ataxia; frontotemporal dementia and other "tauopathies"; Gaucher's disease; Gerstmann's syndrome; giant cell arteritis; giant cell inclusion disease; globoid cell leukodystrophy; Guillain-Barre syndrome; HTLV-1 associated myelopathy; Hallervorden-Spatz disease; head injury; headache; hemifacial spasm; hereditary spastic paraplegia; heredopathia atactica polyneuritiformis; herpes zoster oticus; herpes zoster; Hirayama syndrome; HIV-associated dementia and neuropathy (see also neurological manifestations of AIDS); holoprosencephaly; Huntington's disease and other polyglutamine repeat diseases; hydranencephaly; hydrocephalus; hypercortisolism; hypoxia; immune-mediated encephalomyelitis; inclusion body myositis; incontinentia pigmenti; infantile; phytanic acid storage disease; Infantile Refsum disease; infantile spasms; inflammatory myopathy; intracranial cyst; intracranial hypertension; Joubert syndrome; Kearns-Sayre syndrome; Kennedy disease; Kinsbourne syndrome; Klippel Feil syndrome; Krabbe disease; Kugelberg-Welander disease; kuru; Lafora disease; Lambert-Eaton myasthenic syndrome; Landau-Kleffner syndrome; lateral medullary (Wallenberg) syndrome; learning disabilities; Leigh's disease; Lennox-Gastaut syndrome; Lesch-Nyhan syndrome; leukodystrophy; Lewy body dementia; lissencephaly; locked-in syndrome; Lou Gehrig's disease (aka motor neuron disease or amyotrophic lateral sclerosis); lumbar disc disease; lyme disease-neurological sequelae; Machado-Joseph disease; macrencephaly; megalencephaly; Melkersson-Rosenthal syndrome; Menieres disease; meningitis; Menkes disease; metachromatic leukodystrophy; microcephaly; migraine; Miller Fisher syndrome; mini-strokes; mitochondrial myopathies; Mobius syndrome; monomelic amyotrophy; motor neurone disease; moyamoya disease; mucopolysaccharidoses; multi-infarct dementia; multifocal motor neuropathy; multiple sclerosis and other demyelinating disorders; multiple system atrophy with postural hypotension; muscular dystrophy; myasthenia gravis; myelinoclastic diffuse sclerosis; myoclonic encephalopathy of infants; myoclonus; myopathy; myotonia congenital; narcolepsy; neurofibromatosis; neuroleptic malignant syndrome; neurological manifestations of AIDS; neurological sequelae of lupus; neuromyotonia; neuronal ceroid lipofuscinosis; neuronal migration disorders; Niemann-Pick disease; O'Sullivan-McLeod syndrome; occipital neuralgia; occult spinal dysraphism sequence; Ohtahara syndrome; olivopontocerebellar atrophy; opsoclonus myoclonus; optic neuritis; orthostatic hypotension; overuse syndrome; paresthesia; Parkinson's disease; paramyotonia congenita; paraneoplastic diseases; paroxysmal attacks; Parry Romberg syndrome; Pelizaeus-Merzbacher disease; periodic paralyses; peripheral neuropathy; painful neuropathy and neuropathic pain; persistent vegetative state; pervasive developmental disorders; photic sneeze reflex; phytanic acid storage disease; Pick's disease; pinched nerve; pituitary tumors; polymyositis; porencephaly; Post-Polio syndrome; postherpetic neuralgia (PHN); postinfectious encephalomyelitis; postural hypotension; Prader-Willi syndrome; primary lateral sclerosis; prion diseases; progressive; hemifacial atrophy; progressive multifocal leukoencephalopathy; progressive sclerosing poliodystrophy; progressive supranuclear palsy; pseudotumor cerebri; Ramsay-Hunt syndrome (Type I and Type II); Rasmussen's Encephalitis; reflex sympathetic dystrophy syndrome; Refsum disease; repetitive motion disorders; repetitive stress injuries; restless legs syndrome; retrovirus-associated myelopathy; Rett syndrome; Reye's syndrome; Saint Vitus Dance; Sandhoff disease; Schilder's disease; schizencephaly; septo-optic dysplasia; shaken baby syndrome; shingles; Shy-Drager syndrome; Sjogren's syndrome; sleep apnea; Soto's syndrome; spasticity; spina bifida; spinal cord injury; spinal cord tumors; spinal muscular atrophy; stiff-person syndrome; stroke; Sturge-Weber syndrome; subacute sclerosing panencephalitis; subarachnoid hemorrhage; subcortical arteriosclerotic encephalopathy; sydenham chorea; syncope; syringomyelia; tardive dyskinesia; Tay-Sachs disease; temporal arteritis; tethered spinal cord syndrome; Thomsen disease; thoracic outlet syndrome; tic douloureux; Todd's paralysis; Tourette syndrome; transient ischemic attack; transmissible spongiform encephalopathies; transverse myelitis; traumatic brain injury; tremor; trigeminal neuralgia; tropical spastic paraparesis; tuberous sclerosis; vascular dementia (multi-infarct dementia); vasculitis including temporal arteritis; Von Hippel-Lindau Disease (VHL); Wallenberg's syndrome; Werdnig-Hoffman disease; West syndrome; whiplash; Williams syndrome; Wilson's disease; and Zellweger syndrome.

A "painful condition" includes, but is not limited to, neuropathic pain (e.g., peripheral neuropathic pain), central pain, deafferentiation pain, chronic pain (e.g., chronic nociceptive pain, and other forms of chronic pain such as post-operative pain, e.g., pain arising after hip, knee, or other replacement surgery), pre-operative pain, stimulus of nociceptive receptors (nociceptive pain), acute pain (e.g., phantom and transient acute pain), noninflammatory pain, inflammatory pain, pain associated with cancer, wound pain, burn pain, postoperative pain, pain associated with medical procedures, pain resulting from pruritus, painful bladder syndrome, pain associated with premenstrual dysphoric disorder and/or premenstrual syndrome, pain associated with chronic fatigue syndrome, pain associated with pre-term labor, pain associated with withdrawal symptoms from drug addiction, joint pain, arthritic pain (e.g., pain associated with crystalline arthritis, osteoarthritis, psoriatic arthritis, gouty arthritis, reactive arthritis, rheumatoid arthritis or Reiter's arthritis), lumbosacral pain, musculo-skeletal pain, headache, migraine, muscle ache, lower back pain, neck pain, toothache, dental/maxillofacial pain, visceral pain and the like. One or more of the painful conditions contemplated herein can comprise mixtures of various types of pain provided above and herein (e.g. nociceptive pain, inflammatory pain, neuropathic pain, etc.). In some embodiments, a particular pain can dominate. In other embodiments, the painful condition comprises two or more types of pains without one dominating. A skilled clinician can determine the dosage to achieve a therapeutically effective amount for a particular subject based on the painful condition.

The term "psychiatric disorder" refers to a disease of the mind and includes diseases and disorders listed in the *Diagnostic and Statistical Manual of Mental Disorders—Fourth Edition* (DSM-IV), published by the American Psychiatric Association, Washington D. C. (1994). Psychiatric disorders include, but are not limited to, anxiety disorders (e.g., acute stress disorder agoraphobia, generalized anxiety disorder, obsessive-compulsive disorder, panic disorder, posttraumatic stress disorder, separation anxiety disorder, social phobia, and specific phobia), childhood disorders, (e.g., attention-deficit/hyperactivity disorder, conduct disorder, and oppositional defiant disorder), eating disorders (e.g., anorexia nervosa and bulimia nervosa), mood disorders (e.g., depression, bipolar disorder, cyclothymic disorder, dysthymic disorder, and major depressive disorder), personality disorders (e.g., antisocial personality disorder, avoidant personality disorder, borderline personality disorder, dependent personality disorder, histrionic personality disorder, narcissistic personality disorder, obsessive-compulsive personality disorder, paranoid personality disorder, schizoid personality disorder, and schizotypal personality disorder), psychotic disorders (e.g., brief psychotic disorder, delusional disorder, schizoaffective disorder, schizophreniform disorder, schizophrenia, and shared psychotic disorder), substance-related disorders (e.g., alcohol dependence, amphetamine dependence, cannabis dependence, cocaine dependence, hallucinogen dependence, inhalant dependence, nicotine dependence, opioid dependence, phencyclidine dependence, and sedative dependence), adjustment disorder, autism, delirium, dementia, multi-infarct dementia, learning and memory disorders (e.g., amnesia and age-related memory loss), and Tourette's disorder.

The term "metabolic disorder" refers to any disorder that involves an alteration in the normal metabolism of carbohydrates, lipids, proteins, nucleic acids, or a combination thereof. A metabolic disorder is associated with either a deficiency or excess in a metabolic pathway resulting in an imbalance in metabolism of nucleic acids, proteins, lipids, and/or carbohydrates. Factors affecting metabolism include, and are not limited to, the endocrine (hormonal) control system (e.g., the insulin pathway, the enteroendocrine hormones including GLP-1, PYY or the like), the neural control system (e.g., GLP-1 in the brain), or the like. Examples of metabolic disorders include, but are not limited to, diabetes (e.g., type 1 diabetes, type 2 diabetes, gestational diabetes), hyperglycemia, hyperinsulinemia, insulin resistance, and obesity.

DETAILED DESCRIPTION OF CERTAIN EMBODIMENTS OF THE INVENTION

Figure 1:
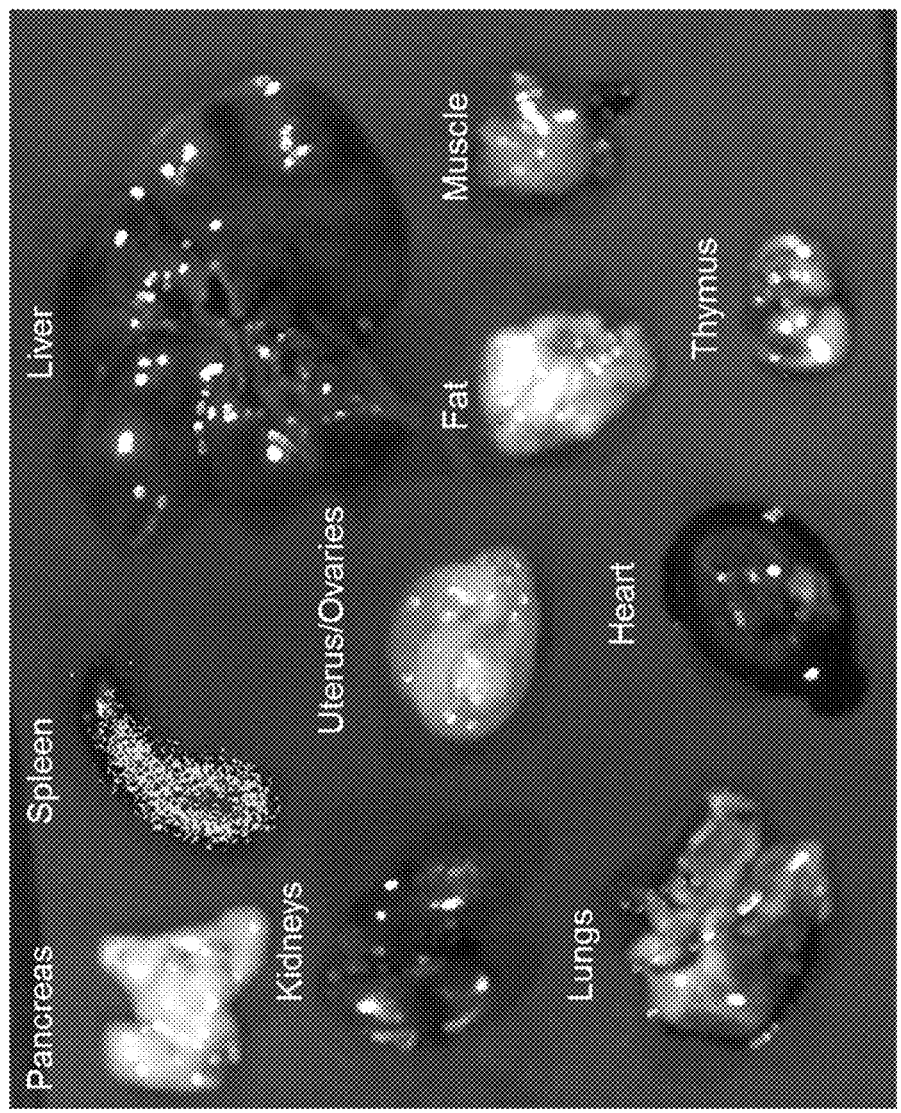
FIG. 1 shows that compound 24C18Oleic exhibited splenic luciferase mRNA expression at 6 hours.

The present disclosure provides compounds and uses thereof. In one aspect, described herein are compounds of Formula (I) or (II). Also described herein are compositions including a compound described herein and optionally an excipient. In certain embodiments, the compositions further include an agent (e.g., a polynucleotide (e.g., an RNA or DNA), small molecule, peptide, or protein). The compounds and compositions have been found to be able to deliver effectively and efficiently an agent to a subject, tissue, or cell. A compound of the disclosure, which includes one or more amino moieties that may be protonated to form positively charged ammonium cation(s), may bind to an agent that includes negatively charged moieties to form a complex. A compound described herein also includes one or more lipid moieties (e.g., substituted or unsubstituted, $C_{4-30}$ alkyl, substituted or unsubstituted, $C_{4-30}$ alkenyl). The lipid moieties are typically hydrophobic and may assist the compound and/or a complex of the compound and the agent to pass through cell membranes and/or mask the charge on the agent to be delivered. A described compound includes R—C(=O)—O— moieties (where R is a lipid moiety), which may be hydrolyzed into non-toxic carboxylic acids (e.g., fatty acids). Therefore, the compounds described herein may be biodegradable and/or non-toxic. In certain embodiments, a composition described herein that includes a plurality of molecules of a compound of the disclosure is in the form of particles. An agent may be encapsulated within or otherwise associated with the particles. In certain embodiments, the compositions are useful in delivering (e.g., selectively delivering) the agent to a subject, tissue (e.g., liver, spleen, or lung), or cell. The compositions (e.g., pharmaceutical compositions) may also be useful in treating and/or preventing a variety of diseases (e.g., genetic diseases, proliferative diseases, hematological diseases, neurological diseases, immunological diseases, gastrointestinal diseases (e.g., liver diseases), spleen diseases, respiratory diseases (e.g., lung diseases)), painful conditions, psychiatric disorders, and metabolic disorders in a subject in need thereof.

Compounds

In one aspect, the present disclosure provides compounds of Formula (I):

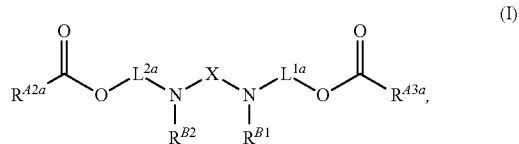

and salts, hydrates, solvates, polymorphs, tautomers, stereoisomers, and isotopically labeled derivatives thereof, wherein:

X is substituted or unsubstituted alkylene, substituted or unsubstituted alkenylene, substituted or unsubstituted alkynylene, substituted or unsubstituted heteroalkylene, substituted or unsubstituted heteroalkenylene, substituted or unsubstituted heteroalkynylene, substituted or unsubstituted carbocyclylene, substituted or unsubstituted heterocyclylene, substituted or unsubstituted arylene, substituted or unsubstituted heteroarylene, a divalent moiety of the formula:

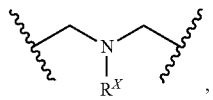

or a combination thereof, wherein each instance of $R^X$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group, or a moiety of the formula:

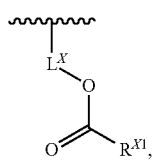

or $R^{B1}$ and an instance of $R^X$ are joined to form a substituted or unsubstituted, heterocyclic ring or a substituted or unsubstituted, heteroaryl ring, or $R^{B2}$ and an instance of $R^X$ are joined to form a substituted or unsubstituted, heterocyclic ring or a substituted or unsubstituted, heteroaryl ring, wherein:

each instance of $L^X$ is independently substituted or unsubstituted alkylene or substituted or unsubstituted heteroalkylene; and each instance of $R^{X1}$ is independently substituted or unsubstituted, $C_{4-30}$ alkyl, substituted or unsubstituted, $C_{4-30}$ alkenyl, or substituted or unsubstituted, $C_{4-30}$ alkynyl;

$L^{1a}$ is substituted or unsubstituted alkylene or substituted or unsubstituted heteroalkylene;

$R^{A1a}$ is substituted or unsubstituted, $C_{4-30}$ alkyl, substituted or unsubstituted, $C_{4-30}$ alkenyl, or substituted or unsubstituted, $C_{4-30}$ alkynyl;

$R^{B1}$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group, or a moiety of the formula:

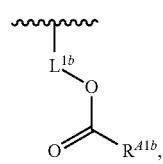

wherein $L^{1b}$ is substituted or unsubstituted alkylene or substituted or unsubstituted heteroalkylene, and $R^{A1b}$ is substituted or unsubstituted, $C_{4-30}$ alkyl, substituted or unsubstituted, $C_{4-30}$ alkenyl, or substituted or unsubstituted, $C_{4-30}$ alkynyl;

$L^{2a}$ is substituted or unsubstituted alkylene or substituted or unsubstituted heteroalkylene;

$R^{A2a}$ is substituted or unsubstituted, $C_{4-30}$ alkyl, substituted or unsubstituted, $C_{4-30}$ alkenyl, or substituted or unsubstituted, $C_{4-30}$ alkynyl; and $R^{B2}$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group, or a moiety of the formula:

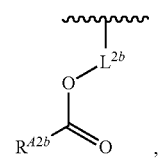

wherein $L^{2b}$ is substituted or unsubstituted alkylene or substituted or unsubstituted heteroalkylene, and $R^{A2b}$ is substituted or unsubstituted, $C_{4-30}$ alkyl, substituted or unsubstituted, $C_{4-30}$ alkenyl, or substituted or unsubstituted, $C_{4-30}$ alkynyl;

or $R^{B1}$ and $R^{B2}$ are joined to form a substituted or unsubstituted, heterocyclic ring or a substituted or unsubstituted, heteroaryl ring.

Formula (I) includes a divalent moiety X. In certain embodiments, X comprises substituted alkylene. In certain embodiments, X comprises a moiety shown in Table 2. In certain embodiments, X comprises unsubstituted alkylene. In certain embodiments, X comprises a moiety shown in Table 1. In certain embodiments, X comprises substituted $C_{1-6}$ alkylene. In certain embodiments, X comprises $C_{1-6}$ alkylene substituted with at least one halogen. In certain embodiments, X comprises $C_{1-6}$ alkylene substituted with at least one fluorine. In certain embodiments, X comprises $C_{1-6}$ perfluoroalkylene. In certain embodiments, X comprises unsubstituted $C_{1-6}$ alkylene. In certain embodiments, X comprises

In certain embodiments, X comprises

In certain embodiments, X comprises

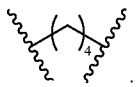

In certain embodiments, X comprises

and/or

In certain embodiments, X is of the formula:

In certain embodiments, X is of the formula:

In certain embodiments, X is of the formula

In certain embodiments, X is of the formula:

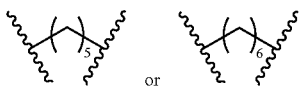

In certain embodiments, X is a moiety shown in Table 1. In certain embodiments, X is a moiety shown in Table 2.

TABLE 1

Exemplary unsubstituted alkylene moieties

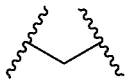

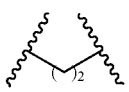

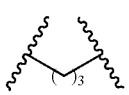

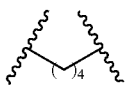

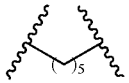

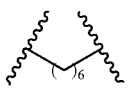

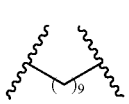

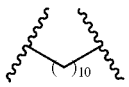

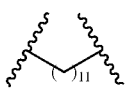

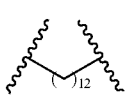

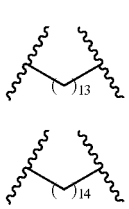

TABLE 1-continued
Exemplary unsubstituted alkylene moieties
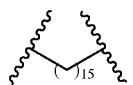
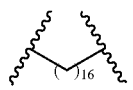
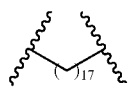
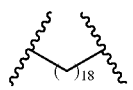
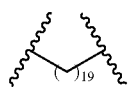
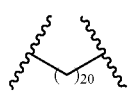
TABLE 2
Exemplary substituted alkylene moieties
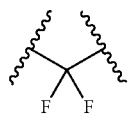 [SMILES: *C(*)(F)F]
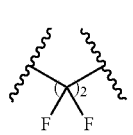
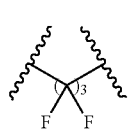
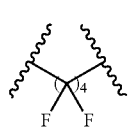
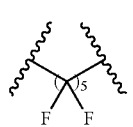
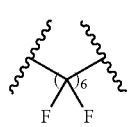
TABLE 2-continued
Exemplary substituted alkylene moieties
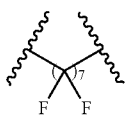
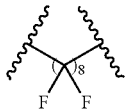
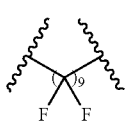
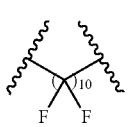
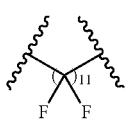
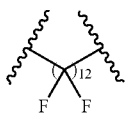
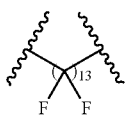
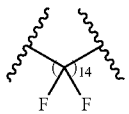
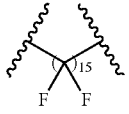
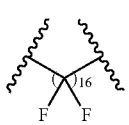
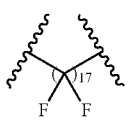
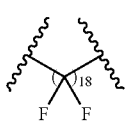

TABLE 2-continued

Exemplary substituted alkylene moieties

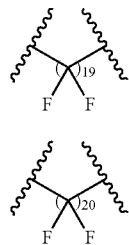

In certain embodiments, X comprises substituted alkenylene. In certain embodiments, X comprises unsubstituted alkenylene. In certain embodiments, X comprises substituted $C_{1-6}$ alkenylene. In certain embodiments, X comprises $C_{2-6}$ alkenylene substituted with at least one halogen. In certain embodiments, X comprises $C_{2-6}$ alkenylene substituted with at least one fluorine. In certain embodiments, X comprises $C_{2-6}$ perfluoroalkenylene. In certain embodiments, X comprises unsubstituted $C_{2-6}$ alkenylene. In certain embodiments, X comprises unsubstituted vinylene. In certain embodiments, X comprises unsubstituted propenylene. In certain embodiments, X comprises unsubstituted butenylene. In certain embodiments, X comprises unsubstituted pentenylene. In certain embodiments, X comprises unsubstituted hexenylene. In certain embodiments, X is unsubstituted vinylene. In certain embodiments, X is unsubstituted propenylene. In certain embodiments, X is unsubstituted butenylene. In certain embodiments, X is unsubstituted pentenylene. In certain embodiments, X is unsubstituted hexenylene.

In certain embodiments, X comprises substituted alkynylene. In certain embodiments, X comprises unsubstituted alkynylene. In certain embodiments, X comprises substituted $C_{1-6}$ alkynylene. In certain embodiments, X comprises $C_{2-6}$ alkynylene substituted with at least one halogen. In certain embodiments, X comprises $C_{2-6}$ alkynylene substituted with at least one fluorine. In certain embodiments, X comprises $C_{2-6}$ perfluoroalkynylene. In certain embodiments, X comprises unsubstituted $C_{2-6}$ alkynylene. In certain embodiments, X comprises —C≡C—. In certain embodiments, X comprises unsubstituted propynylene. In certain embodiments, X comprises unsubstituted butynylene. In certain embodiments, X comprises unsubstituted pentynylene. In certain embodiments, X comprises unsubstituted hexynylene. In certain embodiments, X is —C≡C—. In certain embodiments, X is unsubstituted propynylene. In certain embodiments, X is unsubstituted butynylene. In certain embodiments, X is unsubstituted pentynylene. In certain embodiments, X is unsubstituted hexynylene.

In certain embodiments, X comprises substituted heteroalkylene. In certain embodiments, X comprises unsubstituted heteroalkylene. In certain embodiments, X comprises is a moiety shown in Table 3. In certain embodiments, a heteroalkylene moiety consists of one, two, three, or four heteroatoms in the heteroalkylene chain, wherein the heteroatoms are independently selected from the group consisting of nitrogen, oxygen, or sulfur. In certain embodiments, X comprises substituted $C_{1-6}$ heteroalkylene. In certain embodiments, X comprises $C_{1-6}$ heteroalkylene substituted with at least one halogen. In certain embodiments, X comprises $C_{1-6}$ heteroalkylene substituted with at least one fluorine. In certain embodiments, X comprises unsubstituted $C_{1-6}$ heteroalkylene. In certain embodiments, X is unsubstituted $C_{1-6}$ heteroalkylene. In certain embodiments, X is a moiety shown in Table 3.

TABLE 3

Exemplary unsubstituted heteroalkylene moieties (wherein each instance of $R^X$ is independently unsubstituted $C_{1-6}$ alkyl)

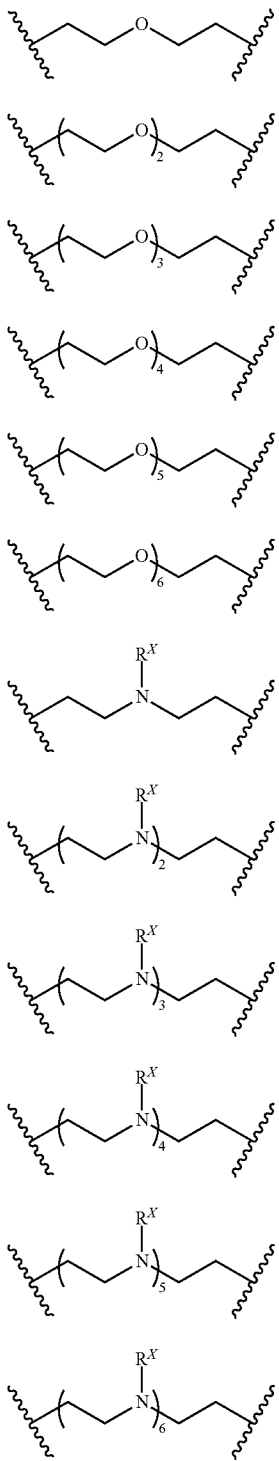

In certain embodiments, X comprises substituted heteroalkenylene. In certain embodiments, X comprises unsubstituted heteroalkenylene. In certain embodiments, a heteroalkenylene moiety consists of one, two, three, or four heteroatoms in the heteroalkenylene chain, wherein the heteroatoms are independently selected from the group consisting of nitrogen, oxygen, or sulfur. In certain embodiments, X comprises substituted $C_{1-6}$ heteroalkenylene. In certain embodiments, X comprises $C_{1-6}$ heteroalkenylene substituted with at least one halogen. In certain embodiments, X comprises $C_{1-6}$ heteroalkenylene substituted with at least one fluorine. In certain embodiments, X comprises unsubstituted $C_{1-6}$ heteroalkenylene. In certain embodiments, X is unsubstituted $C_{1-6}$ heteroalkenylene.

In certain embodiments, X comprises substituted heteroalkynylene. In certain embodiments, X comprises unsubstituted heteroalkynylene. In certain embodiments, a heteroalkynylene moiety consists of one, two, three, or four heteroatoms in the heteroalkynylene chain, wherein the heteroatoms are independently selected from the group consisting of nitrogen, oxygen, or sulfur. In certain embodiments, X comprises substituted $C_{1-6}$ heteroalkynylene. In certain embodiments, X comprises $C_{1-6}$ heteroalkynylene substituted with at least one halogen. In certain embodiments, X comprises $C_{1-6}$ heteroalkynylene substituted with at least one fluorine. In certain embodiments, X comprises unsubstituted $C_{1-6}$ heteroalkynylene. In certain embodiments, X is unsubstituted $C_{1-6}$ heteroalkynylene.

In certain embodiments, X comprises substituted carbocyclylene. In certain embodiments, X comprises unsubstituted carbocyclylene. In certain embodiments, X comprises saturated carbocyclylene. In certain embodiments, X comprises unsaturated carbocyclylene. In certain embodiments, X comprises monocyclic carbocyclylene. In certain embodiments, X comprises 3- to 7-membered, monocyclic carbocyclylene.

In certain embodiments, X comprises substituted heterocyclylene. In certain embodiments, X comprises unsubstituted heterocyclylene. In certain embodiments, X comprises saturated heterocyclylene. In certain embodiments, X comprises unsaturated heterocyclylene. In certain embodiments, X comprises substituted or unsubstituted, 3- to 7-membered, monocyclic heterocyclylene, wherein one, two, or three atoms in the heterocyclylene ring system are independently nitrogen, oxygen, or sulfur. In certain embodiments, X comprises substituted or unsubstituted, 6-membered monocyclic heterocyclylene, wherein one or two atoms in the heterocyclylene ring system are independently nitrogen, oxygen, or sulfur. In certain embodiments, X comprises a divalent moiety of the formula:

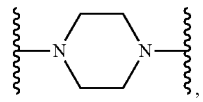

wherein the divalent moiety is substituted (e.g., substituted with one or more halogen, substituted or unsubstituted $C_{1-6}$ alkyl, and/or oxo) or unsubstituted. In certain embodiments, X comprises a divalent moiety of the formula:

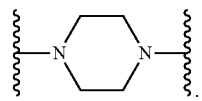

In certain embodiments, X comprises a divalent moiety of the formula:

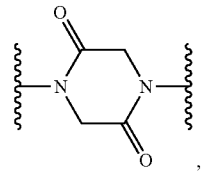 [SMILES: *N1CC(=O)N(*)CC1=O]

wherein the divalent moiety is substituted (e.g., with one or more halogen) or unsubstituted. In certain embodiments, X comprises a divalent moiety of the formula:

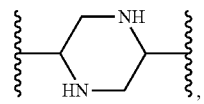

wherein the divalent moiety is substituted (e.g., substituted with one or more halogen, substituted or unsubstituted $C_{1-6}$ alkyl, and/or oxo) or unsubstituted. In certain embodiments, X comprises a divalent moiety of the formula:

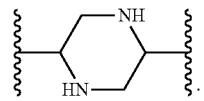

In certain embodiments, X comprises a divalent moiety of the formula:

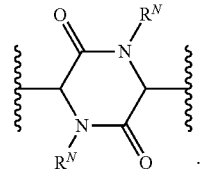

In certain embodiments, X comprises a divalent moiety of the formula:

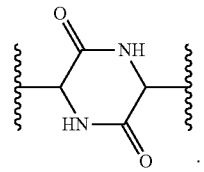

In certain embodiments, all instances of $R^N$ are the same. In certain embodiments, two instances of $R^N$ are different from each other. In certain embodiments, at least one instance of $R^N$ is hydrogen. In certain embodiments, each instance of $R^N$ is hydrogen. In certain embodiments, at least one instance of $R^N$ is substituted or unsubstituted $C_{1-6}$ alkyl (e.g., —$CH_3$, —$CF_3$, unsubstituted ethyl, perfluoroethyl, unsubstituted propyl, perfluoropropyl, unsubstituted butyl, or perfluorobutyl). In certain embodiments, at least one instance of $R^N$ is a nitrogen protecting group (e.g., Bn, Boc, Cbz, Fmoc, trifluoroacetyl, triphenylmethyl, acetyl, or Ts).

In certain embodiments, X comprises substituted arylene. In certain embodiments, X comprises unsubstituted arylene. In certain embodiments, X comprises 6- to 10-membered arylene. In certain embodiments, X comprises substituted phenylene. In certain embodiments, X comprises unsubstituted phenylene. In certain embodiments, X comprises substituted heteroarylene. In certain embodiments, X comprises unsubstituted heteroarylene. In certain embodiments, X comprises heteroarylene, wherein one, two, three, or four atoms in the heteroarylene ring system are independently selected from the group consisting of nitrogen, oxygen, and sulfur. In certain embodiments, X comprises monocyclic heteroarylene. In certain embodiments, X comprises 5-membered, monocyclic heteroarylene. In certain embodiments, X comprises 6-membered, monocyclic heteroarylene. In certain embodiments, X comprises bicyclic heteroarylene, wherein the point of attachment may be on any atom of the bicyclic heteroarylene ring system, as valency permits. In certain embodiments, X comprises 9- or 10-membered, bicyclic heteroarylene.

In certain embodiments, X comprises a divalent moiety of the formula:

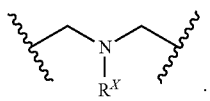

In certain embodiments, X comprises a divalent moiety of the formula:

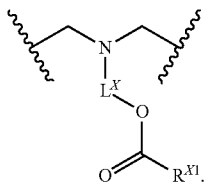

In certain embodiments, all instances of $R^X$ are the same. In certain embodiments, two instances of $R^X$ are different from each other. In certain embodiments, at least one instance of $R^X$ is H. In certain embodiments, at least one instance of $R^X$ is substituted acyl. In certain embodiments, at least one instance of $R^X$ is unsubstituted acyl. In certain embodiments, at least one instance of $R^X$ is acetyl. In certain embodiments, at least one instance of $R^X$ is substituted alkyl. In certain embodiments, at least one instance of $R^X$ is unsubstituted alkyl. In certain embodiments, at least one instance of $R^X$ is unsubstituted $C_{1-6}$ alkyl. In certain embodiments, at least one instance of $R^X$ is methyl. In certain embodiments, at least one instance of $R^X$ is ethyl. In certain embodiments, at least one instance of $R^X$ is propyl. In certain embodiments, at least one instance of $R^X$ is butyl. In certain embodiments, at least one instance of $R^X$ is pentyl. In certain embodiments, at least one instance of $R^X$ is hexyl. In certain embodiments, at least one instance of $R^X$ is substituted or unsubstituted carbocyclyl. In certain embodiments, at least one instance of $R^X$ is saturated carbocyclyl. In certain embodiments, at least one instance of $R^X$ is unsaturated carbocyclyl. In certain embodiments, at least one instance of $R^X$ is 3 to 7 membered, monocyclic carbocyclyl. In certain embodiments, at least one instance of $R^X$ is substituted or unsubstituted heterocyclyl. In certain embodiments, at least one instance of $R^X$ is saturated heterocyclyl. In certain embodiments, at least one instance of $R^X$ is unsaturated heterocyclyl. In certain embodiments, at least one instance of $R^X$ is heterocyclyl, wherein one, two, or three atoms in the heterocyclic ring system are independently selected from the group consisting of nitrogen, oxygen, and sulfur. In certain embodiments, at least one instance of $R^X$ is 3 to 7 membered, monocyclic heterocyclyl. In certain embodiments, at least one instance of $R^X$ is substituted or unsubstituted aryl. In certain embodiments, at least one instance of $R^X$ is 6 to 10 membered aryl. In certain embodiments, at least one instance of $R^X$ is monocyclic aryl. In certain embodiments, at least one instance of $R^X$ is substituted phenyl. In certain embodiments, at least one instance of $R^X$ is unsubstituted phenyl. In certain embodiments, at least one instance of $R^X$ is bicyclic aryl. In certain embodiments, at least one instance of $R^X$ is substituted or unsubstituted heteroaryl. In certain embodiments, at least one instance of $R^X$ is heteroaryl, wherein one, two, three, or four atoms in the heteroaryl ring system are independently selected from the group consisting of nitrogen, oxygen, and sulfur. In certain embodiments, at least one instance of $R^X$ is monocyclic heteroaryl. In certain embodiments, at least one instance of $R^X$ is 5 or 6 membered, monocyclic heteroaryl. In certain embodiments, at least one instance of $R^X$ is bicyclic heteroaryl, wherein the point of attachment may be on any atom of the bicyclic heteroaryl ring system, as valency permits. In certain embodiments, at least one instance of $R^X$ is a nitrogen protecting group. In certain embodiments, at least one instance of $R^X$ is Bn, Boc, Cbz, Fmoc, trifluoroacetyl, triphenylmethyl, acetyl, or Ts. In certain embodiments, at least one instance of $R^X$ is a moiety of the formula:

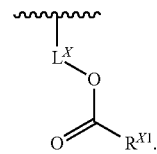

In certain embodiments, $R^{B1}$ and an instance of $R^X$ are joined to form a substituted or unsubstituted, heterocyclic ring. In certain embodiments, $R^{B1}$ and an instance of $R^X$ are joined to form a 3- to 7-membered, monocyclic heterocyclic ring, wherein one, two, or three atoms in the heterocyclic ring system are independently selected from the group consisting of nitrogen, oxygen, and sulfur. In certain embodiments, $R^{B1}$ and an instance of $R^X$ are joined to form a substituted or unsubstituted, heteroaryl ring. In certain embodiments, $R^{B1}$ and an instance of $R^X$ are joined to form a 5- to 6-membered, monocyclic heteroaryl ring, wherein one, two, or three atoms in the heteroaryl ring system are independently selected from the group consisting of nitrogen, oxygen, and sulfur. In certain embodiments, $R^{B1}$ and an instance of $R^X$ are joined to form a 9- to 10-membered, bicyclic heteroaryl ring, wherein one, two, three, or four atoms in the heteroaryl ring system are independently selected from the group consisting of nitrogen, oxygen, and sulfur. In certain embodiments, $R^{B2}$ and an instance of $R^X$ are joined to form a substituted or unsubstituted, heterocyclic ring. In certain embodiments, $R^{B2}$ and an instance of $R^X$ are joined to form a 3- to 7-membered, monocyclic heterocyclic ring, wherein one, two, or three atoms in the heterocyclic ring system are independently selected from the group consisting of nitrogen, oxygen, and sulfur. In certain embodiments, $R^{B2}$ and an instance of $R^X$ are joined to form a substituted or unsubstituted, heteroaryl ring. In certain embodiments, $R^{B2}$ and an instance of $R^X$ are joined to form a 5- to 6-membered, monocyclic heteroaryl ring, wherein one, two, or three atoms in the heteroaryl ring system are independently selected from the group consisting of nitrogen, oxygen, and sulfur. In certain embodiments, $R^{B2}$ and an instance of $R^X$ are joined to form a 9- to 10-membered, bicyclic heteroaryl ring, wherein one, two, three, or four atoms in the heteroaryl ring system are independently selected from the group consisting of nitrogen, oxygen, and sulfur.

In certain embodiments, all instances of $L^X$ are the same. In certain embodiments, two instances of $L^X$ are different from each other. In certain embodiments, at least one instance of $L^X$ is substituted alkylene. In certain embodiments, at least one instance of $L^X$ is a moiety shown in Table 2. In certain embodiments, at least one instance of $L^X$ is unsubstituted alkylene. In certain embodiments, at least one instance of $L^X$ is a moiety shown in Table 1. In certain embodiments, at least one instance of $L^X$ is substituted $C_{1-6}$ alkylene. In certain embodiments, at least one instance of $L^X$ is $C_{1-6}$ alkylene substituted with at least one halogen. In certain embodiments, at least one instance of $L^X$ is $C_{1-6}$ alkylene substituted with at least one fluorine. In certain embodiments, at least one instance of $L^X$ is $C_{1-6}$ perfluoroalkylene. In certain embodiments, at least one instance of $L^X$ is unsubstituted $C_{1-6}$ alkylene. In certain embodiments, at least one instance of $L^X$ is of the formula:

In certain embodiments, at least one instance of $L^X$ is of the formula:

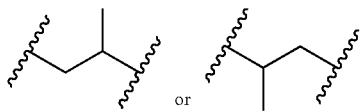

In certain embodiments, at least one instance of $L^X$ is of the formula:

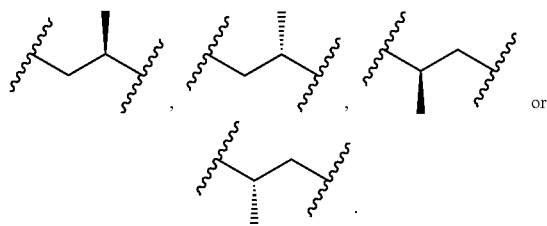

In certain embodiments, at least one instance of $L^X$ is substituted heteroalkylene. In certain embodiments, at least one instance of $L^X$ is unsubstituted heteroalkylene. In certain embodiments, at least one instance of $L^X$ is a moiety shown in Table 3. In certain embodiments, at least one instance of $L^X$ is substituted $C_{1-6}$ heteroalkylene. In certain embodiments, at least one instance of $L^X$ is $C_{1-6}$ heteroalkylene substituted with at least one halogen. In certain embodiments, at least one instance of $L^X$ is $C_{1-6}$ heteroalkylene substituted with at least one fluorine. In certain embodiments, at least one instance of $L^X$ is unsubstituted $C_{1-6}$ heteroalkylene.

In certain embodiments, all instances of $R^{X1}$ are the same. In certain embodiments, two instances of $R^{X1}$ are different from each other. In certain embodiments, at least one instance of $R^{X1}$ is substituted $C_{4-30}$ alkyl. In certain embodiments, at least one instance of $R^{X1}$ is a moiety shown in Table 5. $R^{X1}$ is $C_{4-30}$ alkyl substituted with one or more halogen. In certain embodiments, at least one instance of $R^{X1}$ is $C_{4-30}$ alkyl substituted with one or more fluorine. In certain embodiments, at least one instance of $R^{X1}$ is $C_{4-30}$ perfluoroalkyl. In certain embodiments, at least one instance of $R^{X1}$ is unsubstituted $C_{4-30}$ alkyl. In certain embodiments, at least one instance of $R^{X1}$ is a moiety shown in Table 4. In certain embodiments, at least one instance of $R^{X1}$ is unsubstituted and unbranched $C_{4-30}$ alkyl. In certain embodiments, at least one instance of $R^{X1}$ is substituted $C_{7-24}$ alkyl. In certain embodiments, at least one instance of $R^{X1}$ is $C_{7-24}$ alkyl substituted with one or more halogen. In certain embodiments, at least one instance of $R^{X1}$ is $C_{7-24}$ alkyl substituted with one or more fluorine. In certain embodiments, at least one instance of $R^{X1}$ is $C_{7-24}$ perfluoroalkyl. In certain embodiments, at least one instance of $R^{X1}$ is unsubstituted $C_{7-24}$ alkyl. In certain embodiments, at least one instance of $R^{X1}$ is unsubstituted and unbranched $C_{7-24}$ alkyl. In certain embodiments, at least one instance of $R^{X1}$ is substituted $C_{9-19}$ alkyl. In certain embodiments, at least one instance of $R^{X1}$ is $C_{9-19}$ alkyl substituted with one or more halogen. In certain embodiments, at least one instance of $R^{X1}$ is $C_{9-19}$ alkyl substituted with one or more fluorine. In certain embodiments, at least one instance of $R^{X1}$ is $C_{9-19}$ perfluoroalkyl. In certain embodiments, at least one instance of $R^{X1}$ is unsubstituted $C_{9-19}$ alkyl. In certain embodiments, at least one instance of $R^{X1}$ is unsubstituted and unbranched $C_{9-19}$ alkyl. In certain embodiments, at least one instance of $R^{X1}$ is substituted $C_{4-30}$ alkenyl. In certain embodiments, at least one instance of $R^{X1}$ is $C_{4-30}$ alkenyl substituted with one or more halogen. In certain embodiments, at least one instance of $R^{X1}$ is $C_{4-30}$ alkenyl substituted with one or more fluorine.

In certain embodiments, at least one instance of $R^{X1}$ is $C_{4-30}$ perfluoroalkenyl. In certain embodiments, at least one instance of $R^{X1}$ is unsubstituted $C_{4-30}$ alkenyl. In certain embodiments, at least one instance of $R^{X1}$ is a moiety shown in Table 6. In certain embodiments, at least one instance of $R^{X1}$ is unsubstituted and unbranched $C_{4-30}$ alkenyl. In certain embodiments, at least one instance of $R^{X1}$ is substituted $C_{7-24}$ alkenyl. In certain embodiments, at least one instance of $R^{X1}$ is $C_{7-24}$ alkenyl substituted with one or more halogen. In certain embodiments, at least one instance of $R^{X1}$ is $C_{7-24}$ alkenyl substituted with one or more fluorine. In certain embodiments, at least one instance of $R^{X1}$ is $C_{7-24}$ perfluoroalkenyl. In certain embodiments, at least one instance of $R^{X1}$ is unsubstituted $C_{7-24}$ alkenyl. In certain embodiments, at least one instance of $R^{X1}$ is unsubstituted and unbranched $C_{7-24}$ alkenyl. In certain embodiments, at least one instance of $R^{X1}$ is substituted $C_{9-19}$ alkenyl. In certain embodiments, at least one instance of $R^{X1}$ is $C_{9-19}$ alkenyl substituted with one or more halogen. In certain embodiments, at least one instance of $R^{X1}$ is $C_{9-19}$ alkenyl substituted with one or more fluorine. In certain embodiments, at least one instance of $R^{X1}$ is $C_{9-19}$ perfluoroalkenyl. In certain embodiments, at least one instance of $R^{X1}$ is unsubstituted $C_{9-19}$ alkenyl. In certain embodiments, at least one instance of $R^{X1}$ is unsubstituted and unbranched $C_{9-19}$ alkenyl. In certain embodiments, at least one instance of $R^{X1}$ is alkenyl described herein and includes one, two, three, four, five, or six C=C double bonds. In certain embodiments, at least one instance of $R^{X1}$ is substituted $C_{4-30}$ alkynyl. In certain embodiments, at least one instance of $R^{X1}$ is $C_{4-30}$ alkynyl substituted with one or more halogen. In certain embodiments, at least one instance of $R^{X1}$ is $C_{4-30}$ alkynyl substituted with one or more fluorine. In certain embodiments, at least one instance of $R^{X1}$ is $C_{4-30}$ perfluoroalkynyl. In certain embodiments, at least one instance of $R^{X1}$ is unsubstituted $C_{4-30}$ alkynyl. In certain embodiments, at least one instance of $R^{X1}$ is unsubstituted and unbranched $C_{4-30}$ alkynyl. In certain embodiments, at least one instance of $R^{X1}$ is substituted $C_{7-24}$ alkynyl. In certain embodiments, at least one instance of $R^{X1}$ is $C_{7-24}$ alkynyl substituted with one or more halogen. In certain embodiments, at least one instance of $R^{X1}$ is $C_{7-24}$ alkynyl substituted with one or more fluorine. In certain embodiments, at least one instance of $R^{X1}$ is $C_{7-24}$ perfluoroalkynyl. In certain embodiments, at least one instance of $R^{X1}$ is unsubstituted $C_{7-24}$ alkynyl. In certain embodiments, at least one instance of $R^{X1}$ is unsubstituted and unbranched $C_{7-24}$ alkynyl. In certain embodiments, at least one instance of $R^{X1}$ is substituted $C_{9-19}$ alkynyl. In certain embodiments, at least one instance of $R^{X1}$ is $C_{9-19}$ alkynyl substituted with one or more halogen. In certain embodiments, at least one instance of $R^{X1}$ is $C_{9-19}$ alkynyl substituted with one or more fluorine. In certain embodiments, at least one instance of $R^{X1}$ is $C_{9-19}$ perfluoroalkynyl. In certain embodiments, at least one instance of $R^{X1}$ is unsubstituted $C_{9-19}$ alkynyl. In certain embodiments, at least one instance of $R^{X1}$ is unsubstituted and unbranched $C_{9-19}$ alkynyl.

TABLE 4

Exemplary unsubstituted alkyl moieties

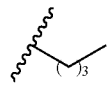
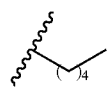
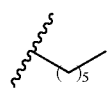
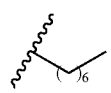
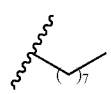
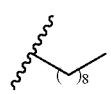
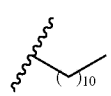

TABLE 4-continued

Exemplary unsubstituted alkyl moieties

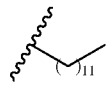
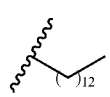
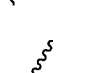
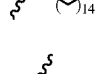
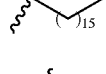
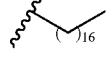
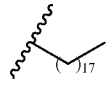
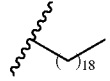

TABLE 5

Exemplary substituted alkyl moieties

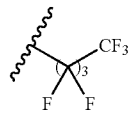
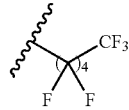
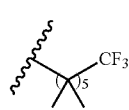
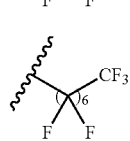

TABLE 5-continued
Exemplary substituted alkyl moieties
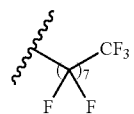
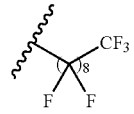
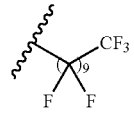
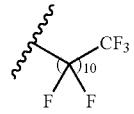
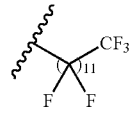
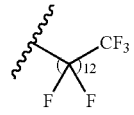
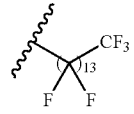
TABLE 5-continued
Exemplary substituted alkyl moieties
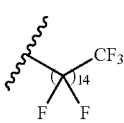
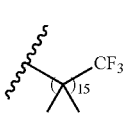
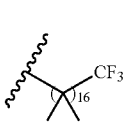
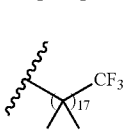
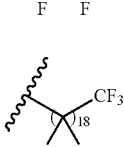
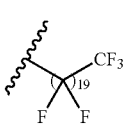
TABLE 6
Exemplary unsubstituted alkenyl moieties
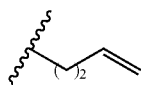
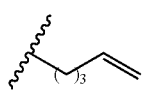
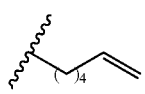
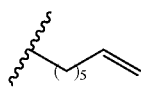
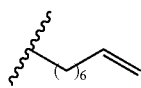
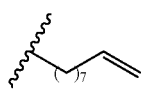

TABLE 6-continued

Exemplary unsubstituted alkenyl moieties

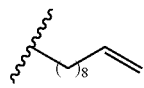

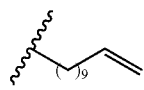

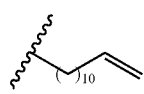

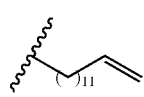

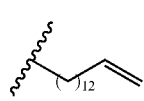

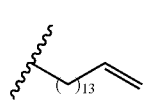

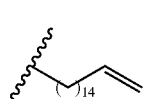

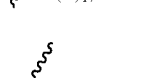

—(CH$_2$)$_7$CH═CH(CH$_2$)$_3$CH$_3$
—(CH$_2$)$_7$CH═CH(CH$_2$)$_5$CH$_3$
—(CH$_2$)$_4$CH═CH(CH$_2$)$_8$CH$_3$
—(CH$_2$)$_7$CH═CH(CH$_2$)$_7$CH$_3$
—(CH$_2$)$_7$CH═CHCH$_2$CH═CH(CH$_2$)$_4$CH$_3$
—(CH$_2$)$_7$CH═CHCH$_2$CH═CHCH$_2$CH═CHCH$_2$CH$_3$
—(CH$_2$)$_3$CH═CHCH$_2$CH═CHCH$_2$CH═CHCH$_2$CH═CH(CH$_2$)$_4$CH$_3$
—(CH$_2$)$_3$CH═CHCH$_2$CH═CHCH$_2$CH═CHCH$_2$CH═CHCH$_2$CH═CHCH$_2$CH$_3$
—(CH$_2$)$_{11}$CH═CH(CH$_2$)$_7$CH$_3$
—(CH$_2$)$_2$CH═CHCH$_2$CH═CHCH$_2$CH═CHCH$_2$CH═CHCH$_2$CH═CHCH$_2$CH═CH—CH$_2$CH$_3$

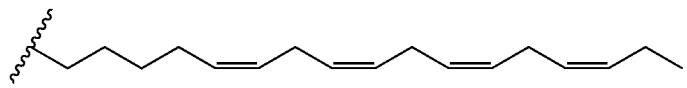

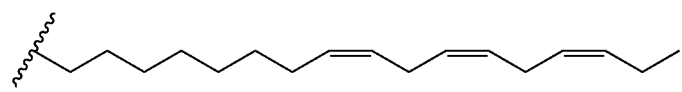

TABLE 6-continued

Exemplary unsubstituted alkenyl moieties

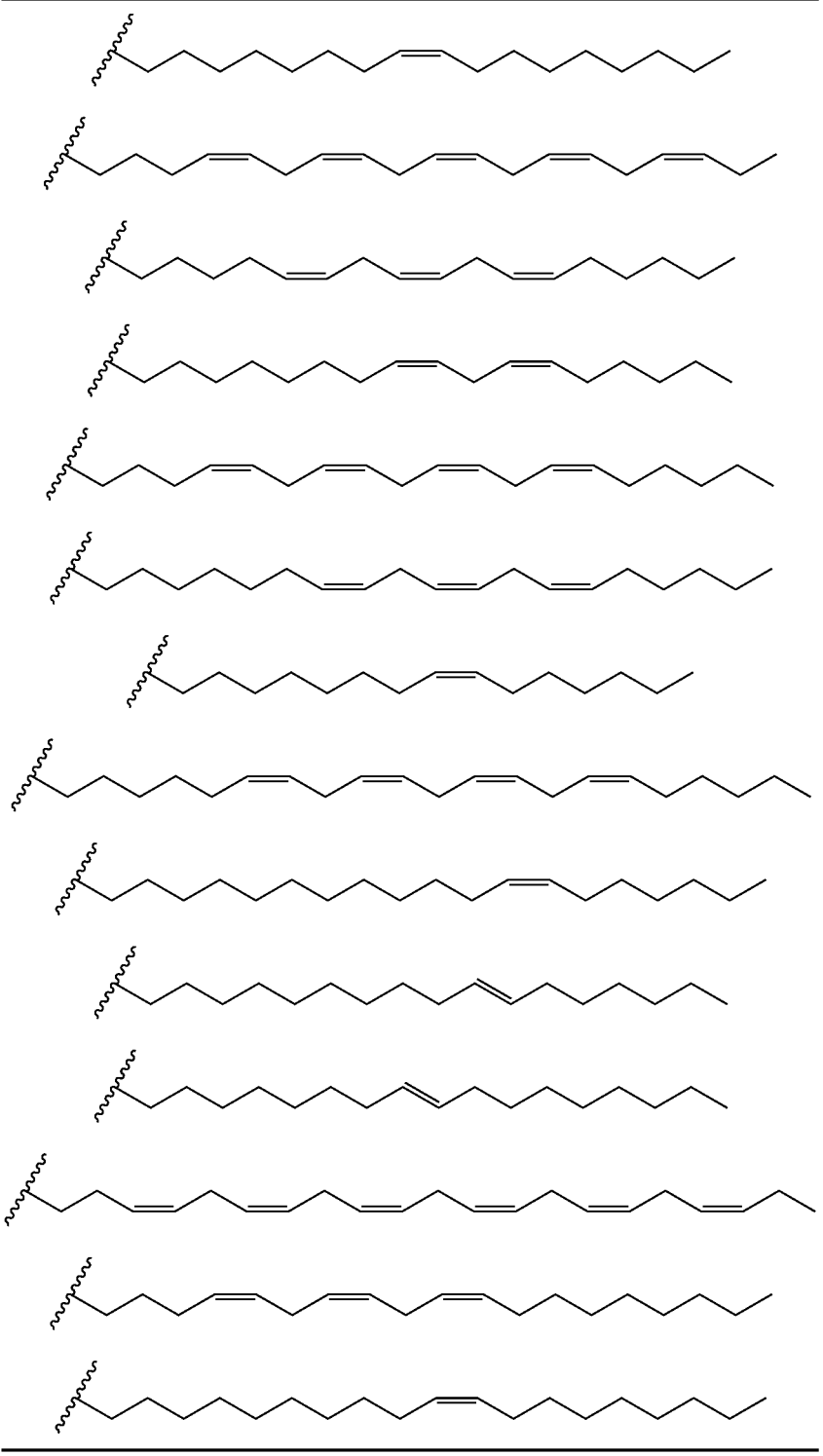

In Formula (I), X may be a combination of two or more divalent moieties described herein. Reference to divalent linker (e.g., X) being a combination of two or more divalent moieties described herein refers to a divalent linker consisting of at least one instance of a first divalent moiety and at least one instance of a second divalent moiety, wherein the first and second divalent moieties are the same or different and are within the scope of the divalent moieties described herein, and the instances of the first and second divalent moieties are consecutive covalently attached to each other. For example, when X is a combination of alkylene and heteroalkylene, divalent linkers -alkylene-alkylene-, -alkylene-heterocyclylene-, -alkylene-(heterocyclylene)$_2$-, and -heterocyclylene-alkylene-heterocyclylene- are all within the scope of X, wherein each instance of alkylene in any one of the divalent linkers may be the same or different, and each instance of heterocyclylene in any one of the divalent linkers may be the same or different. In certain embodiments, X is a combination of one or more substituted or unsubstituted alkylene, one or more substituted or unsubstituted heteroalkylene, and one or more substituted or unsubstituted heterocyclylene. In certain embodiments, X is a combination of one or more substituted or unsubstituted alkylene and one or more substituted or unsubstituted heteroalkylene. In certain embodiments, X is a combination of one or more substituted or unsubstituted alkylene and one or more substituted or unsubstituted heterocyclylene. In certain embodiments, X is a combination of one or more substituted or unsubstituted heteroalkylene and one or more substituted or unsubstituted heterocyclylene. In certain embodiments, X is of the formula:

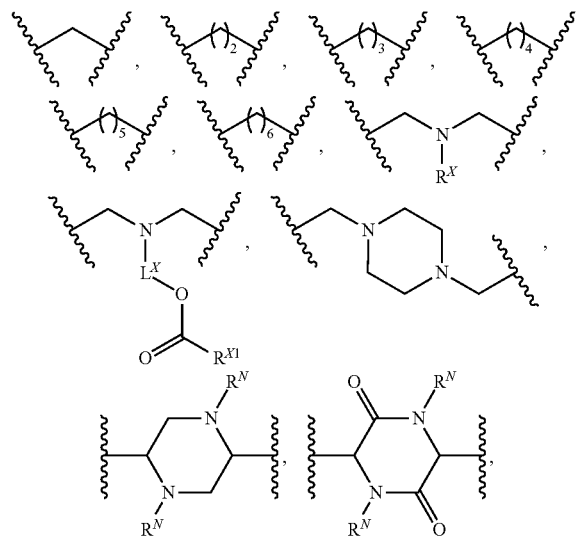

or a combination thereof. In certain embodiments, X is of the formula:

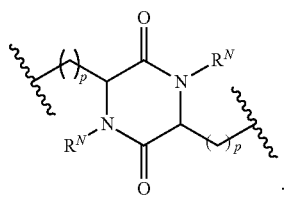

In certain embodiments, X is of the formula:

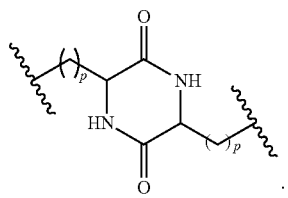

Each instance of p is independently 1, 2, 3, 4, 5, or 6. In certain embodiments, all instances of p are the same. In certain embodiments, two instances of p are different from each other. In certain embodiments, each instance of p is 3, 4, or 5 (e.g., 4). In certain embodiments, X is of the formula:

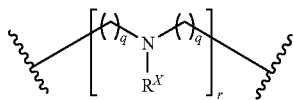

In certain embodiments, X is of the formula:

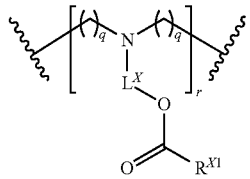

Each instance of q is independently 1, 2, 3, 4, 5, or 6. In certain embodiments, all instances of q are the same. In certain embodiments, two instances of q are different from each other. In certain embodiments, each instance of q is 2, 3, or 4 (e.g., 2). The number r is 1, 2, 3, 4, 5, or 6. In certain embodiments, r is 1. In certain embodiments, r is 2. In certain embodiments, r is 3. In certain embodiments, r is 4. In certain embodiments, r is 5. In certain embodiments, r is 6.

Formula (I) includes divalent linker $L^{1a}$. In certain embodiments, $L^{1a}$ is substituted alkylene. In certain embodiments, $L^{1a}$ is a moiety shown in Table 2. In certain embodiments, $L^{1a}$ is unsubstituted alkylene. In certain embodiments, $L^{1a}$ is a moiety shown in Table 1. In certain embodiments, $L^{1a}$ is substituted $C_{1-6}$ alkylene. In certain embodiments, $L^{1a}$ is $C_{1-6}$ alkylene substituted with at least one halogen. In certain embodiments, $L^{1a}$ is $C_{1-6}$ alkylene substituted with at least one fluorine. In certain embodiments, $L^{1a}$ is $C_{1-6}$ perfluoroalkylene. In certain embodiments, $L^{1a}$ is unsubstituted $C_{1-6}$ alkylene. In certain embodiments, $L^{1a}$ is of the formula:

In certain embodiments, $L^{1a}$ is of the formula:

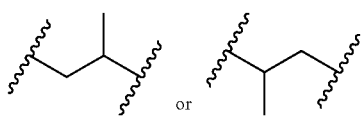

In certain embodiments, $L^{1a}$ is of the formula:

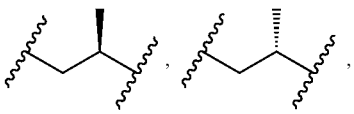

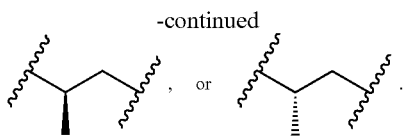

In certain embodiments, $L^{1a}$ is substituted heteroalkylene. In certain embodiments, $L^{1a}$ is unsubstituted heteroalkylene. In certain embodiments, $L^{1a}$ is a moiety shown in Table 3. In certain embodiments, $L^{1a}$ is substituted $C_{1-6}$ heteroalkylene. In certain embodiments, $L^{1a}$ is $C_{1-6}$ heteroalkylene substituted with at least one halogen. In certain embodiments, $L^{1a}$ is $C_{1-6}$ heteroalkylene substituted with at least one fluorine. In certain embodiments, $L^{1a}$ is unsubstituted $C_{1-6}$ heteroalkylene.

Formula (I) includes substituent $R^{A1a}$. In certain embodiments, $R^{A1a}$ is substituted $C_{4-30}$ alkyl. In certain embodiments, $R^{A1a}$ is a moiety shown in Table 5. In certain embodiments, $R^{A1a}$ is $C_{4-30}$ alkyl substituted with one or more halogen. In certain embodiments, $R^{A1a}$ is $C_{4-30}$ alkyl substituted with one or more fluorine. In certain embodiments, $R^{A1a}$ is $C_{4-30}$ perfluoroalkyl. In certain embodiments, $R^{A1a}$ is unsubstituted $C_{4-30}$ alkyl. In certain embodiments, $R^{A1a}$ is a moiety shown in Table 4. In certain embodiments, $R^{A1a}$ is unsubstituted and unbranched $C_{4-30}$ alkyl. In certain embodiments, $R^{A1a}$ is substituted $C_{7-24}$ alkyl. In certain embodiments, $R^{A1a}$ is $C_{7-24}$ alkyl substituted with one or more halogen. In certain embodiments, $R^{A1a}$ is $C_{7-24}$ alkyl substituted with one or more fluorine. In certain embodiments, $R^{A1a}$ is $C_{7-24}$ perfluoroalkyl. In certain embodiments, $R^{A1a}$ is unsubstituted $C_{7-24}$ alkyl. In certain embodiments, $R^{A1a}$ is unsubstituted and unbranched $C_{7-24}$ alkyl. In certain embodiments, $R^{A1a}$ is substituted $C_{9-19}$ alkyl. In certain embodiments, $R^{A1a}$ is $C_{9-19}$ alkyl substituted with one or more halogen. In certain embodiments, $R^{A1a}$ is $C_{9-19}$ alkyl substituted with one or more fluorine. In certain embodiments, $R^{A1a}$ is $C_{9-19}$ perfluoroalkyl. In certain embodiments, $R^{A1a}$ is unsubstituted $C_{9-19}$ alkyl. In certain embodiments, $R^{A1a}$ is unsubstituted and unbranched $C_{9-19}$ alkyl.

In certain embodiments, $R^{A1a}$ is substituted $C_{4-30}$ alkenyl. In certain embodiments, $R^{A1a}$ is $C_{4-30}$ alkenyl substituted with one or more halogen. In certain embodiments, $R^{A1a}$ is $C_{4-30}$ alkenyl substituted with one or more fluorine. In certain embodiments, $R^{A1a}$ is $C_{4-30}$ perfluoroalkenyl. In certain embodiments, $R^{A1a}$ is unsubstituted $C_{4-30}$ alkenyl. In certain embodiments, $R^{A1a}$ is a moiety shown in Table 6. In certain embodiments, $R^{A1a}$ is unsubstituted and unbranched $C_{4-30}$ alkenyl. In certain embodiments, $R^{A1a}$ is substituted $C_{7-24}$ alkenyl. In certain embodiments, $R^{A1a}$ is $C_{7-24}$ alkenyl substituted with one or more halogen. In certain embodiments, $R^{A1a}$ is $C_{7-24}$ alkenyl substituted with one or more fluorine. In certain embodiments, $R^{A1a}$ is $C_{7-24}$ perfluoroalkenyl. In certain embodiments, $R^{A1a}$ is unsubstituted $C_{7-24}$ alkenyl. In certain embodiments, $R^{A1a}$ is unsubstituted and unbranched $C_{7-24}$ alkenyl. In certain embodiments, $R^{A1a}$ is substituted $C_{9-19}$ alkenyl. In certain embodiments, $R^{A1a}$ is $C_{9-19}$ alkenyl substituted with one or more halogen. In certain embodiments, $R^{A1a}$ is $C_{9-19}$ alkenyl substituted with one or more fluorine. In certain embodiments, $R^{A1a}$ is $C_{9-19}$ perfluoroalkenyl. In certain embodiments, $R^{A1a}$ is unsubstituted $C_{9-19}$ alkenyl. In certain embodiments, $R^{A1a}$ is unsubstituted and unbranched $C_{9-19}$ alkenyl. In certain embodiments, $R^{A1a}$ is alkenyl described herein and includes one, two, three, four, five, or six C=C double bonds.

In certain embodiments, $R^{A1a}$ is substituted $C_{4-30}$ alkynyl. In certain embodiments, $R^{A1a}$ is $C_{4-30}$ alkynyl substituted with one or more halogen. In certain embodiments, $R^{A1a}$ is $C_{4-30}$ alkynyl substituted with one or more fluorine. In certain embodiments, $R^{A1a}$ is $C_{4-30}$ perfluoroalkynyl. In certain embodiments, $R^{A1a}$ is unsubstituted $C_{4-30}$ alkynyl. In certain embodiments, $R^{A1a}$ is unsubstituted and unbranched $C_{4-30}$ alkynyl. In certain embodiments, $R^{A1a}$ is substituted $C_{7-24}$ alkynyl. In certain embodiments, $R^{A1a}$ is $C_{7-24}$ alkynyl substituted with one or more halogen. In certain embodiments, $R^{A1a}$ is $C_{7-24}$ alkynyl substituted with one or more fluorine. In certain embodiments, $R^{A1a}$ is $C_{7-24}$ perfluoroalkynyl. In certain embodiments, $R^{A1a}$ is unsubstituted $C_{7-24}$ alkynyl. In certain embodiments, $R^{A1a}$ is unsubstituted and unbranched $C_{7-24}$ alkynyl. In certain embodiments, $R^{A1a}$ is substituted $C_{9-19}$ alkynyl. In certain embodiments, $R^{A1a}$ is $C_{9-19}$ alkynyl substituted with one or more halogen. In certain embodiments, $R^{A1a}$ is $C_{9-19}$ alkynyl substituted with one or more fluorine. In certain embodiments, $R^{A1a}$ is $C_{9-19}$ perfluoroalkynyl. In certain embodiments, $R^{A1a}$ is unsubstituted $C_{9-19}$ alkynyl. In certain embodiments, $R^{A1a}$ is unsubstituted and unbranched $C_{9-19}$ alkynyl.

Formula (I) includes substituent $R^{B1}$. In certain embodiments, $R^{B1}$ is H. In certain embodiments, $R^{B1}$ is substituted acyl. In certain embodiments, $R^{B1}$ is unsubstituted acyl. In certain embodiments, $R^{B1}$ is acetyl. In certain embodiments, $R^{B1}$ is substituted alkyl. In certain embodiments, $R^{B1}$ is unsubstituted alkyl. In certain embodiments, $R^{B1}$ is substituted $C_{1-6}$ alkyl. In certain embodiments, $R^{B1}$ is unsubstituted $C_{1-6}$ alkyl. In certain embodiments, $R^{B1}$ is $C_{1-6}$ alkyl substituted with at least one halogen. In certain embodiments, $R^{B1}$ is substituted methyl. In certain embodiments, $R^{B1}$ is —$CH_2F$, —$CHF_2$, or —$CF_3$. In certain embodiments, $R^{B1}$ is —$CH_3$. In certain embodiments, $R^{B1}$ is ethyl. In certain embodiments, $R^{B1}$ is propyl. In certain embodiments, $R^{B1}$ is butyl. In certain embodiments, $R^{B1}$ is pentyl. In certain embodiments, $R^{B1}$ is hexyl. In certain embodiments, $R^{B1}$ is substituted alkenyl. In certain embodiments, $R^{B1}$ is unsubstituted alkenyl. In certain embodiments, $R^{B1}$ is substituted $C_{1-6}$ alkenyl. In certain embodiments, $R^{B1}$ is unsubstituted $C_{1-6}$ alkenyl. In certain embodiments, $R^{B1}$ is vinyl. In certain embodiments, $R^{B1}$ is substituted alkynyl. In certain embodiments, $R^{B1}$ is unsubstituted alkynyl.

In certain embodiments, $R^{B1}$ is substituted $C_{1-6}$ alkynyl. In certain embodiments, $R^{B1}$ is unsubstituted $C_{1-6}$ alkynyl. In certain embodiments, $R^{B1}$ is substituted carbocyclyl. In certain embodiments, $R^{B1}$ is unsubstituted carbocyclyl. In certain embodiments, $R^{B1}$ is saturated carbocyclyl. In certain embodiments, $R^{B1}$ is unsaturated carbocyclyl. In certain embodiments, $R^{B1}$ is monocyclic carbocyclyl. In certain embodiments, $R^{B1}$ is 3- to 7-membered, monocyclic carbocyclyl. In certain embodiments, $R^{B1}$ is substituted heterocyclyl. In certain embodiments, $R^{B1}$ is unsubstituted heterocyclyl. In certain embodiments, $R^{B1}$ is saturated heterocyclyl. In certain embodiments, $R^{B1}$ is unsaturated heterocyclyl. In certain embodiments, $R^{B1}$ is heterocyclyl, wherein one, two, or three atoms in the heterocyclic ring system are independently selected from the group consisting of nitrogen, oxygen, and sulfur. In certain embodiments, $R^{B1}$ is monocyclic heterocyclyl. In certain embodiments, $R^{B1}$ is 3- to 7-membered, monocyclic heterocyclyl. In certain embodiments, $R^{B1}$ is substituted aryl. In certain embodiments, $R^{B1}$ is unsubstituted aryl. In certain embodiments, $R^{B1}$ is 6- to 10-membered aryl. In certain embodiments, $R^{B1}$ is substituted phenyl. In certain embodiments, $R^{B1}$ is unsubstituted phenyl. In certain embodiments, $R^{B1}$ is substituted heteroaryl. In certain embodiments, $R^{B1}$ is unsubstituted heteroaryl. In certain embodiments, $R^{B1}$ is heteroaryl, wherein one, two, three, or four atoms in the heteroaryl ring system are independently selected from the group consisting of nitrogen, oxygen, and sulfur. In certain embodiments, $R^{B1}$ is monocyclic heteroaryl. In certain embodiments, $R^{B1}$ is 5-membered, monocyclic heteroaryl. In certain embodiments, $R^{B1}$ is 6-membered, monocyclic heteroaryl. In certain embodiments, $R^{B1}$ is bicyclic heteroaryl, wherein the point of attachment may be on any atom of the bicyclic heteroaryl ring system, as valency permits. In certain embodiments, $R^{B1}$ is 9- or 10-membered, bicyclic heteroaryl. In certain embodiments, $R^{B1}$ is a nitrogen protecting group. In certain embodiments, $R^{B1}$ is Bn, Boc, Cbz, Fmoc, trifluoroacetyl, triphenylmethyl, acetyl, or Ts.

In certain embodiments, $R^{B1}$ is a moiety of the formula:

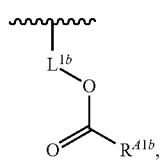

wherein $L^{1b}$ is substituted or unsubstituted alkylene or substituted or unsubstituted heteroalkylene, and $R^{A1b}$ is substituted or unsubstituted, $C_{4-30}$ alkyl, substituted or unsubstituted, $C_{4-30}$ alkenyl, or substituted or unsubstituted, $C_{4-30}$ alkynyl. In certain embodiments, $L^{1b}$ is substituted alkylene. In certain embodiments, $L^{1b}$ is a moiety shown in Table 2. In certain embodiments, $L^{1b}$ is unsubstituted alkylene. In certain embodiments, $L^{1b}$ is a moiety shown in Table 1. In certain embodiments, $L^{1b}$ is substituted $C_{1-6}$ alkylene. In certain embodiments, $L^{1b}$ is $C_{1-6}$ alkylene substituted with at least one halogen. In certain embodiments, $L^{1b}$ is $C_{1-6}$ alkylene substituted with at least one fluorine. In certain embodiments, $L^{1b}$ is $C_{1-6}$ perfluoroalkylene. In certain embodiments, $L^{1b}$ is unsubstituted $C_{1-6}$ alkylene. In certain embodiments, $L^{1b}$ is of the formula:

In certain embodiments, $L^{1b}$ is of the formula:

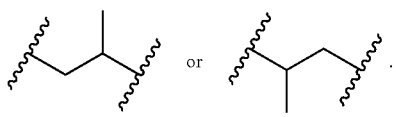

In certain embodiments, L is of the formula:

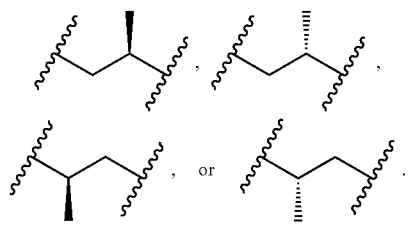

In certain embodiments, $L^{1b}$ is substituted heteroalkylene. In certain embodiments, $L^{1b}$ is unsubstituted heteroalkylene.

In certain embodiments, $L^{1b}$ is a moiety shown in Table 3. In certain embodiments, $L^{1b}$ is substituted $C_{1-6}$ heteroalkylene. In certain embodiments, $L^{1b}$ is $C_{1-6}$ heteroalkylene substituted with at least one halogen. In certain embodiments, $L^{1b}$ is $C_{1-6}$ heteroalkylene substituted with at least one fluorine. In certain embodiments, $L^{1b}$ is unsubstituted $C_{1-6}$ heteroalkylene. In certain embodiments, $R^{A1b}$ is substituted $C_{4-30}$ alkyl. In certain embodiments, $R^{A1b}$ is a moiety shown in Table 5. In certain embodiments, $R^{A1b}$ is $C_{4-30}$ alkyl substituted with one or more halogen. In certain embodiments, $R^{A1b}$ is $C_{4-30}$ alkyl substituted with one or more fluorine. In certain embodiments, $R^{A1b}$ is $C_{4-30}$ perfluoroalkyl. In certain embodiments, $R^{A1b}$ is unsubstituted $C_{4-30}$ alkyl. In certain embodiments, $R^{A1b}$ is a moiety shown in Table 4. In certain embodiments, $R^{A1b}$ is unsubstituted and unbranched $C_{4-30}$ alkyl. In certain embodiments, $R^{A1b}$ is substituted $C_{7-24}$ alkyl. In certain embodiments, $R^{A1b}$ is $C_{7-24}$ alkyl substituted with one or more halogen. In certain embodiments, $R^{A1b}$ is $C_{7-24}$ alkyl substituted with one or more fluorine. In certain embodiments, $R^{A1b}$ is $C_{7-24}$ perfluoroalkyl. In certain embodiments, $R^{A1b}$ is unsubstituted $C_{7-24}$ alkyl. In certain embodiments, $R^{A1b}$ is unsubstituted and unbranched $C_{7-24}$ alkyl. In certain embodiments, $R^{A1b}$ is substituted $C_{9-19}$ alkyl. In certain embodiments, $R^{A1b}$ is $C_{9-19}$ alkyl substituted with one or more halogen. In certain embodiments, $R^{A1b}$ is $C_{9-19}$ alkyl substituted with one or more fluorine. In certain embodiments, $R^{A1b}$ is $C_{9-19}$ perfluoroalkyl. In certain embodiments, $R^{A1b}$ is unsubstituted $C_{9-19}$ alkyl. In certain embodiments, $R^{A1b}$ is unsubstituted and unbranched $C_{9-19}$ alkyl. In certain embodiments, $R^{A1b}$ is substituted $C_{4-30}$ alkenyl. In certain embodiments, $R^{A1b}$ is $C_{4-30}$ alkenyl substituted with one or more halogen. In certain embodiments, $R^{A1b}$ is $C_{4-30}$ alkenyl substituted with one or more fluorine. In certain embodiments, $R^{A1b}$ is $C_{4-30}$ perfluoroalkenyl. In certain embodiments, $R^{A1b}$ is unsubstituted $C_{4-30}$ alkenyl. In certain embodiments, $R^{A1b}$ is a moiety shown in Table 6. In certain embodiments, $R^{A1b}$ is unsubstituted and unbranched $C_{4-30}$ alkenyl. In certain embodiments, $R^{A1b}$ is substituted $C_{7-24}$ alkenyl. In certain embodiments, $R^{A1b}$ is $C_{7-24}$ alkenyl substituted with one or more halogen. In certain embodiments, $R^{A1b}$ is $C_{7-24}$ alkenyl substituted with one or more fluorine. In certain embodiments, $R^{A1b}$ is $C_{7-24}$ perfluoroalkenyl. In certain embodiments, $R^{A1b}$ is unsubstituted $C_{7-24}$ alkenyl. In certain embodiments, $R^{A1b}$ is unsubstituted and unbranched $C_{7-24}$ alkenyl. In certain embodiments, $R^{A1b}$ is substituted $C_{9-19}$ alkenyl. In certain embodiments, $R^{A1b}$ is $C_{9-19}$ alkenyl substituted with one or more halogen. In certain embodiments, $R^{A1b}$ is $C_{9-19}$ alkenyl substituted with one or more fluorine. In certain embodiments, $R^{A1b}$ is $C_{9-19}$ perfluoroalkenyl. In certain embodiments, $R^{A1b}$ is unsubstituted $C_{9-19}$ alkenyl. In certain embodiments, $R^{A1b}$ is unsubstituted and unbranched $C_{9-19}$ alkenyl. In certain embodiments, $R^{A1b}$ is alkenyl described herein and includes one, two, three, four, five, or six C=C double bonds. In certain embodiments, $R^{A1b}$ is substituted $C_{4-30}$ alkynyl. In certain embodiments, $R^{A1b}$ is $C_{4-30}$ alkynyl substituted with one or more halogen. In certain embodiments, $R^{A1b}$ is $C_{4-30}$ alkynyl substituted with one or more fluorine. In certain embodiments, $R^{A1b}$ is $C_{4-30}$ perfluoroalkynyl. In certain embodiments, $R^{A1b}$ is unsubstituted $C_{4-30}$ alkynyl. In certain embodiments, $R^{A1b}$ is unsubstituted and unbranched $C_{4-30}$ alkynyl. In certain embodiments, $R^{A1b}$ is substituted $C_{7-24}$ alkynyl. In certain embodiments, $R^{A1b}$ is $C_{7-24}$ alkynyl substituted with one or more halogen. In certain embodiments, $R^{A1b}$ is $C_{7-24}$ alkynyl substituted with one or more fluorine. In certain embodiments, $R^{A1b}$ is $C_{7-24}$ perfluoroalkynyl. In certain embodiments, $R^{A1b}$ is unsubstituted $C_{7-24}$ alkynyl. In certain embodiments, $R^{A1b}$ is unsubstituted and unbranched $C_{7-24}$ alkynyl. In certain embodiments, $R^{A1b}$ is substituted $C_{9-19}$ alkynyl. In certain embodiments, $R^{A1b}$ is $C_{9-19}$ alkynyl substituted with one or more halogen. In certain embodiments, $R^{A1b}$ is $C_{9-19}$ alkynyl substituted with one or more fluorine. In certain embodiments, $R^{A1b}$ is $C_{9-19}$ perfluoroalkynyl. In certain embodiments, $R^{A1b}$ is unsubstituted $C_{9-19}$ alkynyl. In certain embodiments, $R^{A1b}$ is unsubstituted and unbranched $C_{9-19}$ alkynyl.

In certain embodiments, $R^{B1}$ and $R^{B2}$ are joined to form a substituted or unsubstituted, heterocyclic ring. In certain embodiments, $R^{B1}$ and $R^{B2}$ are joined to form a 3- to 7-membered, monocyclic heterocyclic ring, wherein one, two, or three atoms in the heterocyclic ring system are independently selected from the group consisting of nitrogen, oxygen, and sulfur.

In certain embodiments, $R^{B1}$ and $R^{B2}$ are joined to form a divalent moiety of the formula:

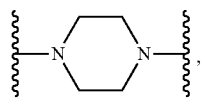

wherein the moiety is substituted (e.g., with one or more halogen and/or oxo) or unsubstituted. In certain embodiments, $R^{B1}$ and $R^{B2}$ are joined to a divalent moiety of the formula:

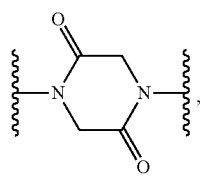 [SMILES: *N1CC(=O)N(*)CC1=O]

wherein the moiety is substituted (e.g., with one or more halogen) or unsubstituted. In certain embodiments, $R^{B1}$ and $R^{B2}$ are joined to form a substituted or unsubstituted, heteroaryl ring. In certain embodiments, $R^{B1}$ and $R^{B2}$ are joined to form a 5- to 6-membered, monocyclic heteroaryl ring, wherein one, two, or three atoms in the heteroaryl ring system are independently selected from the group consisting of nitrogen, oxygen, and sulfur. In certain embodiments, $R^{B1}$ and $R^{B2}$ are joined to form a 9- to 10-membered, bicyclic heteroaryl ring, wherein one, two, three, or four atoms in the heteroaryl ring system are independently selected from the group consisting of nitrogen, oxygen, and sulfur.

Formula (I) includes divalent linker $L^{2a}$. In certain embodiments, $L^{2a}$ is substituted alkylene. In certain embodiments, $L^{2a}$ is a moiety shown in Table 2. In certain embodiments, $L^{2a}$ is unsubstituted alkylene. In certain embodiments, $L^{2a}$ is a moiety shown in Table 1. In certain embodiments, $L^{2a}$ is substituted $C_{1-6}$ alkylene. In certain embodiments, $L^{2a}$ is $C_{1-6}$ alkylene substituted with at least one halogen. In certain embodiments, $L^{2a}$ is $C_{1-6}$ alkylene substituted with at least one fluorine. In certain embodiments, $L^{2a}$ is $C_{1-6}$ perfluoroalkylene. In certain embodiments, $L^{2a}$ is unsubstituted $C_{1-6}$ alkylene. In certain embodiments, $L^{2a}$ is of the formula:

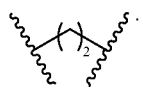

In certain embodiments, $L^{2a}$ is of the formula:

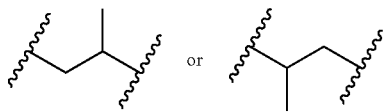

In certain embodiments, $L^{2a}$ is of the formula:

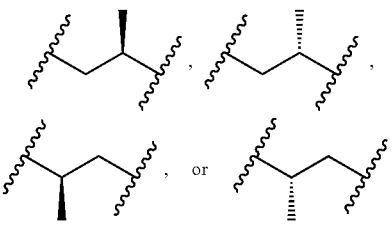

In certain embodiments, $L^{2a}$ is substituted heteroalkylene. In certain embodiments, $L^{2a}$ is unsubstituted heteroalkylene. In certain embodiments, $L^{2a}$ is a moiety shown in Table 3. In certain embodiments, $L^{2a}$ is substituted $C_{1-6}$ heteroalkylene. In certain embodiments, $L^{2a}$ is $C_{1-6}$ heteroalkylene substituted with at least one halogen. In certain embodiments, $L^{2a}$ is $C_{1-6}$ heteroalkylene substituted with at least one fluorine. In certain embodiments, $L^{2a}$ is unsubstituted $C_{1-6}$ heteroalkylene.

Formula (I) includes substituent $R^{A2a}$. In certain embodiments, $R^{A2}$ is substituted $C_{4-30}$ alkyl. In certain embodiments, $R^{A2a}$ is a moiety shown in Table 5. In certain embodiments, $R^{A2a}$ is $C_{4-30}$ alkyl substituted with one or more halogen. In certain embodiments, $R^{A2a}$ is $C_{4-30}$ alkyl substituted with one or more fluorine. In certain embodiments, $R^{A2a}$ is $C_{4-30}$ perfluoroalkyl.

In certain embodiments, $R^{A2a}$ is unsubstituted $C_{4-30}$ alkyl. In certain embodiments, $R^{A2a}$ is a moiety shown in Table 4. In certain embodiments, $R^{A2a}$ is unsubstituted and unbranched $C_{4-30}$ alkyl. In certain embodiments, $R^{A2a}$ is substituted $C_{7-24}$ alkyl. In certain embodiments, $R^{A2a}$ is $C_{7-24}$ alkyl substituted with one or more halogen. In certain embodiments, $R^{A2a}$ is $C_{7-24}$ alkyl substituted with one or more fluorine. In certain embodiments, $R^{A2a}$ is $C_{7-24}$ perfluoroalkyl. In certain embodiments, $R^{A2a}$ is unsubstituted $C_{7-24}$ alkyl. In certain embodiments, $R^{A2a}$ is unsubstituted and unbranched $C_{7-24}$ alkyl. In certain embodiments, $R^{A2a}$ is substituted $C_{9-19}$ alkyl. In certain embodiments, $R^{A2a}$ is $C_{9-19}$ alkyl substituted with one or more halogen. In certain embodiments, $R^{A2a}$ is $C_{9-19}$ alkyl substituted with one or more fluorine. In certain embodiments, $R^{A2a}$ is $C_{9-19}$ perfluoroalkyl. In certain embodiments, $R^{A2a}$ is unsubstituted $C_{9-19}$ alkyl. In certain embodiments, $R^{A2a}$ is unsubstituted and unbranched $C_{9-19}$ alkyl. In certain embodiments, $R^{A2a}$ is substituted $C_{4-30}$ alkenyl. In certain embodiments, $R^{A2a}$ is $C_{4-30}$ alkenyl substituted with one or more halogen. In certain embodiments, $R^{A2a}$ is $C_{4-30}$ alkenyl substituted with one or more fluorine. In certain embodiments, $R^{A2a}$ is $C_{4-30}$ perfluoroalkenyl. In certain embodiments, $R^{A2a}$ is unsubstituted $C_{4-30}$ alkenyl. In certain embodiments, $R^{A2a}$ is a moiety shown in Table 6. In certain embodiments, $R^{A2a}$ is unsubstituted and unbranched $C_{4-30}$ alkenyl. In certain embodiments, $R^{A2a}$ is substituted $C_{7-24}$ alkenyl. In certain embodiments, $R^{A2a}$ is $C_{7-24}$ alkenyl substituted with one or more halogen. In certain embodiments, $R^{A2a}$ is $C_{7-24}$ alkenyl substituted with one or more fluorine. In certain embodiments, $R^{A2a}$ is $C_{7-24}$ perfluoroalkenyl. In certain embodiments, $R^{A2a}$ is unsubstituted $C_{7-24}$ alkenyl. In certain embodiments, $R^{A2a}$ is unsubstituted and unbranched $C_{7-24}$ alkenyl. In certain embodiments, $R^{A2a}$ is substituted $C_{9-19}$ alkenyl. In certain embodiments, $R^{A2a}$ is $C_{9-19}$ alkenyl substituted with one or more halogen. In certain embodiments, $R^{A2a}$ is $C_{9-19}$ alkenyl substituted with one or more fluorine. In certain embodiments, $R^{A2a}$ is $C_{9-19}$ perfluoroalkenyl. In certain embodiments, $R^{A2a}$ is unsubstituted $C_{9-19}$ alkenyl. In certain embodiments, $R^{A2a}$ is unsubstituted and unbranched $C_{9-19}$ alkenyl. In certain embodiments, $R^{A2a}$ is alkenyl described herein and includes one, two, three, four, five, or six C=C double bonds. In certain embodiments, $R^{A2a}$ is substituted $C_{4-30}$ alkynyl. In certain embodiments, $R^{A2a}$ is $C_{4-30}$ alkynyl substituted with one or more halogen. In certain embodiments, $R^{A2a}$ is $C_{4-30}$ alkynyl substituted with one or more fluorine. In certain embodiments, $R^{A2a}$ is $C_{4-30}$ perfluoroalkynyl. In certain embodiments, $R^{A2a}$ is unsubstituted $C_{4-30}$ alkynyl. In certain embodiments, $R^{A2a}$ is unsubstituted and unbranched $C_{4-30}$ alkynyl. In certain embodiments, $R^{A2a}$ is substituted $C_{7-24}$ alkynyl. In certain embodiments, $R^{A2a}$ is $C_{7-24}$ alkynyl substituted with one or more halogen. In certain embodiments, $R^{A2a}$ is $C_{7-24}$ alkynyl substituted with one or more fluorine. In certain embodiments, $R^{A2a}$ is $C_{7-24}$ perfluoroalkynyl. In certain embodiments, $R^{A2a}$ is unsubstituted $C_{7-24}$ alkynyl. In certain embodiments, $R^{A2a}$ is unsubstituted and unbranched $C_{7-24}$ alkynyl. In certain embodiments, $R^{A2a}$ is substituted $C_{9-19}$ alkynyl. In certain embodiments, $R^{A2a}$ is $C_{9-19}$ alkynyl substituted with one or more halogen. In certain embodiments, $R^{A2a}$ is $C_{9-19}$ alkynyl substituted with one or more fluorine. In certain embodiments, $R^{A2a}$ is $C_{9-19}$ perfluoroalkynyl. In certain embodiments, $R^{A2a}$ is unsubstituted $C_{9-19}$ alkynyl. In certain embodiments, $R^{A2a}$ is unsubstituted and unbranched $C_{9-19}$ alkynyl.

Formula (I) includes substituent $R^{B2}$. In certain embodiments, $R^{B2}$ is H. In certain embodiments, $R^{B2}$ is substituted acyl. In certain embodiments, $R^{B2}$ is unsubstituted acyl. In certain embodiments, $R^{B2}$ is acetyl. In certain embodiments, $R^{B2}$ is substituted alkyl. In certain embodiments, $R^{B2}$ is unsubstituted alkyl. In certain embodiments, $R^{B2}$ is substituted $C_{1-6}$ alkyl. In certain embodiments, $R^{B2}$ is unsubstituted $C_{1-6}$ alkyl. In certain embodiments, $R^{B2}$ is $C_{1-6}$ alkyl substituted with at least one halogen. In certain embodiments, $R^{B2}$ is substituted methyl. In certain embodiments, $R^{B2}$ is —CH$_2$F, —CHF$_2$, or —CF$_3$. In certain embodiments, $R^{B2}$ is —CH$_3$. In certain embodiments, $R^{B2}$ is ethyl. In certain embodiments, $R^{B2}$ is propyl. In certain embodiments, $R^{B2}$ is butyl. In certain embodiments, $R^{B2}$ is pentyl. In certain embodiments, $R^{B2}$ is hexyl. In certain embodiments, $R^{B2}$ is substituted alkenyl. In certain embodiments, $R^{B2}$ is unsubstituted alkenyl. In certain embodiments, $R^{B2}$ is substituted $C_{1-6}$ alkenyl. In certain embodiments, $R^{B2}$ is unsubstituted $C_{1-6}$ alkenyl. In certain embodiments, $R^{B2}$ is vinyl. In certain embodiments, $R^{B2}$ is substituted alkynyl. In certain embodiments, $R^{B2}$ is unsubstituted alkynyl. In certain embodiments, $R^{B2}$ is substituted $C_{1-6}$ alkynyl. In certain embodiments, $R^{B2}$ is unsubstituted $C_{1-6}$ alkynyl. In certain embodiments, $R^{B2}$ is substituted carbocyclyl. In certain embodiments, $R^{B2}$ is unsubstituted carbocyclyl. In certain embodiments, $R^{B2}$ is saturated carbocyclyl. In certain embodiments, $R^{B2}$ is unsaturated carbocyclyl. In certain embodiments, $R^{B2}$ is monocyclic carbocyclyl. In certain embodiments, $R^{B2}$ is 3- to 7-membered, monocyclic carbocyclyl. In certain embodiments, $R^{B2}$ is substituted heterocyclyl. In certain embodiments, $R^{B2}$ is unsubstituted heterocyclyl. In certain embodiments, $R^{B2}$ is saturated heterocyclyl. In certain embodiments, $R^{B2}$ is unsaturated heterocyclyl. In certain embodiments, $R^{B2}$ is heterocyclyl, wherein one, two, or three atoms in the heterocyclic ring system are independently selected from the group consisting of nitrogen, oxygen, and sulfur. In certain embodiments, $R^{B2}$ is monocyclic heterocyclyl. In certain embodiments, $R^{B2}$ is 3- to 7-membered, monocyclic heterocyclyl. In certain embodiments, $R^{B2}$ is substituted aryl. In certain embodiments, $R^{B2}$ is unsubstituted aryl. In certain embodiments, $R^{B2}$ is 6- to 10-membered aryl. In certain embodiments, $R^{B2}$ is substituted phenyl. In certain embodiments, $R^{B2}$ is unsubstituted phenyl. In certain embodiments, $R^{B2}$ is substituted heteroaryl. In certain embodiments, $R^{B2}$ is unsubstituted heteroaryl. In certain embodiments, $R^{B2}$ is heteroaryl, wherein one, two, three, or four atoms in the heteroaryl ring system are independently selected from the group consisting of nitrogen, oxygen, and sulfur. In certain embodiments, $R^{B2}$ is monocyclic heteroaryl. In certain embodiments, $R^{B2}$ is 5-membered, monocyclic heteroaryl. In certain embodiments, $R^{B2}$ is 6-membered, monocyclic heteroaryl. In certain embodiments, $R^{B2}$ is bicyclic heteroaryl, wherein the point of attachment may be on any atom of the bicyclic heteroaryl ring system, as valency permits. In certain embodiments, $R^{B2}$ is 9- or 10-membered, bicyclic heteroaryl. In certain embodiments, $R^{B2}$ is a nitrogen protecting group. In certain embodiments, $R^{B2}$ is Bn, Boc, Cbz, Fmoc, trifluoroacetyl, triphenylmethyl, acetyl, or Ts.

In certain embodiments, $R^{B2}$ is a moiety of the formula:

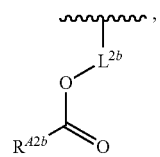

wherein $L^{2b}$ is substituted or unsubstituted alkylene or substituted or unsubstituted heteroalkylene, and $R^{A2b}$ is substituted or unsubstituted, $C_{4-30}$ alkyl, substituted or unsubstituted, $C_{4-30}$ alkenyl, or substituted or unsubstituted, $C_{4-30}$ alkynyl. In certain embodiments, $L^{2b}$ is substituted alkylene. In certain embodiments, $L^{2b}$ is a moiety shown in Table 2. In certain embodiments, $L^{2b}$ is unsubstituted alkylene. In certain embodiments, $L^{2b}$ is a moiety shown in Table 1. In certain embodiments, $L^{2b}$ is substituted $C_{1-6}$ alkylene. In certain embodiments, $L^{2b}$ is $C_{1-6}$ alkylene substituted with at least one halogen. In certain embodiments, $L^{2b}$ is $C_{1-6}$ alkylene substituted with at least one fluorine. In certain embodiments, $L^{2b}$ is $C_{1-6}$ perfluoroalkylene. In certain embodiments, $L^{2b}$ is unsubstituted $C_{1-6}$ alkylene. In certain embodiments, $L^{2b}$ is of the formula:

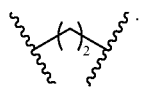

In certain embodiments, $L^{2b}$ is of the formula:

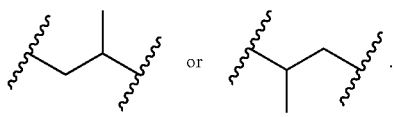

In certain embodiments, $L^{2b}$ is of the formula:

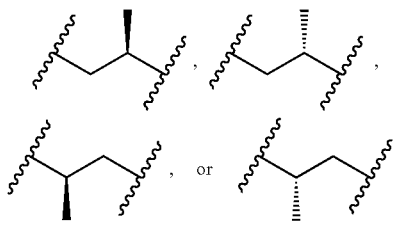

In certain embodiments, $L^{2b}$ is substituted heteroalkylene. In certain embodiments, $L^{2b}$ is unsubstituted heteroalkylene. In certain embodiments, $L^{2b}$ is a moiety shown in Table 3. In certain embodiments, $L^{2b}$ is substituted $C_{1-6}$ heteroalkylene. In certain embodiments, $L^{2b}$ is $C_{1-6}$ heteroalkylene substituted with at least one halogen. In certain embodiments, $L^{2b}$ is $C_{1-6}$ heteroalkylene substituted with at least one fluorine. In certain embodiments, $L^{2b}$ is unsubstituted $C_{1-6}$ heteroalkylene. In certain embodiments, $R^{A2b}$ is substituted $C_{4-30}$ alkyl. In certain embodiments, $R^{A2b}$ is a moiety shown in Table 5. In certain embodiments, $R^{A2b}$ is $C_{4-30}$ alkyl substituted with one or more halogen. In certain embodiments, $R^{A2b}$ is $C_{4-30}$ alkyl substituted with one or more fluorine. In certain embodiments, $R^{A2b}$ is $C_{4-30}$ perfluoroalkyl. In certain embodiments, $R^{A2b}$ is unsubstituted $C_{4-30}$ alkyl. In certain embodiments, $R^{A2b}$ is a moiety shown in Table 4. In certain embodiments, $R^{A2b}$ is unsubstituted and unbranched $C_{4-30}$ alkyl. In certain embodiments, $R^{A2b}$ is substituted $C_{7-24}$ alkyl. In certain embodiments, $R^{A2b}$ is $C_{7-24}$ alkyl substituted with one or more halogen. In certain embodiments, $R^{A2b}$ is $C_{7-24}$ alkyl substituted with one or more fluorine. In certain embodiments, $R^{A2b}$ is $C_{7-24}$ perfluoroalkyl. In certain embodiments, $R^{A2b}$ is unsubstituted $C_{7-24}$ alkyl. In certain embodiments, $R^{A2b}$ is unsubstituted and unbranched $C_{7-24}$ alkyl. In certain embodiments, $R^{A2b}$ is substituted $C_{9-19}$ alkyl. In certain embodiments, $R^{A2b}$ is $C_{9-19}$ alkyl substituted with one or more halogen. In certain embodiments, $R^{A2b}$ is $C_{9-19}$ alkyl substituted with one or more fluorine. In certain embodiments, $R^{A2b}$ is $C_{9-19}$ perfluoroalkyl. In certain embodiments, $R^{A2b}$ is unsubstituted $C_{9-19}$ alkyl. In certain embodiments, $R^{A2b}$ is unsubstituted and unbranched $C_{9-19}$ alkyl. In certain embodiments, $R^{A2b}$ is substituted $C_{4-30}$ alkenyl. In certain embodiments, $R^{A2b}$ is $C_{4-30}$ alkenyl substituted with one or more halogen. In certain embodiments, $R^{A2b}$ is $C_{4-30}$ alkenyl substituted with one or more fluorine. In certain embodiments, $R^{A2b}$ is $C_{4-30}$ perfluoroalkenyl. In certain embodiments, $R^{A2b}$ is unsubstituted $C_{4-30}$ alkenyl. In certain embodiments, $R^{A2b}$ is a moiety shown in Table 6. In certain embodiments, $R^{A2b}$ is unsubstituted and unbranched $C_{4-30}$ alkenyl. In certain embodiments, $R^{A2b}$ is substituted $C_{7-24}$ alkenyl. In certain embodiments, $R^{A2b}$ is $C_{7-24}$ alkenyl substituted with one or more halogen. In certain embodiments, $R^{A2b}$ is $C_{7-24}$ alkenyl substituted with one or more fluorine. In certain embodiments, $R^{A2b}$ is $C_{7-24}$ perfluoroalkenyl. In certain embodiments, $R^{A2b}$ is unsubstituted $C_{7-24}$ alkenyl. In certain embodiments, $R^{A2b}$ is unsubstituted and unbranched $C_{7-24}$ alkenyl. In certain embodiments, $R^{A2b}$ is substituted $C_{9-19}$ alkenyl. In certain embodiments, $R^{A2b}$ is $C_{9-19}$ alkenyl substituted with one or more halogen. In certain embodiments, $R^{A2b}$ is $C_{9-19}$ alkenyl substituted with one or more fluorine. In certain embodiments, $R^{A2b}$ is $C_{9-19}$ perfluoroalkenyl. In certain embodiments, $R^{A2b}$ is unsubstituted $C_{9-19}$ alkenyl. In certain embodiments, $R^{A2b}$ is unsubstituted and unbranched $C_{9-19}$ alkenyl. In certain embodiments, $R^{A2b}$ is substituted $C_{4-30}$ alkynyl. In certain embodiments, $R^{A2b}$ is $C_{4-30}$ alkynyl substituted with one or more halogen. In certain embodiments, $R^{A2b}$ is $C_{4-30}$ alkynyl substituted with one or more fluorine. In certain embodiments, $R^{A2b}$ is $C_{4-30}$ perfluoroalkynyl. In certain embodiments, $R^{A2b}$ is unsubstituted $C_{4-30}$ alkynyl. In certain embodiments, $R^{A2b}$ is unsubstituted and unbranched $C_{4-30}$ alkynyl. In certain embodiments, $R^{A2b}$ is substituted $C_{7-24}$ alkynyl. In certain embodiments, $R^{A2b}$ is $C_{7-24}$ alkynyl substituted with one or more halogen. In certain embodiments, $R^{A2b}$ is $C_{7-24}$ alkynyl substituted with one or more fluorine. In certain embodiments, $R^{A2b}$ is $C_{7-24}$ perfluoroalkynyl. In certain embodiments, $R^{A2b}$ is unsubstituted $C_{7-24}$ alkynyl. In certain embodiments, $R^{A2b}$ is unsubstituted and unbranched $C_{7-24}$ alkynyl. In certain embodiments, $R^{A2b}$ is substituted $C_{9-19}$ alkynyl. In certain embodiments, $R^{A2b}$ is $C_{9-19}$ alkynyl substituted with one or more halogen. In certain embodiments, $R^{A2b}$ is $C_{9-19}$ alkynyl substituted with one or more fluorine. In certain embodiments, $R^{A2b}$ is $C_{9-19}$ perfluoroalkynyl. In certain embodiments, $R^{A2b}$ is unsubstituted $C_{9-19}$ alkynyl. In certain embodiments, $R^{A2b}$ is unsubstituted and unbranched $C_{9-19}$ alkynyl.

In Formula (I), any two of $L^{1a}$, $L^{2a}$, $L^{1b}$, and $L^{2b}$ may be the same or different. In certain embodiments, $L^{1a}$ and $L^{2a}$ are the same. In certain embodiments, each of $L^{1a}$ and $L^{2a}$ is independently substituted or unsubstituted alkylene. In certain embodiments, each of $L^{1a}$ and $L^{2a}$ is of the formula:

In certain embodiments, each of $L^{1a}$ and $L^{2a}$ is of the formula:

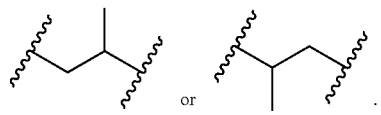

In certain embodiments, each of $L^{1a}$ and $L^{2a}$ is of the formula:

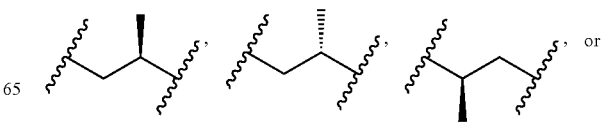

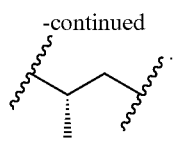

In certain embodiments, $L^{1a}$, $L^{2a}$, and $L^{1b}$ are the same. In certain embodiments, $L^{1a}$, $L^{2a}$, $L^{1b}$, and $L^{2b}$ are the same.

In Formula (I), any two of $R^{1a}$, $R^{A2a}$, $R^{1b}$, and $R^{A2b}$ may be the same or different. In certain embodiments, $R^{A1a}$ and $R^{A2a}$ are the same. In certain embodiments, at least one of $R^{A1a}$ and $R^{A2a}$ is substituted or unsubstituted, $C_{7-24}$ alkyl. In certain embodiments, at least one of $R^{A1a}$ and $R^{A2a}$ is substituted or unsubstituted, $C_{9-19}$ alkyl. In certain embodiments, at least one of $R^{A1a}$ and $R^{A2a}$ is substituted or unsubstituted, $C_{7-24}$ alkenyl. In certain embodiments, at least one of $R^{A1a}$ and $R^{A2a}$ is substituted or unsubstituted, $C_{9-19}$ alkenyl. In certain embodiments, $R^{A1a}$, $R^{A2a}$ and $R^{A1b}$ are the same. In certain embodiments, $R^{A1a}$, $R^{A2a}$, $R^{A1b}$, and $R^{A2b}$ are the same.

In certain embodiments, the compound of Formula (I) is of Formula (I-C):

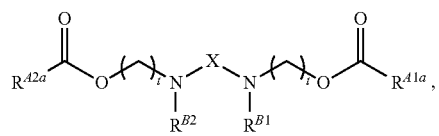

(I-C)

or a salt, hydrate, solvate, polymorph, tautomer, stereoisomer, and isotopically labeled derivative thereof, wherein each instance of t is 2, 3, 4, 5, or 6.

In certain embodiments, the compound of Formula (I) is of Formula (I-D):

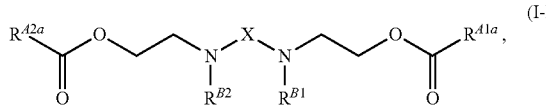

(I-D)

or a salt, hydrate, solvate, polymorph, tautomer, stereoisomer, and isotopically labeled derivative thereof.

In certain embodiments, the compound of Formula (I) is of Formula (I-E):

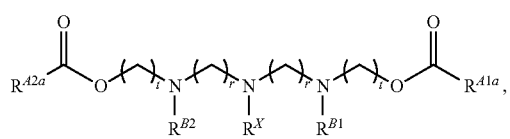

(I-E)

or a salt, hydrate, solvate, polymorph, tautomer, stereoisomer, and isotopically labeled derivative thereof, wherein each instance of t is 2, 3, 4, 5, or 6; and each instance of r is 2, 3, 4, 5, or 6.

In certain embodiments, the compound of Formula (I) is of Formula (I-F):

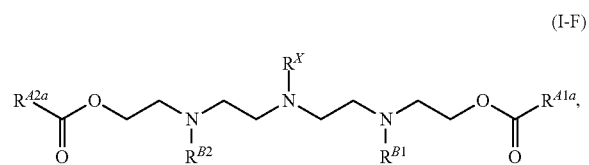

(I-F)

or a salt, hydrate, solvate, polymorph, tautomer, stereoisomer, and isotopically labeled derivative thereof.

In certain embodiments, the compound of Formula (I) is of Formula (I-G):

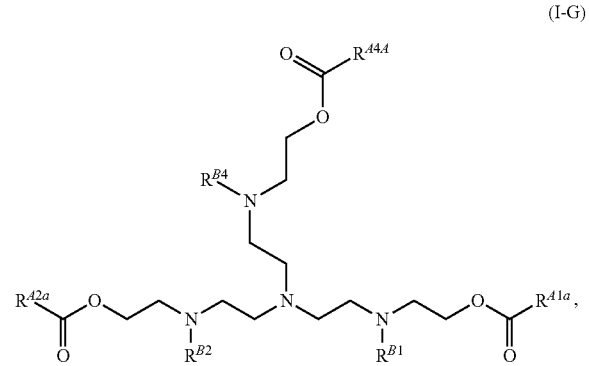

(I-G)

or a salt, hydrate, solvate, polymorph, tautomer, stereoisomer, and isotopically labeled derivative thereof, wherein:

$R^{B4}$ is substituted or unsubstituted $C_{1-6}$ alkyl; and $R^{A4a}$ is substituted or unsubstituted, $C_{4-30}$ alkyl, substituted or unsubstituted, $C_{4-30}$ alkenyl, or substituted or unsubstituted, $C_{4-30}$ alkynyl.

In certain embodiments, a compound of Formula (I) is a compound of any one of Formulae (I-C) to (I-G), wherein each of $R^{B1}$ and $R^{B2}$ is H or substituted or unsubstituted, $C_{1-6}$ alkyl (e.g., methyl).

In certain embodiments, the compound of Formula (I) is of Formula (I-A):

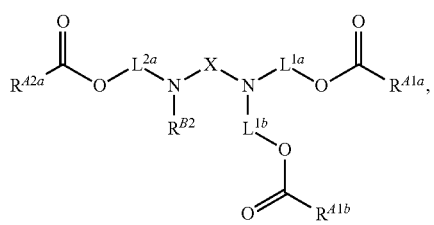

(I-A)

or a salt, hydrate, solvate, polymorph, tautomer, stereoisomer, and isotopically labeled derivative thereof.

In certain embodiments, the compound of Formula (I) is of Formula (I-H):

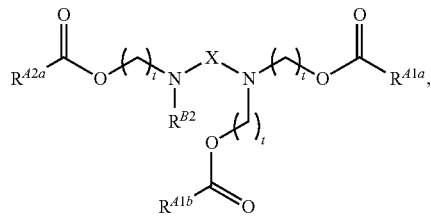

or a salt, hydrate, solvate, polymorph, tautomer, stereoisomer, and isotopically labeled derivative thereof, wherein each instance of t is 2, 3, 4, 5, or 6.

In certain embodiments, the compound of Formula (I) is of Formula (I-I):

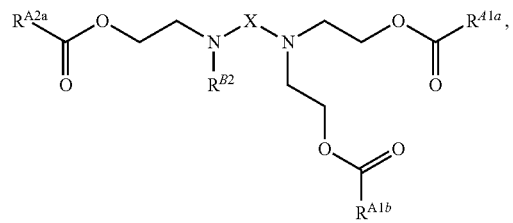

or a salt, hydrate, solvate, polymorph, tautomer, stereoisomer, and isotopically labeled derivative thereof.

In certain embodiments, the compound of Formula (I) is of Formula (I-J):

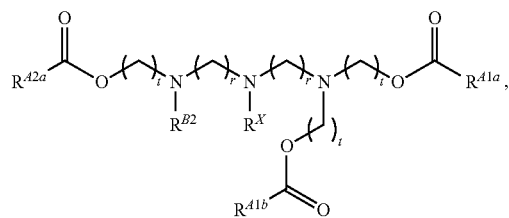

or a salt, hydrate, solvate, polymorph, tautomer, stereoisomer, and isotopically labeled derivative thereof, wherein each instance of t is 2, 3, 4, 5, or 6; and each instance of r is 2, 3, 4, 5, or 6.

In certain embodiments, the compound of Formula (I) is of Formula (I-K):

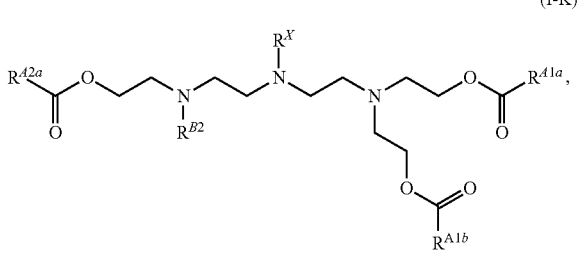

or a salt, hydrate, solvate, polymorph, tautomer, stereoisomer, and isotopically labeled derivative thereof.

In certain embodiments, the compound of Formula (I) is of Formula (I-L):

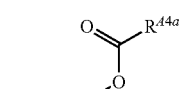

or a salt, hydrate, solvate, polymorph, tautomer, stereoisomer, and isotopically labeled derivative thereof, wherein:

$R^{B4}$ is substituted or unsubstituted $C_{1-6}$ alkyl; and $R^{A4a}$ is substituted or unsubstituted, $C_{4-30}$ alkyl, substituted or unsubstituted, $C_{4-30}$ alkenyl, or substituted or unsubstituted, $C_{4-30}$ alkynyl.

In certain embodiments, a compound of Formula (I) is a compound of any one of Formulae (I-A) and (I-H) to (I-L), wherein $R^{B2}$ is H or substituted or unsubstituted, $C_{1-6}$ alkyl (e.g., methyl).

In certain embodiments, the compound of Formula (I) is of Formula (I-B):

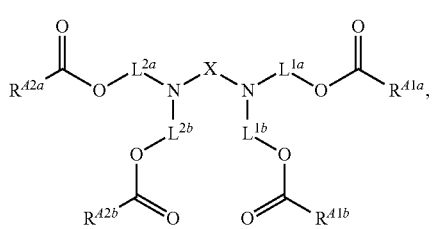

or a salt, hydrate, solvate, polymorph, tautomer, stereoisomer, and isotopically labeled derivative thereof.

In certain embodiments, the compound of Formula (I) is of the formula:

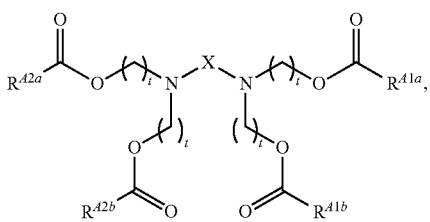

or a salt, hydrate, solvate, polymorph, tautomer, stereoisomer, and isotopically labeled derivative thereof, wherein each instance of t is 2, 3, 4, 5, or 6.

In certain embodiments, the compound of Formula (I) is of the formula:

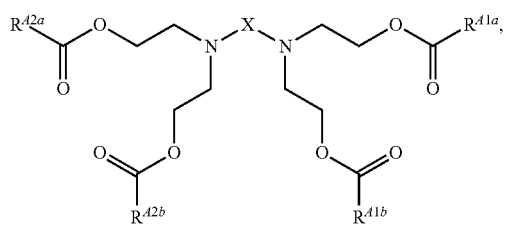

or a salt, hydrate, solvate, polymorph, tautomer, stereoisomer, and isotopically labeled derivative thereof.

In certain embodiments, the compound of Formula (I) is of the formula:

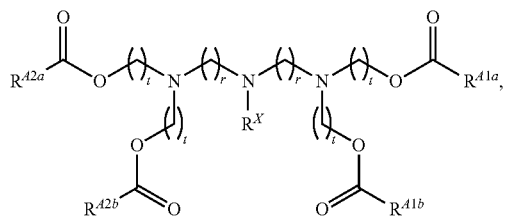

or a salt, hydrate, solvate, polymorph, tautomer, stereoisomer, and isotopically labeled derivative thereof, wherein each instance of t is 2, 3, 4, 5, or 6; and each instance of r is 2, 3, 4, 5, or 6.

In certain embodiments, the compound of Formula (I) is of the formula:

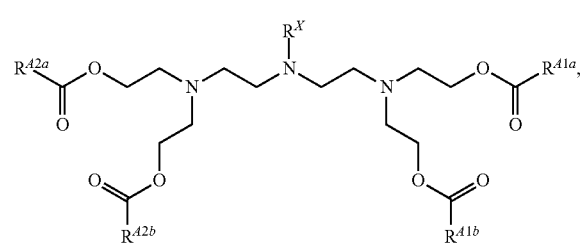

or a salt, hydrate, solvate, polymorph, tautomer, stereoisomer, and isotopically labeled derivative thereof.

In certain embodiments, the compound of Formula (I) is of the formula:

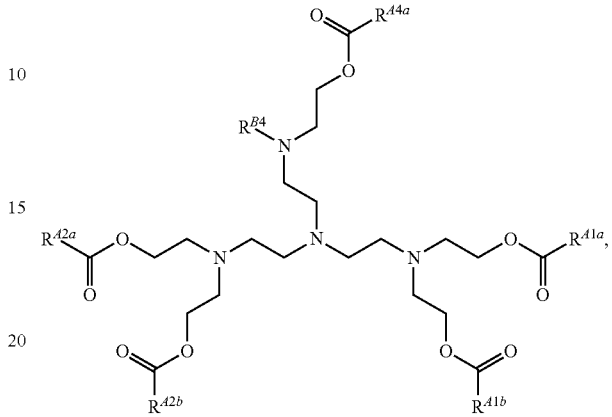

or a salt, hydrate, solvate, polymorph, tautomer, stereoisomer, and isotopically labeled derivative thereof, wherein:

$R^{B4}$ is substituted or unsubstituted $C_{1-6}$ alkyl; and $R^{A4a}$ is substituted or unsubstituted, $C_{4-30}$ alkyl, substituted or unsubstituted, $C_{4-30}$ alkenyl, or substituted or unsubstituted, $C_{4-30}$ alkynyl.

In certain embodiments, the compound of Formula (I) is of the formula:

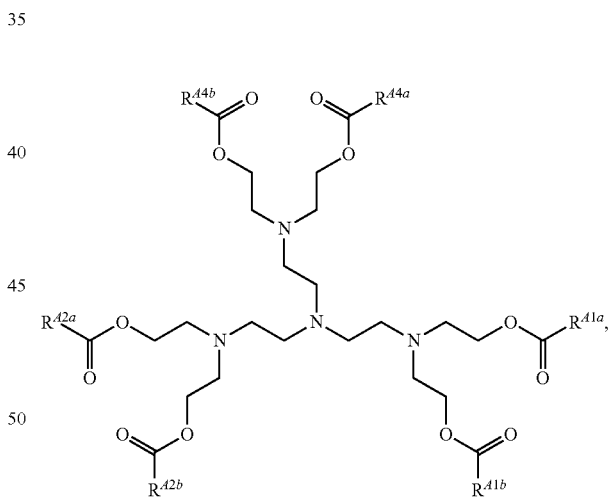

or a salt, hydrate, solvate, polymorph, tautomer, stereoisomer, and isotopically labeled derivative thereof, wherein:

$R^{A4a}$ is substituted or unsubstituted, $C_{4-30}$ alkyl, substituted or unsubstituted, $C_{4-30}$ alkenyl, or substituted or unsubstituted, $C_{4-30}$ alkynyl; and $R^{A4b}$ is substituted or unsubstituted, $C_{4-30}$ alkyl, substituted or unsubstituted, $C_{4-30}$ alkenyl, or substituted or unsubstituted, $C_{4-30}$ alkynyl.

Exemplary compounds of Formula (I) include, but are not limited to:

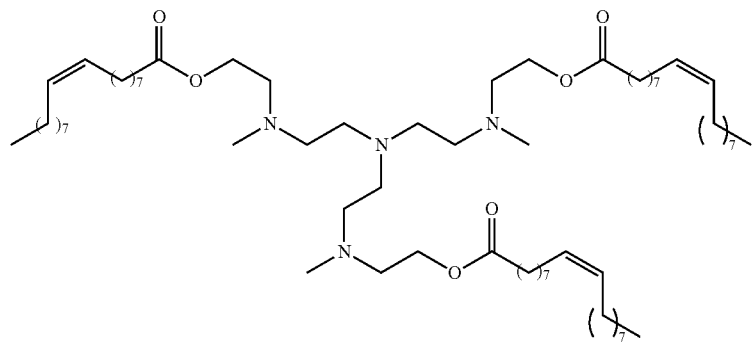
24C18Oleic
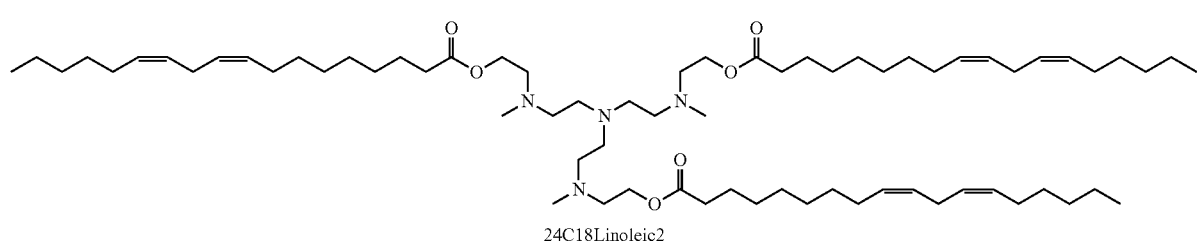
24C18Linoleic2
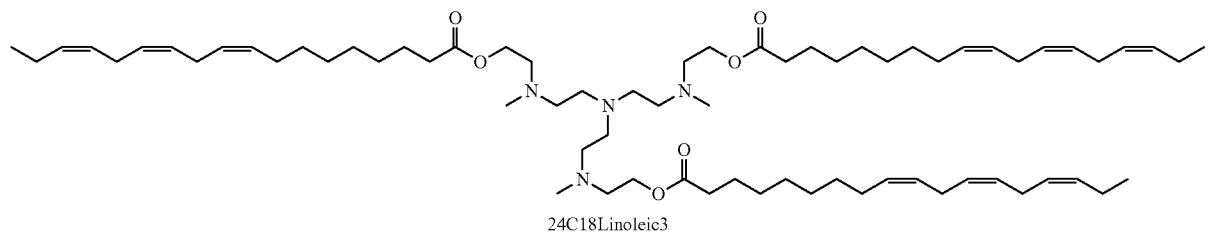
24C18Linoleic3
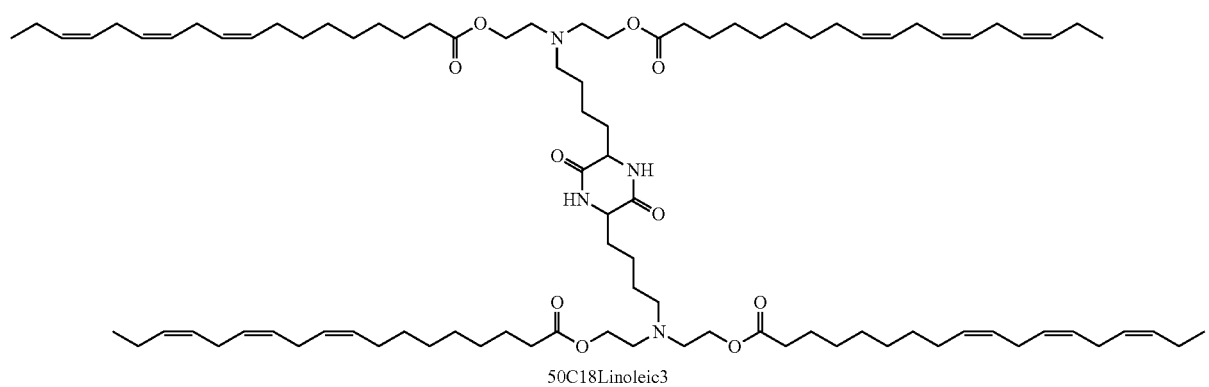
50C18Linoleic3
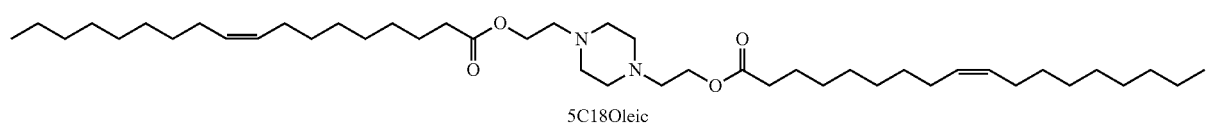
5C18Oleic
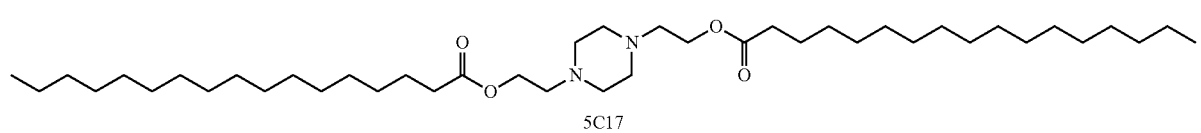
5C17
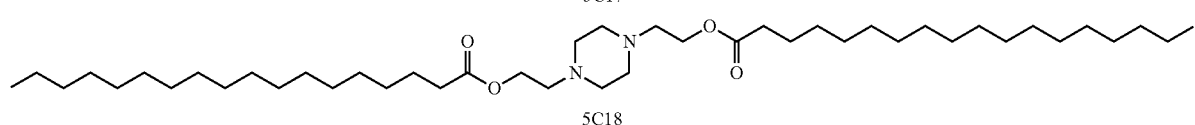
5C18

-continued
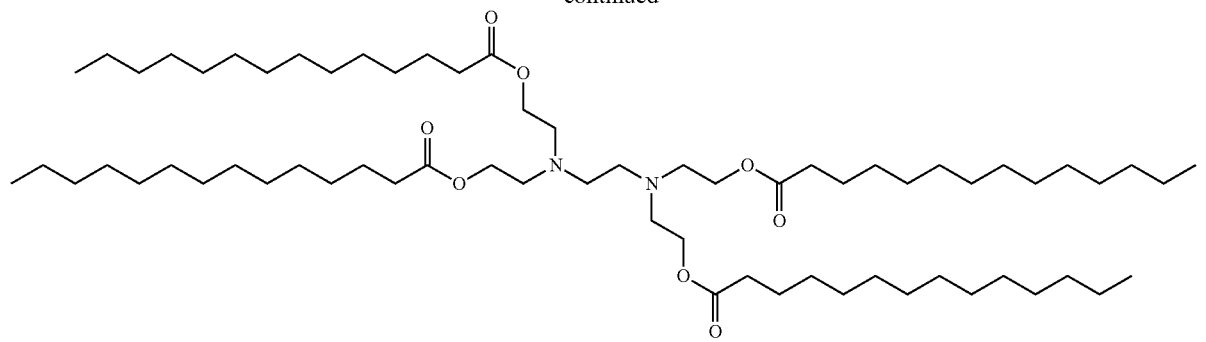
12C14
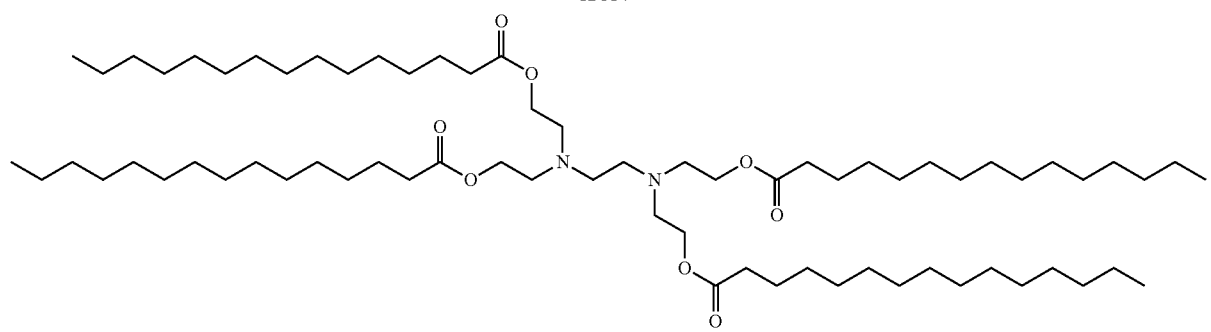
12C15
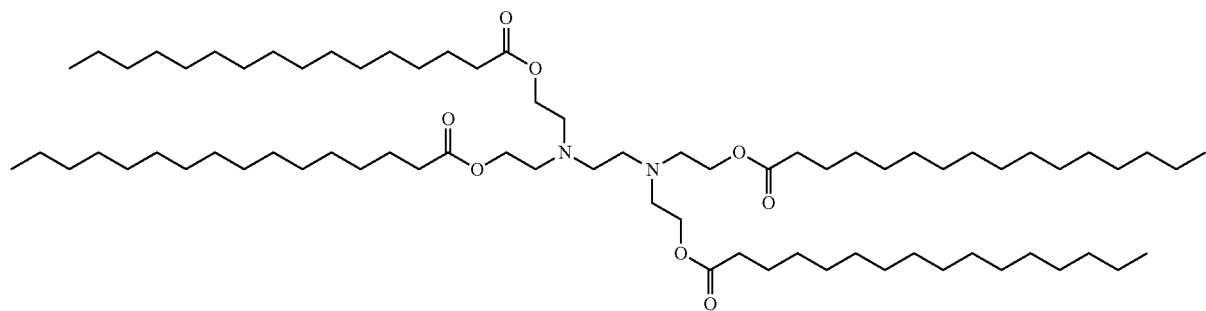
12C16
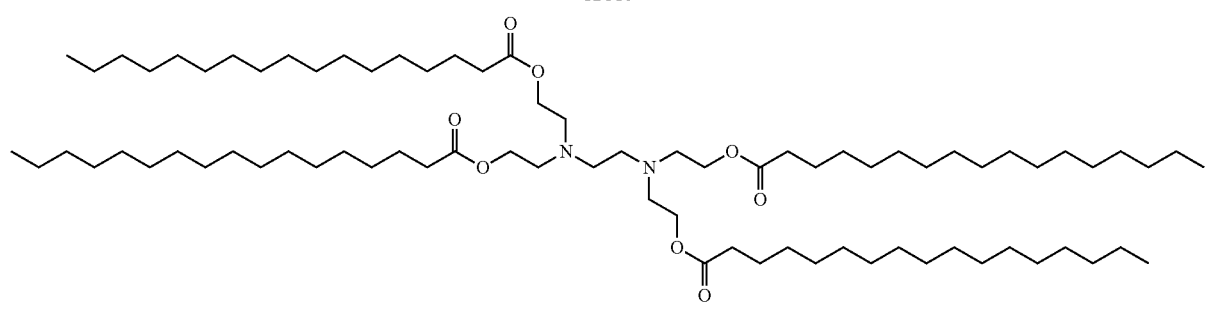
12C17
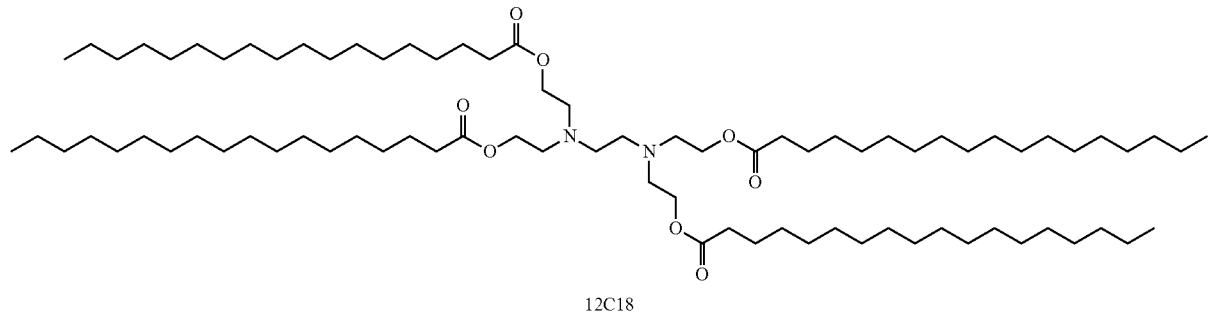
12C18

-continued

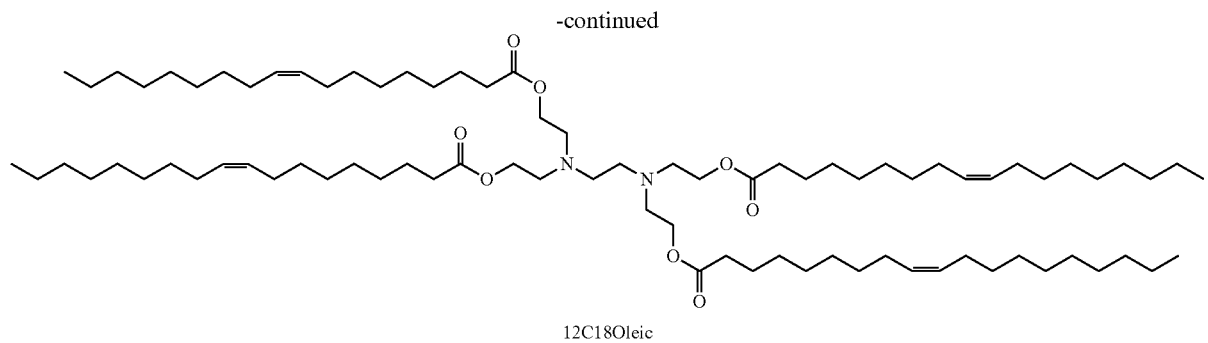

12C18Oleic and salts, hydrates, solvates, polymorphs, tautomers, stereoisomers, and isotopically labeled derivatives thereof.

In another aspect, the present disclosure provides compounds of Formula (II):

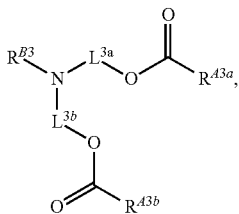
(II)

and salts, hydrates, solvates, polymorphs, tautomers, stereoisomers, and isotopically labeled derivatives thereof, wherein:

Formula (II) includes divalent linker $L^{3a}$. In certain embodiments, $L^{3a}$ is substituted alkylene. In certain embodiments, $L^{3a}$ is a moiety shown in Table 2. In certain embodiments, $L^{3a}$ is unsubstituted alkylene. In certain embodiments, $L^{3a}$ is a moiety shown in Table 1. In certain embodiments, $L^{3a}$ is substituted $C_{1-6}$ alkylene. In certain embodiments, $L^{3a}$ is $C_{1-6}$ alkylene substituted with at least one halogen. In certain embodiments, $L^{3a}$ is $C_{1-6}$ alkylene substituted with at least one fluorine. In certain embodiments, $L^{3a}$ is $C_{1-6}$ perfluoroalkylene. In certain embodiments, $L^{3a}$ is unsubstituted $C_{1-6}$ alkylene. In certain embodiments, $L^{3a}$ is of the formula:

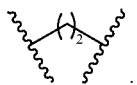

In certain embodiments, $L^{3a}$ is of the formula:

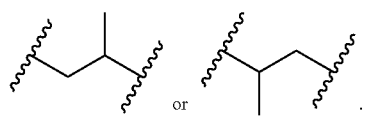

In certain embodiments, $L^{3a}$ is of the formula:

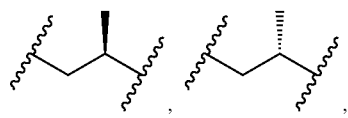

-continued

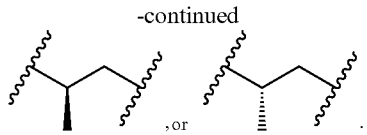
, or

In certain embodiments, $L^{3a}$ is substituted heteroalkylene. In certain embodiments, $L^{3a}$ is unsubstituted heteroalkylene. In certain embodiments, $L^{3a}$ is a moiety shown in Table 3. In certain embodiments, $L^{3a}$ is substituted $C_{1-6}$ heteroalkylene. In certain embodiments, $L^{3a}$ is $C_{1-6}$ heteroalkylene substituted with at least one halogen. In certain embodiments, $L^{3a}$ is $C_{1-6}$ heteroalkylene substituted with at least one fluorine. In certain embodiments, $L^{3a}$ is unsubstituted $C_{1-6}$ heteroalkylene.

Formula (II) includes substituent $R^{43a}$. In certain embodiments, $R^{43a}$ is substituted $C_{4-30}$ alkyl. In certain embodiments, $R^{43a}$ is a moiety shown in Table 5. In certain embodiments, $R^{43a}$ is $C_{4-30}$ alkyl substituted with one or more halogen. In certain embodiments, $R^{43a}$ is $C_{4-30}$ alkyl substituted with one or more fluorine. In certain embodiments, $R^{43a}$ is $C_{4-30}$ perfluoroalkyl. In certain embodiments, $R^{43a}$ is unsubstituted $C_{4-30}$ alkyl. In certain embodiments, $R^{43a}$ is a moiety shown in Table 4. In certain embodiments, $R^{43a}$ is unsubstituted and unbranched $C_{4-30}$ alkyl. In certain embodiments, $R^{43a}$ is substituted $C_{7-24}$ alkyl. In certain embodiments, $R^{43a}$ is $C_{7-24}$ alkyl substituted with one or more halogen. In certain embodiments, $R^{43a}$ is $C_{7-24}$ alkyl substituted with one or more fluorine. In certain embodiments, $R^{43a}$ is $C_{7-24}$ perfluoroalkyl. In certain embodiments, $R^{43a}$ is unsubstituted $C_{7-24}$ alkyl. In certain embodiments, $R^{43a}$ is unsubstituted and unbranched $C_{7-24}$ alkyl. In certain embodiments, $R^{43a}$ is substituted $C_{9-19}$ alkyl.

In certain embodiments, $R^{43a}$ is $C_{9-19}$ alkyl substituted with one or more halogen. In certain embodiments, $R^{43a}$ is $C_{9-19}$ alkyl substituted with one or more fluorine. In certain embodiments, $R^{43a}$ is $C_{9-19}$ perfluoroalkyl. In certain embodiments, $R^{43a}$ is unsubstituted $C_{9-19}$ alkyl. In certain embodiments, $R^{43a}$ is unsubstituted and unbranched $C_{9-19}$ alkyl.

In certain embodiments, $R^{43a}$ is substituted $C_{4-30}$ alkenyl. In certain embodiments, $R^{43a}$ is $C_{4-30}$ alkenyl substituted with one or more halogen. In certain embodiments, $R^{43a}$ is $C_{4-30}$ alkenyl substituted with one or more fluorine. In certain embodiments, $R^{43a}$ is $C_{4-30}$ perfluoroalkenyl. In certain embodiments, $R^{43a}$ is unsubstituted $C_{4-30}$ alkenyl. In certain embodiments, $R^{43a}$ is a moiety shown in Table 6. In certain embodiments, $R^{43a}$ is unsubstituted and unbranched $C_{4-30}$ alkenyl. In certain embodiments, $R^{43a}$ is substituted $C_{7-24}$ alkenyl. In certain embodiments, $R^{43a}$ is $C_{7-24}$ alkenyl substituted with one or more halogen. In certain embodiments, $R^{43a}$ is $C_{7-24}$ alkenyl substituted with one or more fluorine. In certain embodiments, $R^{43a}$ is $C_{7-24}$ perfluoroalkenyl. In certain embodiments, $R^{43a}$ is unsubstituted $C_{7-24}$ alkenyl. In certain embodiments, $R^{A3a}$ is unsubstituted and unbranched $C_{7-24}$ alkenyl. In certain embodiments, $R^{A3a}$ is substituted $C_{9-19}$ alkenyl. In certain embodiments, $R^{A3a}$ is $C_{9-19}$ alkenyl substituted with one or more halogen. In certain embodiments, $R^{A3a}$ is $C_{9-19}$ alkenyl substituted with one or more fluorine. In certain embodiments, $R^{A3a}$ is $C_{9-19}$ perfluoroalkenyl. In certain embodiments, $R^{A3a}$ is unsubstituted $C_{9-19}$ alkenyl. In certain embodiments, $R^{A3a}$ is unsubstituted and unbranched $C_{9-19}$ alkenyl. In certain embodiments, $R^{A3a}$ is alkenyl described herein and includes one, two, three, four, five, or six C=C double bonds.

In certain embodiments, $R^{A3a}$ is substituted $C_{4-30}$ alkynyl. In certain embodiments, $R^{A3a}$ is $C_{4-30}$ alkynyl substituted with one or more halogen. In certain embodiments, $R^{A3a}$ is $C_{4-30}$ alkynyl substituted with one or more fluorine. In certain embodiments, $R^{A3a}$ is $C_{4-30}$ perfluoroalkynyl. In certain embodiments, $R^{A3a}$ is unsubstituted $C_{4-30}$ alkynyl. In certain embodiments, $R^{A3a}$ is unsubstituted and unbranched $C_{4-30}$ alkynyl. In certain embodiments, $R^{A3a}$ is substituted $C_{7-24}$ alkynyl. In certain embodiments, $R^{A3a}$ is $C_{7-24}$ alkynyl substituted with one or more halogen. In certain embodiments, $R^{A3a}$ is $C_{7-24}$ alkynyl substituted with one or more fluorine. In certain embodiments, $R^{A3a}$ is $C_{7-24}$ perfluoroalkynyl. In certain embodiments, $R^{A3a}$ is unsubstituted $C_{7-24}$ alkynyl. In certain embodiments, $R^{A3a}$ is unsubstituted and unbranched $C_{7-24}$ alkynyl. In certain embodiments, $R^{A3a}$ is substituted $C_{9-19}$ alkynyl. In certain embodiments, $R^{A3a}$ is $C_{9-19}$ alkynyl substituted with one or more halogen. In certain embodiments, $R^{A3a}$ is $C_{9-19}$ alkynyl substituted with one or more fluorine. In certain embodiments, $R^{A3a}$ is $C_{9-19}$ perfluoroalkynyl. In certain embodiments, $R^{A3a}$ is unsubstituted $C_{9-19}$ alkynyl. In certain embodiments, $R^{A3a}$ is unsubstituted and unbranched $C_{9-19}$ alkynyl.

Formula (II) includes divalent linker $L^{3b}$. In certain embodiments, $L^{3b}$ is substituted alkylene. In certain embodiments, $L^{3b}$ is a moiety shown in Table 2. In certain embodiments, $L^{3b}$ is unsubstituted alkylene. In certain embodiments, $L^{3b}$ is a moiety shown in Table 1. In certain embodiments, $L^{3b}$ is substituted $C_{1-6}$ alkylene. In certain embodiments, $L^{3b}$ is $C_{1-6}$ alkylene substituted with at least one halogen. In certain embodiments, $L^{3b}$ is $C_{1-6}$ alkylene substituted with at least one fluorine. In certain embodiments, $L^{3b}$ is $C_{1-6}$ perfluoroalkylene. In certain embodiments, $L^{3b}$ is unsubstituted $C_{1-6}$ alkylene. In certain embodiments, $L^{3b}$ is of the formula:

In certain embodiments, $L^{3b}$ is of the formula:

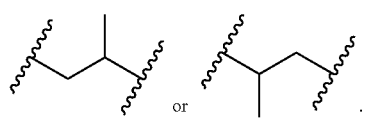

In certain embodiments, $L^{3b}$ is of the formula:

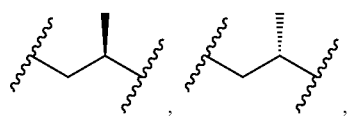

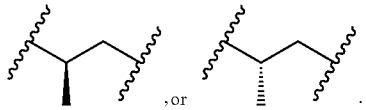

In certain embodiments, $L^{3b}$ is substituted heteroalkylene. In certain embodiments, $L^{3b}$ is unsubstituted heteroalkylene. In certain embodiments, $L^{3b}$ is a moiety shown in Table 3. In certain embodiments, $L^{3b}$ is substituted $C_{1-6}$ heteroalkylene. In certain embodiments, $L^{3b}$ is $C_{1-6}$ heteroalkylene substituted with at least one halogen. In certain embodiments, $L^{3b}$ is $C_{1-6}$ heteroalkylene substituted with at least one fluorine. In certain embodiments, $L^{3b}$ is unsubstituted $C_{1-6}$ heteroalkylene.

Formula (II) includes substituent $R^{A3b}$. In certain embodiments, $R^{A3b}$ is substituted $C_{4-30}$ alkyl. In certain embodiments, $R^{A3b}$ is a moiety shown in Table 5. In certain embodiments, $R^{A3b}$ is $C_{4-30}$ alkyl substituted with one or more halogen. In certain embodiments, $R^{A3b}$ is $C_{4-30}$ alkyl substituted with one or more fluorine. In certain embodiments, $R^{A3b}$ is $C_{4-30}$ perfluoroalkyl. In certain embodiments, $R^{A3b}$ is unsubstituted $C_{4-30}$ alkyl. In certain embodiments, $R^{A3b}$ is a moiety shown in Table 4. In certain embodiments, $R^{3b}$ is unsubstituted and unbranched $C_{4-30}$ alkyl. In certain embodiments, $R^{A3b}$ is substituted $C_{7-24}$ alkyl. In certain embodiments, $R^{A3b}$ is $C_{7-24}$ alkyl substituted with one or more halogen. In certain embodiments, $R^{A3b}$ is $C_{7-24}$ alkyl substituted with one or more fluorine. In certain embodiments, $R^{A3b}$ is $C_{7-24}$ perfluoroalkyl. In certain embodiments, $R^{A3b}$ is unsubstituted $C_{7-24}$ alkyl. In certain embodiments, $R^{A3b}$ is unsubstituted and unbranched $C_{7-24}$ alkyl. In certain embodiments, $R^{A3b}$ is substituted $C_{9-19}$ alkyl. In certain embodiments, $R^{A3b}$ is $C_{9-19}$ alkyl substituted with one or more halogen. In certain embodiments, $R^{A3b}$ is $C_{9-19}$ alkyl substituted with one or more fluorine. In certain embodiments, $R^{A3b}$ is $C_{9-19}$ perfluoroalkyl. In certain embodiments, $R^{A3b}$ is unsubstituted $C_{9-19}$ alkyl. In certain embodiments, $R^{A3b}$ is unsubstituted and unbranched $C_{9-19}$ alkyl.

In certain embodiments, $R^{A3b}$ is substituted $C_{4-30}$ alkenyl. In certain embodiments, $R^{A3b}$ is $C_{4-30}$ alkenyl substituted with one or more halogen. In certain embodiments, $R^{A3b}$ is $C_{4-30}$ alkenyl substituted with one or more fluorine. In certain embodiments, $R^{A3b}$ is $C_{4-30}$ perfluoroalkenyl. In certain embodiments, $R^{A3b}$ is unsubstituted $C_{4-30}$ alkenyl. In certain embodiments, $R^{A3b}$ is a moiety shown in Table 6. In certain embodiments, $R^{A3b}$ is unsubstituted and unbranched $C_{4-30}$ alkenyl. In certain embodiments, $R^{A3b}$ is substituted $C_{7-24}$ alkenyl. In certain embodiments, $R^{A3b}$ is $C_{7-24}$ alkenyl substituted with one or more halogen. In certain embodiments, $R^{3b}$ is $C_{7-24}$ alkenyl substituted with one or more fluorine. In certain embodiments, $R^{A3b}$ is $C_{7-24}$ perfluoroalkenyl. In certain embodiments, $R^{A3b}$ is unsubstituted $C_{7-24}$ alkenyl. In certain embodiments, $R^{A3b}$ is unsubstituted and unbranched $C_{7-24}$ alkenyl. In certain embodiments, $R^{A3b}$ is substituted $C_{9-19}$ alkenyl. In certain embodiments, $R^{A3b}$ is $C_{9-19}$ alkenyl substituted with one or more halogen. In certain embodiments, $R^{A3b}$ is $C_{9-19}$ alkenyl substituted with one or more fluorine. In certain embodiments, $R^{A3b}$ is $C_{9-19}$ perfluoroalkenyl. In certain embodiments, $R^{A3b}$ is unsubstituted $C_{9-19}$ alkenyl. In certain embodiments, $R^{A3b}$ is unsubstituted and unbranched $C_{9-19}$ alkenyl. In certain embodiments, $R^{A3b}$ is alkenyl described herein and includes one, two, three, four, five, or six C=C double bonds.

In certain embodiments, $R^{A3b}$ is substituted $C_{4-30}$ alkynyl. In certain embodiments, $R^{A3b}$ is $C_{4-30}$ alkynyl substituted with one or more halogen. In certain embodiments, $R^{A3b}$ is $C_{4-30}$ alkynyl substituted with one or more fluorine. In certain embodiments, $R^{A3b}$ is $C_{4-30}$ perfluoroalkynyl. In certain embodiments, $R^{A3b}$ is unsubstituted $C_{4-30}$ alkynyl. In certain embodiments, $R^{3b}$ is unsubstituted and unbranched $C_{4-30}$ alkynyl. In certain embodiments, $R^{3b}$ is substituted $C_{7-24}$ alkynyl. In certain embodiments, $R^{A3b}$ is $C_{7-24}$ alkynyl substituted with one or more halogen. In certain embodiments, $R^{A3b}$ is $C_{7-24}$ alkynyl substituted with one or more fluorine. In certain embodiments, $R^{A3b}$ is $C_{7-24}$ perfluoroalkynyl. In certain embodiments, $R^{A3b}$ is unsubstituted $C_{7-24}$ alkynyl. In certain embodiments, $R^{A3b}$ is unsubstituted and unbranched $C_{7-24}$ alkynyl. In certain embodiments, $R^{A3b}$ is substituted $C_{9-19}$ alkynyl. In certain embodiments, $R^{A3b}$ is $C_{9-19}$ alkynyl substituted with one or more halogen. In certain embodiments, $R^{A3b}$ is $C_{9-19}$ alkynyl substituted with one or more fluorine. In certain embodiments, $R^{A3b}$ is $C_{9-19}$ perfluoroalkynyl. In certain embodiments, $R^{A3b}$ is unsubstituted $C_{9-19}$ alkynyl. In certain embodiments, $R^{A3b}$ is unsubstituted and unbranched $C_{9-19}$ alkynyl.

Formula (I) includes substituent $R^{B3}$. In certain embodiments, $R^{B3}$ is H. In certain embodiments, $R^{B3}$ is substituted acyl. In certain embodiments, $R^{B3}$ is unsubstituted acyl. In certain embodiments, $R^{B3}$ is acetyl. In certain embodiments, $R^{B3}$ is substituted alkyl. In certain embodiments, $R^{B3}$ is unsubstituted alkyl. In certain embodiments, $R^{B3}$ is substituted $C_{1-6}$ alkyl. In certain embodiments, $R^{B3}$ is unsubstituted $C_{1-6}$ alkyl. In certain embodiments, $R^{B3}$ is $C_{1-6}$ alkyl substituted with at least one halogen. In certain embodiments, $R^{B3}$ is substituted methyl. In certain embodiments, $R^{B3}$ is —CH$_2$F, —CHF$_2$, or —CF$_3$. In certain embodiments, $R^{B3}$ is —CH$_3$. In certain embodiments, $R^{B3}$ is ethyl. In certain embodiments, $R^{B3}$ is propyl. In certain embodiments, $R^{B3}$ is butyl. In certain embodiments, $R^{B3}$ is pentyl. In certain embodiments, $R^{B3}$ is hexyl. In certain embodiments, $R^{B3}$ is substituted alkenyl. In certain embodiments, $R^{B3}$ is unsubstituted alkenyl. In certain embodiments, $R^{B3}$ is substituted $C_{1-6}$ alkenyl. In certain embodiments, $R^{B3}$ is unsubstituted $C_{1-6}$ alkenyl. In certain embodiments, $R^{B3}$ is vinyl. In certain embodiments, $R^{B3}$ is substituted alkynyl. In certain embodiments, $R^{B3}$ is unsubstituted alkynyl. In certain embodiments, $R^{B3}$ is substituted $C_{1-6}$ alkynyl. In certain embodiments, $R^{B3}$ is unsubstituted $C_{1-6}$ alkynyl. In certain embodiments, $R^{B3}$ is substituted carbocyclyl. In certain embodiments, $R^{B3}$ is unsubstituted carbocyclyl. In certain embodiments, $R^{B3}$ is saturated carbocyclyl. In certain embodiments, $R^{B3}$ is unsaturated carbocyclyl. In certain embodiments, $R^{B3}$ is monocyclic carbocyclyl. In certain embodiments, $R^{B3}$ is 3- to 7-membered, monocyclic carbocyclyl. In certain embodiments, $R^{B3}$ is substituted heterocyclyl. In certain embodiments, $R^{B3}$ is unsubstituted heterocyclyl. In certain embodiments, $R^{B3}$ is saturated heterocyclyl. In certain embodiments, $R^{B3}$ is unsaturated heterocyclyl. In certain embodiments, $R^{B3}$ is heterocyclyl, wherein one, two, or three atoms in the heterocyclic ring system are independently selected from the group consisting of nitrogen, oxygen, and sulfur. In certain embodiments, $R^{B3}$ is monocyclic heterocyclyl. In certain embodiments, $R^{B3}$ is 3- to 7-membered, monocyclic heterocyclyl. In certain embodiments, $R^{B3}$ is substituted aryl. In certain embodiments, $R^{B3}$ is unsubstituted aryl. In certain embodiments, $R^{B3}$ is 6- to 10-membered aryl. In certain embodiments, $R^{B3}$ is substituted phenyl. In certain embodiments, $R^{B3}$ is unsubstituted phenyl. In certain embodiments, $R^{B3}$ is substituted heteroaryl. In certain embodiments, $R^{B3}$ is unsubstituted heteroaryl. In certain embodiments, $R^{B3}$ is heteroaryl, wherein one, two, three, or four atoms in the heteroaryl ring system are independently selected from the group consisting of nitrogen, oxygen, and sulfur. In certain embodiments, $R^{B3}$ is monocyclic heteroaryl. In certain embodiments, $R^{B3}$ is 5-membered, monocyclic heteroaryl. In certain embodiments, $R^{B3}$ is 6-membered, monocyclic heteroaryl. In certain embodiments, $R^{B3}$ is bicyclic heteroaryl, wherein the point of attachment may be on any atom of the bicyclic heteroaryl ring system, as valency permits. In certain embodiments, $R^{B3}$ is 9- or 10-membered, bicyclic heteroaryl. In certain embodiments, $R^{B3}$ is a nitrogen protecting group. In certain embodiments, $R^{B3}$ is Bn, Boc, Cbz, Fmoc, trifluoroacetyl, triphenylmethyl, acetyl, or Ts.

In certain embodiments, $R^{B3}$ is a moiety of the formula:

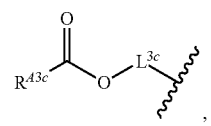

wherein $L^{3c}$ is substituted or unsubstituted alkylene or substituted or unsubstituted heteroalkylene, and $R^{3c}$ is substituted or unsubstituted, $C_{4-30}$ alkyl, substituted or unsubstituted, $C_{4-30}$ alkenyl, or substituted or unsubstituted, $C_{4-30}$ alkynyl. In certain embodiments, $L^{3c}$ is substituted alkylene. In certain embodiments, $L^{3c}$ is a moiety shown in Table 2. In certain embodiments, $L^{3c}$ is unsubstituted alkylene. In certain embodiments, $L^{3c}$ is a moiety shown in Table 1. In certain embodiments, $L^{3c}$ is substituted $C_{1-6}$ alkylene. In certain embodiments, $L^{3c}$ is $C_{1-6}$ alkylene substituted with at least one halogen. In certain embodiments, $L^{3c}$ is $C_{1-6}$ alkylene substituted with at least one fluorine. In certain embodiments, $L^{3c}$ is $C_{1-6}$ perfluoroalkylene. In certain embodiments, $L^{3c}$ is unsubstituted $C_{1-6}$ alkylene. In certain embodiments, $L^{3c}$ is of the formula:

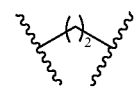

In certain embodiments, $L^{3c}$ is of the formula:

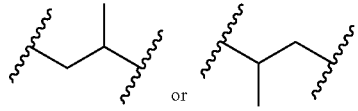

In certain embodiments, $L^{3c}$ is of the formula:

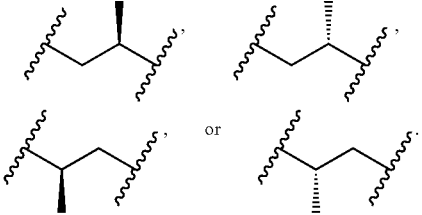

In certain embodiments, $L^{3c}$ is substituted heteroalkylene. In certain embodiments, $L^{3c}$ is unsubstituted heteroalkylene. In certain embodiments, $L^{3c}$ is a moiety shown in Table 3. In certain embodiments, $L^{3c}$ is substituted $C_{1-6}$ heteroalkylene. In certain embodiments, $L^{3c}$ is $C_{1-6}$ heteroalkylene substituted with at least one halogen. In certain embodiments, $L^{3c}$ is $C_{1-6}$ heteroalkylene substituted with at least one fluorine. In certain embodiments, $L^{3c}$ is unsubstituted $C_{1-6}$ heteroalkylene. In certain embodiments, $R^{A3c}$ is substituted C$_{4-30}$ alkyl. In certain embodiments, R$^{A3c}$ is a moiety shown in Table 5. In certain embodiments, R$^{A3c}$ is C$_{4-30}$ alkyl substituted with one or more halogen. In certain embodiments, R$^{A3c}$ is C$_{4-30}$ alkyl substituted with one or more fluorine. In certain embodiments, R$^{A3c}$ is C$_{4-30}$ perfluoroalkyl. In certain embodiments, R$^{A3c}$ is unsubstituted C$_{4-30}$ alkyl. In certain embodiments, R$^{A3c}$ is a moiety shown in Table 4. In certain embodiments, R$^{A3c}$ is unsubstituted and unbranched C$_{4-30}$ alkyl. In certain embodiments, R$^{3c}$ is substituted C$_{7-24}$ alkyl. In certain embodiments, R$^{A3c}$ is C$_{7-24}$ alkyl substituted with one or more halogen. In certain embodiments, R$^{A3c}$ is C$_{7-24}$ alkyl substituted with one or more fluorine. In certain embodiments, R$^{A3c}$ is C$_{7-24}$ perfluoroalkyl. In certain embodiments, R$^{A3c}$ is unsubstituted C$_{7-24}$ alkyl. In certain embodiments, R$^{A3c}$ is unsubstituted and unbranched C$_{7-24}$ alkyl. In certain embodiments, R$^{A3c}$ is substituted C$_{9-19}$ alkyl. In certain embodiments, R$^{A3c}$ is C$_{9-19}$ alkyl substituted with one or more halogen. In certain embodiments, R$^{A3c}$ is C$_{9-19}$ alkyl substituted with one or more fluorine. In certain embodiments, R$^{A3c}$ is C$_{9-19}$ perfluoroalkyl. In certain embodiments, R$^{A3c}$ is unsubstituted C$_{9-19}$ alkyl. In certain embodiments, R$^{A3c}$ is unsubstituted and unbranched C$_{9-19}$ alkyl.

In certain embodiments, R$^{3c}$ is substituted C$_{4-30}$ alkenyl. In certain embodiments, R$^{A3c}$ is C$_{4-30}$ alkenyl substituted with one or more halogen. In certain embodiments, R$^{A3c}$ is C$_{4-30}$ alkenyl substituted with one or more fluorine. In certain embodiments, R$^{A3c}$ is C$_{4-30}$ perfluoroalkenyl. In certain embodiments, R$^{A3c}$ is unsubstituted C$_{4-30}$ alkenyl. In certain embodiments, R$^{A3c}$ is a moiety shown in Table 6. In certain embodiments, R$^{A3c}$ is unsubstituted and unbranched C$_{4-30}$ alkenyl. In certain embodiments, R$^{A3c}$ is substituted C$_{7-24}$ alkenyl. In certain embodiments, R$^{A3c}$ is C$_{7-24}$ alkenyl substituted with one or more halogen. In certain embodiments, R$^{A3c}$ is C$_{7-24}$ alkenyl substituted with one or more fluorine. In certain embodiments, R$^{A3c}$ is C$_{7-24}$ perfluoroalkenyl. In certain embodiments, R$^{A3c}$ is unsubstituted C$_{7-24}$ alkenyl. In certain embodiments, R$^{A3c}$ is unsubstituted and unbranched C$_{7-24}$ alkenyl. In certain embodiments, R$^{A3c}$ is substituted C$_{9-19}$ alkenyl. In certain embodiments, R$^{A3c}$ is C$_{9-19}$ alkenyl substituted with one or more halogen. In certain embodiments, R$^{A3c}$ is C$_{9-19}$ alkenyl substituted with one or more fluorine. In certain embodiments, R$^{A3c}$ is C$_{9-19}$ perfluoroalkenyl. In certain embodiments, R$^{A3c}$ is unsubstituted C$_{9-19}$ alkenyl. In certain embodiments, R$^{A3c}$ is unsubstituted and unbranched C$_{9-19}$ alkenyl. In certain embodiments, R$^{A3c}$ is alkenyl described herein and includes one, two, three, four, five, or six C=C double bonds.

In certain embodiments, R$^{3c}$ is substituted C$_{4-30}$ alkynyl. In certain embodiments, R$^{A3c}$ is C$_{4-30}$ alkynyl substituted with one or more halogen. In certain embodiments, R$^{A3c}$ is C$_{4-30}$ alkynyl substituted with one or more fluorine. In certain embodiments, R$^{A3c}$ is C$_{4-30}$ perfluoroalkynyl. In certain embodiments, R$^{A3c}$ is unsubstituted C$_{4-30}$ alkynyl. In certain embodiments, R$^{A3c}$ is unsubstituted and unbranched C$_{4-30}$ alkynyl. In certain embodiments, R$^{A3c}$ is substituted C$_{7-24}$ alkynyl. In certain embodiments, R$^{A3c}$ is C$_{7-24}$ alkynyl substituted with one or more halogen. In certain embodiments, R$^{A3c}$ is C$_{7-24}$ alkynyl substituted with one or more fluorine. In certain embodiments, R$^{A3c}$ is C$_{7-24}$ perfluoroalkynyl. In certain embodiments, R$^{A3c}$ is unsubstituted C$_{7-24}$ alkynyl. In certain embodiments, R$^{A3c}$ is unsubstituted and unbranched C$_{7-24}$ alkynyl. In certain embodiments, R$^{3c}$ is substituted C$_{9-19}$ alkynyl. In certain embodiments, R$^{A3c}$ is C$_{9-19}$ alkynyl substituted with one or more halogen. In certain embodiments, R$^{A3c}$ is C$_{9-19}$ alkynyl substituted with one or more fluorine. In certain embodiments, R$^{A3c}$ is C$_{9-19}$ perfluoroalkynyl. In certain embodiments, R$^{A3c}$ is unsubstituted C$_{9-19}$ alkynyl. In certain embodiments, R$^{A3c}$ is unsubstituted and unbranched C$_{9-19}$ alkynyl.

In Formula (II), any two of L$^{3a}$, L$^{3b}$, and L$^{3c}$ may be the same or different. In certain embodiments, L$^{3a}$ and L$^{3b}$ are the same. In certain embodiments, each of L$^{3a}$ and L$^{3b}$ is independently substituted or unsubstituted alkylene. In certain embodiments, each of L$^{3a}$ and L$^{3b}$ is of the formula:

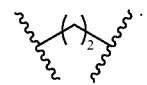

In certain embodiments, each of L$^{3a}$ and L$^{3b}$ is of the formula:

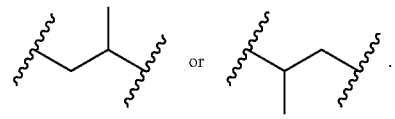

In certain embodiments, each of L$^{3a}$ and L$^{3b}$ is of the formula:

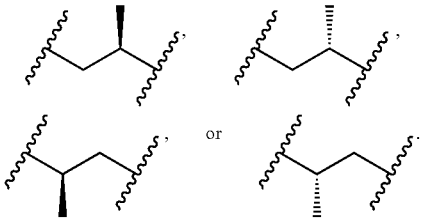

In certain embodiments, L$^{3a}$, L$^{3b}$, and L$^{3c}$ are the same.

In Formula (II), any two of R$^{A3a}$, R$^{A3b}$, and R$^{A3c}$ may be the same or different. In certain embodiments, R$^{A3a}$ and R$^{A3b}$ are the same. In certain embodiments, at least one of R$^{A3a}$ and R$^{A3b}$ is substituted or unsubstituted, C$_{7-24}$ alkyl. In certain embodiments, at least one of R$^{A3a}$ and R$^{A3b}$ is substituted or unsubstituted, C$_{9-19}$ alkyl. In certain embodiments, at least one of R$^{A3a}$ and R$^{A3b}$ is substituted or unsubstituted, C$_{7-24}$ alkenyl. In certain embodiments, at least one of R$^{A3a}$ and R$^{A3b}$ is substituted or unsubstituted, C$_{9-19}$ alkenyl. In certain embodiments, R$^{A3a}$, R$^{A3b}$ and R$^{A3c}$ are the same.

In certain embodiments, the compound of Formula (II) is of formula:

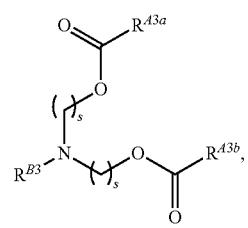

or a salt, hydrate, solvate, polymorph, tautomer, stereoisomer, and isotopically labeled derivative thereof, wherein each instance of s is 2, 3, 4, 5, or 6.

In certain embodiments, the compound of Formula (II) is of the formula:

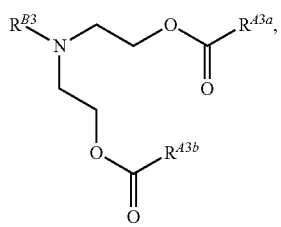

or a salt, hydrate, solvate, polymorph, tautomer, stereoisomer, and isotopically labeled derivative thereof.

In certain embodiments, the compound of Formula (II) is of Formula (II-A):

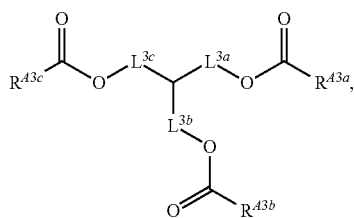
(II-A)

or a salt, hydrate, solvate, polymorph, tautomer, stereoisomer, and isotopically labeled derivative thereof.

In certain embodiments, the compound of Formula (I) is of the formula:

In certain embodiments, the compound of Formula (II) is of the formula:

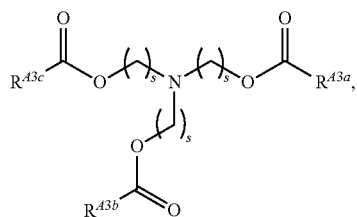

or a salt, hydrate, solvate, polymorph, tautomer, stereoisomer, and isotopically labeled derivative thereof, wherein each instance of s is 2, 3, 4, 5, or 6.

In certain embodiments, the compound of Formula (II) is of the formula:

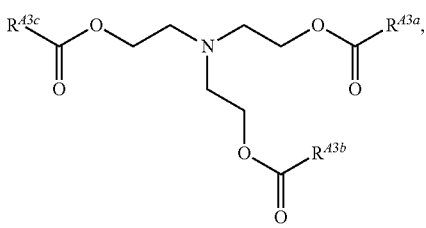

or a salt, hydrate, solvate, polymorph, tautomer, stereoisomer, and isotopically labeled derivative thereof.

Exemplary compounds of Formula (II) include, but are not limited to:

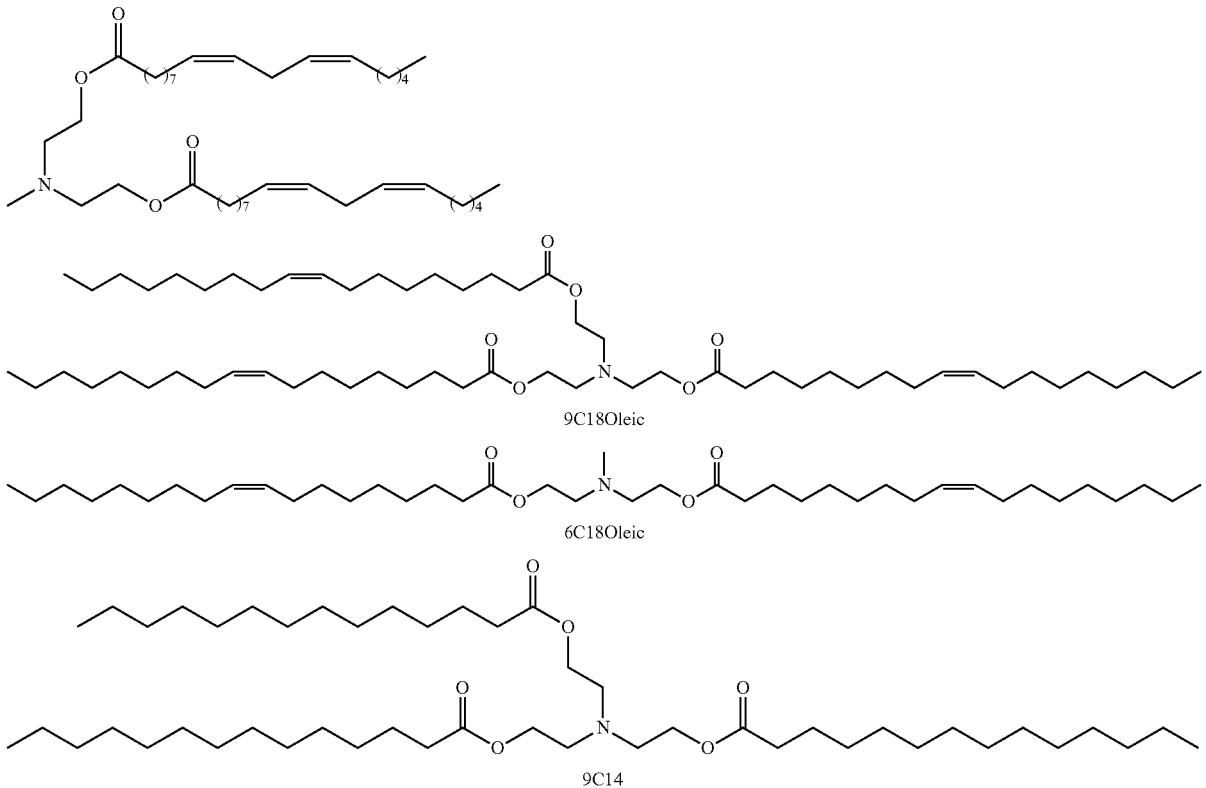

9C18Oleic

6C18Oleic

9C14

-continued

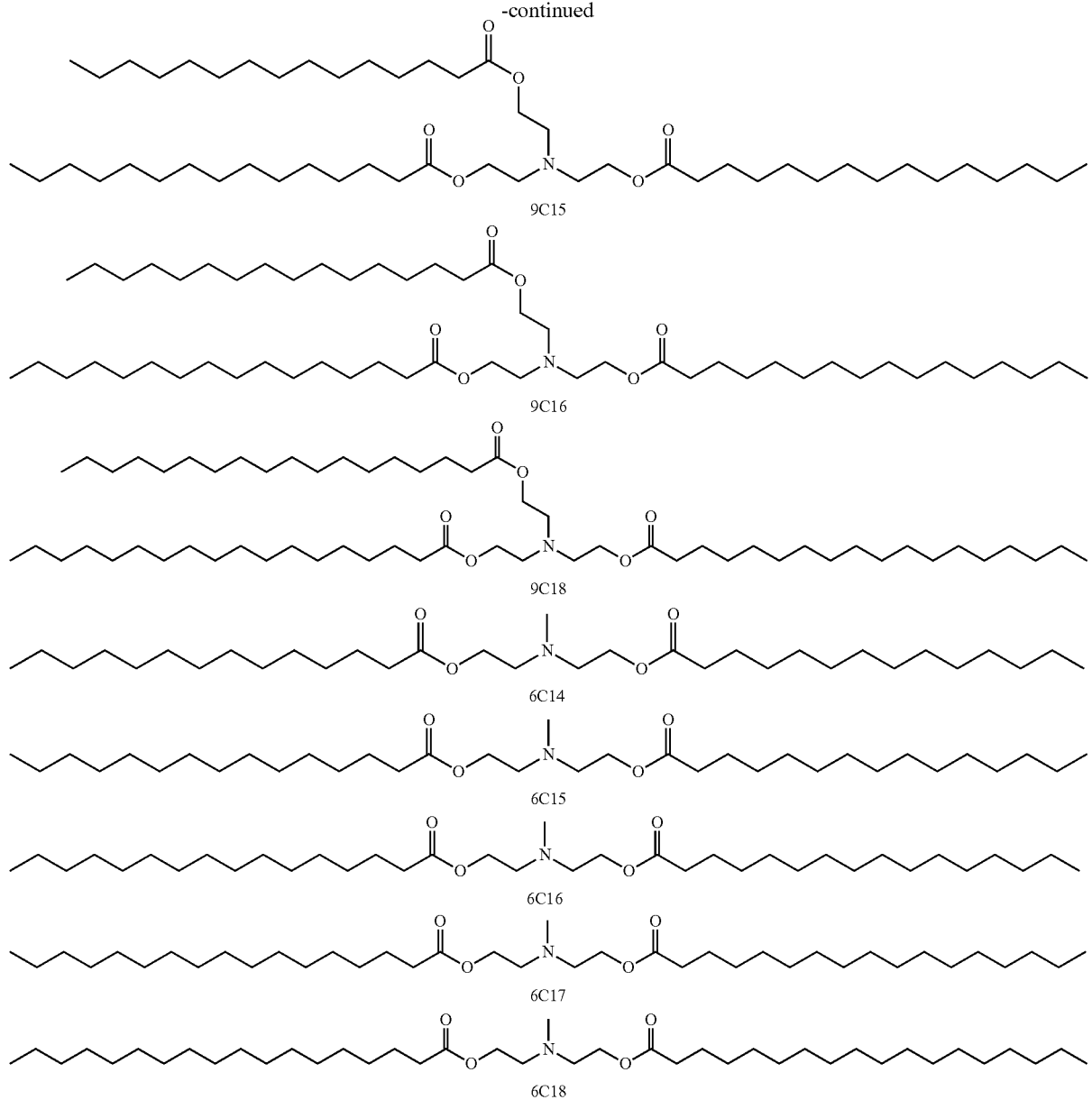

and salts, hydrates, solvates, polymorphs, tautomers, stereoisomers, and isotopically labeled derivatives thereof.

In another aspect, the present disclosure provides compounds listed in Table 6A, and salts, hydrates, solvates, polymorphs, tautomers, stereoisomers, and isotopically labeled derivatives thereof.

TABLE 6A

Single-tailed lipidoids of the present disclosure

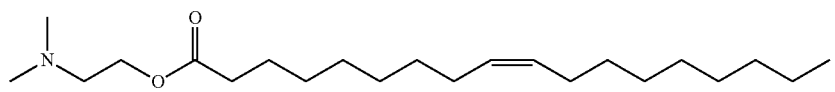 [SMILES: CCCCCCCC/C=C\CCCCCCCC(=O)OCCN(C)C]

TABLE 6A-continued

Single-tailed lipidoids of the present disclosure

| Structure | Name |
|---|---|
| | 3C18Oleic |
| | 30C18Oleic |
| | 1C18 |
| | 1C14 |
| | 1C16 |
| | 1C18Elaidic |
| | 1C15 |
| | 1C18Oleic |
| | 3C14 |
| | 3C15 |
| | 3C16 |
| | 3C17 |
| | 3C18 |

TABLE 6A-continued

Single-tailed lipidoids of the present disclosure

30C14

30C15

30C16

30C17

30C18

In certain embodiments, a compound described herein is a compound of Formula (I), or a salt, hydrate, solvate, polymorph, tautomer, stereoisomer, and isotopically labeled derivative thereof. In certain embodiments, a compound described herein is a compound of Formula (I), or a salt thereof. In certain embodiments, a compound described herein is a compound of Formula (I), or a pharmaceutically acceptable salt thereof. In certain embodiments, a compound described herein is a compound of Formula (II), or a salt, hydrate, solvate, polymorph, tautomer, stereoisomer, and isotopically labeled derivative thereof. In certain embodiments, a compound described herein is a compound of Formula (II), or a salt thereof. In certain embodiments, a compound described herein is a compound of Formula (II), or a pharmaceutically acceptable salt thereof. In certain embodiments, a compound described herein is a compound listed in Table 6A, or a salt, hydrate, solvate, polymorph, tautomer, stereoisomer, and isotopically labeled derivative thereof. In certain embodiments, a compound described herein is a compound listed in Table 6A, or a salt thereof. In certain embodiments, a compound described herein is a compound listed in Table 6A, or a pharmaceutically acceptable salt thereof.

The compounds described herein may be useful in delivering an agent, such as a polynucleotide (e.g., DNA (e.g., plasmid DNA) or RNA (e.g., an siRNA, mRNA), or a combination thereof), to a subject, tissue, or cell. The compounds described herein may also be useful in treating and/or preventing a disease (e.g., a genetic disease, proliferative disease, hematological disease, or neurological disease) in a subject in need thereof. In certain embodiments, the compounds described herein are useful in gene therapy.

Delivery of an agent to a subject, tissue, or cell using multi-tailed lipidoids have been reported. However, the toxicity of lipidoids still remain a problem (Lv et al., Control. Release, 114, 100-109 (2006); Ma et. al., Biochem. Biophys. Res. Commun., 330, 755-759 (2005); Akhtar et al., Adv. Drug Deliv. Rev., 59, 164-182 (2007)). For example, polyamine-acrylamide derived lipidoids do not readily hydrolyze under physiological conditions due to their amide bond linkage. Therefore, these polyamine-acrylamides accumulate in the kidneys at sometimes hazardous levels due to inefficient renal clearance (Scheme 1).

Scheme 1. Inefficient amide bond hydrolysis of polyamine-acrylamide derived lipidoids may result in renal accumulation

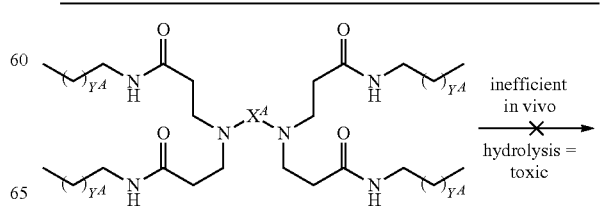

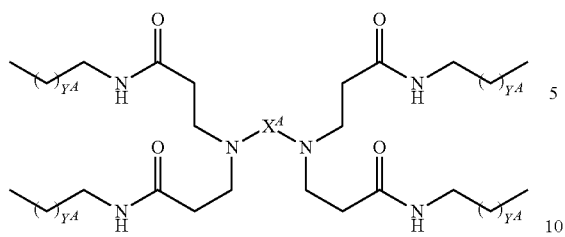

$X^A$ = aliphatic, heterocyclic, heteroaliphatic, etc.
$Y^A$ = 4-20

Polyamine-acrylate derived lipidoids typically degrade more readily under physiological conditions than polyamine-acrylamide derived lipidoids, due to the hydrolysable ester bond linkage. However, current polyamine-acrylate derived lipidoids include "external" ester moieties R—O—C(=O)— (wherein R is a lipid moiety) and may hydrolyze into aliphatic alcohols ROH due to the "external" orientation of the ester (Scheme 2), and the resulting aliphatic alcohols are often toxic.

Scheme 2. In vivo hydrolysis of polyamine-acrylate derived lipidoids generates toxic alcohols

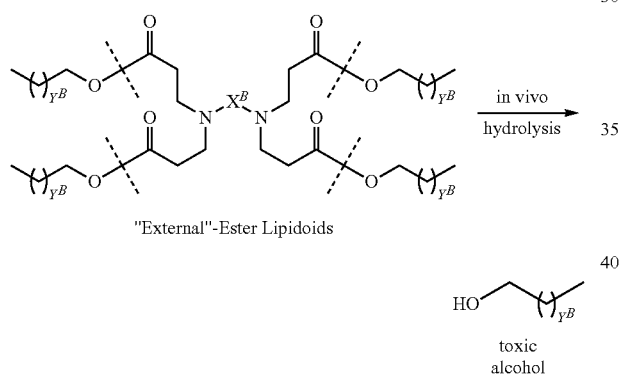

$X^B$ = aliphatic, heterocyclic, heteroaliphatic, etc.
$Y^B$ = 4-20

The compounds of the present disclosure are advantageous over reported lipidoids in delivering an agent to a subject, tissue, or cell. Instead of an amide linkage or an "external" ester linkage, the compounds described herein include "internal" ester linkage, i.e., a lipid moiety (R) of a compound described herein is directly attached to a —C(=O)—O— moiety to form an R—C(=O)—O— moiety ("internal"), rather than to form an R—O—C(=O)— moiety ("external"). By "internalizing" the ester linkage, the compounds of the disclosure may hydrolyze into carboxylic acids (e.g., fatty acids), which are typically non-toxic, thereby decreasing the toxicity associated with lipidoid delivery systems (see, e.g., Scheme 3). Therefore, the compounds of the disclosure are typically biodegradable and non-toxic.

Scheme 3. Exemplary compounds of the disclosure may hydrolyze into non-toxic carboxylic acid

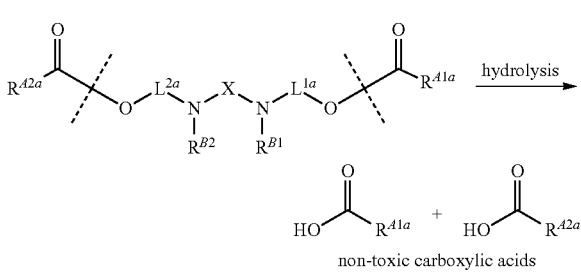

In certain embodiments, a compound Formula (I) is a compound of formula:

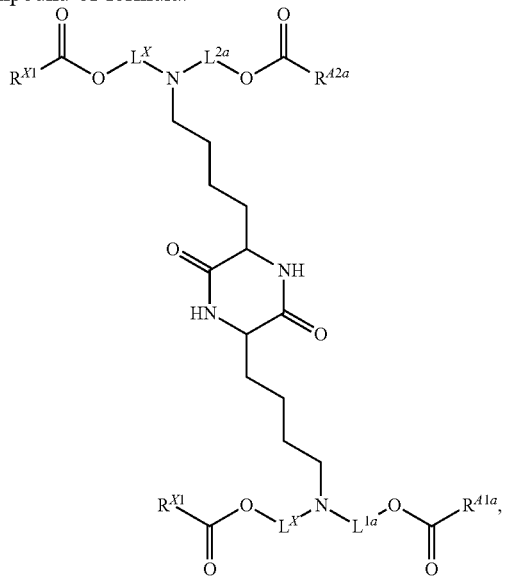

or a salt thereof, wherein $L^X$, $L^{1a}$, $L^{2a}$, $R^{X1}$, $R^{A1a}$, and $R^{A2a}$ are as defined herein.

In certain embodiments, a compound Formula (I) is a compound of formula:

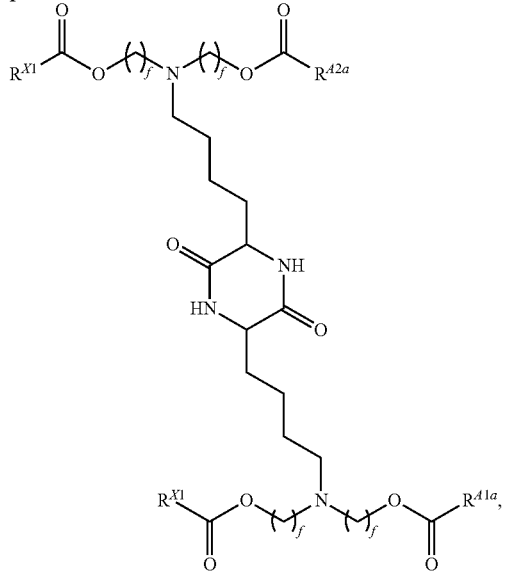

or a salt thereof, wherein f is 2, 3, 4, or 5, and wherein $R^X$, $R^{A1a}$, and $R^{A2a}$ are as defined herein.
In certain embodiments, a compound Formula (I) is a compound of formula:
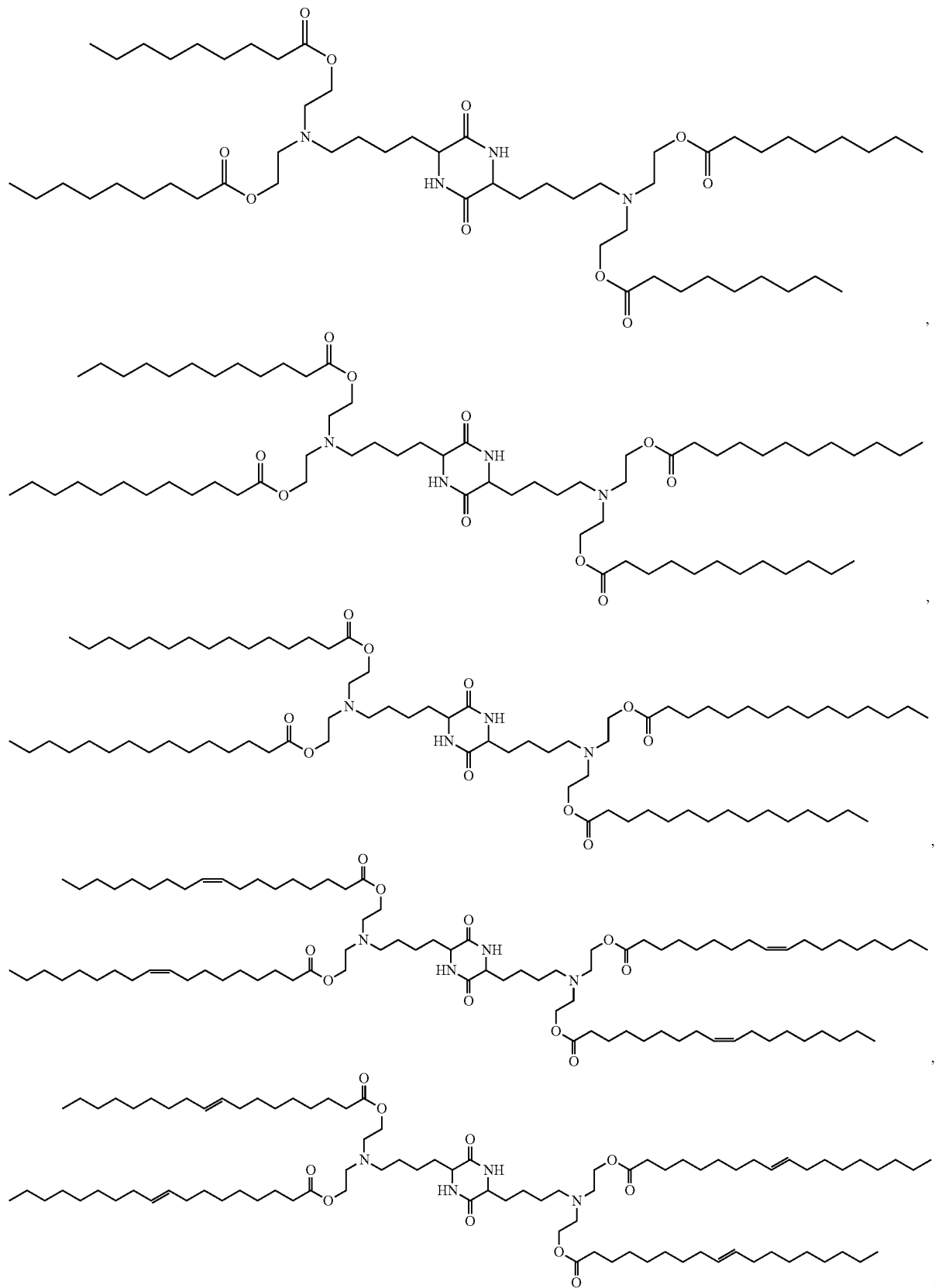

-continued
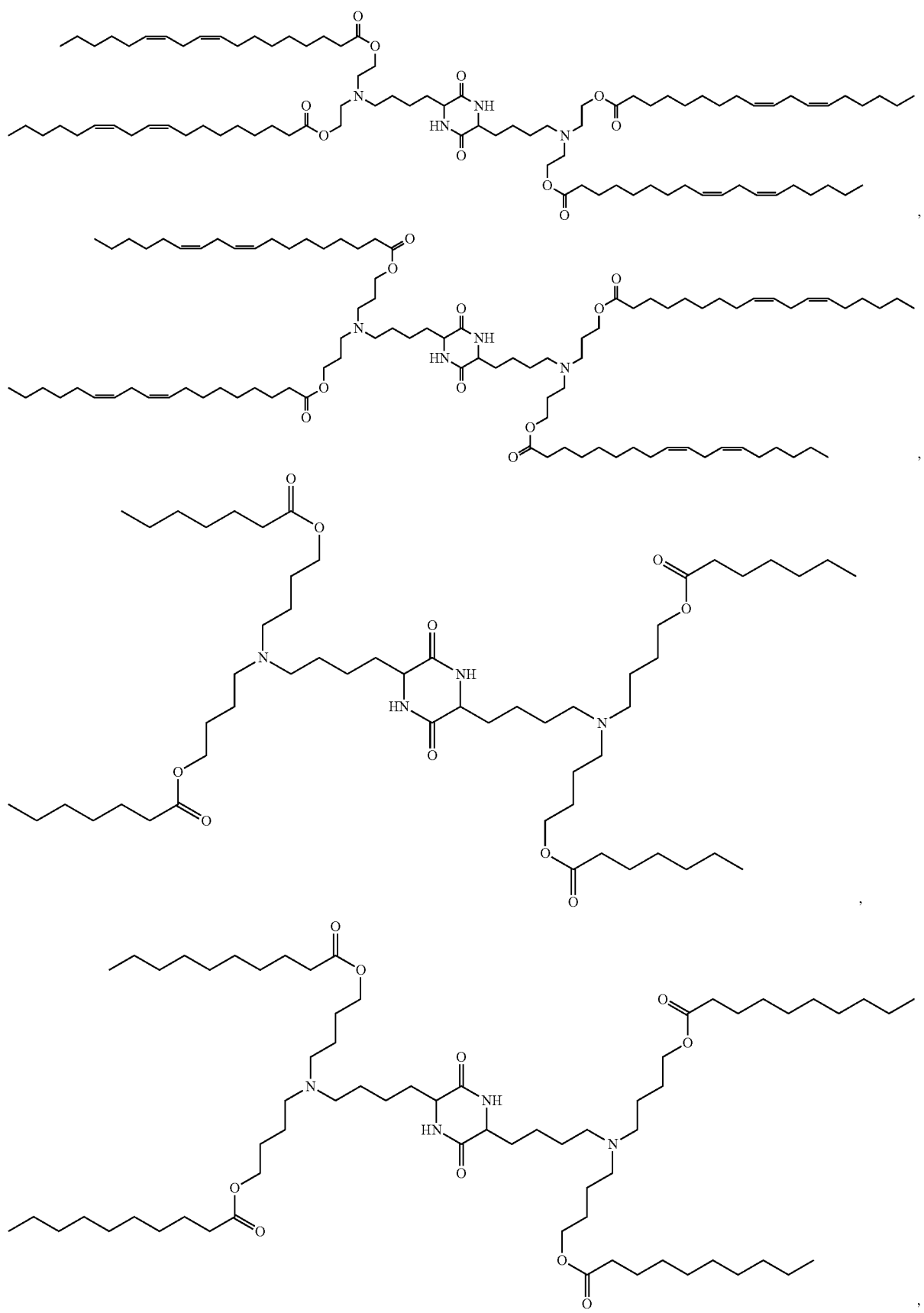

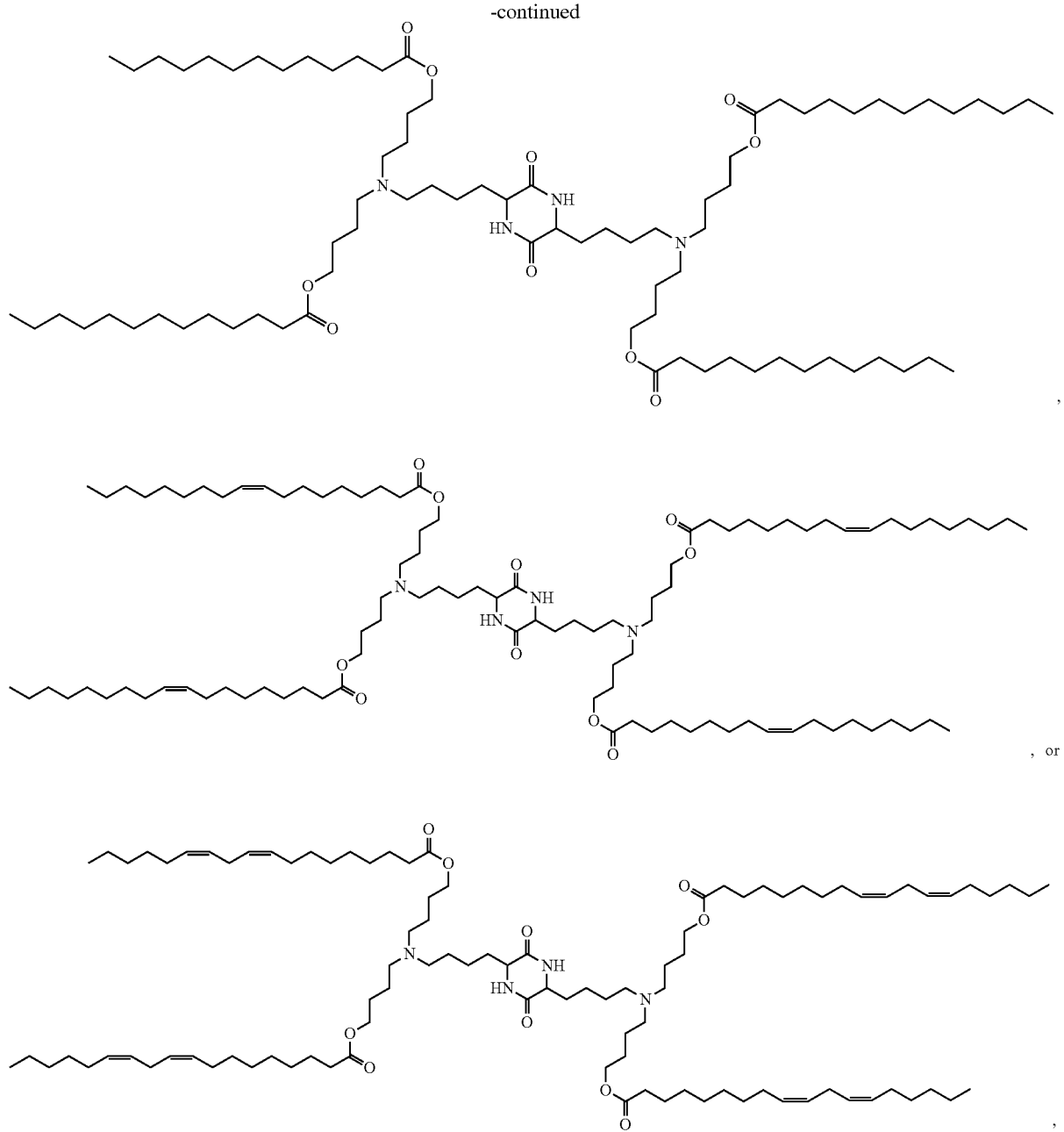

Methods of Preparing the Compounds and Compounds Prepared by the Methods

Compounds described herein may be prepared using esterification (e.g., Methods A and D), alkylation (e.g., Methods B and E), or reductive amination (e.g., Methods C and F) reactions. In another aspect, the present disclosure also provides methods of preparing the compounds described herein. In certain embodiments, described herein are methods of preparing the compounds of Formula (I), and salts, stereoisomers, and isotopically labeled derivatives thereof (Method A), the methods including esterifying an alcohol of Formula (A), or a salt, stereoisomer, and isotopically labeled derivative thereof, with a carboxylic acid of Formula (B), or a salt, stereoisomer, and isotopically labeled derivative thereof:

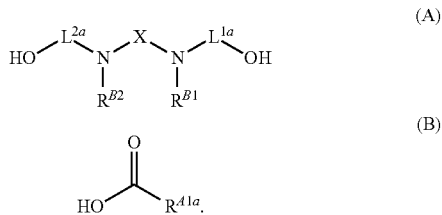

In certain embodiments, described herein are methods of preparing the compounds of Formula (I), and salts, stereoisomers, and isotopically labeled derivatives thereof (Method B), the methods including alkylating an amine of Formula (C), or a salt, stereoisomer, and isotopically labeled derivative thereof, with a compound of Formula (D), or a salt, stereoisomer, and isotopically labeled derivative thereof:

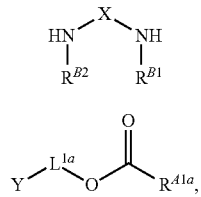

(C)

(D)

wherein Y is a leaving group.

Formula (D) includes substituent Y. In certain embodiments, Y is Cl, Br, I, or —OS(=O)$_u$R$^Y$, wherein u is 1 or 2; and R$^Y$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl. In certain embodiments, Y is Cl. In certain embodiments, Y is Br. In certain embodiments, Y is I (iodine). In certain embodiments, Y is —OS(=O)$_u$R$^Y$. In certain embodiments, Y is —OS(=O) R$^Y$. In certain embodiments, Y is —OS(=O)$_2$R$^Y$. In certain embodiments, Y is —OTs, —OMs, —OBs, or —OTf.

In certain embodiments, u is 1. In certain embodiments, u is 2.

In certain embodiments, R$^Y$ is substituted alkyl. In certain embodiments, R$^Y$ is unsubstituted alkyl. In certain embodiments, R$^Y$ is substituted C$_{1-6}$ alkyl. In certain embodiments, R$^Y$ is unsubstituted C$_{1-6}$ alkyl. In certain embodiments, R$^Y$ is C$_{1-6}$ alkyl substituted with at least one halogen. In certain embodiments, R$^Y$ is substituted methyl. In certain embodiments, R$^Y$ is —CH$_2$F, —CHF$_2$, or —CF$_3$. In certain embodiments, R$^Y$ is —CH$_3$. In certain embodiments, R$^Y$ is ethyl. In certain embodiments, R$^Y$ is propyl. In certain embodiments, R$^Y$ is butyl. In certain embodiments, R$^Y$ is pentyl. In certain embodiments, R$^Y$ is hexyl.

In certain embodiments, described herein are methods of preparing the compounds of Formula (I), and salts, stereoisomers, and isotopically labeled derivatives thereof (Method C), the methods including reacting an amine of Formula (C), or a salt thereof, with an aldehyde of Formula (K), or a salt thereof, in the presence of a reductant:

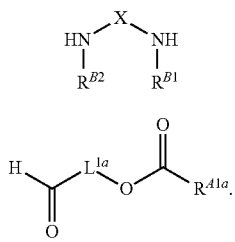

(C)

(K)

In certain embodiments, the reductant is a borohydride (e.g., sodium borohydride, potassium borohydride, calcium borohydride, magnesium borohydride, tetramethylammonium borohydride, tetraethylammonium borohydride, tetrabutylammonium borohydride, methyltrioctylammonium borohydride, cetyltrimethylammonium borohydride, bis(triphenylphosphine)copper(I) borohydride, potassium tri(1-pyrazolyl)borohydride, potassium tri(3,5-dimethyl-1-pyrazolyl)borohydride, sodium cyanoborohydride, sodium triacetoxyborohydride, or polymer-supported borohydride). In certain embodiments, the reductant is a borane (e.g., a borane tetrahydrofuran complex, borane dimethyl sulfide complex, borane dimethylamine complex, borane pyridine complex, borane trimethylamine complex, borane triethylamine complex, borane morpholine complex, borane tert-butylamine complex, borane-ammonia complex, borane triphenylphosphine complex, borane N,N-diethylaniline complex, borane di(tert-butyl)phosphine complex, borane diphenylphosphine complex, borane 4-methylmorpholine complex, borane N,N-diisopropylethylamine complex, borane isoamylsulfide complex, borane ethylenediamine complex, acetylthiomethyl-diphenylphosphine borane complex, 2-methylpyridine borane complex, tert-butyldimethylphosphine borane, 5-ethyl-2-methylpyridine borane complex, lithium ammonia borane, (11bR)-4,5-dihydro-3H-dinaphtho[2,1-c: 1',2'-e]phosphepine borane, (methoxycarbonyl)borane trimethylamine complex, dibromoborane dimethyl sulfide complex, mono-bromoborane methyl sulfide complex, dichloroborane methyl sulfide complex, 1,3-dimethylimidazol-2-ylidene borane). In certain embodiments, the reductant is a silane. In certain embodiments, the silane is of the formula: HSi(R$^1$)$_3$, wherein each instance of R$^1$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or —OR$^{1a}$, wherein each instance of R$^{1a}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or an oxygen protecting group). In certain embodiments, the silane is a monoalkylsilane (e.g., BuSiH$_3$), dialkylsilane (e.g., Et$_2$SiH$_2$), trialkylsilane (e.g., Me$_3$SiH or Et$_3$SiH). In certain embodiments, the silane is a poly(alkylhydrosiloxane) (e.g., poly(methylhydrosiloxane) (PMHS)). In certain embodiments, the reductant is an alcohol. In certain embodiments, the alcohol is of the formula: (R$^2$)$_2$CHOH, wherein each instance of R$^2$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl. In certain embodiments, the alcohol is methanol, ethanol, propanol (e.g., isopropanol), or butanol. In certain embodiments, the reductant is H$_2$. In certain embodiments, the reductant is commercially available.

In certain embodiments, described herein are methods of preparing the compounds of Formula (II), and salts, stereoisomers, and isotopically labeled derivatives thereof (Method D), the methods including esterifying an alcohol of Formula (E), or a salt, stereoisomer, and isotopically labeled derivative thereof, with a carboxylic acid of Formula (F), or a salt, stereoisomer, and isotopically labeled derivative thereof:

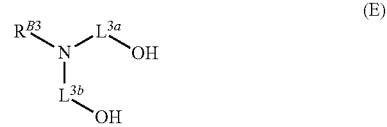

(E)

-continued

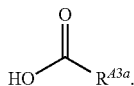
(F)

In certain embodiments, described herein are methods of preparing the compounds of Formula (II), and salts, stereoisomers, and isotopically labeled derivatives thereof (Method E), the methods including alkylating an amine of Formula (G), or a salt, stereoisomer, and isotopically labeled derivative thereof, with a compound of Formula (H), or a salt, stereoisomer, and isotopically labeled derivative thereof:

(G)

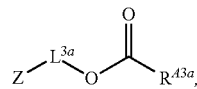
(H)

wherein Z is a leaving group.

Formula (H) includes substituent Z. In certain embodiments, Z is Cl, Br, I, or —OS(=O)$_v$R$^Z$, wherein v is 1 or 2; and R$^Z$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl. In certain embodiments, Z is Cl. In certain embodiments, Z is Br. In certain embodiments, Z is I (iodine). In certain embodiments, Z is —OS(=O)$_v$R$^Z$. In certain embodiments, Z is —OS(=O)R$^Z$. In certain embodiments, Z is —OS(=O)$_2$R$^Z$. In certain embodiments, Z is —OTs, —OMs, —OBs, or —OTf.

In certain embodiments, v is 1. In certain embodiments, v is 2.

In certain embodiments, R$^Z$ is substituted alkyl. In certain embodiments, R$^Z$ is unsubstituted alkyl. In certain embodiments, R$^Z$ is substituted C$_{1-6}$ alkyl. In certain embodiments, R$^Z$ is unsubstituted C$_{1-6}$ alkyl. In certain embodiments, R$^Z$ is C$_{1-6}$ alkyl substituted with at least one halogen. In certain embodiments, R$^Z$ is substituted methyl. In certain embodiments, R$^Z$ is —CH$_2$F, —CHF$_2$, or —CF$_3$. In certain embodiments, R$^Z$ is —CH$_3$. In certain embodiments, R$^Z$ is ethyl. In certain embodiments, R$^Z$ is propyl. In certain embodiments, R$^Z$ is butyl. In certain embodiments, R$^Z$ is pentyl. In certain embodiments, R$^Z$ is hexyl.

In certain embodiments, described herein are methods of preparing the compounds of Formula (II), and salts, stereoisomers, and isotopically labeled derivatives thereof (Method F), the methods including reacting an amine of Formula (G), or a salt thereof, with an aldehyde of Formula (J), or a salt thereof, in the presence of a reductant:

(G)

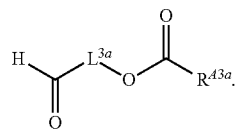
(J)

Certain embodiments of a compound of Formula (I) may be prepared according to Scheme 4. In certain embodiments, the X is a compound of formula:

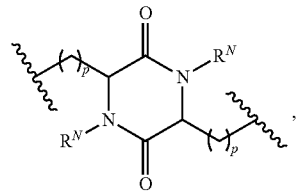

wherein each instance of p is independently 1, 2, 3, 4, 5, or 6. For example, X may be a bis-lysine diketopiperzine based moiety, of formula:

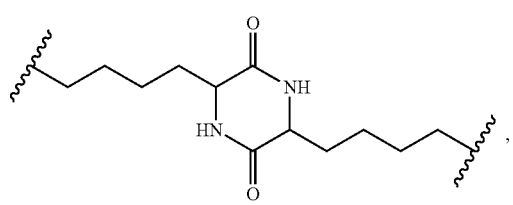 [SMILES: *CCCCC1NC(=O)C(CCCC*)NC1=O]

Scheme 4.

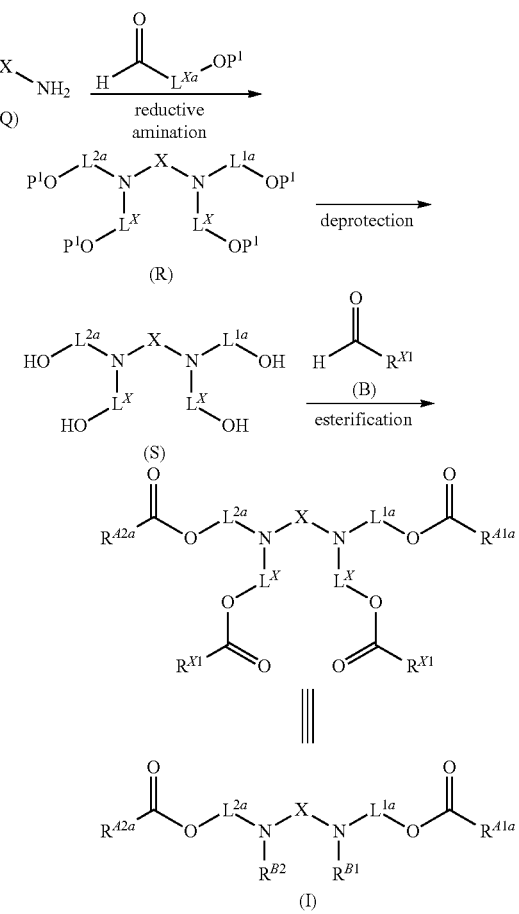

Thus, in another aspect, described herein is a method of preparing the compound of Formula (I), or a salt, stereoisomer, or isotopically labeled derivative thereof, the method comprising esterifying an alcohol of Formula (S):

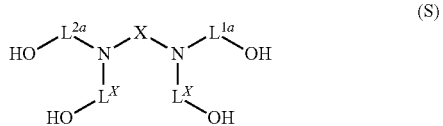

or a salt, stereoisomer, or isotopically labeled derivative thereof, with a carboxylic acid of Formula (B):

or a salt, stereoisomer, or isotopically labeled derivative thereof, wherein X, $L^X$, $L^{1a}$, $L^{2a}$, and $R^{X1}$ are as described herein, to provide a compound of Formula (I). In some embodiments, the step of esterifying is performed in the presence of a base. In some embodiments, the base is an organic base. In certain embodiments, the organic base is an aliphatic amine or aromatic amine. In certain embodiments, the organic base is a primary amine, secondary amine, or tertiary amine. In certain embodiments, the organic base is triethylamine, N,N-diisopropylethylamine, 1,8-diazabicyclo[5.4.0]undec-7-ene (DBU), pyridine, 2,6-lutidine, or 4-dimethylaminopyridine (DMAP). In some embodiments, the step of esterifying is performed in the presence of a carbodiimide (e.g., N,N'-dicyclohexylcarbodiimide (DCC), 1-ethyl-3-(3-dimethylaminopropyl)carbodiimide (EDC), or N,N'-diisopropylcarbodiimide (DIC)). In some embodiments, the step of esterigying is performed in the presence of a catalyst (e.g., DMAP, 1-hydroxybenzotriazole (HOBt), or 1-hydroxy-7-azabenzotriazole (HOAt)).

In another aspect, the method of preparing a compound of Formula (I) further comprises deprotecting a compound of Formula (R):

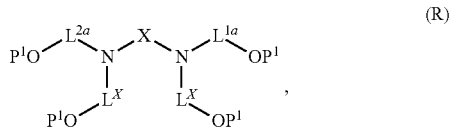

or a salt, stereoisomer, or isotopically labeled derivative thereof, wherein each $P^1$ is independently hydrogen, optionally substituted alkyl, or an oxygen protecting group, and X, $L^X$, $L^{1a}$, $L^{2a}$ are as described herein, to provide a compound of Formula (S). In certain embodiments, the oxygen protecting group is silyl (e.g., TMS, TES, TIPS, TBDMS). In certain embodiments, the step of deprotecting is performed in the presence of an acid. In certain embodiments, the step of deprotecting is performed in the presence of a base. In certain embodiments, the step of deprotecting is performed in the presence of a reductant. In certain embodiments, the step of deprotecting is performed in the presence of a fluoride source (e.g., tetrabutylammonium fluoride (TBAF)).

In another aspect, the method of preparing a compound of Formula (I) further comprises contacting a compound of Formula (Q):

or a salt, stereoisomer, or isotopically labeled derivative thereof, wherein X is as described herein, with a compound of Formula (P):

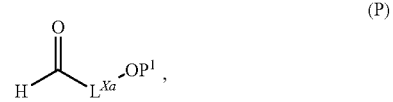

or a salt, stereoisomer, or isotopically labeled derivative thereof, wherein $P^1$ is hydrogen, optionally substituted alkyl, or an oxygen protecting group, and $L^{Xa}$ is substituted or unsubstituted alkylene or substituted or unsubstituted heteroalkylene, in the presence of a reductant, to provide a compound of Formula (R). In certain embodiments, the oxygen protecting group is silyl (e.g., TMS, TES, TIPS, TBDMS). In some embodiments, the step of esterifying is performed in the presence of a base. In some embodiments, the base is an organic base. In certain embodiments, the organic base is an aliphatic amine or aromatic amine. In certain embodiments, the organic base is a primary amine, secondary amine, or tertiary amine. In certain embodiments, the organic base is triethylamine, N,N-diisopropylethylamine, 1,8-diazabicyclo[5.4.0]undec-7-ene (DBU), pyridine, 2,6-lutidine, or 4-dimethylaminopyridine (DMAP). In certain embodiments, the reductant is a reductant described herein. In certain embodiments, the reductant is a borohydride or borane. In some embodiments, the reductant is sodium borohydride or sodium triacetoxyborohydride.

The step(s) of the methods of preparing the compounds described herein may be performed under any suitable conditions. A suitable condition is a combination of physical and chemical parameters under which an intended product (e.g., a compound described herein) or intermediate may be formed using the methods. A suitable condition may include the presence of a base. In certain embodiments, the base is an inorganic base. In certain embodiments, the inorganic base is an alkali metal carbonate (e.g., $Li_2CO_3$, $Na_2CO_3$, $K_2CO_3$, $Rb_2CO_3$, or $Cs_2CO_3$). In certain embodiments, the inorganic base is an alkali metal bicarbonate (e.g., $LiHCO_3$, $NaHCO_3$, $KHCO_3$, $RbHCO_3$, or $CsHCO_3$). In certain embodiments, the inorganic base is an alkaline earth metal carbonate (e.g., $BeCO_3$, $MgCO_3$, $CaCO_3$, $SrCO_3$, or $BaCO_3$). In certain embodiments, the inorganic base is an alkaline earth metal bicarbonate (e.g., $Be(HCO_3)_2$, $Mg(HCO_3)_2$, $Ca(HCO_3)_2$, $Sr(HCO_3)_2$, or $Ba(HCO_3)_2$). In certain embodiments, the base is an organic base. In certain embodiments, the organic base is an aliphatic amine or aromatic amine. In certain embodiments, the organic base is a primary amine, secondary amine, or tertiary amine. In certain embodiments, the organic base is triethylamine, N,N-diisopropylethylamine, 1,8-diazabicyclo[5.4.0]undec-7-ene (DBU), pyridine, 2,6-lutidine, or 4-dimethylaminopyridine (DMAP). A base described herein may be present in a stoichiometric amount (e.g., at least 1 equivalent compared to the amount of a compound of Formula (B), (D), (F), (H), (Q), or (S)) or catalytic amount (e.g., less than 1 equivalent compared to the amount of a compound of Formula (B), (D), (F), (H), (Q), or (S)).

A suitable condition may include the presence of a carbodiimide (e.g., N,N'-dicyclohexylcarbodiimide (DCC), 1-ethyl-3-(3-dimethylaminopropyl)carbodiimide (EDC), or N,N'-diisopropylcarbodiimide (DIC)).

A suitable condition may include the presence of a catalyst (e.g., DMAP, 1-hydroxybenzotriazole (HOBt), or 1-hydroxy-7-azabenzotriazole (HOAt)).

A suitable condition may include the absence of a solvent (i.e., neat). A suitable condition may include a suitable solvent. In certain embodiments, the suitable solvent is an organic solvent. In certain embodiments, the suitable solvent is an aprotic organic solvent (e.g., acetonitrile, N,N-dimethylformamide (DMF), N,N-dimethylacetamide (DMA), N-methyl-2-pyrrolidone (NMP), dimethyl sulfoxide (DMSO), tetrahydrofuran (THF), 2-methyl-tetrahydrofuran, tetrahydropyran, dioxane, diethyl ether, methyl t-butyl ether (MTBE), dimethoxyethane (DME), diglyme, acetone, butanone, dichloromethane, chloroform, carbon tetrachloride, or 1,2-dichloroethane). In certain embodiments, the suitable solvent is a protic organic solvent (e.g., an alcohol, such as methanol, ethanol, propanol, or butanol). In certain embodiments, the suitable solvent is an inorganic solvent (e.g., water). In certain embodiments, the suitable solvent is a mixture of two or more solvents. In certain embodiments, the suitable solvent is commercially available.

A suitable condition may also include a suitable temperature under which a step of a method of preparing a compound described herein is performed. In certain embodiments, the suitable temperature is at least about 0° C., at least about 23° C., at least about 40° C., at least about 60° C., at least about 80° C., or at least about 100° C. In certain embodiments, the suitable temperature is at most about 100° C., at most about 80° C., at most about 60° C., at most about 40° C., at most about 23° C., or at most about 0° C. Combinations of the above-referenced ranges (e.g., at least about 23° C. and at most about 80° C.) are also within the scope of the disclosure. A suitable temperature may be a variable temperature (e.g., from 23° C. to about 80° C.) during a step of a method of preparing a compound described herein.

A suitable condition may also include a suitable pressure under which a step of a method of preparing a compound described herein is performed. In certain embodiments, the suitable pressure is about 1 atmosphere.

A suitable condition may also include a suitable atmosphere under which a step of a method of preparing a compound described herein is performed. In certain embodiments, the suitable atmosphere is air. In certain embodiments, the suitable atmosphere is an inert atmosphere. In certain embodiments, the suitable atmosphere is a nitrogen or argon atmosphere.

A suitable condition may also include a suitable time duration that a step of a method of preparing a compound described herein lasts. In certain embodiments, the suitable time duration is in the order of minutes (e.g., about 10 minutes or about 30 minutes), hours (e.g., about 1 hour, about 2 hours, about 3 hours, about 4 hours, about 6 hours, or about 12 hours), or days (e.g., about 1 day or 2 days).

One or more intermediates resulting from a step of a method of preparing the compounds described herein may be isolated and/or purified, and the isolated and/or purified intermediates may be reacted in a next step of the method. The isolated and/or purified intermediates may be substantially free of impurities or may contain one or more other components, such as reagents and solvents employed in the step yielding the intermediates, and byproducts. The intermediates may also be reacted in a next step without being isolated and/or purified. The intermediates and/or intended products of a method of preparing a compound described herein may be isolated and/or purified using methods known in the art, such as distillation, chromatography (e.g., normal phase chromatography (e.g., silica gel flash chromatography), reverse phase chromatography (e.g., high performance liquid chromatography (HPLC)), precipitation, decanting, filtration, centrifuge, trituration, crystallization, recrystallization, liquid-liquid phase separation, evaporation, and drying. In certain embodiments, an intended product described herein is substantially pure (e.g., substantially free of impurities) (e.g., at least about 90%, at least about 95%, at least about 98%, at least about 99%, at least about 99.5%, at least about 99.9%, or more pure) prior to or without purification.

Another aspect of the present disclosure relates to compounds prepared by a method described herein (e.g., any one of Methods A to F). In certain embodiments, described herein are compounds prepared by a method described herein, wherein the alcohol of Formula (A) or (E) is a compound in Table 7, or a salt, stereoisomer, and isotopically labeled derivative thereof, and the carboxylic acid of Formula (B) or (F) is a compound in Table 8, or a salt, stereoisomer, and isotopically labeled derivative thereof.

TABLE 7

Exemplary alcohols that are useful in preparing a compound of the disclosure

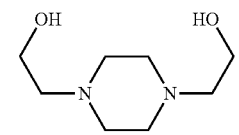 [SMILES: OCCN1CCN(CCO)CC1]

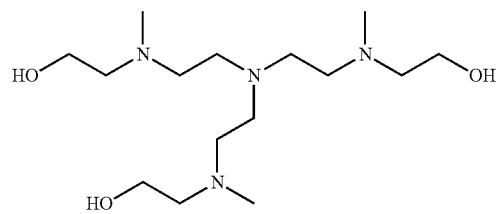 [SMILES: CN(CCO)CCN(CCN(C)CCO)CCN(C)CCO]

117                                                                                                     118
TABLE 7-continued
Exemplary alcohols that are useful in preparing a compound of the disclosure
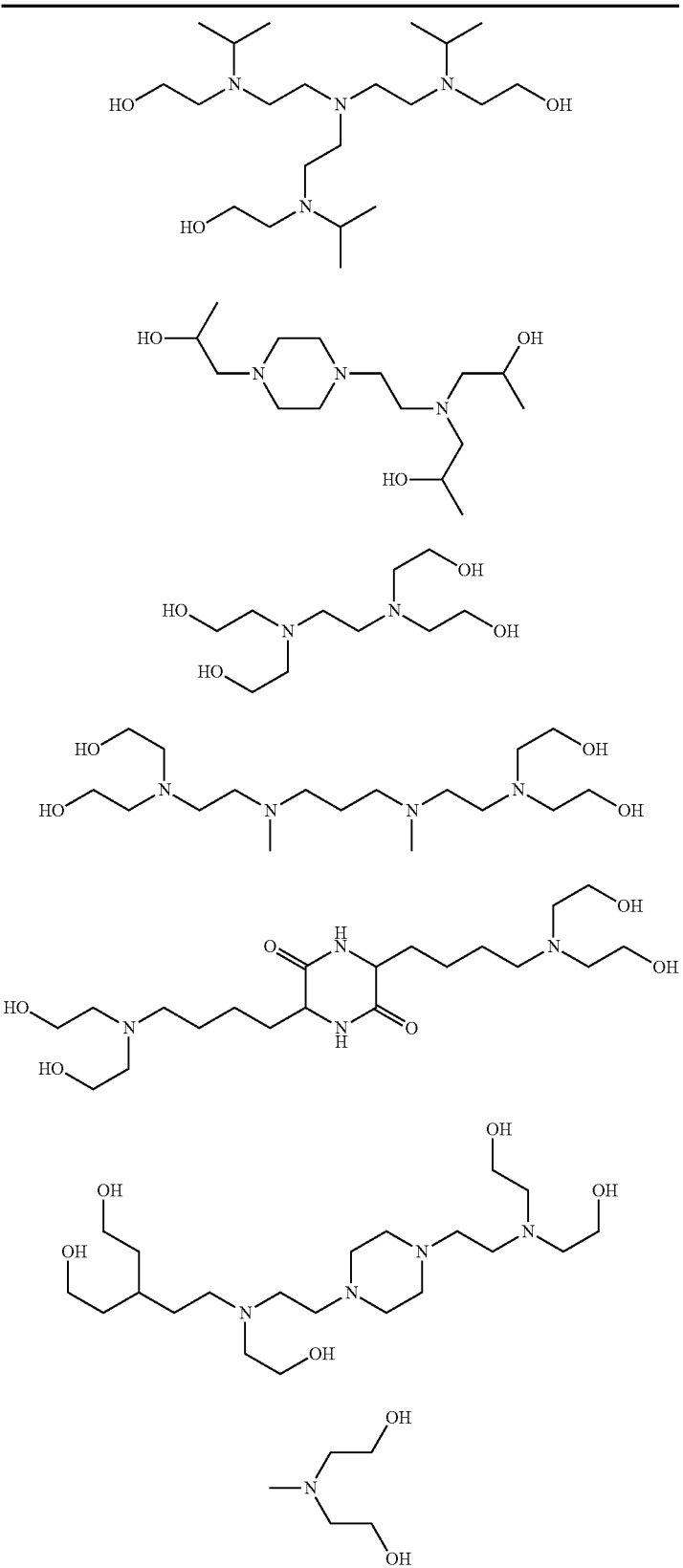

TABLE 7-continued
Exemplary alcohols that are useful in preparing a compound of the disclosure
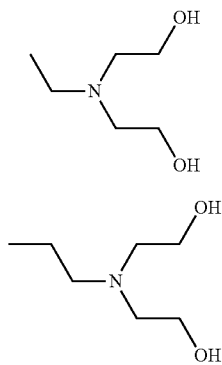
TABLE 8
Exemplary carboxylic acids that are useful in preparing a compound of the disclosure
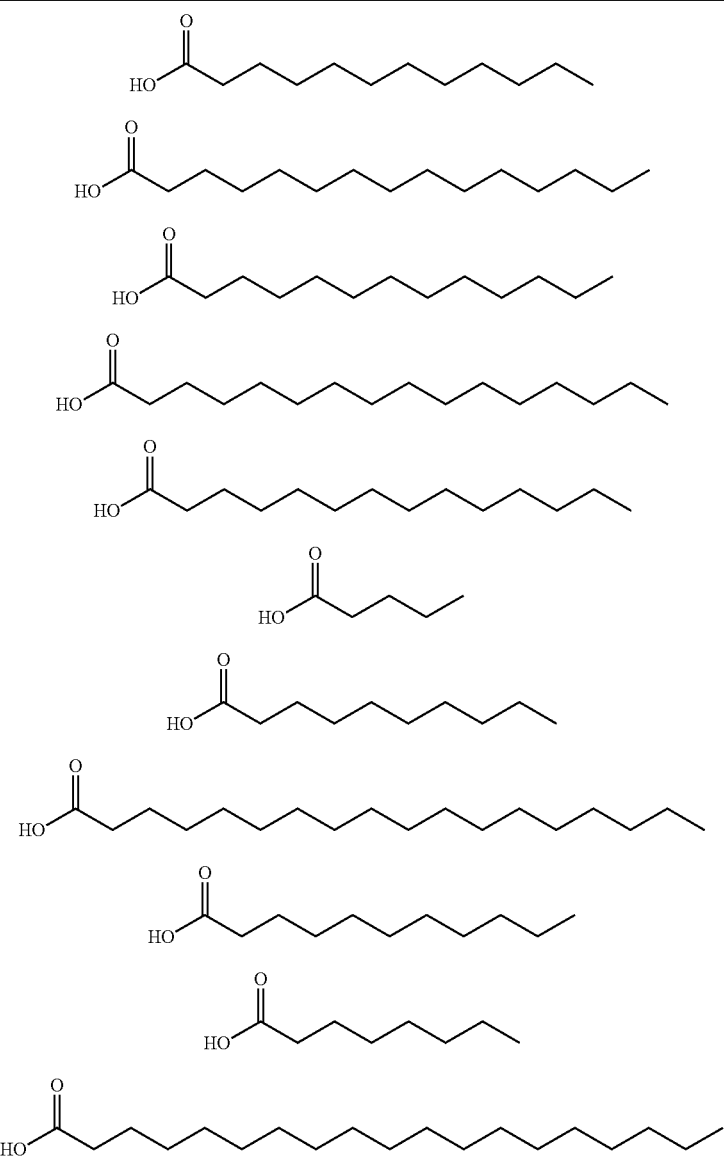

TABLE 8-continued
Exemplary carboxylic acids that are useful in preparing a compound of the disclosure
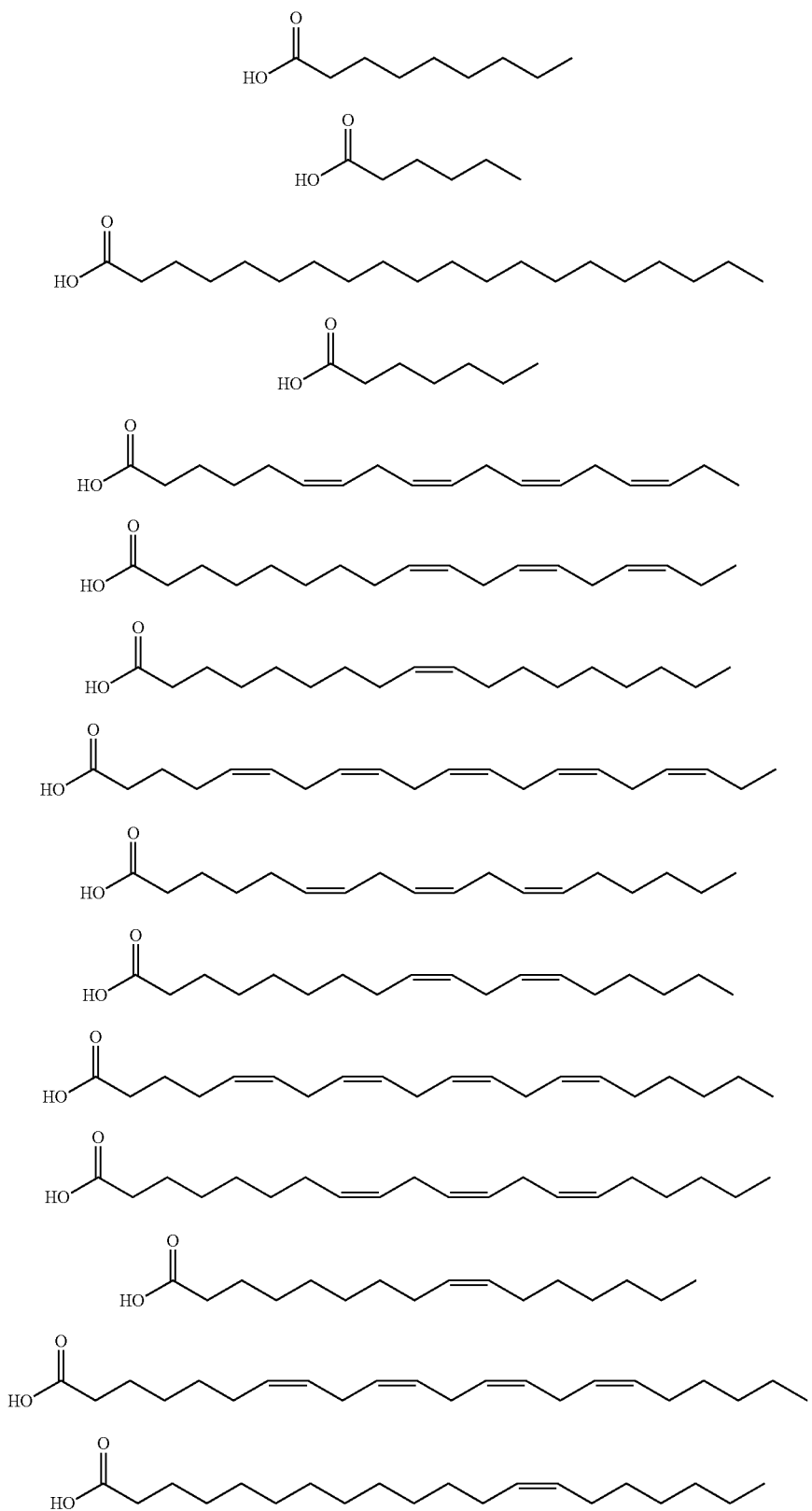

TABLE 8-continued

Exemplary carboxylic acids that are useful in preparing a compound of the disclosure

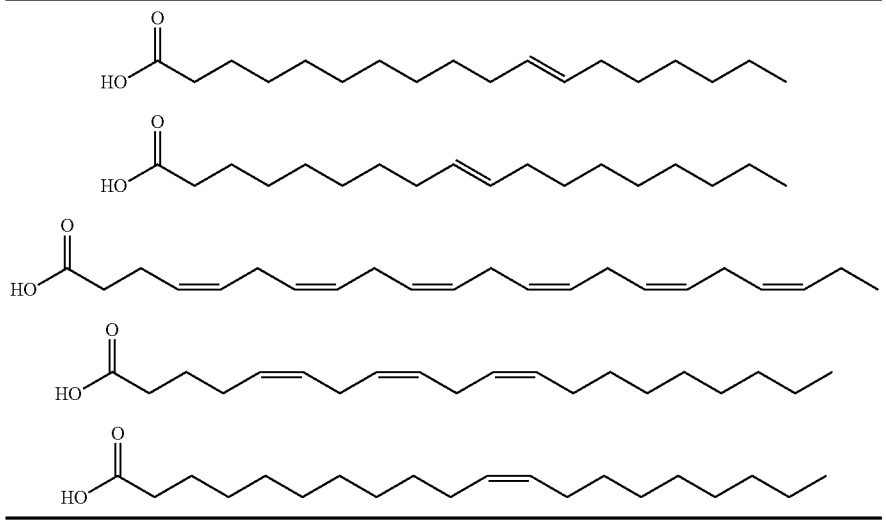

Compositions

In another aspect, the present disclosure provides compositions comprising a compound described herein and optionally an excipient. In certain embodiments, a composition described herein comprises a compound described herein and an excipient. In certain embodiments, a composition described herein is a pharmaceutical composition. In certain embodiments, a composition described herein comprises a compound described herein and a pharmaceutically acceptable excipient. In certain embodiments, a composition described herein is a composition for non-medical applications. In certain embodiments, a composition described herein is a cosmetic composition. In certain embodiments, a composition described herein comprises a compound described herein and a cosmetically acceptable excipient. In certain embodiments, a composition described herein is a dietary composition. In certain embodiments, a composition described herein comprises a compound described herein and a dietarily acceptable excipient. In certain embodiments, a composition described herein is a nutraceutical composition. In certain embodiments, a composition described herein comprises a compound described herein and a nutraceutically acceptable excipient.

A composition described herein may further comprise an agent (e.g., a pharmaceutical agent or diagnostic agent). In a composition described herein, an agent may form a complex with a compound described herein. In certain embodiments, a composition described herein is useful in the delivery of the agent to a subject, tissue, or cell. In certain embodiments, a composition described herein is useful in the delivery of an effective amount of the agent to the subject, tissue, or cell.

Compositions of the disclosure may improve or increase the delivery of an agent described herein to a subject, tissue, or cell. In certain embodiments, the compositions increase the delivery of the agent to a target tissue or target cell. In certain embodiments, the target tissue is liver, spleen, and/or lung. In certain embodiments, the target cell is a liver cell, spleen cell, and/or lung cell. In certain embodiments, the compositions selectively deliver the agent to the target tissue or target cell (e.g., the compositions deliver the agent to the target tissue in a greater quantity in unit time than to a non-target tissue or deliver the agent to the target cell in a greater quantity in unit time than to a non-target cell).

The delivery of an agent described herein may be characterized in various ways, such as the exposure, concentration, and bioavailability of the agent. The exposure of an agent in a subject, tissue, or cell may be defined as the area under the curve (AUC) of the concentration of the agent in the subject, tissue, or cell after administering or dosing the agent. In general, an increase in exposure may be calculated by first taking the difference in: (1) a first AUC, which is the AUC measured in a subject, tissue, or cell administered or dosed with a composition described herein; and (2) a second AUC, which is the AUC measured in a subject, tissue, or cell administered or dosed with a control composition; and then by dividing the difference by the second AUC. Exposure of an agent may be measured in an appropriate animal model. The concentration of an agent and, when appropriate, its metabolite(s), in a subject, tissue, or cell is measured as a function of time after administering or dosing the agent.

Concentration of an agent, and, when appropriate, of its metabolite(s), in a subject, tissue, or cell, may be measured as a function of time in vivo using an appropriate animal model. In certain embodiments, the concentration of the agent is the concentration of the agent in a target tissue or target cell. One exemplary method of determining the concentration of an agent involves dissecting of a tissue. The concentration of the agent may be determined by HPLC or LC/MS analysis.

In some embodiments, a composition of the disclosure increases the delivery of an agent described herein to a subject, tissue, or cell by due to the presence of a compound described herein. In some embodiments, the composition increases the delivery of the agent due to the presence of a complex formed between the compound and the agent. In some embodiments, the presence of a compound described herein increase the delivery of the agent by at least about 10%, at least about 20%, at least about 30%, at least about 40%, at least about 50%, at least about 100%, at least about 2-fold, at least about 3-fold, at least about 10-fold, at least about 30-fold, at least about 100-fold, at least about 300-fold, or at least about 1000-fold. In certain embodiments, a compound described herein is present in the composition in an amount sufficient to increase the delivery of the agent by an amount described herein when administered in the composition compared to the delivery of the agent when administered in the absence of the compound.

Compositions described herein may deliver an agent selectively to a tissue or cell. In certain embodiments, the tissue or cell to which the agent is selectively delivered is a target tissue or target cell, respectively. In certain embodiments, the compositions deliver at least about 10%, at least about 20%, at least about 30%, at least about 40%, at least about 50%, at least about 70%, at least about 100%, at least about 3-fold, at least about 10-fold, at least about 30-fold, at least about 100-fold, at least about 300-fold, or at least about 1000-fold more amount of the agent in unit time to a target tissue than to a non-target tissue or to a target cell than to a non-target cell. The amount of agent may be measured by the exposure, concentration, and/or bioavailability of the agent in a tissue or cell as described herein.

The compositions described herein (e.g., pharmaceutical compositions) including one or more agents (e.g., pharmaceutical agents) may be useful in treating and/or preventing a disease. In certain embodiments, the compositions are useful in gene therapy. In certain embodiments, the compositions are useful for treating and/or preventing a genetic disease. In certain embodiments, the compositions are useful for treating and/or preventing a proliferative disease. In certain embodiments, the compositions are useful for treating and/or preventing cancer. In certain embodiments, the compositions are useful for treating and/or preventing a benign neoplasm. In certain embodiments, the compositions are useful for treating and/or preventing pathological angiogenesis. In certain embodiments, the compositions are useful for treating and/or preventing an inflammatory disease. In certain embodiments, the compositions are useful for treating and/or preventing an autoimmune disease. In certain embodiments, the compositions are useful for treating and/or preventing a hematological disease. In certain embodiments, the compositions are useful for treating and/or preventing a neurological disease. In certain embodiments, the compositions are useful for treating and/or preventing an immunological disease. In certain embodiments, the compositions are useful for treating and/or preventing a gastrointestinal disease. In certain embodiments, the compositions are useful for treating and/or preventing a liver disease. In certain embodiments, the compositions are useful for treating and/or preventing a spleen disease. In certain embodiments, the compositions are useful for treating and/or preventing a respiratory disease. In certain embodiments, the compositions are useful for treating and/or preventing a lung disease. In certain embodiments, the compositions are useful for treating and/or preventing a painful condition. In certain embodiments, the compositions are useful for treating and/or preventing a psychiatric disorder. In certain embodiments, the compositions are useful for treating and/or preventing a metabolic disorder. In certain embodiments, the compositions are useful for treating and/or preventing hepatic carcinoma, hypercholesterolemia, refractory anemia, or familial amyloid neuropathy.

The agents may be provided in an effective amount in a composition described herein. In certain embodiments, the effective amount is a therapeutically effective amount. In certain embodiments, the effective amount is a prophylactically effective amount. In certain embodiments, the effective amount is an amount effective for treating a disease described herein. In certain embodiments, the effective amount is an amount effective for preventing a disease described herein.

An effective amount of an agent may vary from about 0.001 mg/kg to about 1000 mg/kg in one or more dose administrations for one or several days (depending on the mode of administration). In certain embodiments, the effective amount per dose varies from about 0.001 to about 1000 mg/kg, from about 0.01 to about 750 mg/kg, from about 0.1 to about 500 mg/kg, from about 1.0 to about 250 mg/kg, and from about 10.0 to about 150 mg/kg.

A composition of the disclosure may include a particle described herein. In certain embodiments, the composition is in the form of a particle. In certain embodiments, the particle is a nanoparticle or microparticle. In certain embodiments, a composition described herein is in the form of liposomes or micelles. It is understood that, in certain embodiments, the particles, micelles, or liposomes result from self-assembly of the components of the composition. In certain embodiments, the particle, micelle, or liposome encapsulates an agent. The agent to be delivered by the particle, micelle, or liposome may be in the form of a gas, liquid, or solid. The compounds described herein may be combined with polymers (synthetic or natural), surfactants, substituted or unsubstituted cholesterols, steroids, carbohydrates, proteins, lipids, lipidoids, etc. to form the particles. These particles may be further combined with an excipient to form the composition. The particles, micelles, and liposomes are described in more detail herein.

The compositions described herein (e.g., pharmaceutical compositions) can be prepared by any method known in the art (e.g., pharmacology). In certain embodiments, such preparatory methods include the steps of bringing a compound described herein into association with an agent described herein (i.e., the "active ingredient"), optionally with a carrier or excipient, and/or one or more other accessory ingredients, and then, if necessary and/or desirable, shaping, and/or packaging the product into a desired single- or multi-dose unit.

Compositions can be prepared, packaged, and/or sold in bulk, as a single unit dose, and/or as a plurality of single unit doses. A unit dose is a discrete amount of the composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the excipient (e.g., the pharmaceutically or cosmetically acceptable excipient), and/or any additional ingredients in a composition described herein will vary, depending upon the identity, size, and/or condition of the subject to whom the composition is administered and further depending upon the route by which the composition is to be administered. The composition may comprise between 0.1% and 100% (w/w) active ingredient.

Excipients used in the manufacture of provided compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween® 20), polyoxyethylene sorbitan (Tween® 60), polyoxyethylene sorbitan monooleate (Tween® 80), sorbitan monopalmitate (Span® 40), sorbitan monostearate (Span® 60), sorbitan tristearate (Span® 65), glyceryl monooleate, sorbitan monooleate (Span® 80), polyoxyethylene esters (e.g., polyoxyethylene monostearate (Myrj® 45), polyoxyethylene hydrogenated castor oil, polyethoxylated castor oil, polyoxymethylene stearate, and Solutol®), sucrose fatty acid esters, polyethylene glycol fatty acid esters (e.g., Cremophor®), polyoxyethylene ethers, (e.g., polyoxyethylene lauryl ether (Brij® 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F-68, Poloxamer P-188, cetrimonium bromide, cetylpyridinium chloride, benzalkonium chloride, docusate sodium, and mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan), alginates, polyethylene oxide, polyethylene glycol, inorganic calcium salts, silicic acid, polymethacrylates, waxes, water, alcohol, and mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, sodium sulfite, and mixtures thereof.

Exemplary chelating agents include ethylenediaminetetraacetic acid (EDTA) and salts and hydrates thereof (e.g., sodium edetate, disodium edetate, trisodium edetate, calcium disodium edetate, and dipotassium edetateke), citric acid and salts and hydrates thereof (e.g., citric acid monohydrate), fumaric acid and salts and hydrates thereof, malic acid and salts and hydrates thereof, phosphoric acid and salts and hydrates thereof, tartaric acid and salts and hydrates thereof, and mixtures thereof.

Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, thimerosal, and mixtures thereof.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, sorbic acid, and mixtures thereof.

Exemplary alcohol preservatives include ethanol, polyethylene glycol, phenol, phenolic compounds, bisphenol, chlorobutanol, hydroxybenzoate, phenylethyl alcohol, and mixtures thereof.

Exemplary acidic preservatives include vitamin A, vitamin C, vitamin E, beta-carotene, citric acid, acetic acid, dehydroacetic acid, ascorbic acid, sorbic acid, phytic acid, and mixtures thereof.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant® Plus, Phenonip®, methylparaben, Germall® 115, Germaben® II, Neolone®, Kathon®, Euxyl®, and mixtures thereof.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Additionally, the composition may further comprise an apolipoprotein. Previous studies have reported that Apolipoprotein E (ApoE) was able to enhance cell uptake and gene silencing for a certain type of materials. See, e.g., Akinc, A., et al., *Targeted delivery of RNAi therapeutics with endogenous and exogenous ligand-based mechanisms*. Mol Ther. 18(7): p. 1357-64. In certain embodiments, the apolipoprotein is ApoA, ApoB, ApoC, ApoE, or ApoH, or an isoform thereof.

Liquid dosage forms for oral and parenteral administration include emulsions, microemulsions, solutions, suspensions, syrups and elixirs. In certain embodiments, the emulsions, microemulsions, solutions, suspensions, syrups and elixirs are or cosmetically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates described herein are mixed with solubilizing agents such as Cremophor®, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Compositions for rectal or vaginal administration are typically suppositories which can be prepared by mixing the conjugates with suitable non-irritating excipients or carriers such as cocoa butter, polyethylene glycol, or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, excipient or carrier (e.g., pharmaceutically or cosmetically acceptable excipient or carrier) such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the formulation art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Dosage forms for topical and/or transdermal administration of a composition of this disclosure may include ointments, pastes, creams, lotions, gels, powders, solutions, sprays, inhalants, and/or patches. Generally, the active ingredient is admixed under sterile conditions with a carrier or excipient and/or any needed preservatives and/or buffers as can be required. Additionally, the present disclosure contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions can be administered by devices which limit the effective penetration length of a needle into the skin, such as those described in PCT publication WO 99/34850 and functional equivalents thereof. Alternatively or additionally, conventional syringes can be used in the classical mantoux method of intradermal administration. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate the agent in powder form through the outer layers of the skin to the dermis are suitable.

Formulations suitable for topical administration include, but are not limited to, liquid and/or semi-liquid preparations such as liniments, lotions, oil-in-water and/or water-in-oil emulsions such as creams, ointments, and/or pastes, and/or solutions and/or suspensions. Topically administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A composition described herein can be prepared, packaged, and/or sold in a formulation suitable for pulmonary administration via the buccal cavity. Such a formulation may comprise dry particles which comprise the active ingredient. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Compositions described herein formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a composition described herein. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein. A composition described herein can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A composition described herein can be prepared, packaged, and/or sold in a formulation for ophthalmic administration. Such formulations may, for example, be in the form of eye drops including, for example, a 0.1/1.0% (w/w) solution and/or suspension of the active ingredient in an aqueous or oily liquid carrier or excipient. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are also contemplated as being within the scope of this disclosure.

Although the descriptions of compositions provided herein are principally directed to compositions which are suitable for administration to humans, it will be understood by the skilled artisan that such compositions are generally suitable for administration to animals of all sorts. Modification of compositions suitable for administration to humans in order to render the compositions suitable for administration to various animals is well understood, and the ordinarily skilled veterinary pharmacologist can design and/or perform such modification with ordinary experimentation.

Compounds described herein are typically formulated in dosage unit form for ease of administration and uniformity of dosage. It will be understood, however, that the total daily usage of the compositions of the present disclosure will be decided by the attending physician within the scope of sound medical judgment. The specific therapeutically effective dose level for any particular subject or organism will depend upon a variety of factors including the disease being treated and the severity of the disorder, the activity of the specific active ingredient employed, the specific composition employed, the age, body weight, general health, sex, and diet of the subject, the time of administration, route of administration, and rate of excretion of the specific active ingredient employed, the duration of the treatment, drugs used in combination or coincidental with the specific active ingredient employed, and like factors well known in the medical arts.

The compositions described herein can be administered by any suitable route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. In certain embodiments, the compositions are administered by oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration).

The exact amount of an agent required to achieve an effective amount will vary from subject to subject, depending, for example, on species, age, and general condition of a subject, severity of the side effects or disorder, identity of the particular agent, mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of an agent for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of an agent per unit dosage form.

In certain embodiments, the agents described herein may be at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic and/or prophylactic effect.

It will be appreciated that dose ranges as described herein provide guidance for the administration of provided compositions to an adult. The amount to be administered to, for example, a child or an adolescent can be determined by a medical practitioner or person skilled in the art and can be lower or the same as that administered to an adult.

Compositions described herein may further include a hydrophilic polymer (e.g., polyethylene glycol (PEG)). The compositions described herein may further include a lipid (e.g., a substituted or unsubstituted cholesterol, a steroid, or a polyethylene glycol (PEG)-containing material). In certain embodiments, the lipid included in the compositions is a triglyceride, a driglyceride, a PEGylated lipid, dimyristoyl-PEG2000 (DMG-PEG2000), a phospholipid (e.g., 1,2-distearoyl-sn-glycero-3-phosphocholine (DSPC)), dioleoyl-phosphatidylethanolamine (DOPE), a substituted or unsubstituted cholesterol, a steroid an apolipoprotein, or a combination thereof. In certain embodiments, the compositions include two components selected from the group consisting of the following components: a hydrophilic polymer, a triglyceride, a driglyceride, a PEGylated lipid, a phospholipid, a substituted or unsubstituted cholesterol, a steroid, and an apolipoprotein. In certain embodiments, the compositions include three components selected from the group consisting of the following components: a hydrophilic polymer, a triglyceride, a driglyceride, a PEGylated lipid, a phospholipid, a substituted or unsubstituted cholesterol, a steroid, and an apolipoprotein. In certain embodiments, the compositions include at least four components selected from the group consisting of the following components: a hydrophilic polymer, a triglyceride, a driglyceride, a PEGylated lipid, a phospholipid, a substituted or unsubstituted cholesterol, a steroid, and an apolipoprotein. In certain embodiments, the compositions include a hydrophilic polymer, a phospholipid, a substituted or unsubstituted cholesterol, and a steroid. In certain embodiments, the compositions include PEG, DSPC, and cholesterol.

Compositions described herein may be useful in other applications, e.g., non-medical applications. Nutraceutical compositions described herein may be useful in the delivery of an effective amount of a nutraceutical, e.g., a dietary supplement, to a subject in need thereof. Cosmetic compositions described herein may be formulated as a cream, ointment, balm, paste, film, or liquid, etc., and may be useful in the application of make-up, hair products, and materials useful for personal hygiene, etc. Compositions described herein may be useful for other non-medical applications, e.g., such as an emulsion, emulsifier, or coating, useful, for example, as a food component, for extinguishing fires, for disinfecting surfaces, for oil cleanup, and/or as a bulk material.

Agents

Agents that are delivered by the systems (e.g., pharmaceutical compositions) described herein may be pharmaceutical (e.g., therapeutic or prophylactic), diagnostic, cosmetic, or nutraceutical agents. Any chemical compound to be administered to a subject or to be contacted with a tissue or cell may be delivered using the compositions, complexes, particles, micelles, or liposomes described herein. The agent may be a small molecule (e.g., a small organic molecule or small inorganic molecule), protein, peptide, polynucleotide, targeting agent, isotopically labeled chemical compound, vaccine, or immunological agent. The agent may be an agent useful in bioprocessing (e.g., intracellular manufacturing of proteins, such as a cell's bioprocessing of a commercially useful chemical or fuel). For example, intracellular delivery of an agent may be useful in bioprocessing by maintaining the cell's health and/or growth, e.g., in the manufacturing of proteins. Any chemical compound to be administered to a subject or contacted with a tissue or cell may be delivered to the subject, tissue, or cell using the compositions described herein.

Exemplary agents that may be included in a composition described herein include, but are not limited to, small molecules, organometallic compounds, polynucleotides, proteins, peptides, carbohydrates, monosaccharides, oligosaccharides, polysaccharides, nucleoproteins, mucoproteins, lipoproteins, small molecules linked to proteins, glycoproteins, steroids, nucleotides, oligonucleotides, polynucleotides, nucleosides, antisense oligonucleotides, lipids, hormones, vitamins, cells, metals, targeting agents, isotopically labeled chemical compounds, drugs (e.g., compounds approved for human or veterinary use by the U.S. Food and Drug Administration as provided in the Code of Federal Regulations), vaccines, immunological agents, agents useful in bioprocessing, and mixtures thereof. The targeting agents are described in more detail herein. In certain embodiments, the agents are nutraceutical agents. In certain embodiments, the agents are pharmaceutical agents (e.g., a therapeutic or prophylactic agent). In certain embodiments, the agent is an antibiotic agent (e.g., an anti-bacterial, anti-viral, or anti-fungal agent), anesthetic, steroidal agent, anti-proliferative agent, anti-inflammatory agent, anti-angiogenesis agent, anti-neoplastic agent, anti-cancer agent, anti-diabetic agent, antigen, vaccine, antibody, decongestant, antihypertensive, sedative, birth control agent, progestational agent, anti-cholinergic, analgesic, immunosuppressant, anti-depressant, anti-psychotic, β-adrenergic blocking agent, diuretic, cardiovascular active agent, vasoactive agent, non-steroidal, nutritional agent, anti-allergic agent, or pain-relieving agent. Vaccines may comprise isolated proteins or peptides, inactivated organisms and viruses, dead organisms and viruses, genetically altered organisms or viruses, and cell extracts. Therapeutic and prophylactic agents may be combined with interleukins, interferon, cytokines, and adjuvants such as cholera toxin, alum, and Freund's adjuvant, etc.

In certain embodiments, an agent described herein is a polynucleotide. In certain embodiments, the agent is a DNA. In certain embodiments, the agent is plasmid DNA (pDNA). In certain embodiments, the agent is single-stranded DNA (ssDNA), double-stranded DNA (dsDNA), genomic DNA (gDNA), complementary DNA (cDNA), antisense DNA, chloroplast DNA (ctDNA or cpDNA), microsatellite DNA, mitochondrial DNA (mtDNA or mDNA), kinetoplast DNA (kDNA), provirus, lysogen, repetitive DNA, satellite DNA, or viral DNA. In certain embodiments, the agent is an RNA. In certain embodiments, the agent is siRNA. In certain embodiments, the agent is mRNA. In certain embodiments, the agent is single-stranded RNA (ssRNA), double-stranded RNA (dsRNA), small interfering RNA (siRNA), precursor messenger RNA (pre-mRNA), small hairpin RNA or short hairpin RNA (shRNA), microRNA (miRNA), guide RNA (gRNA), transfer RNA (tRNA), antisense RNA (asRNA), heterogeneous nuclear RNA (hnRNA), coding RNA, non-coding RNA (ncRNA), long non-coding RNA (long ncRNA or lncRNA), satellite RNA, viral satellite RNA, signal recognition particle RNA, small cytoplasmic RNA, small nuclear RNA (snRNA), ribosomal RNA (rRNA), Piwi-interacting RNA (piRNA), polyinosinic acid, ribozyme, flexizyme, small nucleolar RNA (snoRNA), spliced leader RNA, viral RNA, or viral satellite RNA. In certain embodiments, the agent is a pDNA, siRNA, or a combination thereof. In certain embodiments, the agent is a pDNA, siRNA, mRNA, or a combination thereof. In certain embodiments, the agent is an RNA that carries out RNA interference (RNAi). The phenomenon of RNAi is discussed in greater detail, for example, in the following references: Elbashir et al., 2001, *Genes Dev.*, 15:188; Fire et al., 1998, *Nature*, 391:806; Tabara et al., 1999, *Cell*, 99:123; Hammond et al., *Nature*, 2000, 404:293; Zamore et al., 2000, *Cell*, 101:25; Chakraborty, 2007, *Curr. Drug Targets*, 8:469; and Morris and Rossi, 2006, *Gene Ther.*, 13:553. In certain embodiments, the agent is an siRNA. In certain embodiments, the agent is a dsRNA. In certain embodiments, the agent is an shRNA. In certain embodiments, the agent is an miRNA. miRNAs are genomically encoded non-coding RNAs of about 21-23 nucleotides in length that help regulate gene expression, particularly during development. See, e.g., Bartel, 2004, *Cell*, 116:281; Novina and Sharp, 2004, *Nature*, 430:161; and U.S. Patent Application Publication, US 2005/0059005; Wang et al., 2007, *Front. Biosci.*, 12:3975; and Zhao, 2007, *Trends Biochem. Sci.*, 32:189. In certain embodiments, the agent is an mRNA. In certain embodiments, the agent is a tRNA. In certain embodiments, the agent is an asRNA. In certain embodiments, the agent is a combination of pDNA and siRNA. In certain embodiments, upon delivery of an RNA into a subject, tissue, or cell, the RNA is able to interfere with the expression of a specific gene in the subject, tissue, or cell.

In certain embodiments, the polynucleotide may be provided as an antisense agent or RNAi. See, e.g., Fire et al., *Nature* 391:806-811, 1998. Antisense therapy is meant to include, e.g., administration or in situ provision of single- or double-stranded polynucleotides, or derivatives thereof, which specifically hybridize, e.g., bind, under cellular conditions, with cellular mRNA and/or genomic DNA, or mutants thereof, so as to inhibit the expression of the encoded protein, e.g., by inhibiting transcription and/or translation. See, e.g., Crooke, "Molecular mechanisms of action of antisense drugs," *Biochim. Biophys. Acta* 1489(1): 31-44, 1999; Crooke, "Evaluating the mechanism of action of anti-proliferative antisense drugs," *Antisense Nucleic Acid Drug Dev.* 10(2):123-126, discussion 127, 2000; *Methods in Enzymology* volumes 313-314, 1999. The binding may be by conventional base pair complementarity, or, for example, in the case of binding to DNA duplexes, through specific interactions in the major groove of the double helix (i.e., triple helix formation). See, e.g., Chan et al., *J. Mol. Med.* 75(4):267-282, 1997.

The siRNA, dsRNA, shRNA, miRNA, mRNA, tRNA, asRNA, and/or RNAi described herein can be designed and/or predicted using one or more of a large number of available algorithms. To give but a few examples, the following resources can be utilized to design and/or predict polynucleotides: algorithms found at Alnylum Online; Dharmacon Online; OligoEngine Online; Molecula Online; Ambion Online; BioPredsi Online; RNAi Web Online; Chang Bioscience Online; Invitrogen Online; LentiWeb Online GenScript Online; Protocol Online; Reynolds et al., 2004, *Nat. Biotechnol.*, 22:326; Naito et al., 2006, *Nucleic Acids Res.*, 34:W448; Li et al., 2007, *RNA*, 13:1765; Yiu et al., 2005, *Bioinformatics*, 21:144; and Jia et al., 2006, *BMC Bioinformatics*, 7: 271.

The polynucleotide included in a composition described herein may be of any size or sequence, and they may be single- or double-stranded. In certain embodiments, the polynucleotide includes at least about 30, at least about 100, at least about 300, at least about 1,000, at least about 3,000, or at least about 10,000 base pairs. In certain embodiments, the polynucleotide includes less than about 10,000, less than about 3,000, less than about 1,000, less than about 300, less than about 100, or less than about 30 base pairs. Combinations of the above ranges (e.g., at least about 100 and less than about 1,000) are also within the scope of the disclosure. The polynucleotide may be provided by any suitable means known in the art. In certain embodiments, the polynucleotide is engineered using recombinant techniques. See, e.g., Ausubel et al., *Current Protocols in Molecular Biology* (John Wiley & Sons, Inc., New York, 1999); *Molecular Cloning: A Laboratory Manual*, 2nd Ed., ed. by Sambrook, Fritsch, and Maniatis (Cold Spring Harbor Laboratory Press: 1989). The polynucleotide may also be obtained from natural sources and purified from contaminating components found normally in nature. The polynucleotide may also be chemically synthesized in a laboratory. In certain embodiments, the polynucleotide is synthesized using standard solid phase chemistry. The polynucleotide may be isolated and/or purified. In certain embodiments, the polynucleotide is substantially free of impurities. In certain embodiments, the polynucleotide is at least about 50%, at least about 60%, at least about 70%, at least about 80%, at least about 90%, at least about 95%, or at least about 99% free of impurities.

The polynucleotide may be modified by physical, chemical, and/or biological means. The modifications include methylation, phosphorylation, and/or end-capping, etc. In certain embodiments, the modifications lead to increased stability of the polynucleotide.

Wherever a polynucleotide is employed in the present disclosure, a derivative of the polynucleotide may also be used. These derivatives include products resulted from modifications of the polynucleotide in the base moieties, sugar moieties, and/or phosphate moieties of the polynucleotide. Modified base moieties include, but are not limited to, 2-aminoadenosine, 2-thiothymidine, inosine, pyrrolo-pyrimidine, 3-methyl adenosine, 5-methylcytidine, C5-bromouridine, C5-fluorouridine, C5-iodouridine, C5-propynyl-uridine, C5-propynyl-cytidine, C5-methylcytidine, 7-deazaadenosine, 7-deazaguanosine, 8-oxoadenosine, 8-oxoguanosine, 0(6)-methylguanine, and 2-thiocytidine. Modified sugar moieties include, but are not limited to, 2'-fluororibose, ribose, 2'-deoxyribose, 3'-azido-2',3'-dideoxyribose, 2',3'-dideoxyribose, arabinose (the 2'-epimer of ribose), acyclic sugars, and hexoses. The nucleosides may be strung together by linkages other than the phosphodiester linkage found in naturally occurring DNA and RNA. Modified linkages include, but are not limited to, phosphorothioate and 5'-N-phosphoramidite linkages. Combinations of the various modifications may be used in a single polynucleotide. These modified polynucleotides may be provided by any suitable means known in the art; however, as will be appreciated by those of skill in the art, the modified polynucleotides may be prepared using synthetic chemistry in vitro.

The polynucleotide described herein may be in any form, such as a circular plasmid, a linearized plasmid, a cosmid, a viral genome, a modified viral genome, or an artificial chromosome.

The polynucleotide described herein may be of any sequence. In certain embodiments, the polynucleotide encodes a protein or peptide. The encoded protein may be an enzyme, structural protein, receptor, soluble receptor, ion channel, active (e.g., pharmaceutically active) protein, cytokine, interleukin, antibody, antibody fragment, antigen, coagulation factor, albumin, growth factor, hormone, or insulin, etc. The polynucleotide may also comprise regulatory regions to control the expression of a gene. These regulatory regions may include, but are not limited to, promoters, enhancer elements, repressor elements, TATA boxes, ribosomal binding sites, and stop sites for transcription. In certain embodiments, the polynucleotide is not intended to encode a protein. For example, the polynucleotide may be used to fix an error in the genome of the cell being transfected.

In certain embodiments, the polynucleotide described herein comprises a sequence encoding an antigenic peptide or protein. A composition containing the polynucleotide can be delivered to a subject to induce an immunologic response sufficient to decrease the chance of a subsequent infection and/or lessen the symptoms associated with such an infection. The polynucleotide of these vaccines may be combined with interleukins, interferon, cytokines, and/or adjuvants described herein.

The antigenic protein or peptides encoded by the polynucleotide may be derived from bacterial organisms, such as *Streptocococcus pneumoniae, Haemophilus influenzae, Staphylococcus aureus, Streptococcus pyrogenes, Corynebacterium diphtheriae, Listeria monocytogenes, Bacillus anthracis, Clostridium tetani, Clostridium botulinum, Clostridium perfringens, Neisseria meningitidis, Neisseria gonorrhoeae, Streptococcus mutans, Pseudomonas aeruginosa, Salmonella typhi, Haemophilus parainfluenzae, Bordetella pertussis, Francisella tularensis, Yersinia pestis, Vibrio cholerae, Legionella pneumophila, Mycobacterium tuberculosis, Mycobacterium leprae, Treponema pallidum, Leptospirosis interrogans, Borrelia burgdorferi*, and *Camphylobacter jejuni*; from viruses, such as smallpox virus, influenza A virus, influenza B virus, respiratory syncytial virus, parainfluenza virus, measles virus, HIV virus, varicella-zoster virus, herpes simplex 1 virus, herpes simplex 2 virus, cytomegalovirus, Epstein-Barr virus, rotavirus, rhinovirus, adenovirus, papillomavirus, poliovirus, mumps virus, rabies virus, rubella virus, coxsackieviruses, equine encephalitis virus, Japanese encephalitis virus, yellow fever virus, Rift Valley fever virus, hepatitis A virus, hepatitis B virus, hepatitis C virus, hepatitis D virus, and hepatitis E virus; and from fungal, protozoan, or parasitic organisms, such as *Cryptococcus neoformans, Histoplasma capsulatum, Candida albicans, Candida tropicalis, Nocardia asteroides, Rickettsia ricketsii, Rickettsia typhi, Mycoplasma pneumoniae, Chlamydial psittaci, Chlamydial trachomatis, Plasmodium falciparum, Trypanosoma brucei, Entamoeba histolytica, Toxoplasma gondii, Trichomonas vaginalis*, and *Schistosoma mansoni*.

An agent described herein may be covalently or non-covalently (e.g., complexed or encapsulated) attached to a compound described herein, or included in a composition described herein. In certain embodiments, upon delivery of the agent into a cell, the agent is able to interfere with the expression of a specific gene in the cell.

In certain embodiments, an agent described herein may be a mixture of two or more agents that may be useful as, e.g., combination therapies. A composition including the mixture can be used to achieve a synergistic effect. In certain embodiments, the composition including the mixture can be used to improve the activity and/or bioavailability, reduce and/or modify the metabolism, inhibit the excretion, and/or modify the distribution of at least one of the two or more agents in a subject, tissue, or cell to which the mixture is administered or dosed. It will also be appreciated that the composition including the mixture may achieve a desired effect for the same disorder, and/or it may achieve different effects. The two or more agents in the mixture may be useful for treating and/or preventing a same disease or different diseases described herein.

The compositions (e.g., pharmaceutical compositions) described herein can be administered concurrently with, prior to, or subsequent to the one or more agents (e.g., pharmaceutical agents). Each one of the agents may be administered at a dose and/or on a time schedule determined for that agent. The agents may also be administered together with each other and/or with the composition described herein in a single dose or administered separately in different doses. The particular combination to employ in a regimen will take into account compatibility of the agents and/or the desired therapeutic and/or prophylactic effect to be achieved. In general, it is expected that the agents utilized in combination be utilized at levels that do not exceed the levels at which they are utilized individually. In some embodiments, the levels utilized in combination will be lower than those utilized individually.

Targeting Agents

Since it is often desirable to target a particular cell, collection of cells, or tissue, compounds described herein, and the compositions, complexes, liposomes, micelles, and particles thereof, may be modified to include targeting moieties. For example, the compounds may include a targeting moiety. The targeting agent may be included throughout a particle of a compound described herein or may be only on the surface (e.g., outer or inner surface) of the particle. A targeting agent may be a protein, peptide, carbohydrate, glycoprotein, lipid, small molecule, or polynucleotide, and a targeting moiety may be a fragment of the targeting agent. The targeting moiety or targeting agent may be used to target specific cells or tissues or may be used to promote endocytosis or phagocytosis of the particle. The targeting moieties or targeting agents include the ones known in the art. See, e.g., Cotten et al., *Methods Enzym.* 217:618, 1993. Examples of the targeting moieties and targeting agents include, but are not limited to, antibodies, antibodies, proteins, peptides, carbohydrates, receptor ligands, sialic acid, aptamers, and fragments thereof. If a targeting agent is included throughout a particle, the targeting agent may be included in the mixture that is used to form the particle. If the targeting agent is only on the surface of a particle, the targeting agent may be associated with (e.g., by covalent or non-covalent (e.g., electrostatic, hydrophobic, hydrogen bonding, van der Waals, π-π stacking) interactions) the formed particle using standard chemical techniques.

Complexes of a Lipidoid and an Agent

The present disclosure contemplates that the compounds described herein are useful in the delivery of an agent described herein to a subject, tissue, or cell. Without wishing to be bound by any particular theory, the compounds have several desirable properties that make a composition that includes the compound and an agent suitable for delivering the agent to a subject, tissue, or cell. The desirable properties include: 1) the ability of the compound to complex with and "protect" the agent that may otherwise be labile; 2) the ability of the compound to buffer the pH in an endosome of the cell; 3) the ability of the compound to act as a "proton sponge" and cause endosomolysis; and 4) the ability of the compound to substantially neutralize the negative charges of the agent.

A compound and agent described herein may form a complex in a composition of the disclosure. For example, a compound described herein comprises secondary or tertiary amino moieties, which may be useful in enhancing the ability of a composition that includes an agent to deliver the agent to a subject, tissue, or cell. The amino moieties, sterically hindered or not, may non-covalently interact with the agent, such as a polynucleotide. The agent may be contacted with the compound under conditions suitable to form a complex. In certain embodiments, the agent binds to the compound to form a complex through non-covalent interactions. In certain embodiments, the agent binds to the compound to form a complex through electrostatic interactions. Without wishing to be bound by any particular theory, one or more amino moieties of a compound described herein may be positively charged, and an agent described herein may be negatively charged (e.g., at the monophosphate, diphosphate, and/or triphosphate moieties of a polynucleotide), when the compound, or a composition thereof, is delivered to a subject, tissue, or cell (e.g., under physiological conditions). The agent may bind to the compound to form a complex through electrostatic interactions between the negative charges of the compound and the positive charges of the agent. By substantially neutralizing the charges (e.g., negative charges) of the agent, the resulting complex may be able to more easily pass through the hydrophobic membranes (e.g., cytoplasmic, lysosomal, endosomal, or nuclear) of a cell, compared to an agent whose charges are not neutralized. In certain embodiments, the complex is substantially neutral. In certain embodiments, the complex is slightly positively charged. In certain embodiments, the complex has a positive ζ-potential. In certain embodiments the ζ-potential is between 0 and +30.

An agent described herein, such as a polynucleotide, may be degraded chemically and/or enzymatically (e.g., by nucleases). The interaction of a compound described herein with the agent is thought to at least partially prevent the degradation of the agent.

A compound described herein may be at least partially provided as a salt (e.g., being protonated) so as to form a complex with a negatively charged agent. In certain embodiments, the complex form particles that are useful in the delivery of the agent to a subject, tissue, or cell. In certain embodiments, more than one compound described herein are associated with an agent. For example, the complex may include 1-10, 1-100, 1-1,000, 10-1,000, 100-1,000, or 100-10,000 compounds described herein associated with an agent.

The ratio of the amount of a compound described herein to the amount of an agent to be delivered in a described composition that includes the compound and agent (e.g., as a complex) may be adjusted so that the agent may be more efficiently delivered to a subject, tissue, or cell and/or the toxicity of the composition is decreased. In certain embodiments, the ratio of the compound to the agent is at least about 1:1, at least about 2:1, at least about 5:1, at least about 10:1, at least about 20:1, at least about 50:1, at least about 100:1, at least about 200:1, or at least about 500:1 mol/mol. In certain embodiments, the ratio of the compound to the agent is less than about 500:1, less than about 200:1, less than about 100:1, less than about 50:1, less than about 20:1, less than about 10:1, less than about 5:1, less than about 2:1, or less than about 1:1 mol/mol. Combinations of the above ranges (e.g., at least about 10:1 and less than about 100:1) are also within the scope of the disclosure.

The ratio of the amount of the amino moieties of a compound described herein to the amount of the phosphate moieties of a polynucleotide (i.e., nitrogen:phosphate ratio) in a described composition that includes the compound and polynucleotide (e.g., as a complex) may also be adjusted so that the polynucleotide may be more efficiently delivered to a subject, tissue, or cell and/or the toxicity of the composition is decreased. See, e.g., Incani et al., *Soft Matter* (2010) 6:2124-2138. In certain embodiments, the nitrogen:phosphate ratio is at least about 1:1, at least about 2:1, at least about 5:1, at least about 10:1, at least about 20:1, at least about 50:1, at least about 100:1, at least about 200:1, or at least about 500:1 mol/mol. In certain embodiments, the nitrogen:phosphate ratio is less than about 500:1, less than about 200:1, less than about 100:1, less than about 50:1, less than about 20:1, less than about 10:1, less than about 5:1, less than about 2:1, or less than about 1:1 mol/mol. Combinations of the above ranges (e.g., at least about 10:1 and less than about 100:1) are also within the scope of the disclosure.

Particles

A composition that includes a compound and agent described herein may be in the form of a particle. In certain embodiments, the compound is in the form of a particle. In certain embodiments, the agent is in the form of a particle. In certain embodiments, the compound and agent form a complex, and the complex is in the form of a particle. In certain embodiments, the compound encapsulates the agent and is in the form of a particle. In certain embodiments, the compound is mixed with the agent, and the mixture is in the form of a particle.

Encapsulation of an agent (e.g., a polynucleotide, such as an siRNA) within particles (e.g., nanoparticles) may offer numerous benefits for delivering the agent to a subject, tissue, or cell, including protection from degradation of the agent by ubiquitous nucleases, passive and active targeting, and/or evasion of endosomal Toll-like receptors (1-9). To date, several polymeric, lipid, and dendritic nanoparticles have been developed for the encapsulation and delivery of siRNAs (1, 3, 5, 7-15). Despite the delivery successes met by some of these carriers, challenges to efficient delivery exist, including particle dissociation via serum proteins, cellular uptake, endosomal escape, and appropriate intracellular disassembly. To address some of these challenges, single parameter studies that evaluate the effect of chemical structure on a single biological property or on delivery performance have been reported (10-17). Furthermore, high-throughput synthetic methods have been exploited for the accelerated discovery of potent lipid nanoparticles (LNPs) and evaluation of structure activity relationships (SARs) (16-20). In spite of these efforts, the relationships between physicochemical properties of nanoparticles and biological barriers, and that between biological barriers and gene silencing activity remain unclear. This lack of clarity has also resulted in poor in vitro-in vivo translation.

In certain embodiments, a compound described herein (e.g., a plurality of molecules of the compound) is in the form of a particle. In certain embodiments, a complex of a compound and agent described herein in a described composition is in the form of a particle. In certain embodiments, the particle is a microparticle. In certain embodiments, the particle is a nanoparticle. Such a nanoparticle may be referred to as a "lipid nanoparticle" (LNP). In certain embodiments, the average diameter of the particle is less than about 1 mm, less than about 300 m, less than about 100 µm, less than about 30 µm less than about 10 µm, less than about 3 µm, less than about 1 µm, less than about 300 nm, less than about 100 nm, less than about 30 nm, or less than about 10 nm. In certain embodiments, the average diameter of the particle is at least about 10 nm, at least about 30 nm, at least about 100 nm, at least about 300 nm, at least about 1 µm, at least about 3 µm, at least about 10 µm, at least about 30 µm, at least about 100 µm, at least about 300 µm, or at least about 1 mm. Combinations of the above ranges (e.g., at least about 100 nm and less than about 1 km) are also within the scope of the present disclosure.

In certain embodiments, a particle described herein includes an agent described herein. The particle may encapsulate the agent. A particle described herein may further include additional materials such as polymers (e.g., synthetic polymers (e.g., PEG, PLGA) and natural polymers (e.g., phospholipids, proteins)). In certain embodiments, the particle further includes a lipid (e.g., a substituted or unsubstituted cholesterol, a steroid, or a polyethylene glycol (PEG)-containing material). In certain embodiments, the additional materials are approved by a regulatory agency, such as the U.S. FDA, for human and/or veterinary use.

A particle described herein may be prepared using any suitable method known in the art, such as precipitation, milling, spray drying, single and double emulsion solvent evaporation, solvent extraction, phase separation, and simple and complex coacervation. In certain embodiments, methods of preparing the particles are the double emulsion process and spray drying. The conditions used in preparing the particles may be altered to yield particles of a desired size or property (e.g., hydrophobicity, hydrophilicity, external morphology, "stickiness", shape, and polydispersity). The method of preparing the particles and the conditions (e.g., solvent, temperature, concentration, and air flow rate) used may also depend on the agent being complexed, encapsulated, or mixed, and/or the composition of the matrix.

Methods developed for making particles for delivery of agents that are included in the particles are described in the literature. See, e.g., Doubrow, M., Ed., "Microcapsules and Nanoparticles in Medicine and Pharmacy," CRC Press, Boca Raton, 1992; Mathiowitz and Langer, *J. Controlled Release* 5:13-22, 1987; Mathiowitz et al., *Reactive Polymers* 6:275-283, 1987; Mathiowitz et al., *J. Appl. Polymer Sci.* 35:755-774, 1988.

If the particles prepared by any of the methods described herein have a size range outside of the desired range, the particles can be sized, for example, using a sieve. The particles may also be coated. In certain embodiments, the particles are coated with a targeting agent. In certain embodiments, the particles are coated with a surface-altering agent. In some embodiments, the particles are coated to achieve desirable surface properties (e.g., a particular charge).

Particles described herein may also be a micelle, liposome, or lipoplex.

Micelles, Liposomes, and Lipoplexes

A composition including a compound and agent described herein may be in the form of a micelle or liposome. In certain embodiments, the compound is in the form of a micelle or liposome. An agent described herein may be inside a micelle or liposome, and a lipidoid described herein may be inside the micelle or liposome. In certain embodiments, in a micelle or liposome, an agent is encapsulated in a lipidoid. Micelles and liposomes are typically useful in delivering an agent, such as a hydrophobic agent, to a subject, tissue, or cell. When the micelle or liposome is complexed with (e.g., encapsulates or covers) a polynucleotide, the resulting complex may be referred to as a "lipoplex." Many techniques for preparing micelles and liposomes are known in the art, and any such method may be used to make micelles and liposomes.

In certain embodiments, liposomes are formed through spontaneous assembly. In some embodiments, liposomes are formed when thin lipid films or lipid cakes are hydrated and stacks of lipid crystalline bilayers become fluid and swell. The hydrated lipid sheets detach during agitation and self-close to form large, multilamellar vesicles (LMV). This may prevent interaction of water with the hydrocarbon core of the bilayers at the edges. Once these liposomes have formed, reducing the size of the liposomes can be modified through input of sonic energy (sonication) or mechanical energy (extrusion). See, e.g., Walde, P. "Preparation of Vesicles (Liposomes)" In *Encylopedia of Nanoscience and Nanotechnology*; Nalwa, H. S. Ed. American Scientific Publishers: Los Angeles, 2004; Vol. 9, pp. 43-79; Szoka et al., "Comparative Properties and Methods of Preparation of Lipid Vesicles (Liposomes)" *Ann. Rev. Biophys. Bioeng.* 9:467-508, 1980; each of which is incorporated herein by reference. The preparation of lipsomes may involve preparing a compound described herein for hydration, hydrating the compound with agitation, and sizing the vesicles to achieve a homogenous distribution of liposomes. A compound described herein may be first dissolved in a solvent in a container to result in a homogeneous mixture. The solvent is then removed to form a film. This film is thoroughly dried to remove residual amount of the solvent, e.g., by placing the container in vacuo for a period of time. Hydration of the film may be accomplished by adding an aqueous medium and agitating the resulting mixture. Disruption of LMV suspensions using sonic energy typically produces small unilamellar vesicles (SUV) with diameters in the range of 15-50 nm. Lipid extrusion is a technique in which a lipid suspension is forced through a polycarbonate filter with a defined pore size to yield particles having a diameter near the pore size of the filter used. Extrusion through filters with 100 nm pores typically yields large, unilamellar vesicles (LUV) with a mean diameter of 120-140 nm. In certain embodiments, the amount of a compound described herein in the liposome is between about 30 mol % and about 80 mol %, between about 40 mol % and about 70 mol %, or between about 60 mol % and about 70 mol %, inclusive. In certain embodiments, the compound further complexes an agent, such as a polynucleotide.

Liposomes and micelles may also be prepared according to methods in the following scientific papers: Narang et al., "Cationic Lipids with Increased DNA Binding Affinity for Nonviral Gene Transfer in Dividing and Nondividing Cells," *Bioconjugate Chem.* 16:156-68, 2005; Hofland et al., "Formation of stable cationic lipid/DNA complexes for gene transfer," *Proc. Natl. Acad. Sci. USA* 93:7305-7309, July 1996; Byk et al., "Synthesis, Activity, and Structure—Activity Relationship Studies of Novel Cationic Lipids for DNA Transfer," *J. Med. Chem.* 41(2):224-235, 1998; Wu et al., "Cationic Lipid Polymerization as a Novel Approach for Constructing New DNA Delivery Agents," *Bioconjugate Chem.* 12:251-57, 2001; Lukyanov et al., "Micelles from lipid derivatives of water-soluble polymers as delivery systems for poorly soluble drugs," *Advanced Drug Delivery Reviews* 56:1273-1289, 2004; Tranchant et al., "Physicochemical optimisation of plasmid delivery by cationic lipids," *J. Gene Med.* 6:S24-S35, 2004; van Balen et al., "Liposome/Water Lipophilicity: Methods, Information Content, and Pharmaceutical Applications," *Medicinal Research Rev.* 24(3):299-324, 2004.

Kits

Also described herein are kits (e.g., packs). The kits provided may comprise a compound or composition described herein and a container (e.g., a vial, ampule, bottle, syringe, and/or dispenser package, or other suitable container). In some embodiments, a kit described herein further includes a second container comprising an excipient for dilution or suspension of a compound or composition described herein. In some embodiments, the compound or composition provided in the first container and the compound or composition provided in the second container are combined to form one unit dosage form.

In certain embodiments, the kits described herein are useful for delivering an agent to a subject, tissue, or cell. In certain embodiments, the kits are useful for delivering an agent to a target tissue described herein. In certain embodiments, the kits are useful for treating a disease described herein. In certain embodiments, the kits are useful for preventing a disease described herein.

In certain embodiments, the described kits further include instructions for administering a compound or composition described herein. The kits may also include information as required by a regulatory agency such as the U.S. Food and Drug Administration (FDA). In certain embodiments, the information included in the kits is prescribing information. In certain embodiments, the kits, including the instructions, provide for delivering an agent described herein to a subject, tissue, or cell. In certain embodiments, the kits, including the instructions, provide for treating a disease described herein. In certain embodiments, the kits, including the instructions, provide for preventing a disease described herein. The kit described herein may include one or more agents described herein as a separate composition.

Methods of Treatment and Uses

It is estimated that over 10,000 human diseases are caused by genetic disorders, which are abnormalities in genes or chromosomes. See, e.g., McClellan, J. and M. C. King, *Genetic heterogeneity in human disease.* Cell. 141(2): p. 210-7; Leachman, S. A., et al., *J. Dermatol. Sci.,* 2008. 51(3): p. 151-7. Many of these diseases are fatal, such as cancer, severe hypercholesterolemia, and familial amyloidotic polyneuropathy. See, e.g., Frank-Kamenetsky, M., et al., *Proc. Natl. Acad. Sci. U.S.A.* 2008. 105(33): p. 11915-20; Coelho, T., *Curr. Opin. Neurol.,* 1996. 9(5): p. 355-9. Since the discovery of gene expression silencing via RNA interference (RNAi) by Fire and Mello (Fire, A., et al., *Nature,* 1998. 391(6669): p. 806-11), there has been extensive effort toward developing therapeutic applications for RNAi in humans. See, e.g., Davis, M. E., *Mol. Pharm.* 2009. 6(3): p. 659-68; Whitehead, K. A., R. Langer, and D. G. Anderson, *Nat. Rev. Drug Discovery,* 2009. 8(2): p. 129-138; Tan, S. J., et al., *Small.* 7(7): p. 841-56; Castanotto, D. and J. J. Rossi, *Nature,* 2009. 457(7228): p. 426-33; Chen, Y. and L. Huang, *Expert Opin. Drug Deliv.* 2008. 5(12): p. 1301-11; Weinstein, S. and D. Peer, Nanotechnology. 21(23): p. 232001; Fenske, D. B. and P. R. Cullis, *Expert Opin. Drug Deliv.* 2008. 5(1): p. 25-44; and Thiel, K. W. and P. H. Giangrande, *Oligonucleotides,* 2009. 19(3): p. 209-22. Currently, there are more than 20 clinical trials ongoing or completed involving siRNA therapeutics, which have shown promising results for the treatment of various diseases. See, e.g., Burnett, J. C., J. J. Rossi, and K. Tiemann, *Biotechnol. J.* 6(9): p. 1130-46. However, the efficient and safe delivery of siRNA is still a key challenge in the development of siRNA therapeutics. See, e.g., Juliano, R., et al., *Mol. Pharm.* 2009. 6(3): p. 686-95.

In another aspect, the present disclosure provides methods of delivering an agent described herein (e.g., polynucleotide) to a subject, tissue, or cell. In certain embodiments, described herein are methods of delivering the agent to a target tissue or target cell described herein. In certain embodiments, described herein are methods of selectively delivering the agent to a target tissue, compared to a non-target tissue. In certain embodiments, described herein are methods of selectively delivering the agent to a target cell, compared to a non-target cell. In certain embodiments, the agent is delivered into the subject, tissue, or cell by the methods described herein. In certain embodiments, the agent is selectively delivered into the target tissue or target cell by the methods described herein, compared to a non-target tissue or non-target cell, respectively.

Another aspect of the present disclosure relates to methods of increasing the delivery of an agent to a subject, tissue, or cell. In certain embodiments, the delivery of the agent to the subject, tissue, or cell is increased by a method described herein. In certain embodiments, the delivery of the agent to the subject, tissue, or cell by a method described herein is increased compared to the delivery of the agent to the subject, tissue, or cell by a control method that does not involve a compound described herein.

In another aspect, the present disclosure provides methods of treating a disease described herein in a subject in need thereof. In certain embodiments, the present disclosure provides methods of preventing a disease described herein in a subject in need thereof. In certain embodiments, the disease is treated by the methods. In certain embodiments, a symptom of the disease is reduced or eliminated by the methods. In certain embodiments, the progression of the disease is slowed by the methods. In certain embodiments, the disease is prevented by the methods. In certain embodiments, the onset of the disease is delayed by the methods.

In another aspect, the present disclosure provides methods of reducing the risk of developing a disease described herein in a subject in need thereof. In certain embodiments, the risk of developing the disease is reduced by the methods.

In certain embodiments, a disease described herein is a genetic disease. In certain embodiments, the genetic disease is a genetic disease described herein. In certain embodiments, the disease is cancer. In certain embodiments, the cancer is a cancer described herein. In certain embodiments, the disease is a benign neoplasm. In certain embodiments, the benign neoplasm is a benign neoplasm described herein. In certain embodiments, the disease is pathological angiogenesis. In certain embodiments, the pathological angiogenesis is pathological angiogenesis described herein. In certain embodiments, the disease is an inflammatory disease. In certain embodiments, the disease is an autoimmune disease. In certain embodiments, the disease is a hematological disease. In certain embodiments, the disease is a neurological disease. In certain embodiments, the disease is an immunological disease. In certain embodiments, the disease is a gastrointestinal disease. In certain embodiments, the disease is a liver disease. In certain embodiments, the disease is a spleen disease. In certain embodiments, the disease is a respiratory disease. In certain embodiments, the disease is a painful condition. In certain embodiments, the painful condition is a painful condition described herein. In certain embodiments, the painful condition is inflammatory pain. In certain embodiments, the painful condition (e.g., inflammatory pain) is associated with an inflammatory disorder and/or an autoimmune disorder. In certain embodiments, the disease is a psychiatric disorder. In certain embodiments, the disease is a metabolic disorder. In certain embodiments, the disease is hepatic carcinoma. In certain embodiments, the disease is hypercholesterolemia. In certain embodiments, the disease is refractory anemia. In certain embodiments, the disease is familial amyloid neuropathy.

Another aspect of the present disclosure relates to methods of genetically engineering a subject. In certain embodiments, the subject is genetically engineered to increase the growth of the subject. In certain embodiments, the subject is genetically engineered to increase the subject's resistance to pathogenic organisms and/or microorganisms (e.g., viruses, bacteria, fungi, protozoa, and parasites.

In certain embodiments, a method described herein includes administering to the subject a composition described herein. In certain embodiments, a method described herein includes administering to the subject an effective amount of a composition described herein. In certain embodiments, a method described herein includes administering to the subject a therapeutically effective amount of a pharmaceutical composition described herein.

In certain embodiments, a method described herein includes contacting the tissue with a composition described herein. In certain embodiments, a method described herein includes contacting the tissue with an effective amount of a composition described herein. In certain embodiments, a method described herein includes contacting the tissue with a therapeutically effective amount of a pharmaceutical composition described herein.

In certain embodiments, a method described herein includes contacting the cell with a composition described herein. In certain embodiments, a method described herein includes contacting the cell with an effective amount of a composition described herein. In certain embodiments, a method described herein includes contacting the cell with a therapeutically effective amount of a pharmaceutical composition described herein.

In certain embodiments, a subject described herein is a human. In certain embodiments, the subject is an animal. In certain embodiments, the subject is a non-human animal. The animal may be of either sex and may be at any stage of development. In certain embodiments, the subject is a fish. In certain embodiments, the subject is a mammal. In certain embodiments, the subject is a non-human mammal. In certain embodiments, the subject is a domesticated animal, such as a dog, cat, cow, pig, horse, sheep, or goat. In certain embodiments, the subject is a companion animal such as a dog or cat. In certain embodiments, the subject is a livestock animal such as a cow, pig, horse, sheep, or goat. In certain embodiments, the subject is a zoo animal. In another embodiment, the subject is a research animal such as a rodent (e.g., mouse, rat), dog, pig, or non-human primate. In certain embodiments, the animal is a genetically engineered animal. In certain embodiments, the animal is a transgenic animal. In certain embodiments, the subject is a human with a disease described herein. In certain embodiments, the subject is a human suspected of having a disease described. In certain embodiments, the subject is a human at risk of developing a disease described herein.

In certain embodiments, a cell described herein is in vivo. In certain embodiments, a cell described herein is in vitro.

Another aspect of the present disclosure relates to methods of screening a library of compounds to identify a compound that is useful in the methods described herein. In certain embodiments, the methods of screening a library of compounds are useful in identifying a compound with desired or undesired properties. In certain embodiments, the desired property is solubility in water, solubility at different pH, ability to bind polynucleotides, ability to bind heparin, ability to bind small molecules, ability to bind protein, ability to form microparticles, ability to increase transfection efficiency, ability to support normal cell growth, ability to inhibit abnormal cell growth, ability to support cell attachment, ability to support tissue growth, and/or intracellular delivery of an agent described herein and/or an agent complexed or attached thereto to aid in bioprocessing. In certain embodiments, the undesired property is the lack of a desired property. In certain embodiments, the compound identified is useful for delivering an agent described herein to a subject, tissue, or cell. In certain embodiments, the compound identified is useful for treating and/or preventing a disease described herein. In certain embodiments, the library of compounds is a library of compounds described herein. In certain embodiments, the methods of screening a library include providing at least two different compounds described herein; and performing at least one assay using the compounds. In certain embodiments, at least one assay is useful in identifying a compound that is useful in a method described herein. The assay may be an immunoassay, such as a sandwich-type assay, competitive binding assay, one-step direct test, two-step test, or blot assay. The step of performing at least one assay may be performed robotically or manually.

EXAMPLES

In order that the invention described herein may be more fully understood, the following examples are set forth. The synthetic and biological examples described in this application are offered to illustrate the compounds, pharmaceutical compositions, and methods provided herein and are not to be construed in any way as limiting their scope.

Example 1. Preparation of the Compounds

The compounds provided herein can be prepared from readily available starting materials using the following general methods (e.g., the method shown in Scheme E1, E2, or E3).

It will be appreciated that where typical or preferred process conditions (e.g., reaction temperatures, times, mole ratios of reactants, solvents, and pressures) are given, other process conditions can also be used unless otherwise stated. Optimum reaction conditions may vary with the particular reactants or solvents used, but such conditions can be determined by those skilled in the art by routine optimization.

Proton nuclear magnetic resonance ($^1$H NMR) spectra were recorded with a Varian INOVA-500 spectrometer and are reported in parts per million (ppm) on the δ scale, and are referenced from the residual protium in the NMR solvent (CDCl$_3$: δ 7.26 (CHCl$_3$).

Example 1.1. Preparation of the Compounds by Esterification

Compounds described herein (e.g., compounds of Formula (I) or (II)) may be prepared by esterification reactions (see, e.g., Neises et al., *Angew. Chem. Int. Ed.* 1978, 17, 522), such as the ones illustrated in Scheme 4.

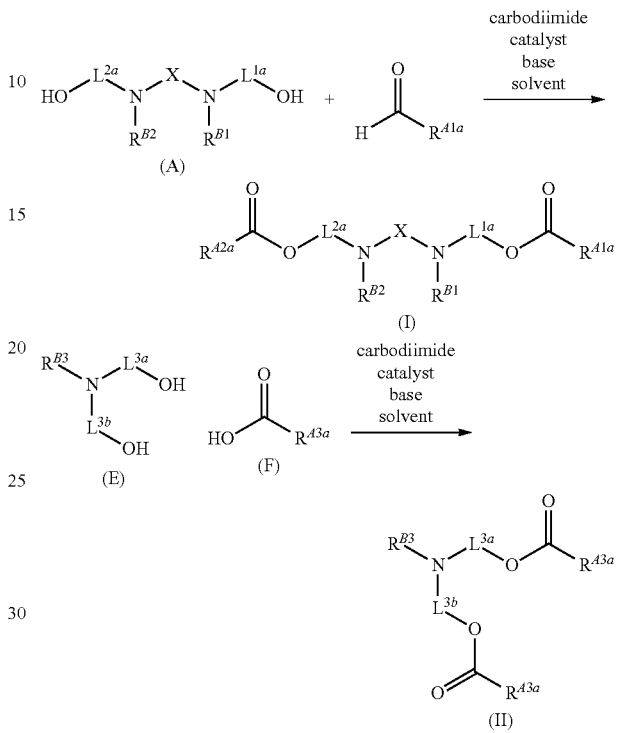

Scheme E1. Exemplary synthesis of compounds described herein by esterification

Figure 4A:
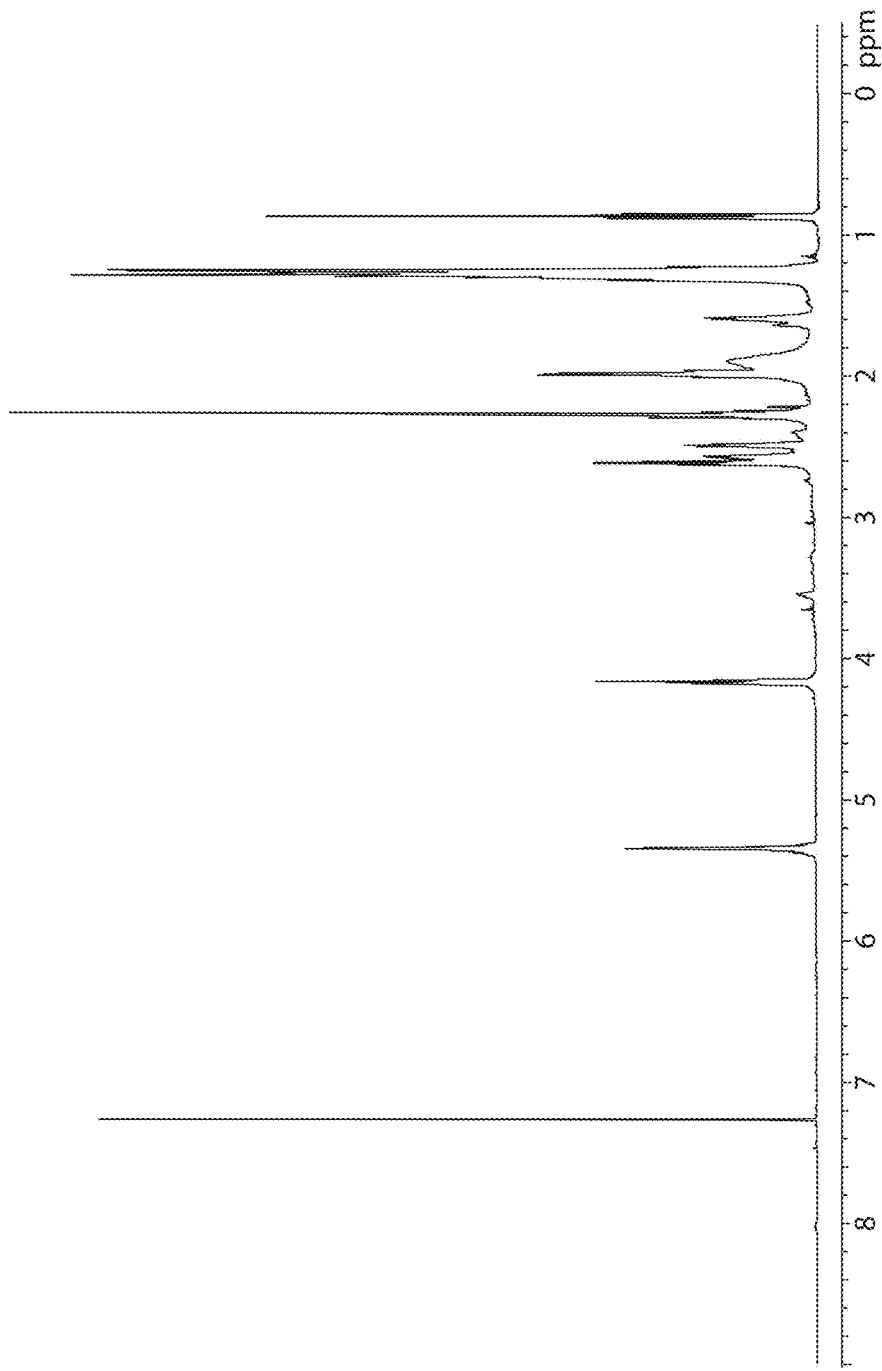
FIGS. 4A to 4C show exemplary proton nuclear magnetic resonance (CDCl$_3$) spectra of compounds 24C18Oleic (FIG. 4A), 24C18Linoleic3 (FIG. 4B), and 50C18Linoleic3 (FIG. 4C).
Figure 4B:
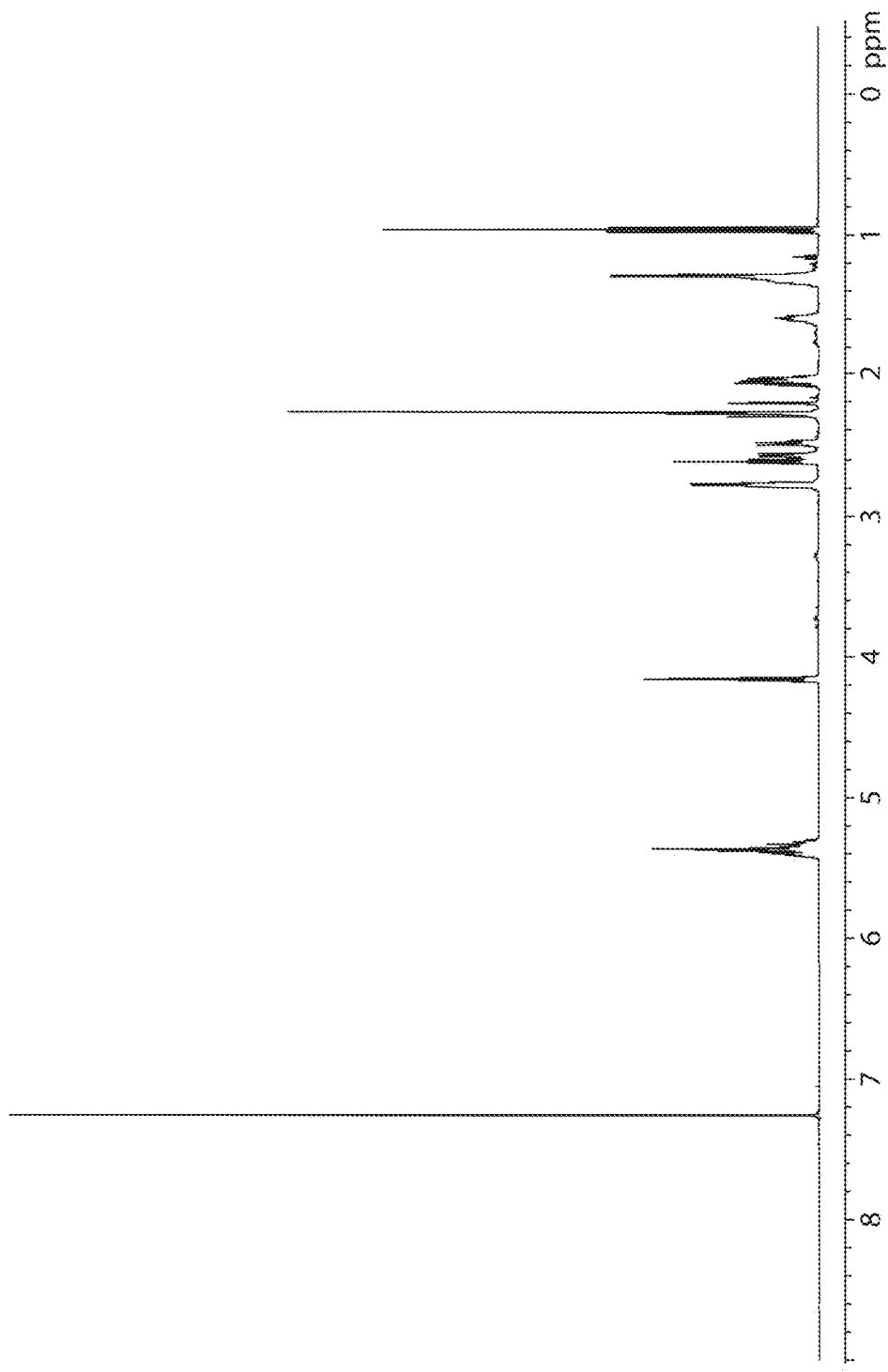
Figure 4C:
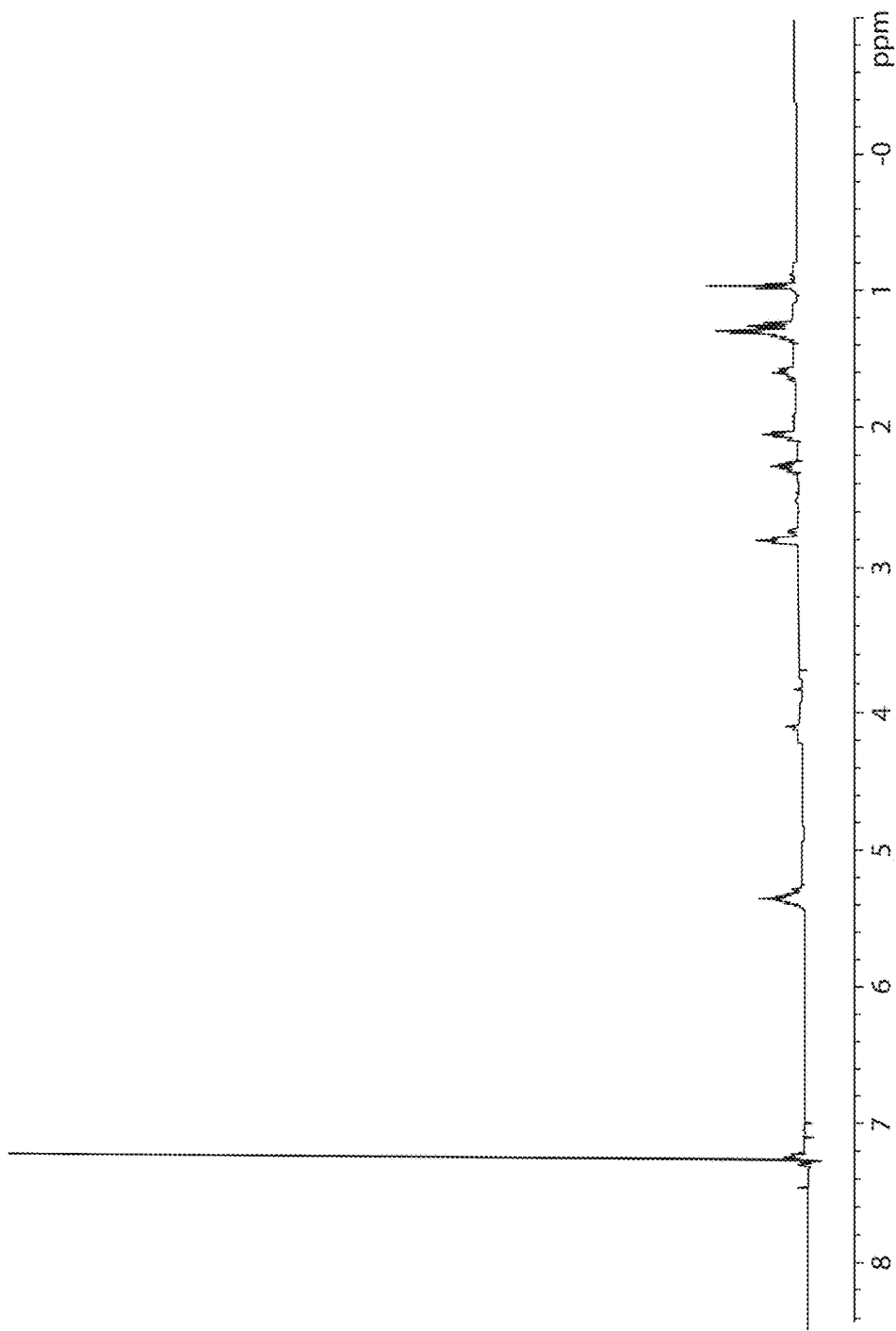
Figure 5A:
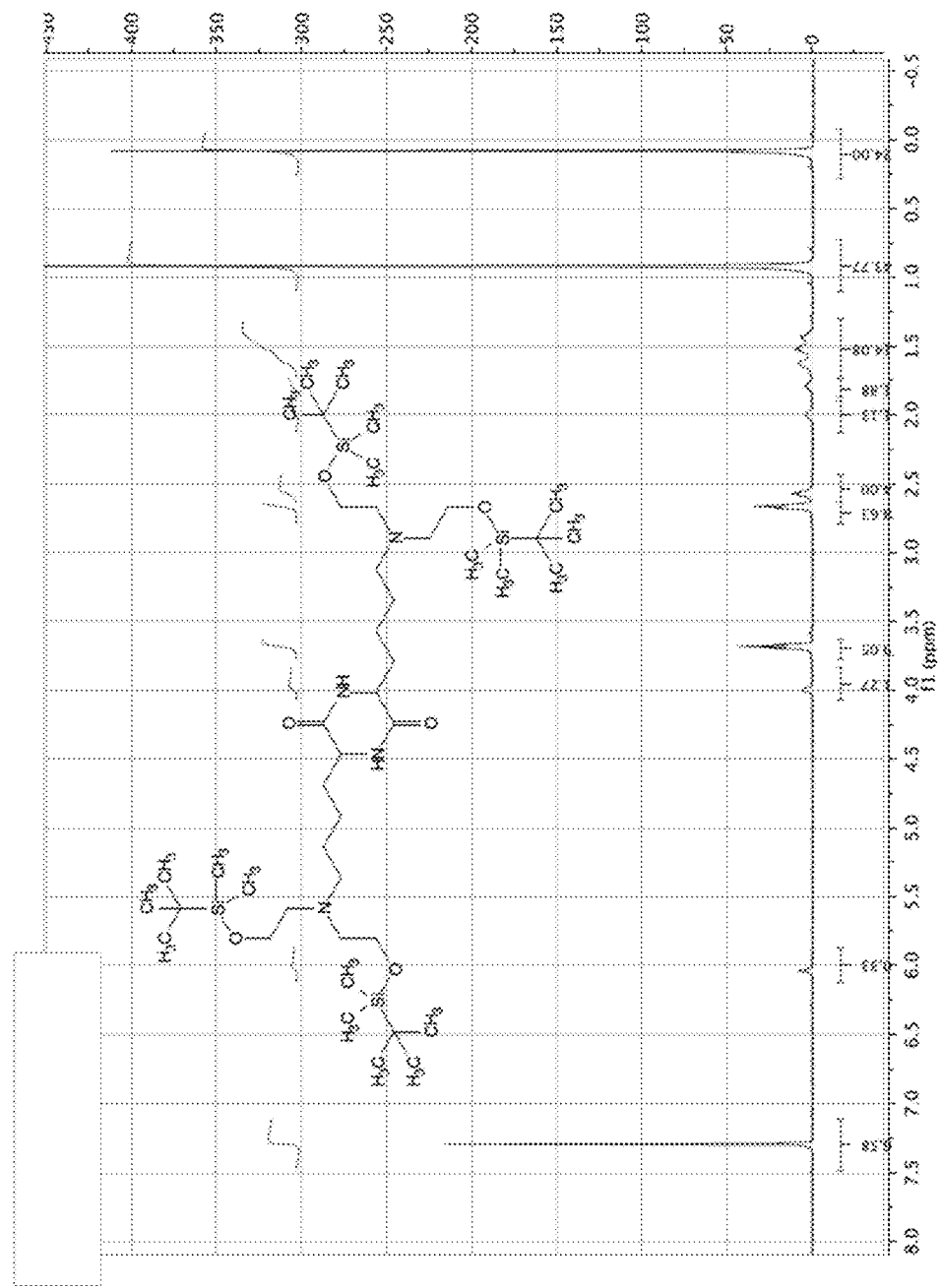
FIGS. 5A to 5P show exemplary proton nuclear magnetic resonance spectra of compounds (A) 50-C2-CC-DD core, (B) 50-C3-CC-DD core, (C) 50-C4-CC-DD core, (D) 50-C5-CC-DD core, (E) 50-C2-C9-4tail, (F) 50-C2-C12-4tail, (G) 50-C2-C15-4tail, (H) 50-C2-C18oleic-4tail, (I) 50-C2-C18elaidic-4tail, (J) 50-C2-C18lin2-4tail, (K) 50-C3-C18lin2-4tail, (L) 50-C4-C7-4tail, (M) 50-C4-C10-4tail, (N) 50-C4-C13-4tail, (O) 50-C4-C18oleic-4tail, and (P) 50-C4-C18lin2-4tail.
Figure 5B:
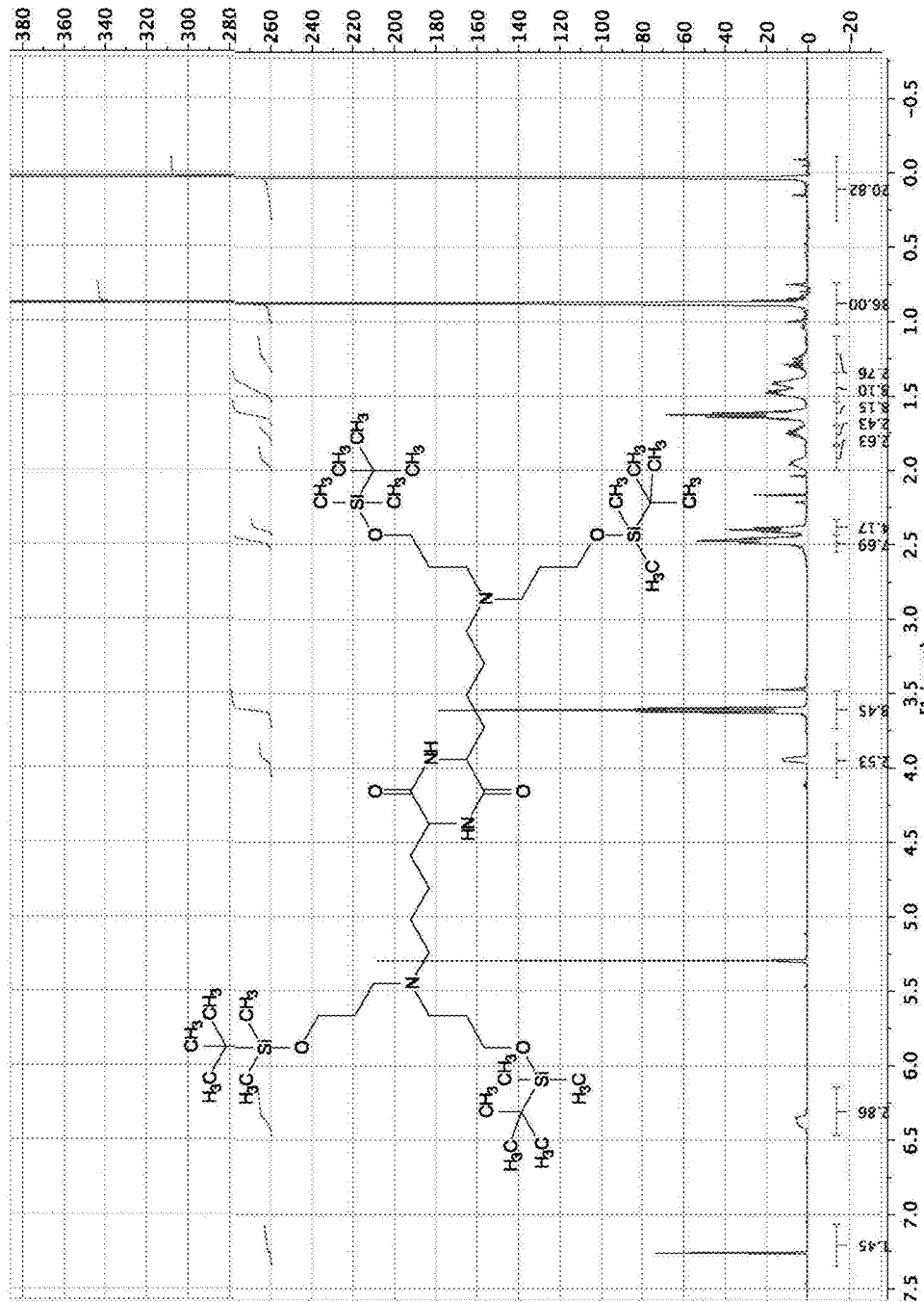
Figure 5C:
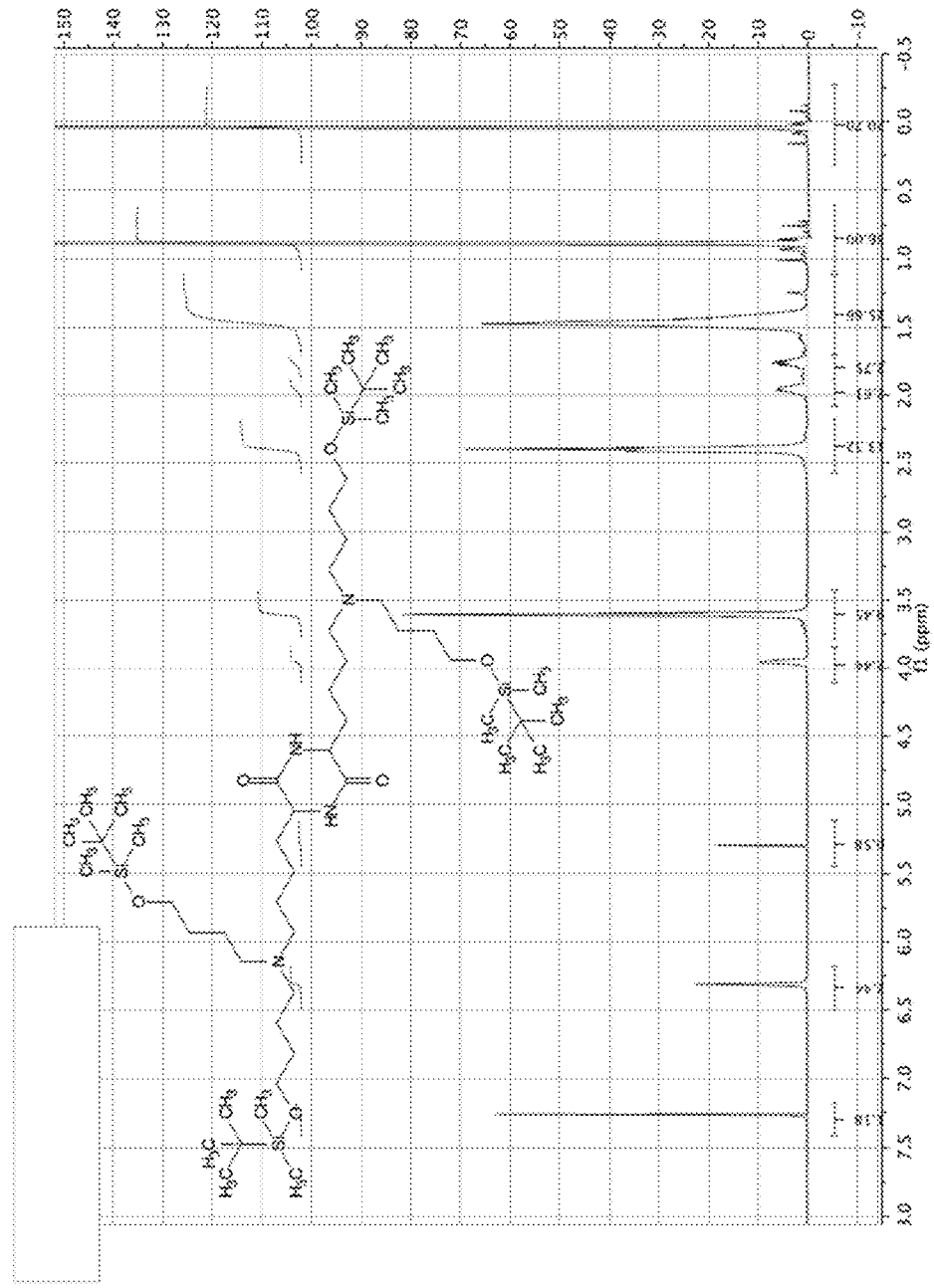
Figure 5D:
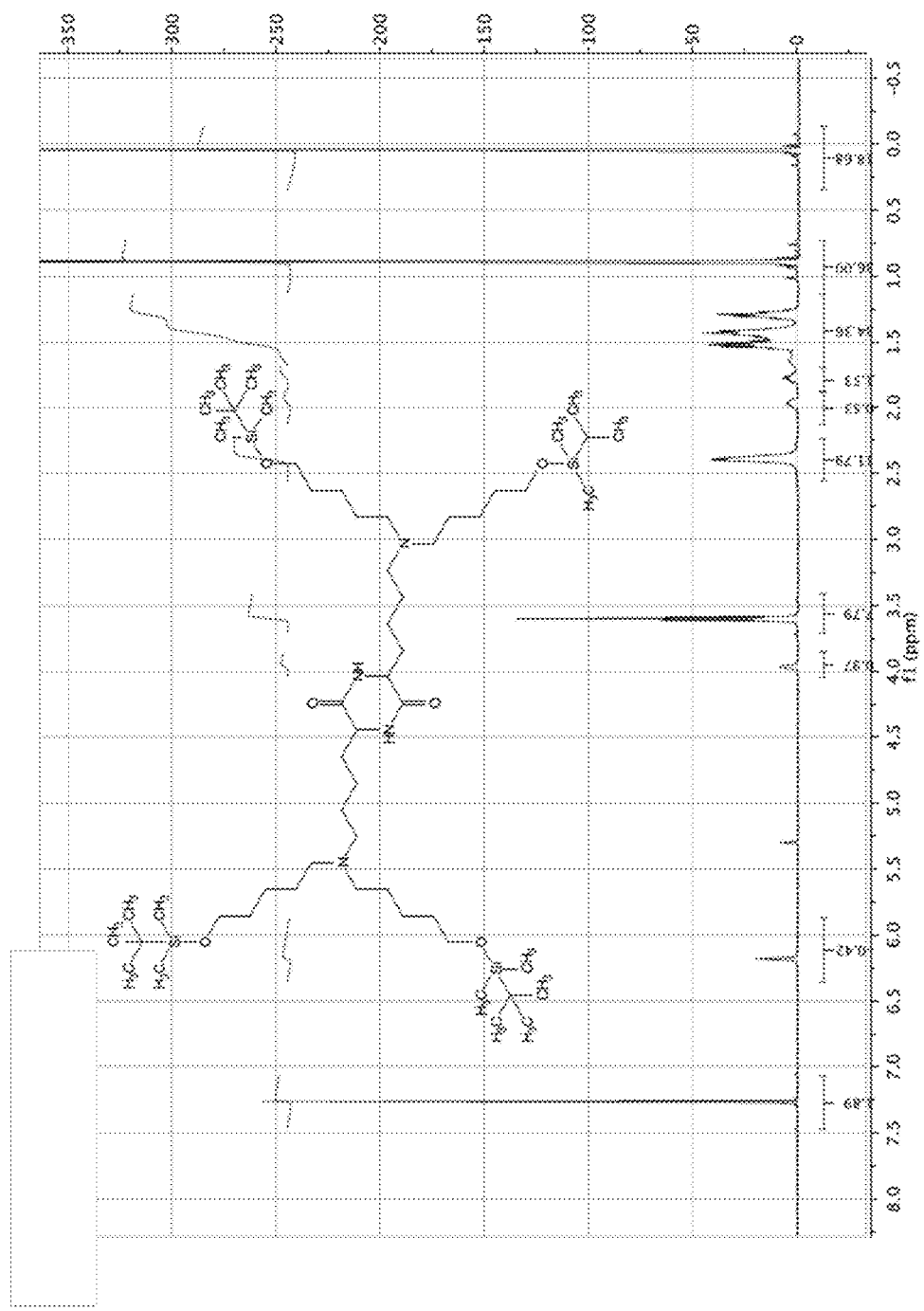
Figure 5E:
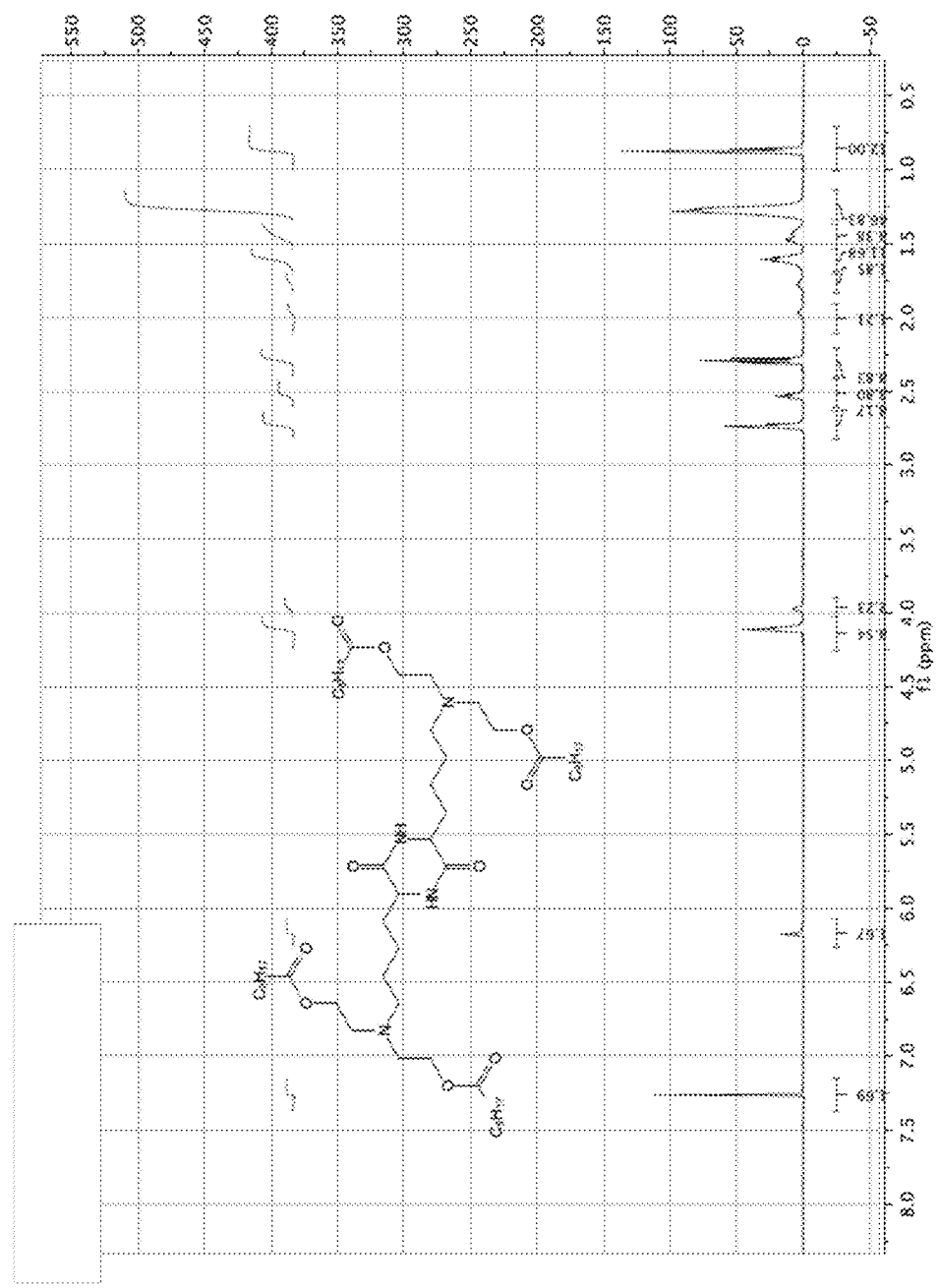
Figure 5F:
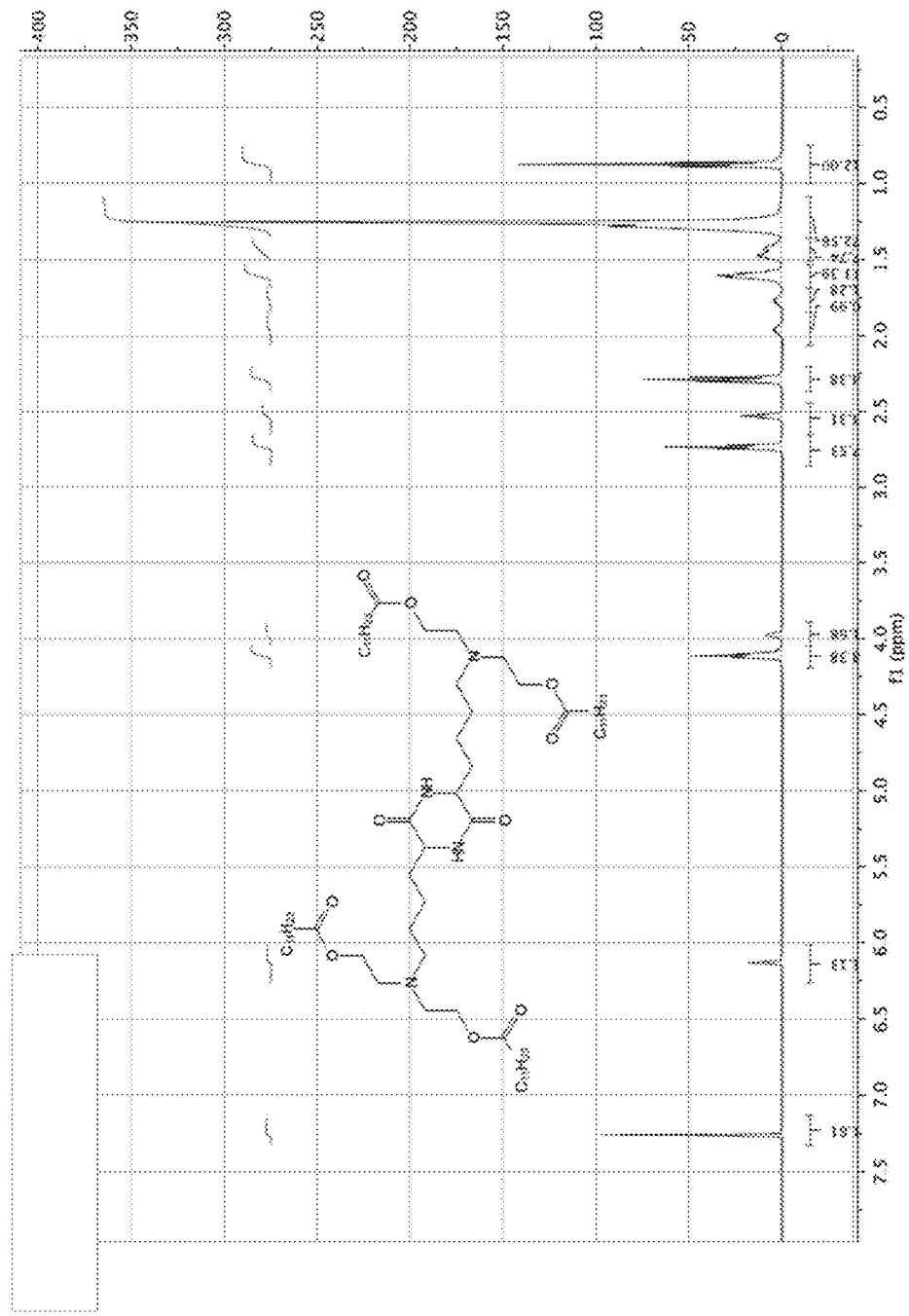
Figure 5G:
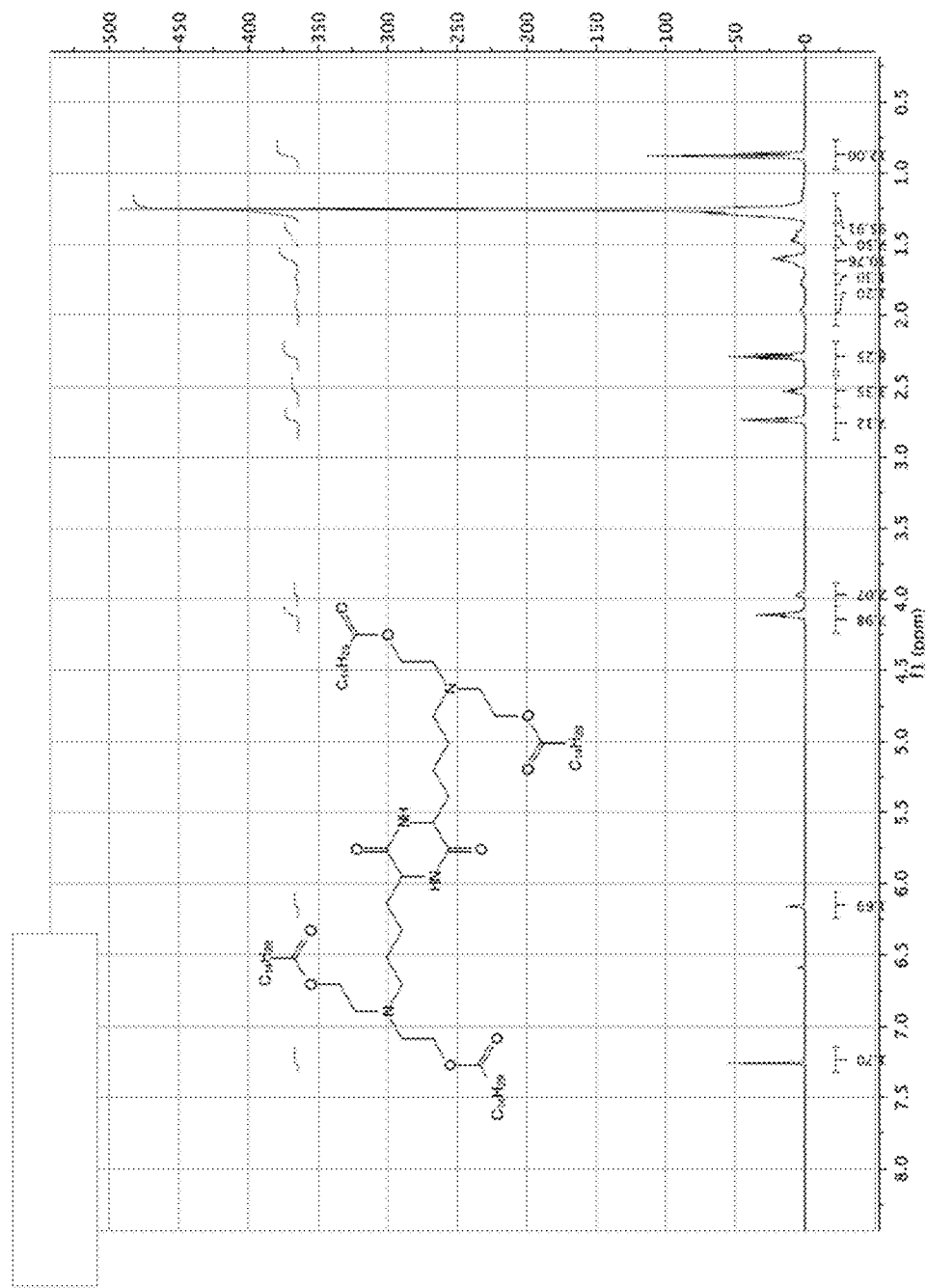
Figure 5H:
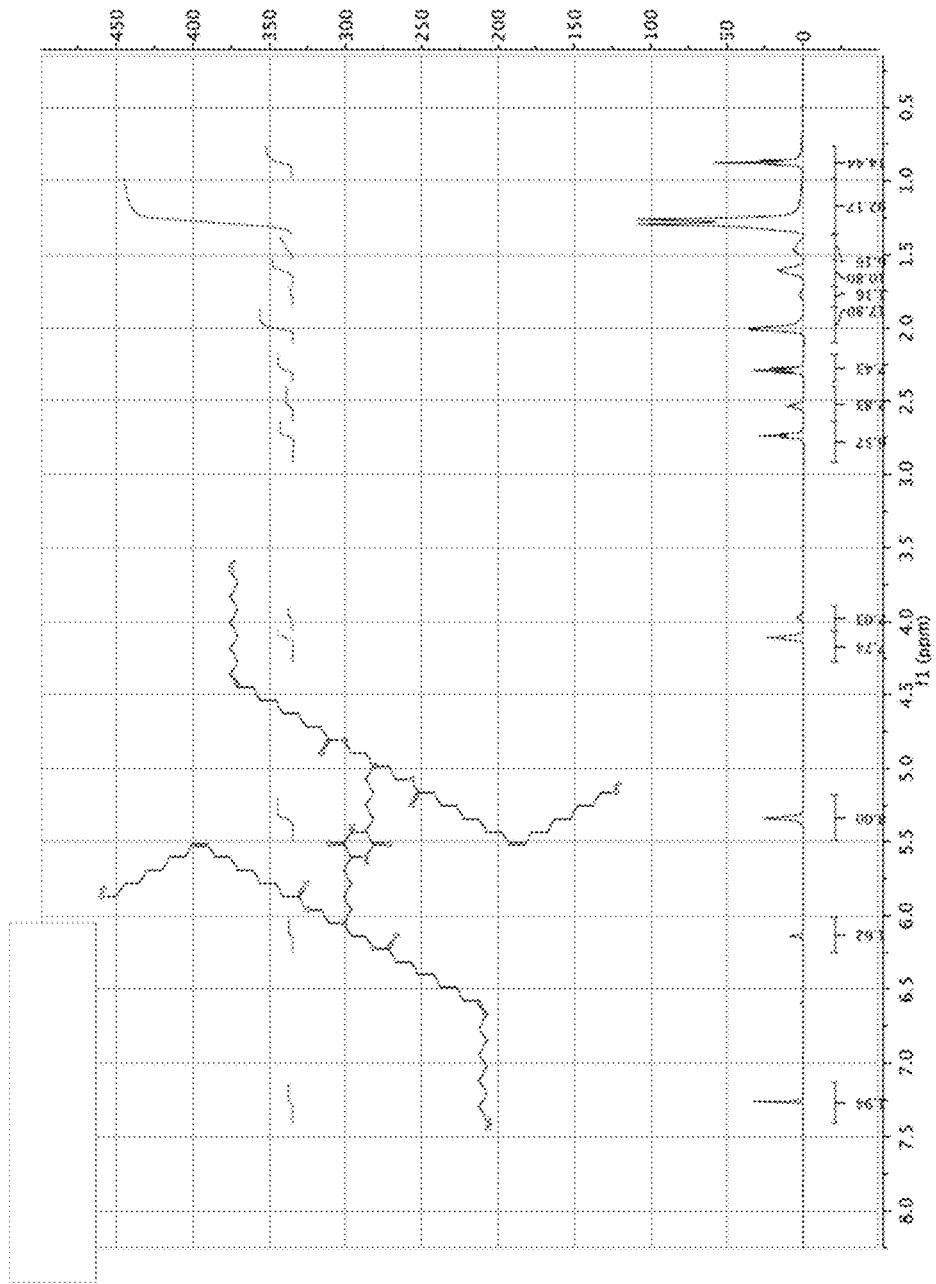
Figure 5I:
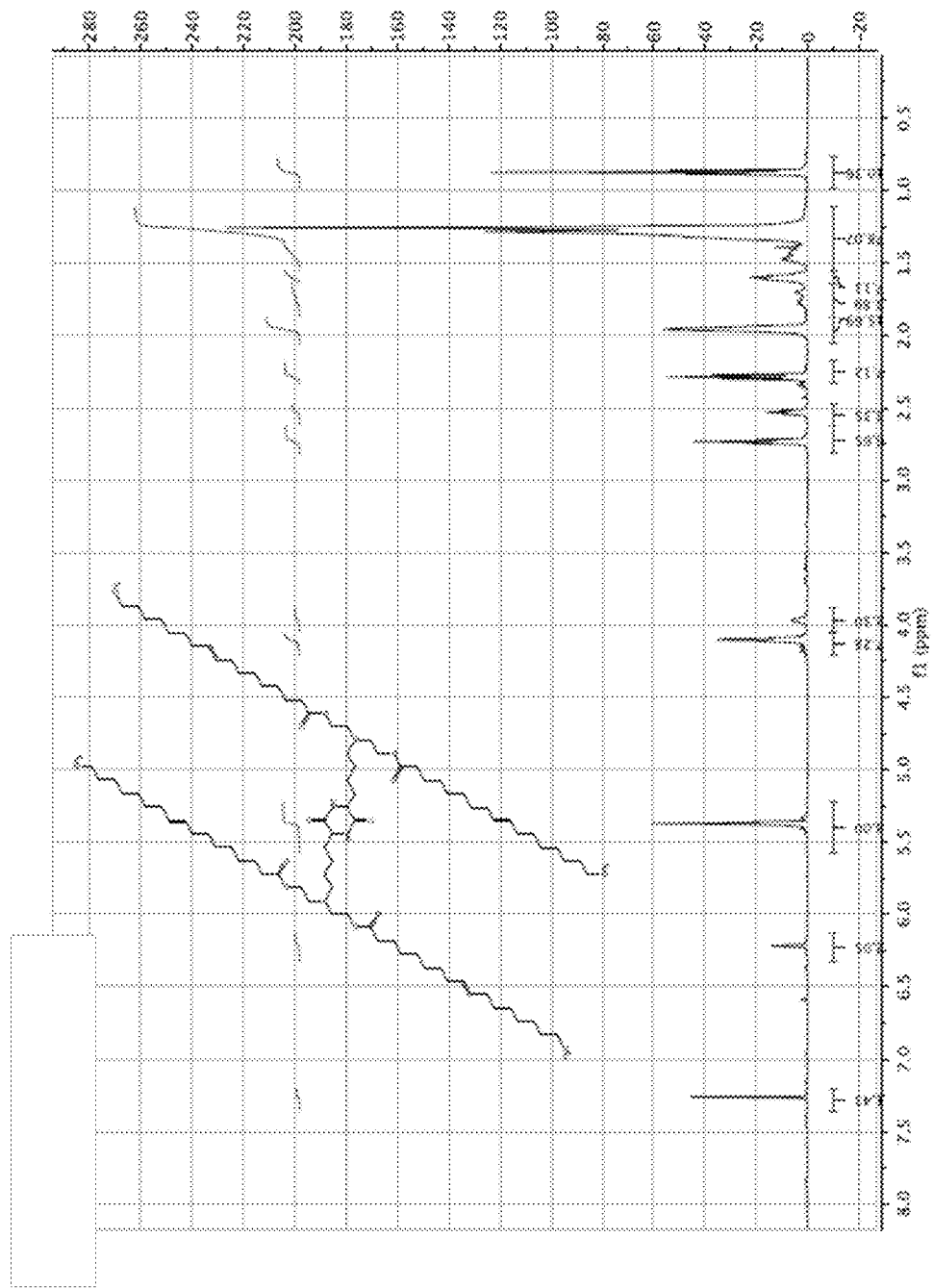
Figure 5J:
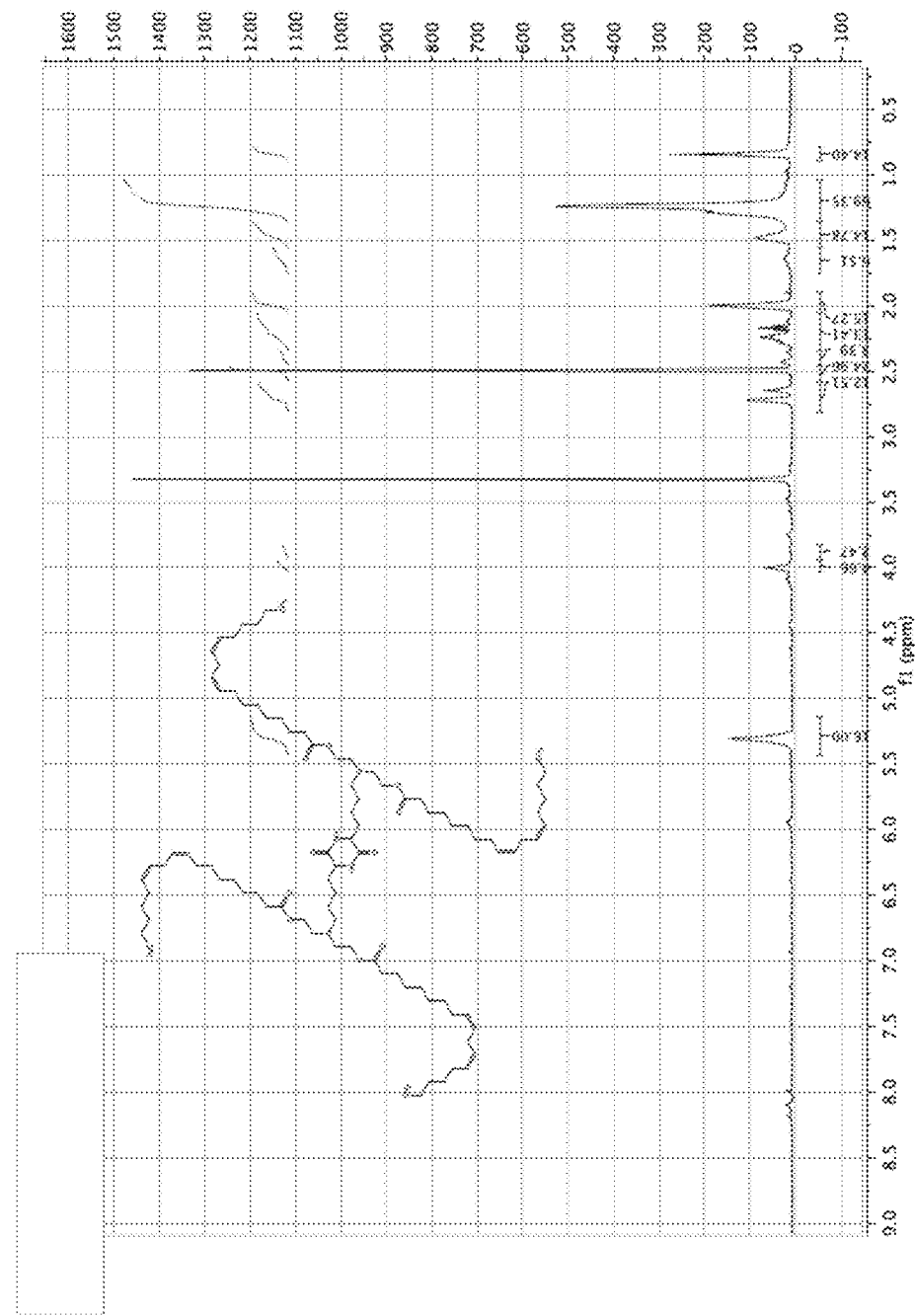
Figure 5K:
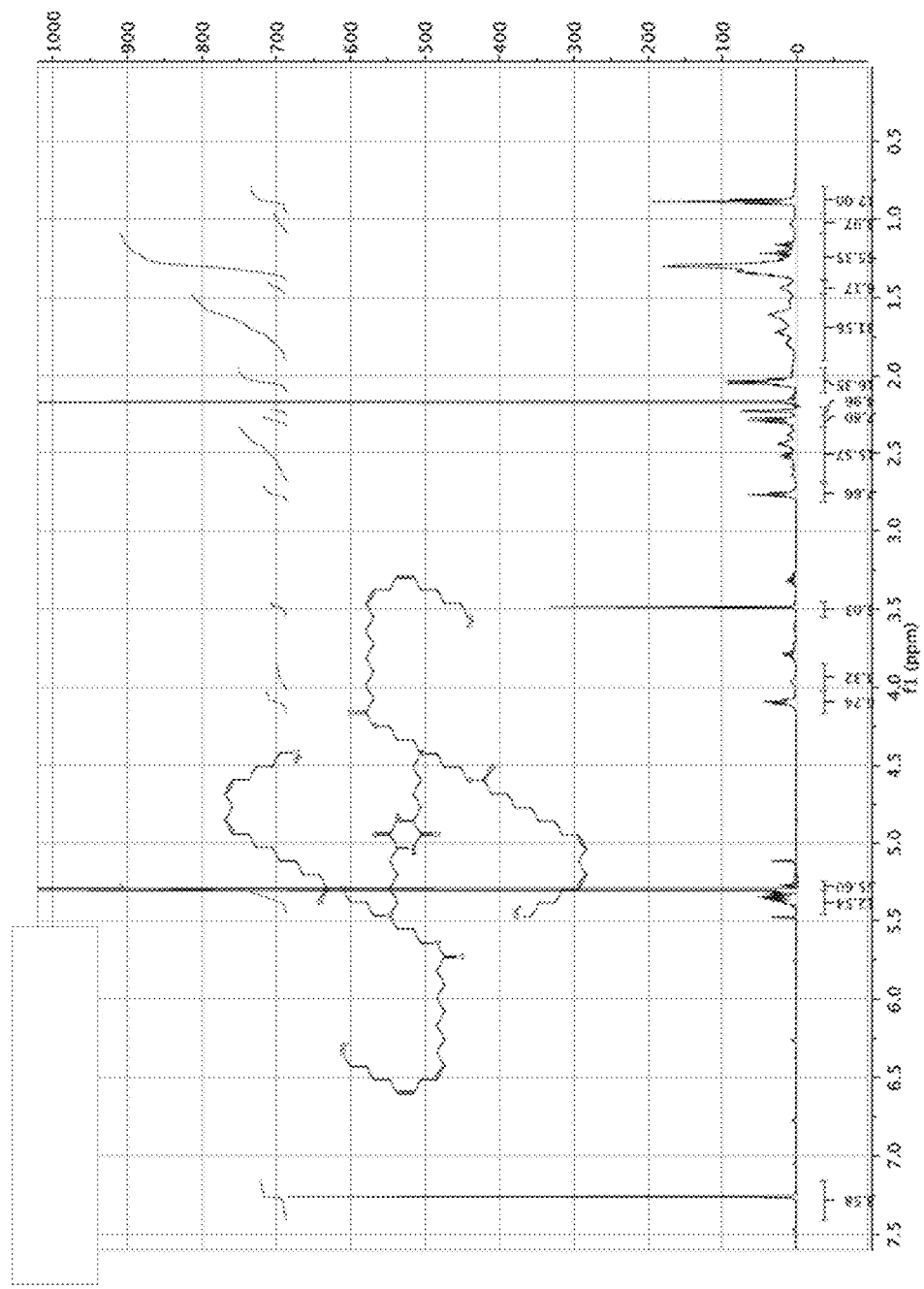
Figure 5L:
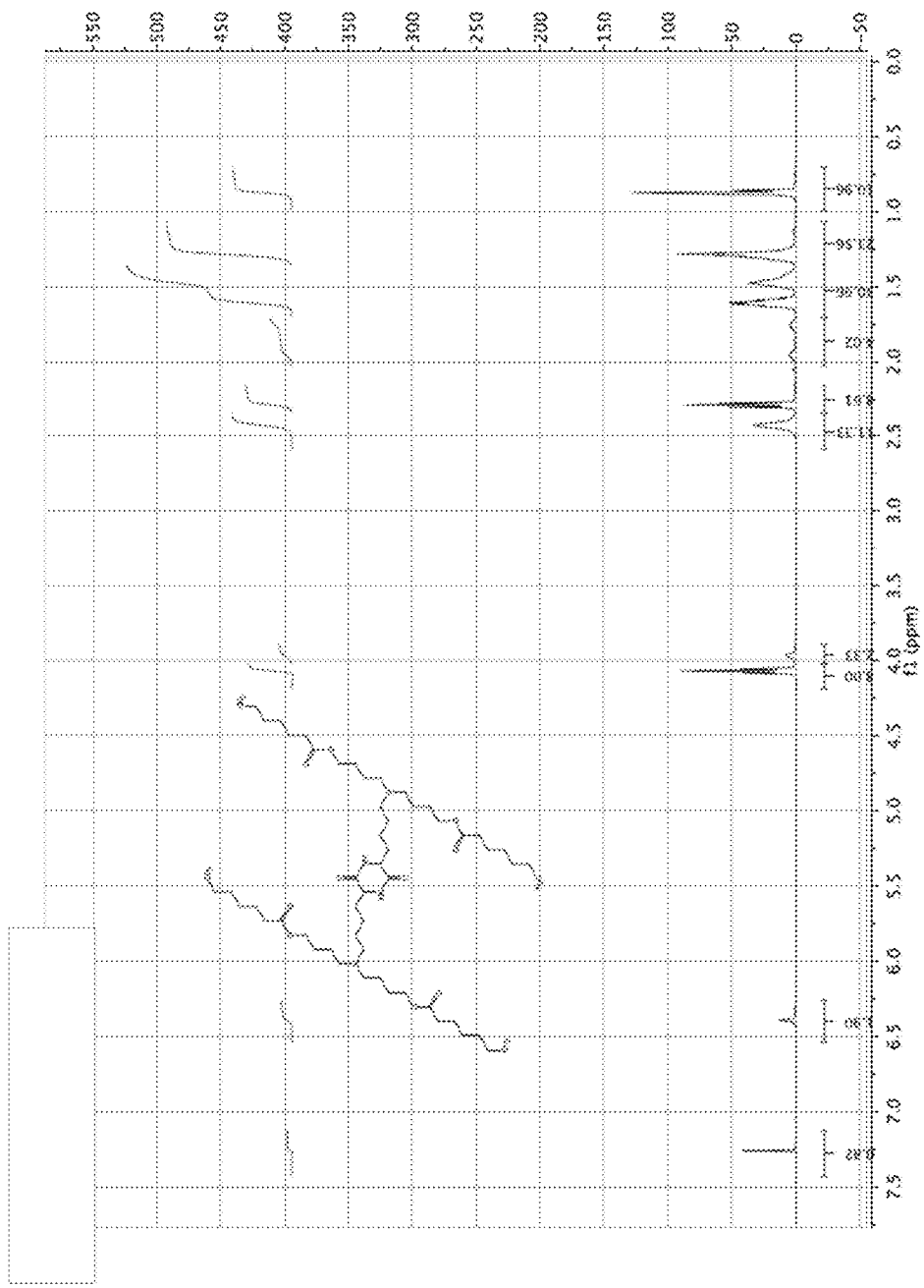
Figure 5M:
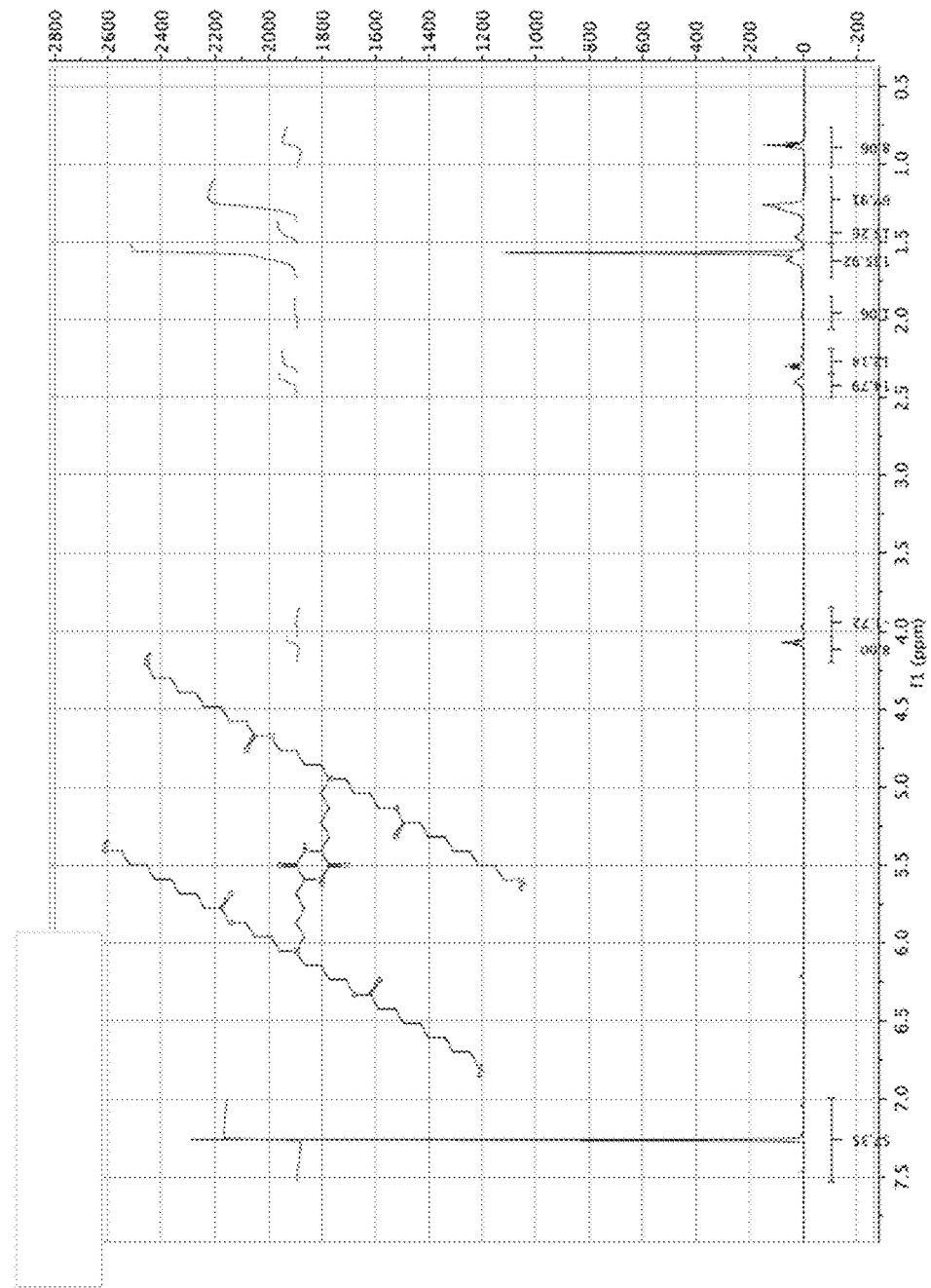
Figure 5N:
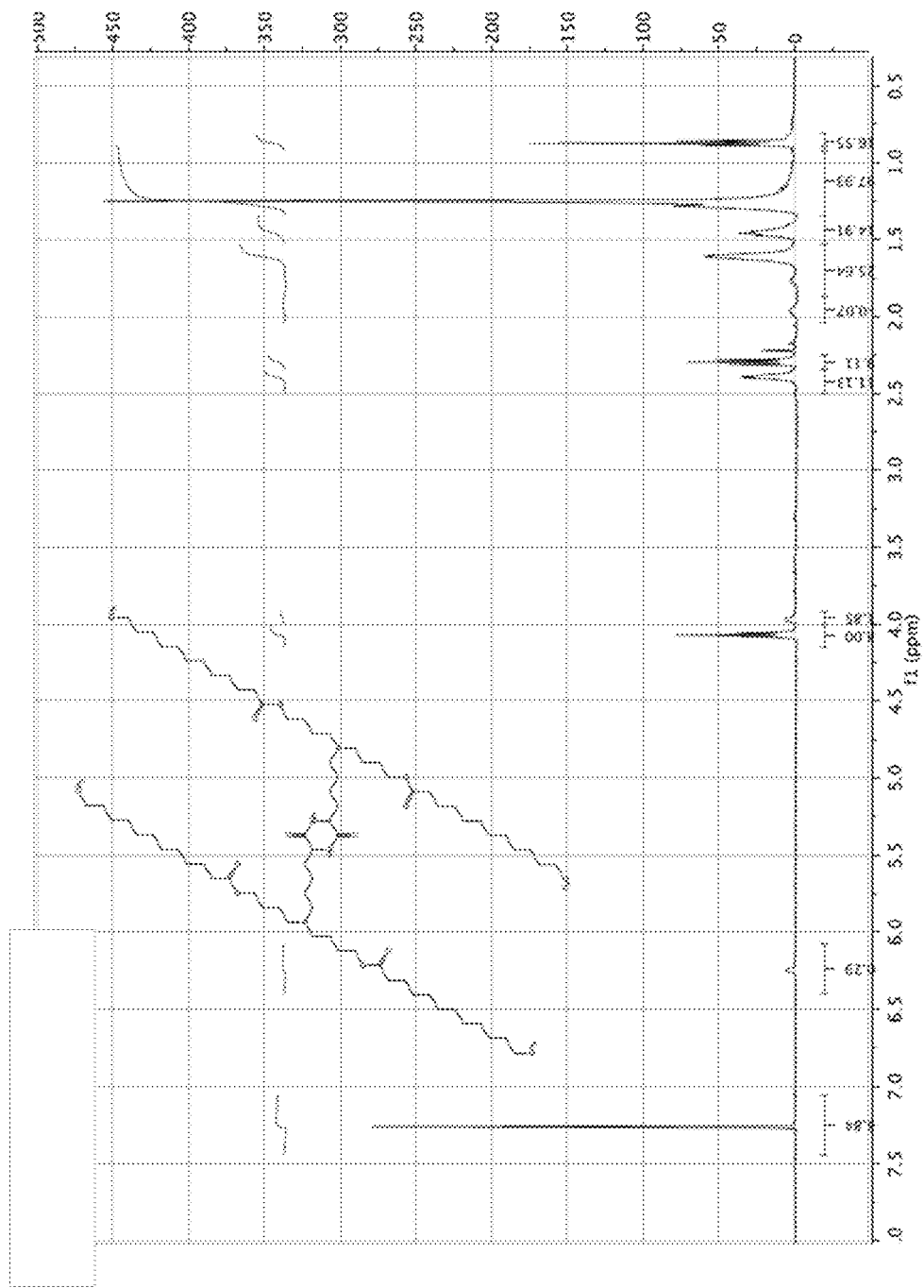
Figure 50:
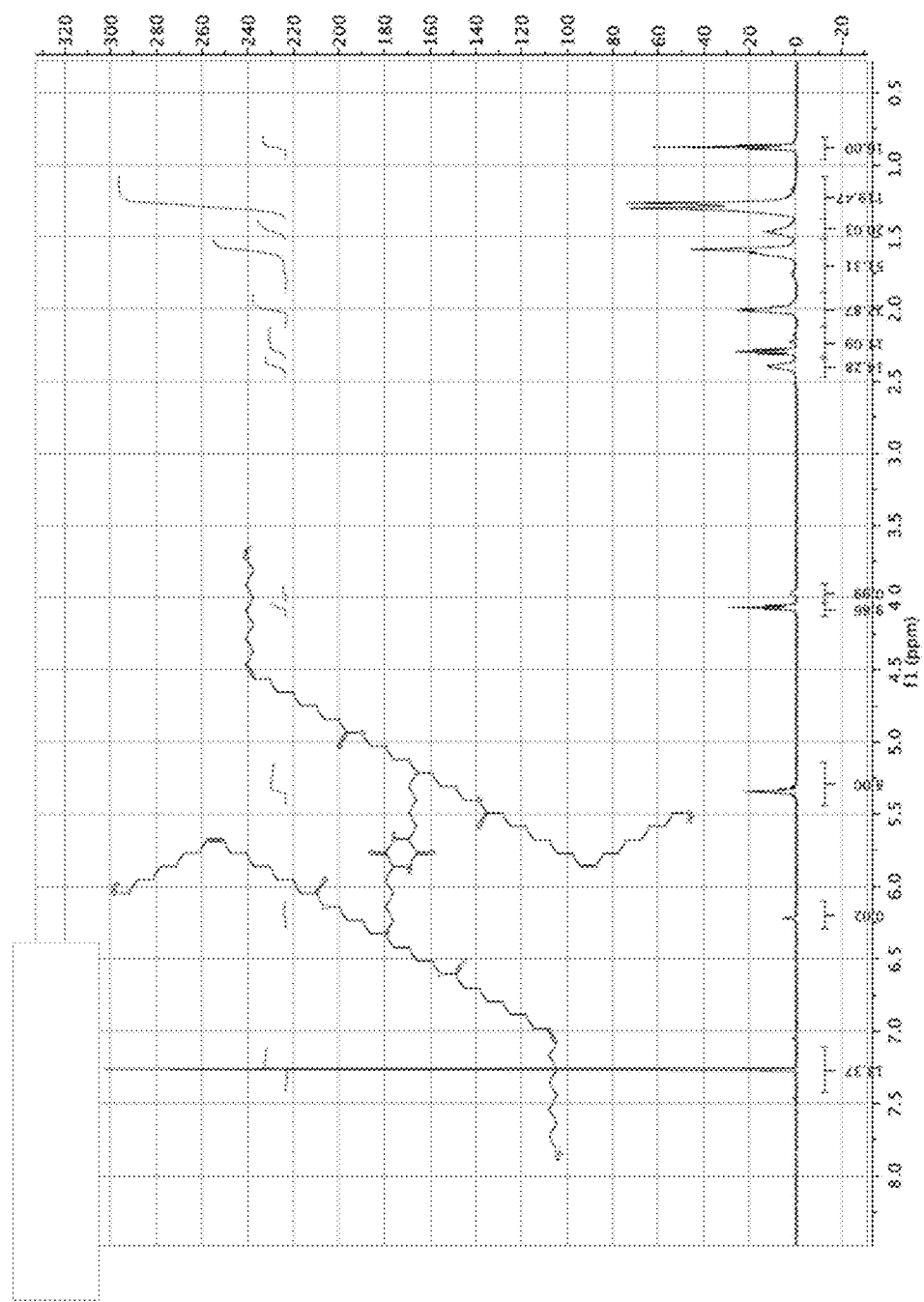
Figure 5P:
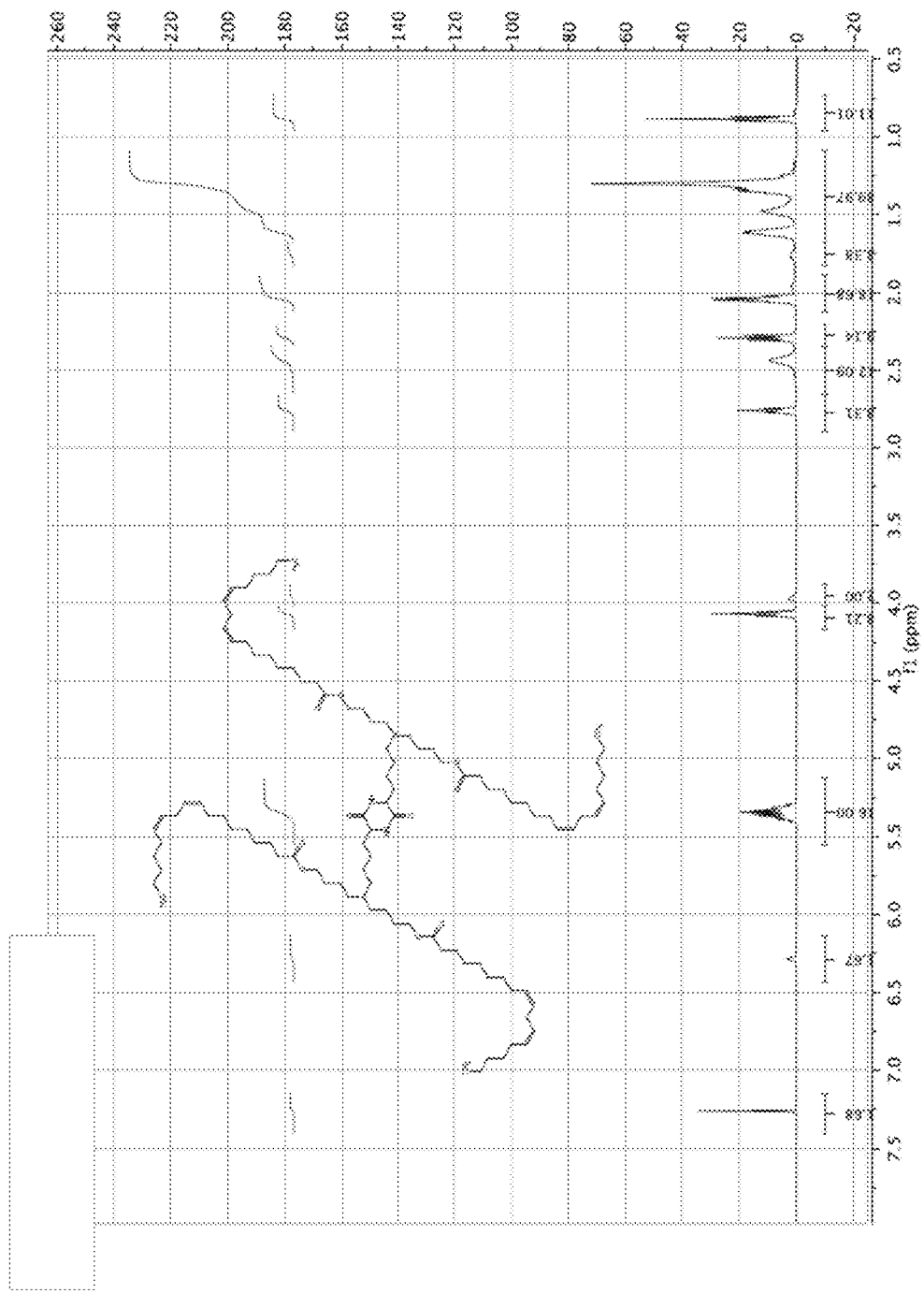

In an exemplary synthesis, an alcohol of Formula (A) or (E) (1 equivalent) was dissolved in a solvent (e.g., dichloromethane, in which the concentration of the alcohol of Formula (A) or (E) was about 0.1 M). To this solution was added a carbodiimide (e.g., EDC (about 2a equivalents, where a is the number of hydroxyl moieties of a molecule of the alcohol of Formula (A)), a catalyst (e.g., HOBt (about 2a equivalents), and a carboxylic acid of Formula (B) or (F) (about 2a equivalents). A base (e.g., triethylamine (about 6a equivalents) was then added dropwise to the resulting mixture. The reaction mixture was stirred at room temperature for about 24 hours. Liquid chromatography/mass spectrometry was used to assess if the reaction was complete, and if it was not, additional amounts (e.g., 1 to 6a equivalents) of the carbodiimide, catalyst, carboxylic acid of Formula (B) or (F), and/or base were added so that the conversion of the alcohol of Formula (A) or (E) was close to 100% (e.g., at least about 90% or at least about 95%). Upon completion, the reaction mixture was diluted with the solvent (e.g., dichloromethane) and washed with an aqueous solution of 1 N hydrochloric acid, an aqueous solution of saturated sodium bicarbonate, and saturated sodium chloride. The organic layer was dried over anhydrous sodium sulfate, filtered through cotton, and concentrated under reduced pressure. $^1$H NMR spectroscopy was used to assess the purity of the crude product. If the crude product included impurities, the crude product was purified via silica gel chromatography eluted with a 2% to 100% gradient of dichloromethane/ULTRA (where ULTRA is a solution consisting of 75% dichloromethane, 22% methanol, and 3% concentrated ammonium hydroxide) to yield the desired product. For example, compounds 24C18Oleic, 24C18Linoleic3, and 50C18Linoleic3 were prepared, and the $^1$H NMR (CDCl$_3$) spectra of these compounds are shown in FIGS. 4A to 4C, respectively.

Example 1.2. Preparation of the Compounds by Alkylation

Compounds described herein (e.g., compounds of Formula (I) or (II)) may be prepared by alkylation reactions, such as the ones illustrated in Scheme 5.

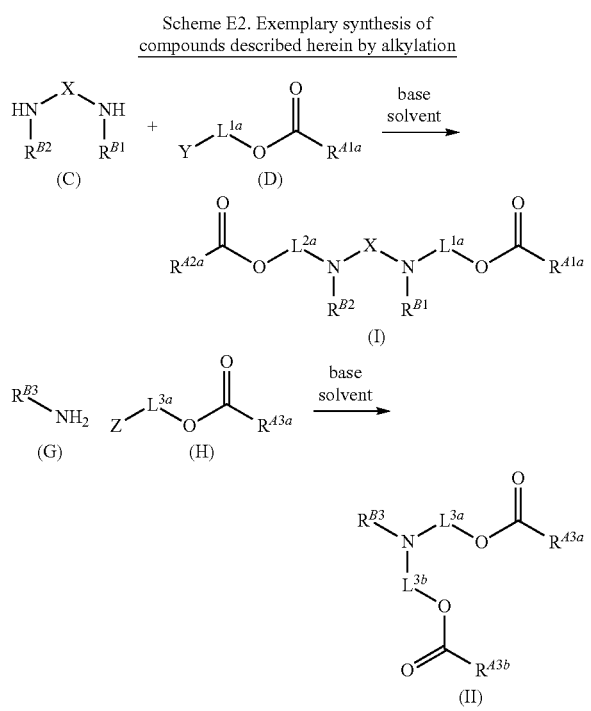

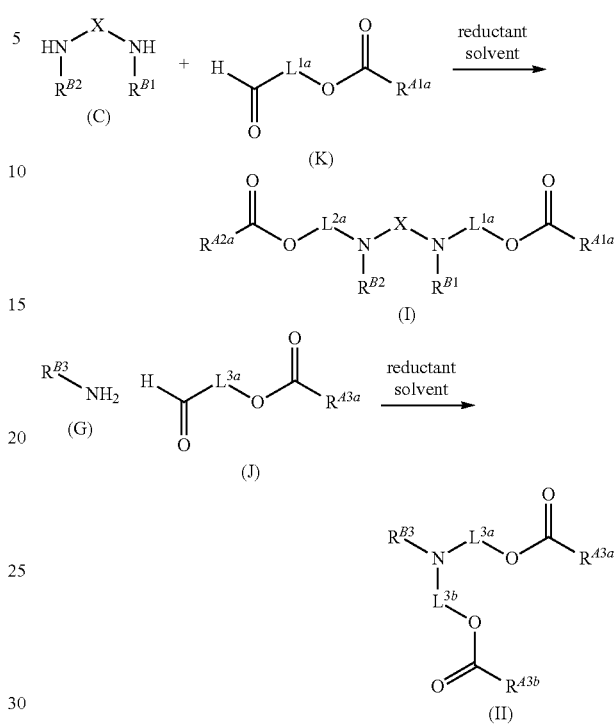

In an exemplary synthesis, an amine of Formula (C) or (G) (1 equivalent) was dissolved in a solvent (e.g., DMF). A base (e.g., solid sodium carbonate (about 4b equivalents, where b is the number of amino protons of a molecule of the amine of Formula (C) or (G)) was added, followed by the addition of a compound of Formula (D) or (H) (about 2b equivalents). The resulting mixture was stirred vigorously at elevated temperature (e.g., about 50° C. or higher) for about 48 hours, cooled to room temperature, and filtered. The filtrate was concentrated under reduced pressure. The resulting residue was purified via silica gel chromatography eluted with a 2% to 100% gradient of dichloromethane/ULTRA to yield the desired product.

Example 1.3. Preparation of the Compounds by Reductive Amination

Compounds described herein (e.g., compounds of Formula (I) or (II)) may be prepared by reductive amination reactions, such as the ones illustrated in Scheme E3.

In an exemplary synthesis, an amine of Formula (C) or (G) (1 equivalent) was dissolved in a solvent (e.g., THF, in which the concentration of the amine of Formula (C) or (G) was about 0.1 M). An aldehyde of Formula (K) or (J) (about 3c equivalents, where c is the number of amino moieties of a molecule of the amine of Formula (C) or (G)) was added to the resulting mixture, followed by the addition of a reductant (e.g., sodium triacetoxy borohydride (about 2.7c equivalents)). The reaction mixture was stirred at room temperature for about 24 hours. Liquid chromatography/mass spectrometry was used to assess the conversion of the reaction, and more amounts (e.g., 1 to 3c equivalents) of the aldehyde of Formula (K) or (J) and the reductant were added to attempt to so that the conversion of the amine of Formula (C) or (G) was close to 100% (e.g., at least about 90% or at least about 95%). After completion, the reaction mixture was diluted with ethyl acetate, and the organic layer was washed with an aqueous solution of sodium chloride. The organic layer was dried over anhydrous sodium sulfate, filtered, and concentrated under reduced pressure. The resulting residue was purified via silica gel chromatography eluted with a 2% to 100% gradient of dichloromethane/ULTRA to yield the desired product.

Example 1.4.1. Nomenclature and Synthetic Considerations

The following nomenclature system is one means of identifying the compounds of the invention. The nomenclature structure is in a general format as follows: AA-BB-CC- DD, wherein: AA refers to the specific core, e.g., core 50, which refers to a bis-lysine diketopiperazine based core. BB refers to the number of carbons between the lysine nitrogens and the alcohol oxygen. CC refers to the tail length of the fatty acid used for esterification, and, in cases wherein multiple tails exist with the same tail length, the specific tail name is used. DD refers to the total number of tails off of the diketopiperazine core.

Example 1.4.2. Reductive Amination Protocol for the 50-C2-CC-DD, 50-C4-CC-DD, and 50-C5-CC-DD Cores To the bis-lysine diketopiperazine core (1 equiv.) in THF was added $NEt_3$ (2.2 equiv.). The reaction mixture was stirred for 30 minutes, until the solid was nearly fully dissolved, and then to it was added the aldehyde (6.9 equiv.), followed by $NaB(OAc)_3H$ (5 equiv.). The solution was stirred overnight. It was then diluted in EtOAc, washed with brine, filtered over $Na_2SO_4$, and concentrated in vacuo to yield the product. The crude product mixtures were purified using silica gel chromatography eluting with a gradient of dichloromethane to dichloromethane:methanol:ammonium hydroxide (75%:22%:3% v:v:v).

50-C2-CC-DD Core

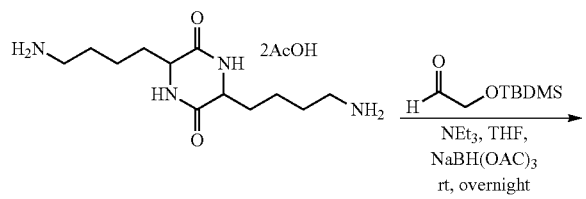

To the bis-lysine diketopiperazine core (1.000 g, 2.66 mmol, 1 equiv.) in THF (88 ml) was added $NEt_3$ (823 al, 5.90 mmol, 2.2 equiv.). The reaction mixture was stirred for 1.5 h, until the solid was nearly fully dissolved, and then to it was added the C2 protected aldehyde (3.49 ml, 18.3 mmol, 6.9 equiv.), followed by $NaB(OAc)_3H$ (2.814 g, 13.3 mmol, 5 equiv.). The solution was stirred overnight. It was then diluted in EtOAc, washed with brine, filtered over $Na_2SO_4$, and concentrated in vacuo. The crude product mixture was purified using silica gel chromatography eluting with a 0→100% gradient of dichlormethane/methanol/ammonium hydroxide (75%/22%/3% v/v/v):dichloromethane. Fractions were concentrated under reduced pressure to afford the desired products in 58% yield. $^1$H NMR (500 MHz, $CDCl_3$, ppm): 6.15 (br, 2H, NH), 3.99 (br, 2H, COCHN), 3.8 (t, 8H, $NCH_2CH_2OSi$), 2.65 (t, 8H, $NCH_2CH_2OSi$), 2.55 (t, 4H, $NCH_2$), 1.99 (m, 2H, $COCHCH_2$), 1.8 (m, 2H, $COCHCH_2$), 1.45 (m, 4H, $NCH_2CH_2CH_2CH_2$), 1.40 (m, 4H, $NCH_2CH_2CH_2CH_2$), 0.89 (s, 36H, $OSi(CH_3)_2C(CH_3)_3$), 0.04 (s, 36H, $OSi(CH_3)_2C(CH_3)_3$).

50-C4-CC-DD Core

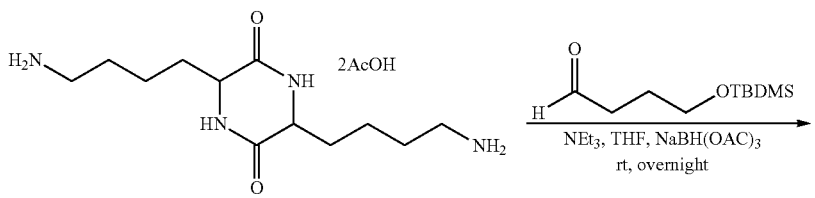

To the bis-lysine diketopiperazine core (373 mg, 0.99 mmol, 1 equiv.) in THF (33 ml) was added NEt₃ (307 μl, 2.18 mmol, 2.2 equiv). The reaction mixture was stirred for 30 minutes, until the solid was nearly fully dissolved, and then to it was added the C4 protected aldehyde (1.382 g, 6.83 mmol, 6.9 equiv.), followed by NaB(OAc)₃H (1.05 g, 4.95 mmol, 5 equiv.). The solution was stirred overnight. It was then diluted in EtOAc, washed with brine, filtered over Na₂SO₄, and concentrated in vacuo. The crude product mixture was purified using silica gel chromatography eluting with a 0→100% gradient of dichlormethane/methanol/ammonium hydroxide (75%/22%/3% v/v/v):dichloromethane. Fractions were concentrated under reduced pressure to afford the desired products in 41% yield. ¹H NMR (500 MHz, CDCl₃, ppm): 6.4 (br, 2H, NH), 3.95 (br, 2H, COCHN), 3.62 (t, 8H, CH₂OSi), 2.40 (m, 12H, NCH₂), 1.98 (m, 4H, COCHCH₂), 1.33-1.84 (m, 24H, CH₂), 0.89 (s, 36H, OSi(CH₃)₂C(CH₃)₃), 0.04 (s, 24H, OSi(CH₃)₂C(CH₃)₃).

50-C5-CC-DD Core:

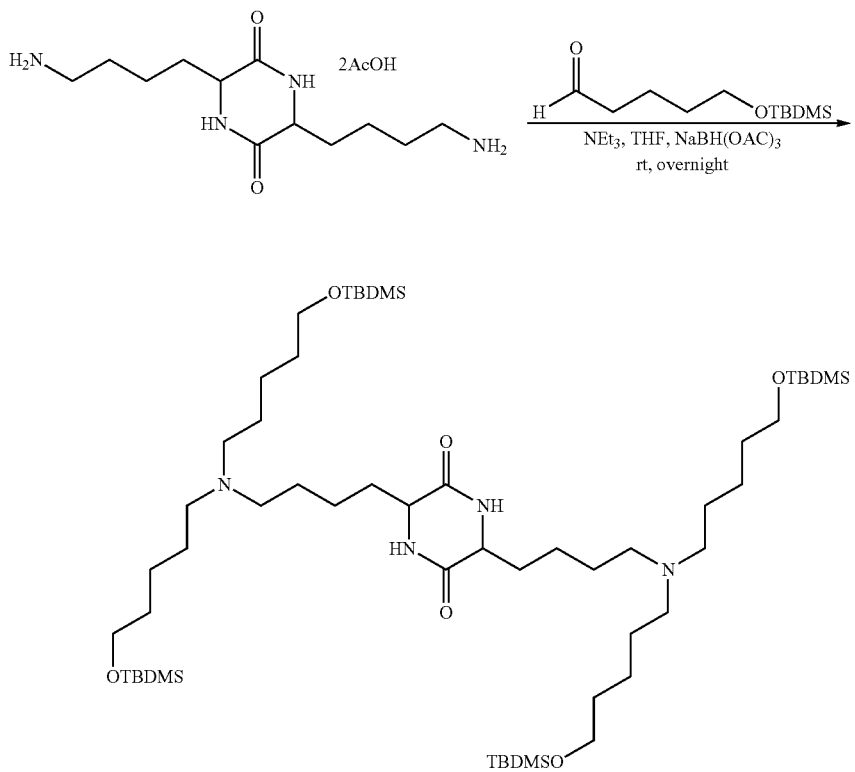

To the bis-lysine diketopiperazine core (373 mg, 0.99 mmol, 1 equiv.) in THF (33 ml) was added NEt₃ (307 μl, 2.18 mmol, 2.2 equiv.). The reaction mixture was stirred for 30 minutes, until the solid was nearly fully dissolved, and then to it was added the protected aldehyde (1.477 g, 6.83 mmol, 6.9 equiv.), followed by NaB(OAc)₃H (1.050 g, 4.95 mmol, 5 equiv.). The solution was stirred overnight. It was then diluted in EtOAc, washed with brine, filtered over Na₂SO₄, and concentrated under reduced pressure. The crude product mixture was purified using silica gel chromatography eluting with a 0→100% gradient of dichlormethane/methanol/ammonium hydroxide (75%/22%/3% v/v/v):dichloromethane. Fractions were concentrated under reduced pressure to afford the desired products in 19% yield. ¹H NMR (500 MHz, CDCl₃, ppm): 6.17 (br, 2H, NH), 3.97 (br, 2H, COCHN), 3.59 (t, 8H, CH₂OSi), 2.39 (m, 12H, NCH₂), 1.24-1.99 (m, 36H, CH₂), 0.89 (s, 36H, OSi(CH₃)₂C(CH₃)₃), 0.04 (s, 24H, OSi(CH₃)₂C(CH₃)₃).

Example 1.4.3. Alkylation Protocol for the 50-C3-CC-DD Core

50-C3-CC-DD Core.

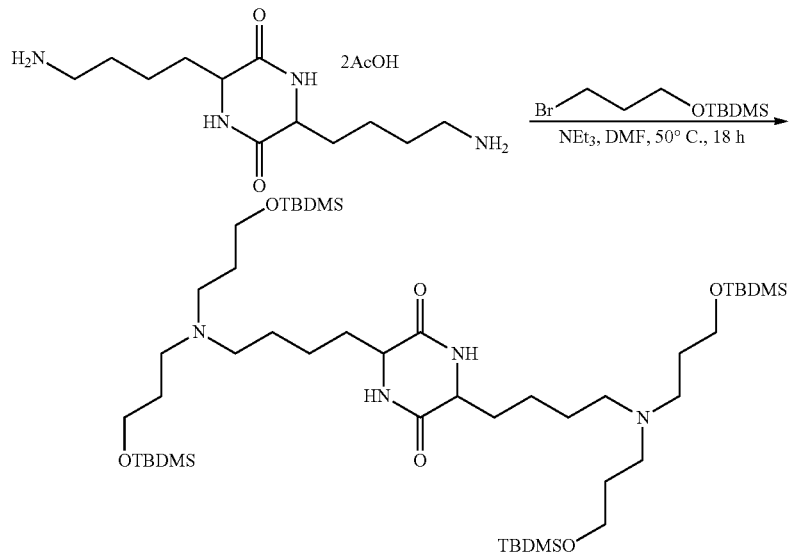

To the bis-lysine diketopiperazine core (263.4 mg, 0.7 mmol, 1 equiv.) in DMF (10 ml) was added NEt$_3$ (1.32 ml, 9.45 mmol, 13.5 equiv.). The mixture was stirred at room temperature for 15 minutes. To the flask was then added (3-bromopropoxy)(tert-butyl)dimethylsilane (1.297 ml, 5.6 mmol, 8 equiv.), and the reaction was stirred at 50° C. for 18 hours. The mixture was diluted in ethyl acetate, washed with brine, filtered through Na$_2$SO$_4$, and concentrated under reduced pressure. The crude product mixture was purified using silica gel chromatography eluting with a 0→100% gradient of dichlormethane/methanol/ammonium hydroxide (75%/22%/3% v/v/v):dichloromethane. Fractions were concentrated under reduced pressure to afford the desired products in 13% yield. $^1$H NMR (500 MHz, CDCl$_3$, ppm): 6.5 (br, 2H, NH), 3.93 (br, 2H, COCHN), 3.58 (t, 8H, NCH$_2$CH$_2$CH$_2$OSi), 2.49 (t, 8H, NCH$_2$CH$_2$CH$_2$OSi), 2.40 (t, 4H, NCH$_2$), 1.97 (m, 2H, COCHCH$_2$), 1.75 (m, 2H, COCHCH$_2$), 1.64 (quintet, 8H, NCH$_2$CH$_2$CH$_2$OSi), 1.48 (m, 4H, NCH$_2$CH$_2$CH$_2$CH$_2$), 1.42 (m, 4H, NCH$_2$CH$_2$CH$_2$CH$_2$), 0.89 (s, 36H, OSi(CH$_3$)$_2$C(CH$_3$)$_3$), 0.04 (s, 36H, OSi(CH$_3$)$_2$C(CH$_3$)$_3$).

Example 1.4.4. Desilylation-Esterification Protocol

To the protected alcohols (0.088 mmol, 1 equiv.) in THF (6 ml) was added TBAF (1.75 ml, IM in THF, 1.75 mmol, 12 equiv.). The solution was stirred for one hour and the reaction was then quenched with 1 drop of H$_2$O.

To a solution of the deprotected alcohol in CH$_2$Cl$_2$ (6 ml) was added HOBt (120.7 mg, 0.88 mmol, 10 equiv.), EDC (168.7 mg, 0.88 mmol, 10 equiv.), a carboxylic acid (0.88 mmol, 10 equiv.), and then NEt$_3$ (178 al, 2.2 mmol, 25 equiv.). The reaction was stirred overnight, and was then diluted with ethyl acetate. The organic phase was washed with 1 N HCl, with saturated sodium bicarbonate, and then with brine. The organic phase was dried over sodium sulfate, was filtered through cotton, and was concentrated under reduced pressure. The crude product mixture was purified using silica gel chromatography eluting with a 0→100% gradient of dichlormethane/methanol/ammonium hydroxide (75%/22%/3% v/v/v):dichloromethane. Fractions were concentrated under reduced pressure to afford the desired products in moderate yield.

50-C2-C9-4Tail

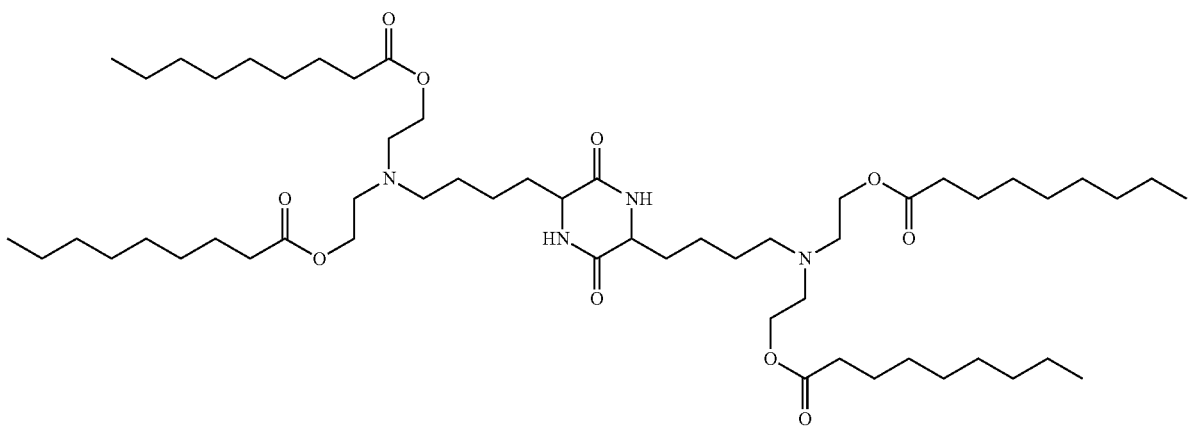 [SMILES: CCCCCCCCC(=O)OCCN(CCCCC1NC(=O)C(CCCCN(CCOC(=O)CCCCCCCC)CCOC(=O)CCCCCCCC)NC1=O)CCOC(=O)CCCCCCCC]

C9 refers to nonanoic acid. 1H NMR (500 MHz, CDCl$_3$, ppm): 6.15 (br, 2H, NH), 4.1 (m, 8H, NCH$_2$CH$_2$OCO), 3.99 (br, 2H, COCHN), 2.73 (t, 8H, OCOCH$_2$), 2.53 (t, 4H, NCH$_2$), 2.29 (t, 8H, NCH$_2$CH$_2$OCO), 1.96 (m, 2H, COCHCH$_2$), 1.78 (m, 2H, COCHCH$_2$), 1.61 (m, 4H, NCH$_2$CH$_2$CH$_2$), 1.77 (m, 4H, NCH$_2$CH$_2$CH$_2$), 1.1-1.35 (m, 48H, CH$_2$), 0.88 (t, 12H, CH$_3$).

50-C2-C12-4Tail

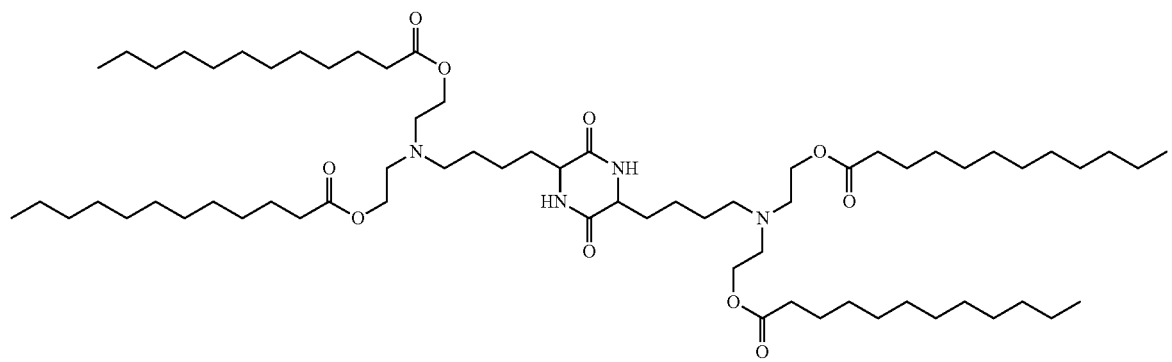 [SMILES: CCCCCCCCCCCC(=O)OCCN(CCCCC1NC(=O)C(CCCCN(CCOC(=O)CCCCCCCCCCC)CCOC(=O)CCCCCCCCCCC)NC1=O)CCOC(=O)CCCCCCCCCCC]

C12 refers to dodecanoic acid. $^1$H NMR (500 MHz, CDCl$_3$, ppm): 6.12 (br, 2H, NH), 4.11 (m, 8H, NCH$_2$CH$_2$OCO), 3.97 (br, 2H, COCHN), 2.75 (t, 8H, OCOCH$_2$), 2.54 (t, 4H, NCH$_2$), 2.29 (t, 8H, NCH$_2$CH$_2$OCO), 1.97 (m, 2H, COCHCH$_2$), 1.77 (m, 2H, COCHCH$_2$), 1.61 (m, 4H, NCH$_2$CH$_2$CH$_2$), 1.45 (m, 4H, NCH$_2$CH$_2$CH$_2$), 1.1-1.17 (m, 72H, CH$_2$), 0.9 (t, 12H, CH$_3$).

50-C2-C15-4Tail

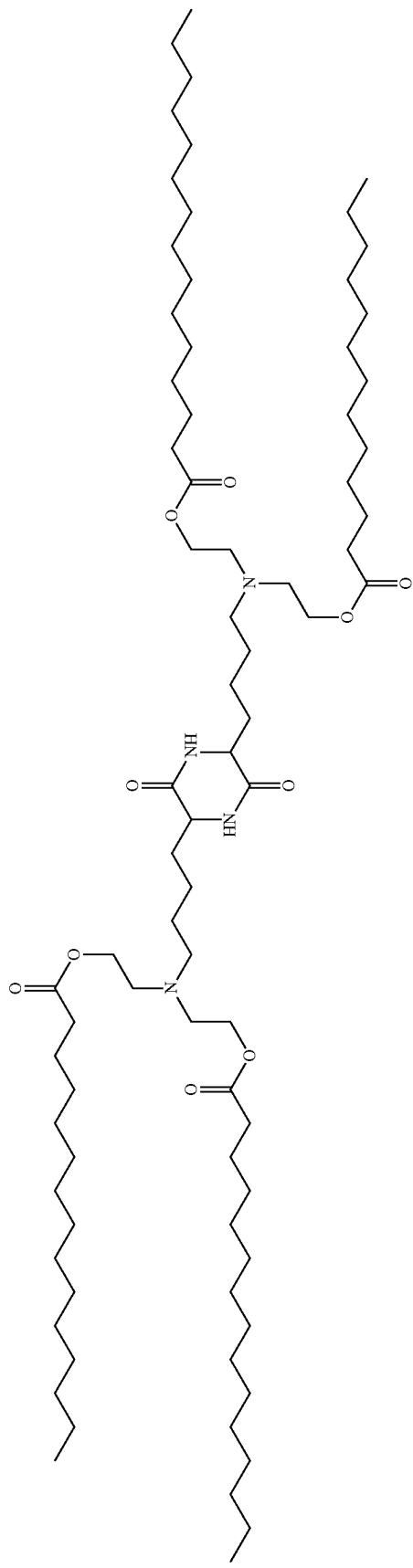

C15 refers to pentadecanoic acid. $^1$H NMR (500 MHz, CDCl$_3$, ppm): 6.17 (br, 2H, NH), 4.11 (m, 8H, NCH$_2$CH$_2$OCO), 3.97 (br, 2H, COCHN), 2.74 (t, 8H, OCOCH$_2$), 2.53 (t, 4H, NCH$_2$), 2.29 (t, 8H, NCH$_2$CH$_2$OCO), 1.97 (m, 2H, COCHCH$_2$), 1.76 (m, 2H, COCHCH$_2$), 1.59 (m, 4H, NCH$_2$CH$_2$CH$_2$CH$_2$), 1.45 (m, 4H, NCH$_2$CH$_2$CH$_2$CH$_2$), 1.17-1.34 (m, 96H, CH$_2$), 0.9 (t, 12H, CH$_3$).
50-C2-C18oleic-4Tail

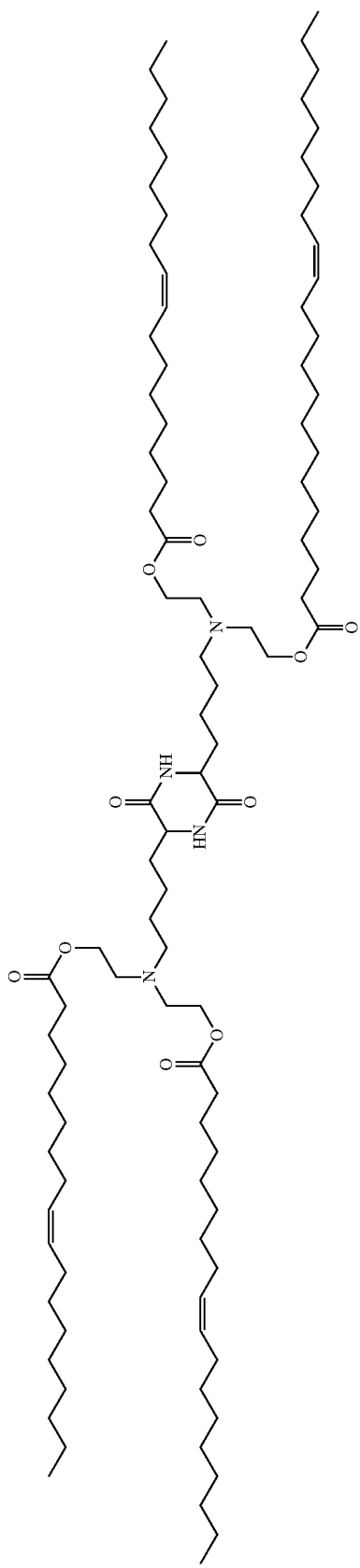

C18oleic refers to oleic acid. 1H NMR (500 MHz, CDCl$_3$, ppm): 6.13 (br, 2H, NH), 5.34 (m, 8H, CH$_2$CHCHCH$_2$), 4.11 (m, 8H, NCH$_2$CH$_2$OCO), 3.98 (br, 2H, COCHN), 2.74 (t, 8H, OCOCH$_2$), 2.53 (t, 4H, NCH$_2$), 2.29 (t, 8H, NCH$_2$CH$_2$OCO), 2.00 (m, 16H, CH$_2$CHCHCH$_2$), 1.94 (m, 2H, COCHCH$_2$), 1.77 (m, 2H, COCHCH$_2$), 1.61 (m, 4H, NCH$_2$CH$_2$CH$_2$CH$_2$), 1.45 (m, 4H, NCH$_2$CH$_2$CH$_2$CH$_2$), 1.21-1.36 (m, 88H, CH$_2$), 0.9 (t, 12H, CH$_3$).

50-C2-C18elaidic-4Tail

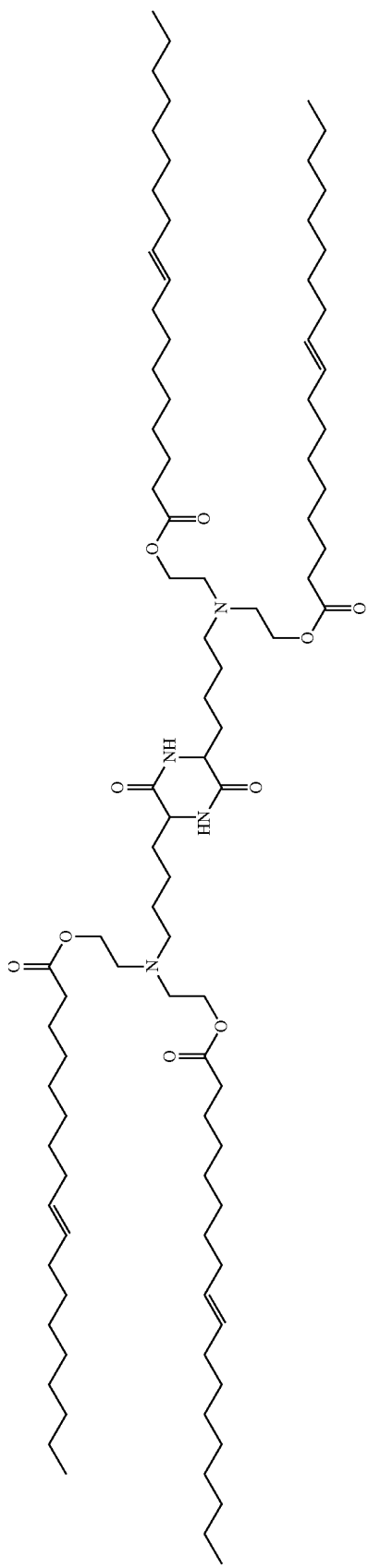

C18elaidic refers to elaidic acid. 1H NMR (500 MHz, CDCl$_3$, ppm): 6.13 (br, 2H, NH), 5.39 (m, 8H, CH$_2$CHCHCH$_2$), 4.10 (m, 8H, NCH$_2$CH$_2$OCO), 3.97 (br, 2H, COCHN), 2.74 (t, 8H, OCOCH$_2$), 2.52 (t, 4H, NCH$_2$), 2.27 (t, 8H, NCH$_2$CH$_2$OCO), 1.95 (m, 16H, CH$_2$CHCHCH$_2$), 1.78 (m, 2H, COCHCH$_2$), 1.69 (m, 2H, COCHCH$_2$), 1.60 (m, 4H, NCH$_2$CH$_2$CH$_2$CH$_2$), 1.45 (m, 4H, NCH$_2$CH$_2$CH$_2$CH$_2$), 1.20-1.37 (m, 88H, CH$_2$), 0.87 (t, 12H, CH$_3$).

50-C2-C18lin2-4Tail

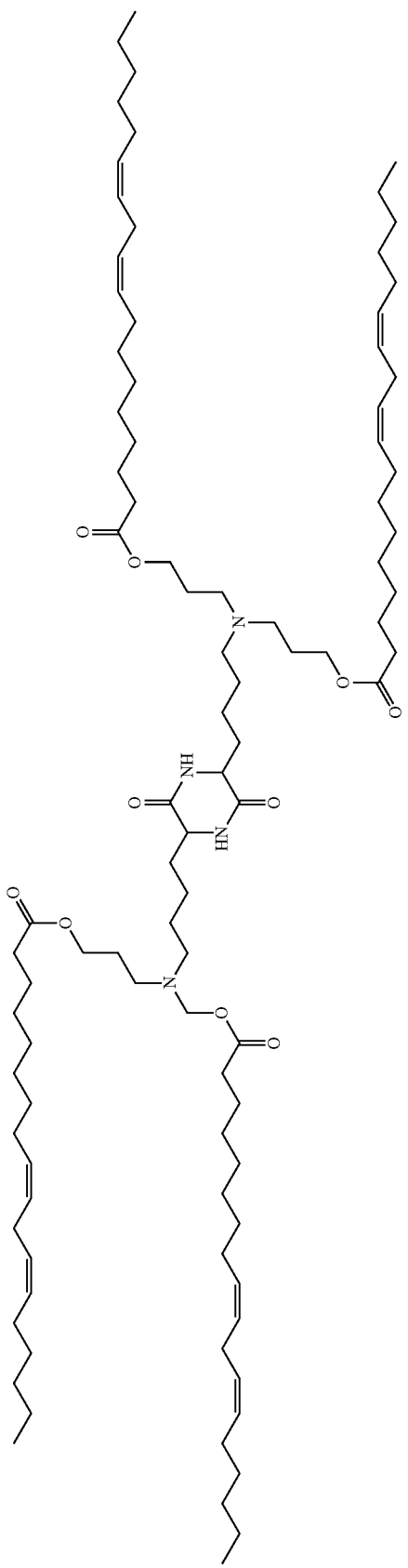

C18lin2 refers to linoleic acid. 1H NMR (500 MHz, DMSO-d$_6$, ppm): 6.13 (br, 2H, NH), 5.34 (m, 16H, CH$_2$CHCHCH$_2$), 4.11 (m, 8H, NCH$_2$CH$_2$OCO), 3.98 (br, 2H, COCHN), 2.74 (t, 8H, OCOCH$_2$), 2.53 (t, 8H, NCH$_2$CH$_2$OCO), 2.29 (t, 4H, NCH$_2$), 2.00 (m, 16H, CH$_2$CHCHCH$_2$CHCHCH$_2$), 1.94 (m, 2H, COCHCH$_2$), 1.77 (m, 2H, COCHCH$_2$), 1.61 (m, 4H, NCH$_2$CH$_2$CH$_2$), 1.45 (m, 4H, NCH$_2$CH$_2$CH$_2$), 1.21-1.36 (m, 88H, CH$_2$), 0.9 (t, 12H, CH$_3$).

50-C3-C18Lin2-4Tail

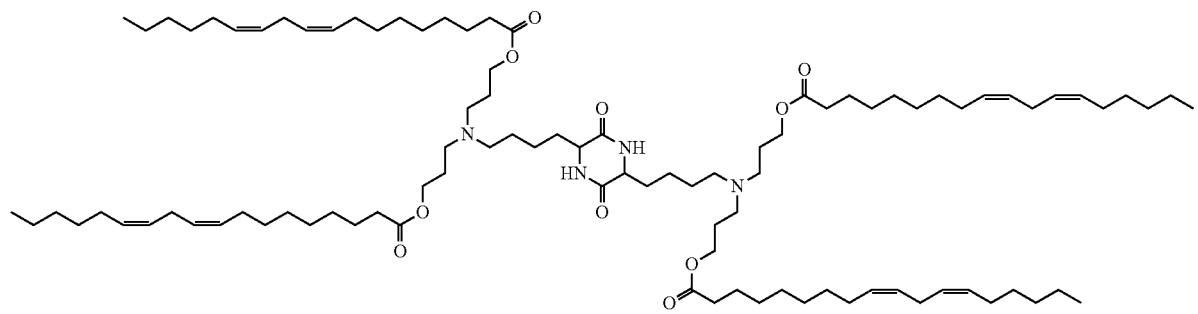 [SMILES: CCCCC/C=C\C/C=C\CCCCCCCC(=O)OCCCN(CCCCC1NC(=O)C(CCCCN(CCCOC(=O)CCCCCCC/C=C\C/C=C\CCCCC)CCCOC(=O)CCCCCCC/C=C\C/C=C\CCCCC)NC1=O)CCCOC(=O)CCCCCCC/C=C\C/C=C\CCCCC]

C18lin2 refers to linoleic acid. H NMR (500 MHz, CDCl$_3$, ppm): 6.27 (br, 2H, NH), 5.34 (m, 16H, CH$_2$CHCHCH$_2$), 4.09 (m, 8H, NCH$_2$CH$_2$OCO), 3.97 (br, 2H, COCHN), 2.76 (t, 8H, OCOCH$_2$), 2.26-2.57 (t, 12H, NCH$_2$), 2.22 (m, 8H, CHCH$_2$CH, 2.04 (m, 16H, CH$_2$CHCHCH$_2$CHCHCH$_2$), 1.14-1.85 (m, 84H, CH$_2$), 0.9 (t, 12H, CH$_3$).

50-C4-C7-4Tail

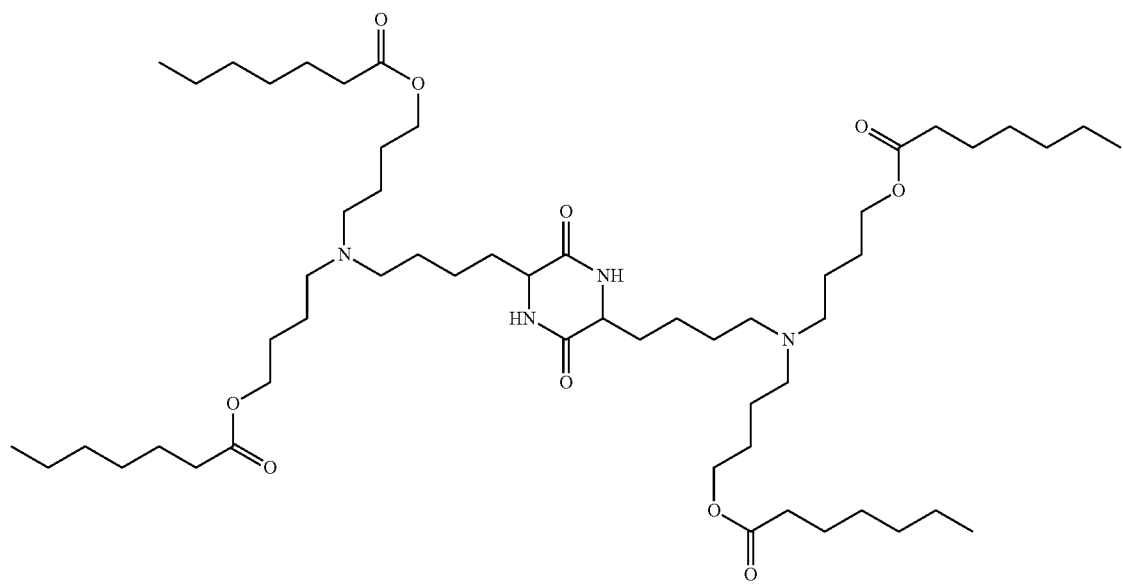 [SMILES: CCCCCCC(=O)OCCCCN(CCCCOC(=O)CCCCCC)CCCCC1NC(=O)C(CCCCN(CCCCOC(=O)CCCCCC)CCCCOC(=O)CCCCCC)NC1=O]

C7 refers to heptanoic acid. $^1$H NMR (500 MHz, CDCl$_3$, ppm): 6.15 (br, 2H, NH), 4.07 (m, 8H, NCH$_2$CH$_2$OCO), 3.97 (br, 2H, COCHN), 2.43 (br, 12H, NCH$_2$), 2.30 (t, 8H, t, 8H, OCOCH$_2$), 1.96 (m, 2H, COCHCH$_2$), 1.76 (m, 2H, COCHCH$_2$), 1.1-1.67 (m, 64H, CH$_2$), 0.9 (t, 12H, CH$_3$).

50-C4-C10-4Tail
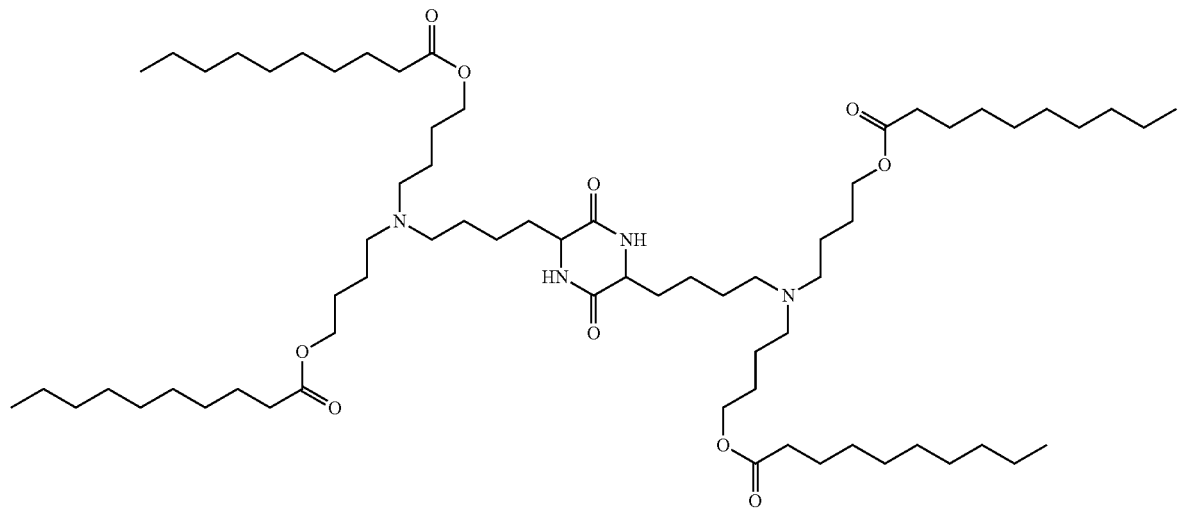 [SMILES: CCCCCCCCCC(=O)OCCCCN(CCCCOC(=O)CCCCCCCCC)CCCCC1NC(=O)C(CCCCN(CCCCOC(=O)CCCCCCCCC)CCCCOC(=O)CCCCCCCCC)NC1=O]
C10 refers to decanoic acid. $^1$H NMR (500 MHz, CDCl$_3$, ppm): 6.23 (br, 2H, NH), 4.07 (m, 8H, NCH$_2$CH$_2$OCO), 3.97 (br, 2H, COCHN), 2.40 (br, 12H, NCH$_2$), 2.30 (t, 8H, t, 8H, OCOCH$_2$), 1.97 (m, 2H, COCHCH$_2$), 1.77 (m, 2H, COCHCH$_2$), 1.14-1.69 (m, 80H, CH$_2$), 0.88 (t, 12H, CH$_3$).
50-C4-C13-Tail
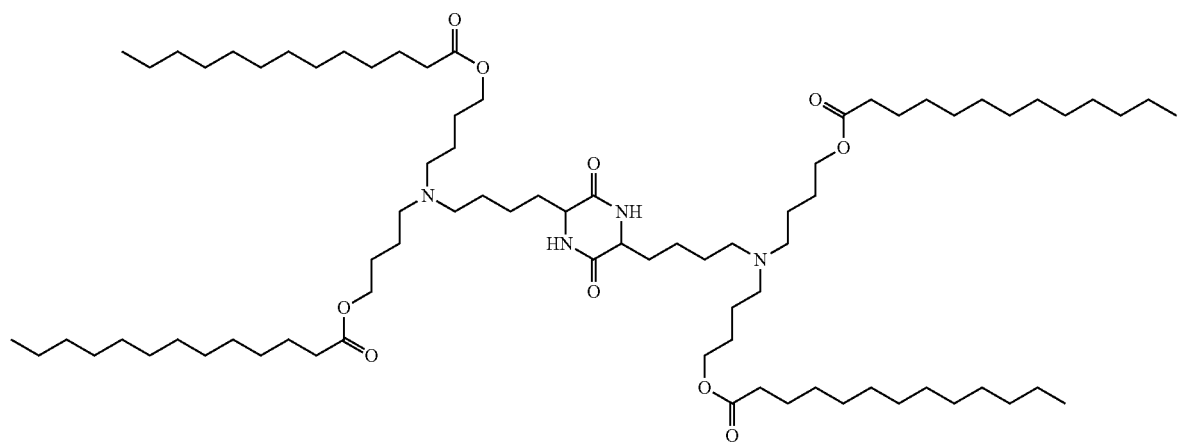 [SMILES: CCCCCCCCCCCCC(=O)OCCCCN(CCCCOC(=O)CCCCCCCCCCCC)CCCCC1NC(=O)C(CCCCN(CCCCOC(=O)CCCCCCCCCCCC)CCCCOC(=O)CCCCCCCCCCCC)NC1=O]
C13 refers to tridecanoic acid. 1H NMR (500 MHz, CDCl$_3$, ppm): 6.25 (br, 2H, NH), 4.07 (m, 8H, NCH$_2$CH$_2$OCO), 3.96 (br, 2H, COCHN), 2.39 (br, 12H, NCH$_2$), 2.29 (t, 8H, t, 8H, OCOCH$_2$), 1.96 (m, 2H, COCHCH$_2$), 1.75 (m, 2H, COCHCH$_2$), 1.13-1.68 (m, 104H, CH$_2$), 0.88 (t, 12H, CH$_3$).

50-C4-C18oleic-4Tail

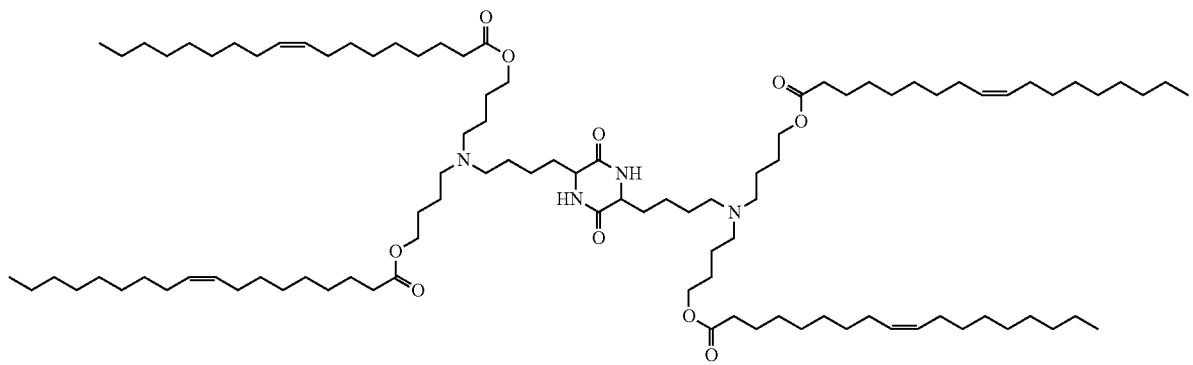 [SMILES: CCCCCCCC/C=C\CCCCCCCC(=O)OCCCCN(CCCCOC(=O)CCCCCCC/C=C\CCCCCCCC)CCCCC1NC(=O)C(CCCCN(CCCCOC(=O)CCCCCCC/C=C\CCCCCCCC)CCCCOC(=O)CCCCCCC/C=C\CCCCCCCC)NC1=O]

C18oleic refers to oleic acid. 1H NMR (500 MHz, CDCl$_3$, ppm): 6.22 (br, 2H, NH), 5.35 (m, 8H, CH$_2$CHCHCH$_2$), 4.07 (m, 8H, CH$_2$CH$_2$OCO), 3.98 (br, 2H, COCHN), 2.39 (br, 12H, NCH$_2$), 2.29 (t, 8H, OCOCH$_2$), 2.04 (m, 16H, CH$_2$CHCH), 1.96 (m, 2H, COCHCH$_2$), 1.77 (m, 2H, COCHCH$_2$), 1.18-1.70 (m, 110H, CH$_2$), 0.88 (t, 12H, CH$_3$).

50-C4-C18lin2-4Tail

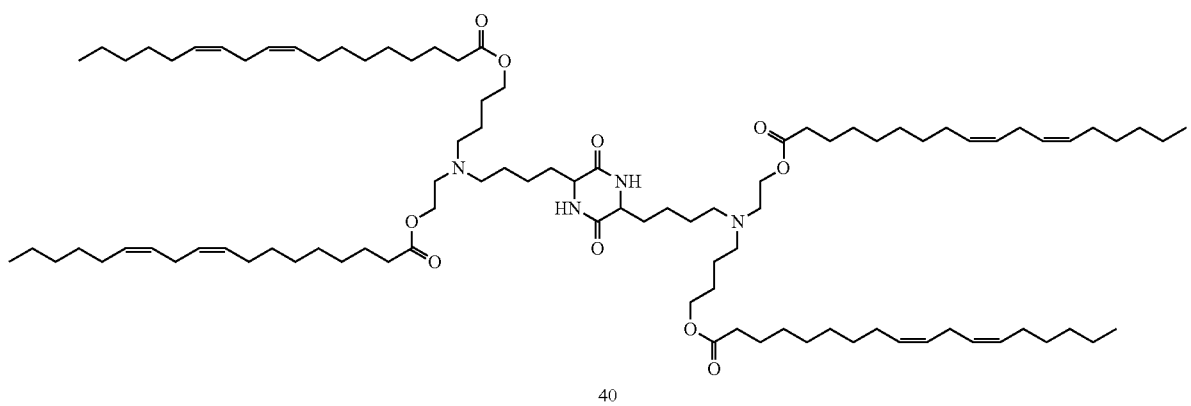

C18lin2 refers to linoleic acid. 1H NMR (500 MHz, CDCl$_3$, ppm): 6.29 (br, 2H, NH), 5.35 (m, 16H, CH$_2$CHCHCH$_2$), 4.07 (m, 8H, CH$_2$CH$_2$OCO), 3.96 (br, 2H, COCHN), 2.77 (t, 8H, OCOCH$_2$), 2.44 (br, 12H, NCH$_2$), 2.29 (t, 8H, CHCH$_2$CH), 2.04 (m, 16H, CH$_2$CHCHCH$_2$CHCHCH$_2$), 1.96 (m, 2H, COCHCH$_2$), 1.77 (m, 2H, COCHCH$_2$), 1.22-1.68 (m, 88H, CH$_2$), 0.88 (t, 12H, CH$_3$).

Example 2. Biological Assays of the Compounds

In addition to the polyamine-fatty acid derived lipidoids (e.g., compounds of Formula (I) or (II)), helper lipids were used to generate the liposomal nanoparticles: cholesterol, dimyristoyl-PEG2000 (DMG-PEG2000), distearoylphosphatidylcholine (DSPC), and dioleoylphosphatidylethanolamine (DOPE). The lipids (e.g., the lipidoids and helper lipids) were solubilized in ethanol and combined. The RNA (e.g., mRNA) was dissolved in water and then added to a citric acid buffer (pH 3.0). Two methods (Methods (a) and (b)) were used to formulate the liposomal nanoparticles, with both methods requiring the use of syringe pumps and a microfluidics device (Chen et al., J. Am. Chem. Soc. 2012, 134, 6948-6951). In Method (a), the lipid and RNA solutions were pumped into the microfluidics device in a 1:1 ratio at 300 μl/minute, followed by addition of PBS at 600 μL/minute. In Method (b), the RNA and lipids were pumped in at a ratio of 3:1 at 900 μL/minute and 300 μL/minute, respectively. After formulating, the liposomal nanoparticles are dialyzed in 20 k MW cutoff dialysis cassettes against PBS for 2 hours. Entrapment and mRNA concentration were determined via RIBOGREEN assay; particle size was determined using a ZETASIZER (Malvern).

Figure 3:
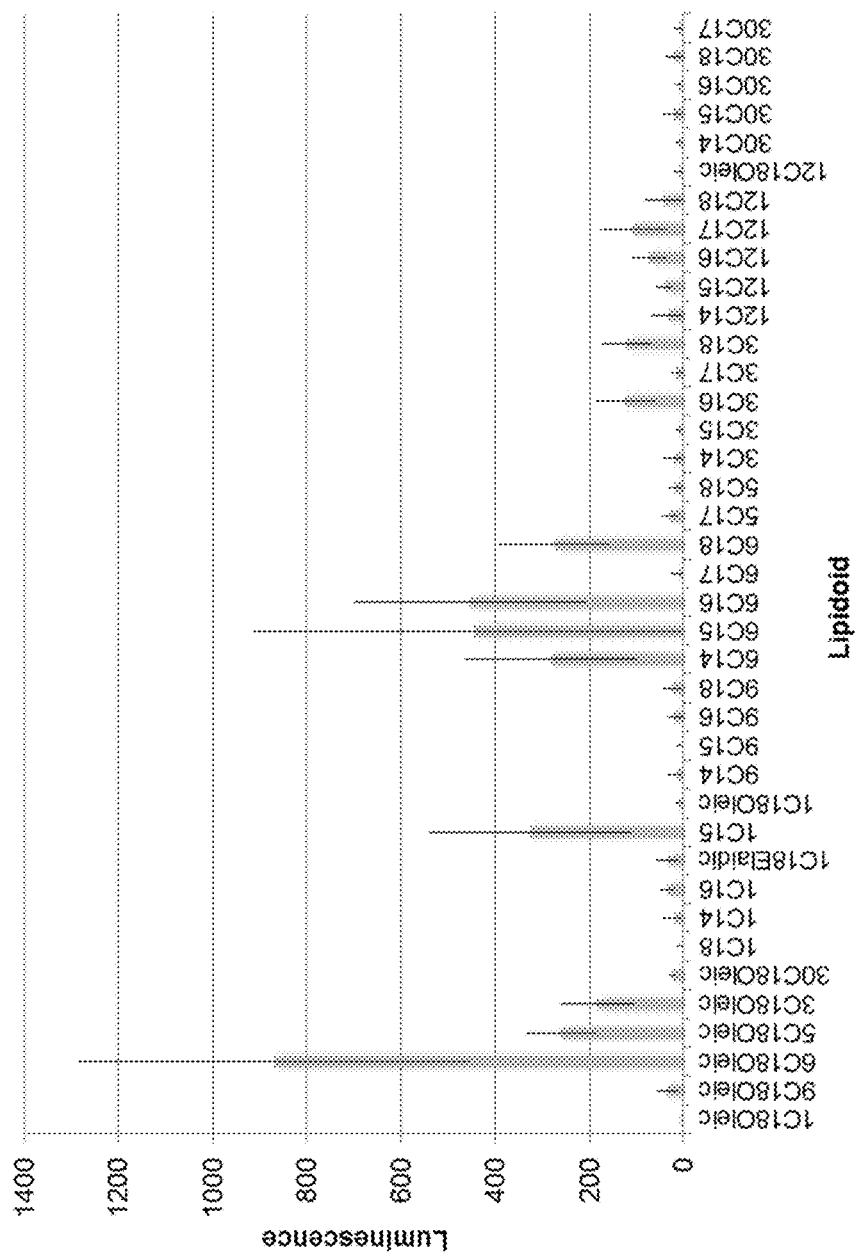
FIG. 3 shows exemplary HeLa cell luminescence results at 24 hours after treating HeLa cells with 10 ng of a composition that includes luciferase mRNA and an exemplary compound of the disclosure.

Exemplary lipidoids (e.g., compounds of Formula (I) or (II)) of the disclosure were examined for efficacy in vitro. HeLa cells were transfected with 10 ng of formulated luciferase mRNA, and examined for luminescence 24 hours later. Exemplary results are shown in FIG. 3.

Figure 2:
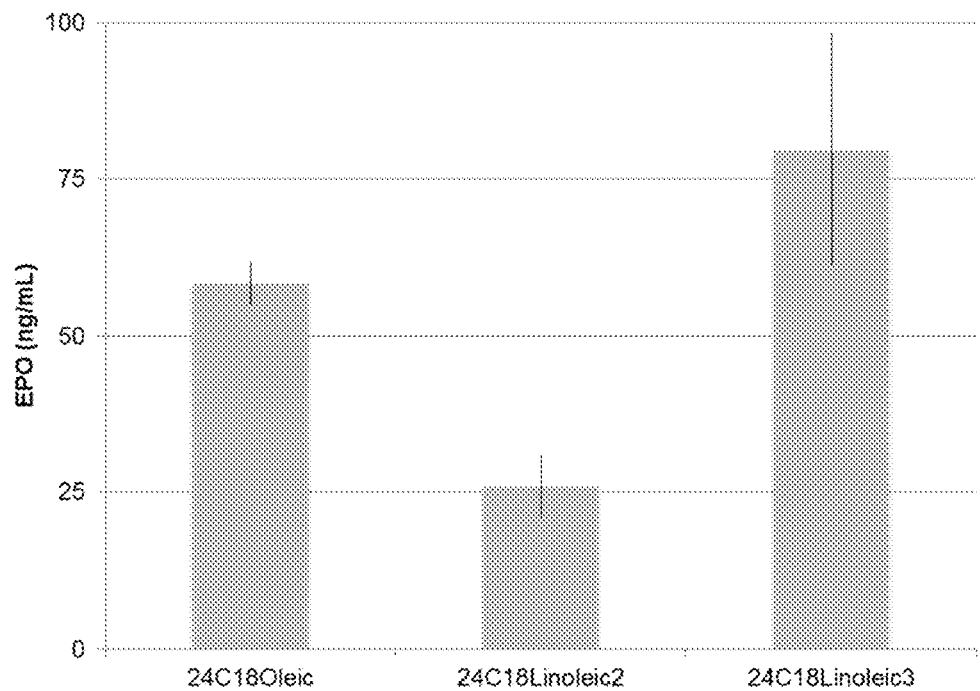
FIG. 2 shows exemplary erythropoietin (EPO) serum levels at 6 hours after a 1 mg/kg injection of a composition that includes EPO mRNA and compound 24C18Oleic, 24C18Linoleic2, or 24C18Linoleic3.

Mice were injected with formulated luciferase mRNA using the compound 24C18Oleic at a dose of 1 mg/kh mRNA; after 6 hours, the murine organs were examined ex vivo, and luminescence was successfully seen in the spleen of the treated mice (FIG. 1). The EPO levels of mice were examined 6 hours after treatment with formulated human EPO mRNA at a dose of 1 mg/kg. Several lipidoids (e.g., compounds 24C18Oleic, 24C18Linoleic2, and 24C18Linoleic3) were examined, resulting in EPO levels ranging from 25 ng/mL to over 75 ng/mL (FIG. 2).

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects described herein, is/are referred to as comprising particular elements and/or features, certain embodiments described herein or aspects described herein consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments described herein, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment described herein can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A compound of Formula (I):

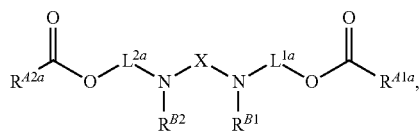

or a salt thereof, wherein:
X is of the formula:

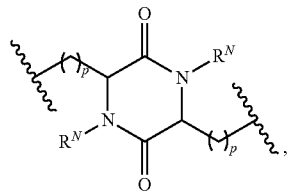

wherein:
each instance of p is independently 1, 2, 3, 4, 5, or 6; and
each instance of $R^N$ is independently hydrogen, substituted or unsubstituted $C_{1-6}$ alkyl, or a nitrogen protecting group;
$L^{1a}$ is substituted or unsubstituted alkylene or substituted or unsubstituted heteroalkylene;
$R^{A1a}$ is substituted or unsubstituted, $C_{4-30}$ alkyl, substituted or unsubstituted, $C_{4-30}$ alkenyl, or substituted or unsubstituted, $C_{4-30}$ alkynyl;
$R^{B1}$ is hydrogen, substituted or unsubstituted acyl, substituted or unsubstituted alkyl, substituted or unsubstituted alkenyl, substituted or unsubstituted alkynyl, a nitrogen protecting group, or a moiety of the formula:

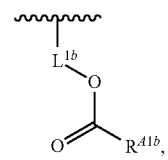

wherein $L^{1b}$ is substituted or unsubstituted alkylene or substituted or unsubstituted heteroalkylene, and $R^{A1b}$ is substituted or unsubstituted, $C_{4-30}$ alkyl, substituted or unsubstituted, $C_{4-30}$ alkenyl, or substituted or unsubstituted, $C_{4-30}$ alkynyl;
$L^{2a}$ is substituted or unsubstituted alkylene or substituted or unsubstituted heteroalkylene;
$R^{A2a}$ is substituted or unsubstituted, $C_{4-30}$ alkyl, substituted or unsubstituted, $C_{4-30}$ alkenyl, or substituted or unsubstituted, $C_{4-30}$ alkynyl; and
$R^{B2}$ is hydrogen, substituted or unsubstituted acyl, substituted or unsubstituted alkyl, substituted or unsubstituted alkenyl, substituted or unsubstituted alkynyl, a nitrogen protecting group, or a moiety of the formula:

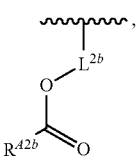

wherein $L^{2b}$ is substituted or unsubstituted alkylene or substituted or unsubstituted heteroalkylene, and $R^{A2b}$ is substituted or unsubstituted, $C_{4-30}$ alkyl, substituted or unsubstituted, $C_{4-30}$ alkenyl, or substituted or unsubstituted, $C_{4-30}$ alkynyl.

2. The compound of claim 1, wherein the compound is of Formula (I-B):

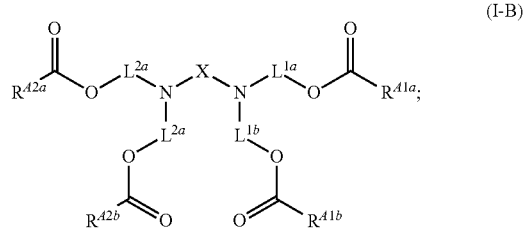

(I-B)

or a salt thereof.

3. The compound of claim 1, wherein each of $L^{1a}$ and $L^{2a}$ is independently substituted or unsubstituted alkylene; or a salt thereof.

4. The compound of claim 2, wherein each of $L^{1a}$, $L^{a2}$, $L^{1b}$, and $L^{2b}$ is independently substituted or unsubstituted alkylene; or a salt thereof.

5. The compound of claim 1, wherein at least one of $R^{A1a}$ and $R^{A2a}$ is substituted or unsubstituted, $C_{7-24}$ alkyl, or substituted or unsubstituted, $C_{7-24}$ alkenyl; or a salt thereof.

6. The compound of claim 1, wherein each one of $R^{B1}$ and $R^{B2}$ is independently hydrogen or substituted or unsubstituted alkyl; or a salt thereof.

7. The compound of claim 1, wherein the compound is of the formula:

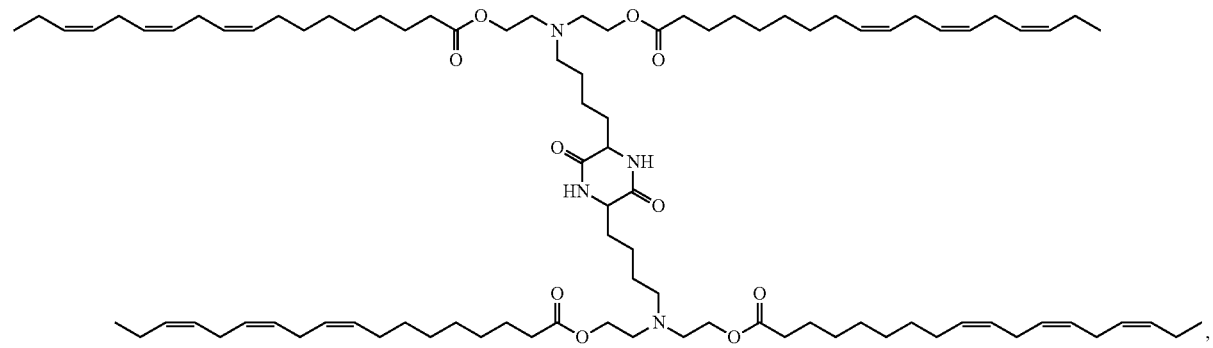 [SMILES: CC/C=C\C/C=C\C/C=C\CCCCCCCC(=O)OCCN(CCCCC1NC(=O)C(CCCCN(CCOC(=O)CCCCCCC/C=C\C/C=C\C/C=C\CC)CCOC(=O)CCCCCCC/C=C\C/C=C\C/C=C\CC)NC1=O)CCOC(=O)CCCCCCC/C=C\C/C=C\C/C=C\CC]

or a salt thereof.

8. The compound of claim 1, wherein the compound is of formula:

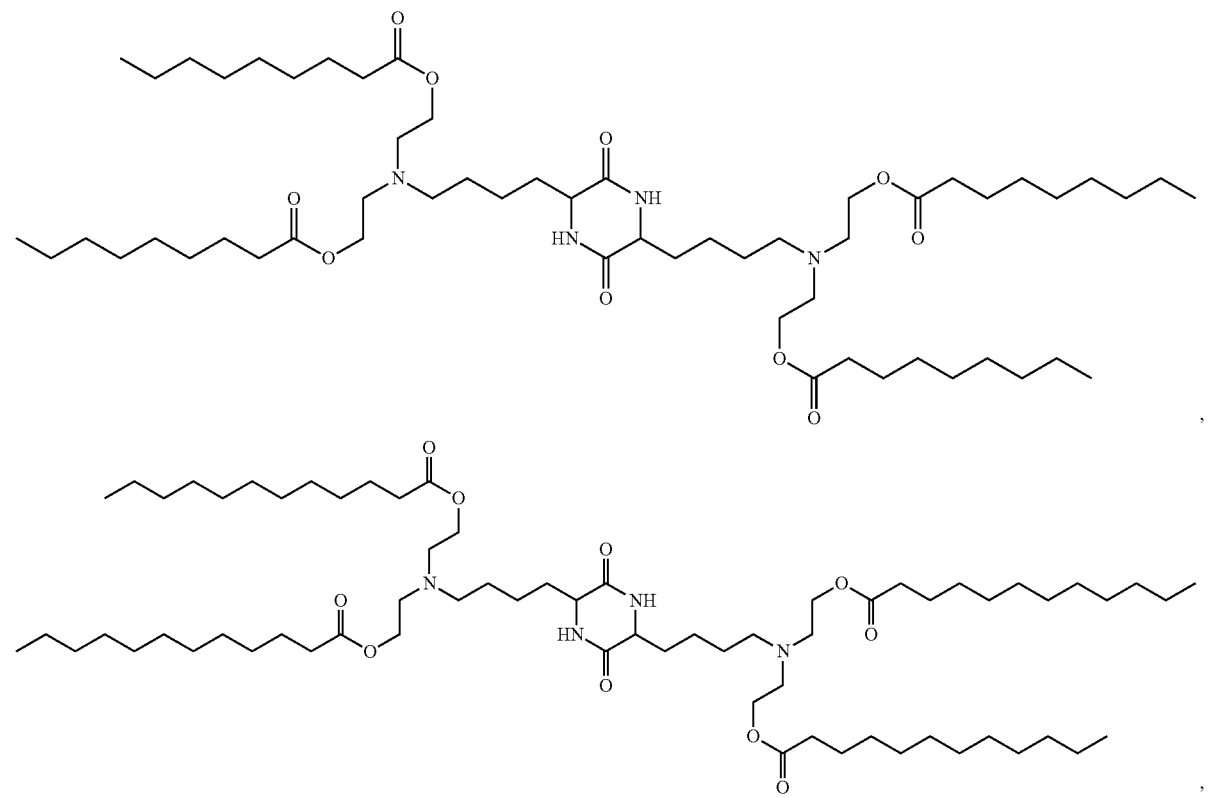

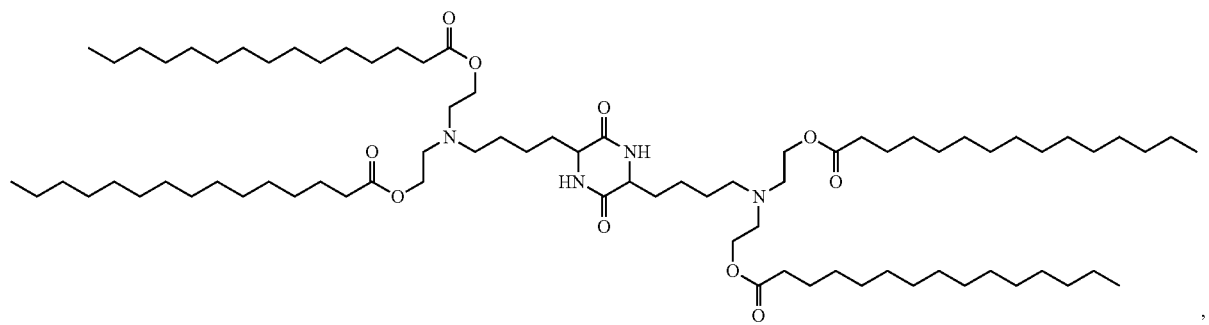
,
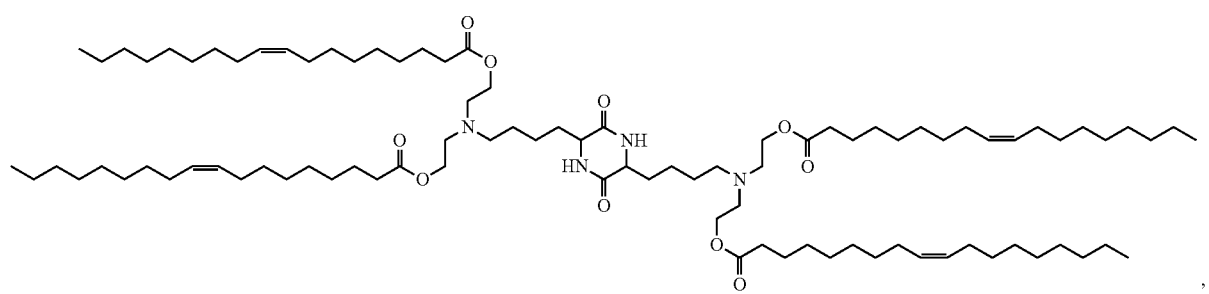
,
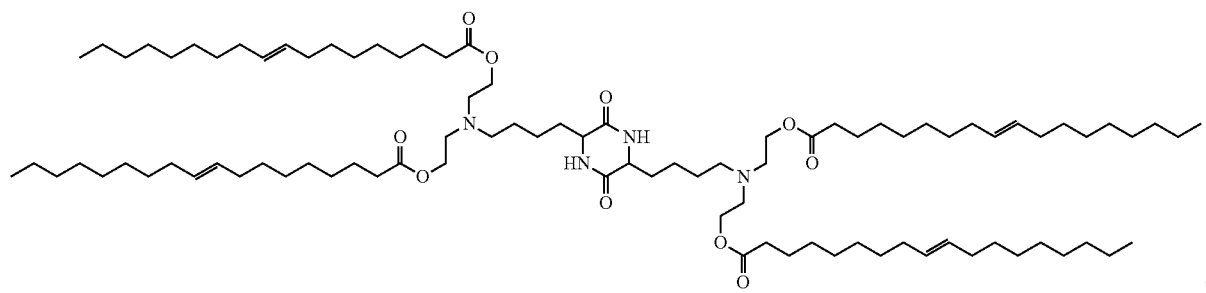
,
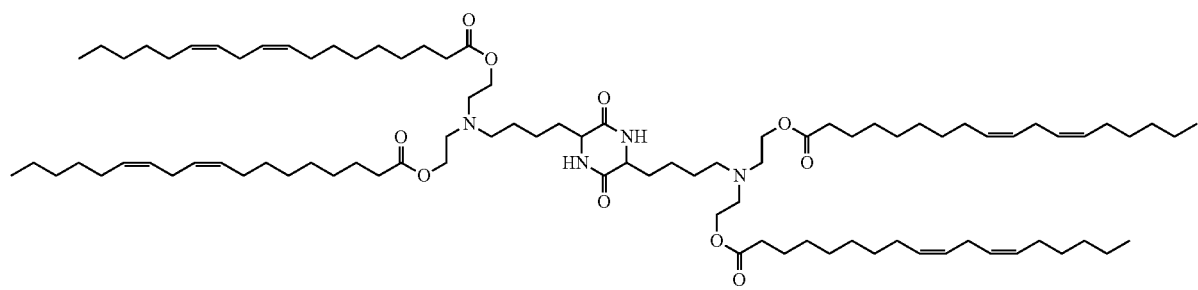
,
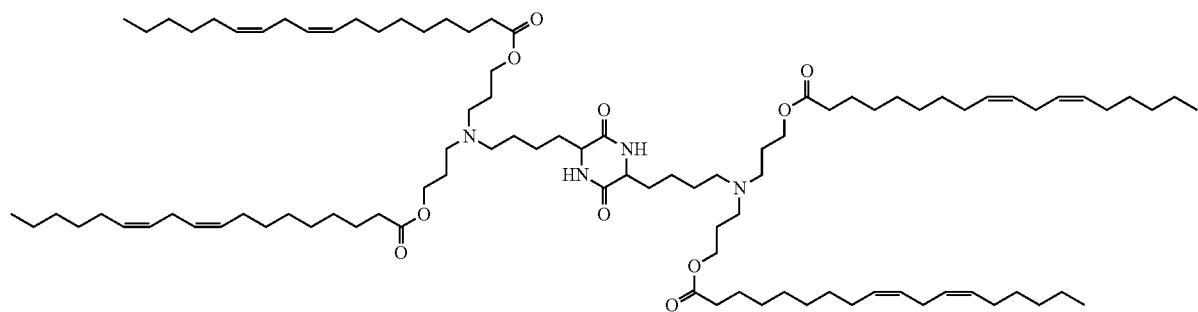
,

185
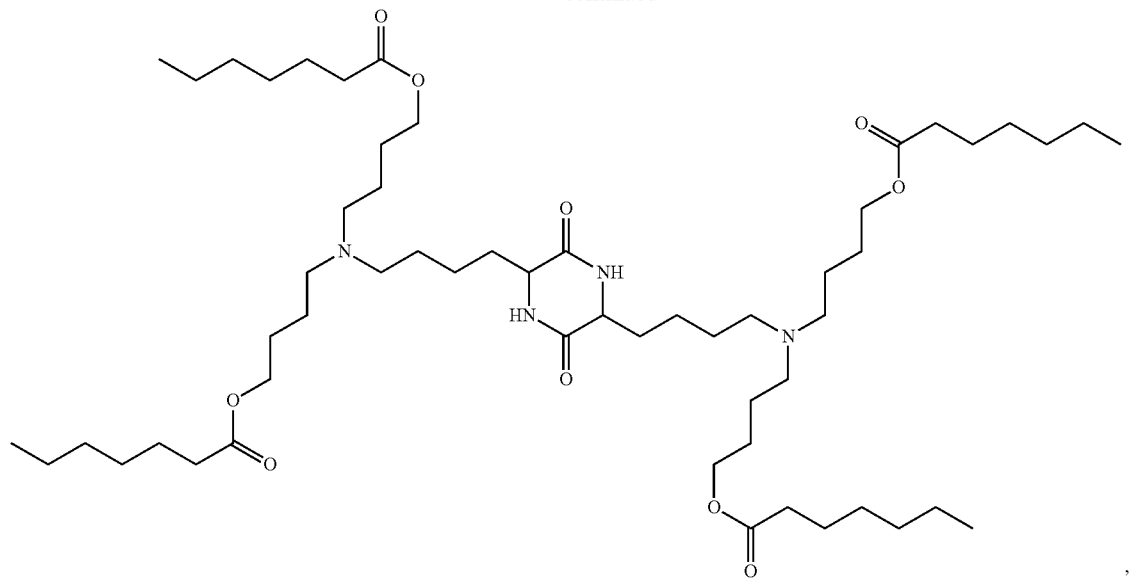
186
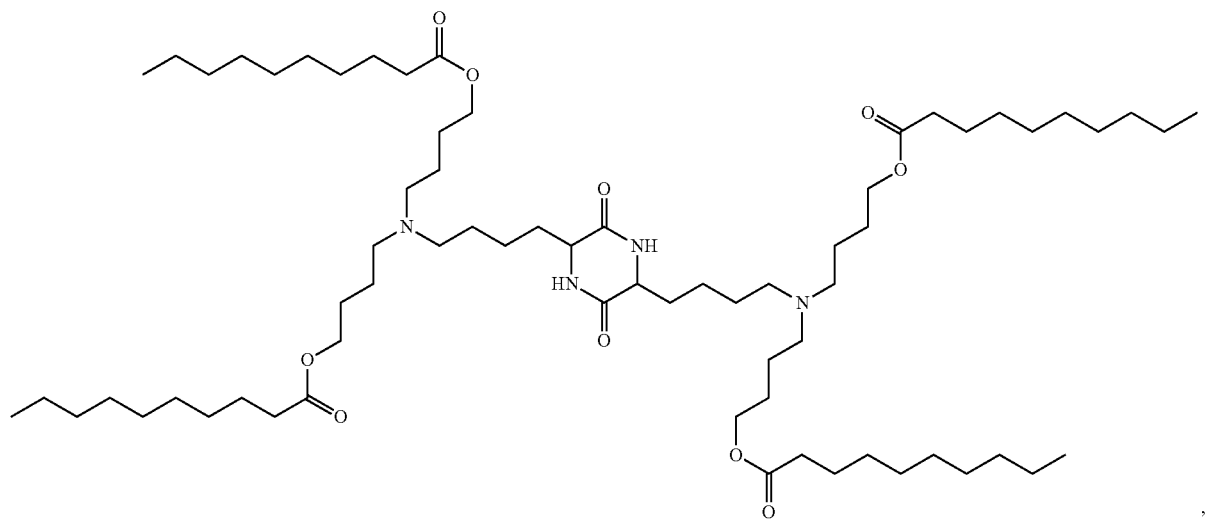
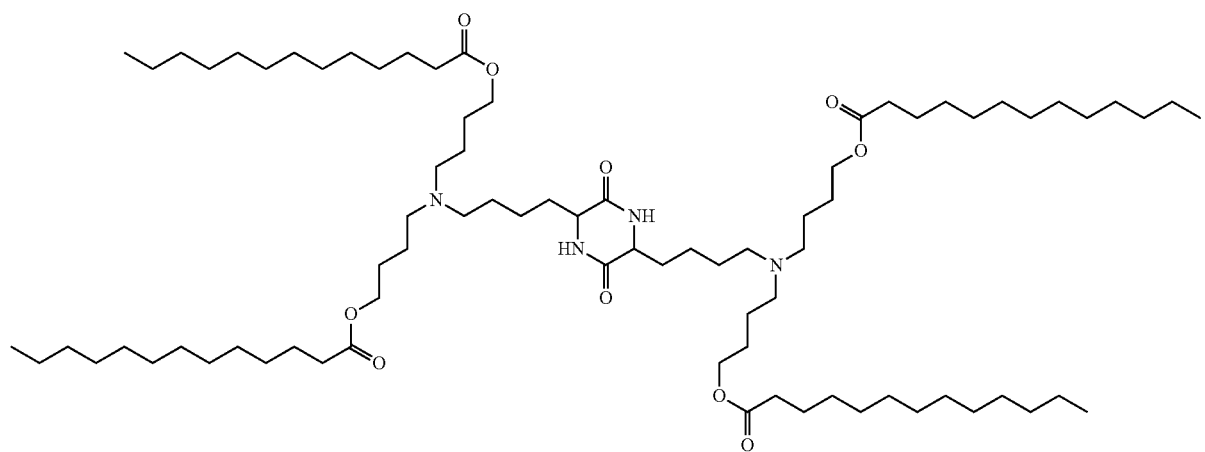

-continued

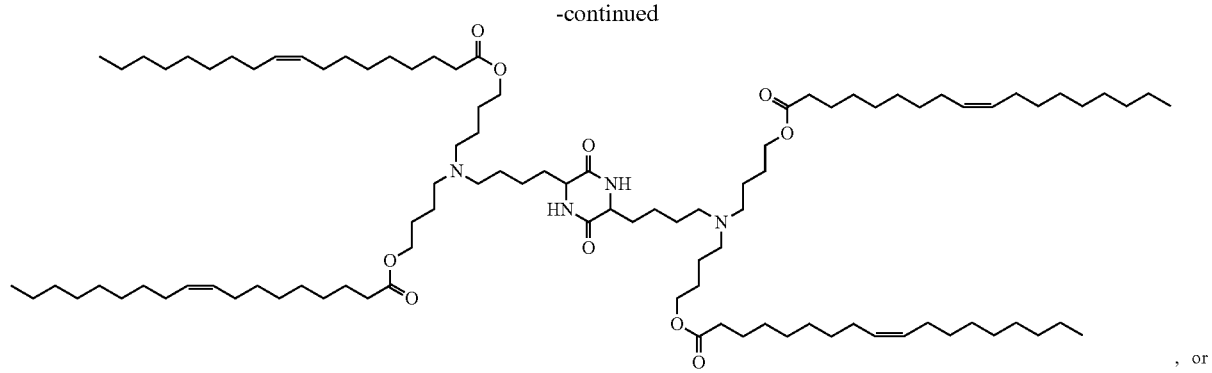

, or

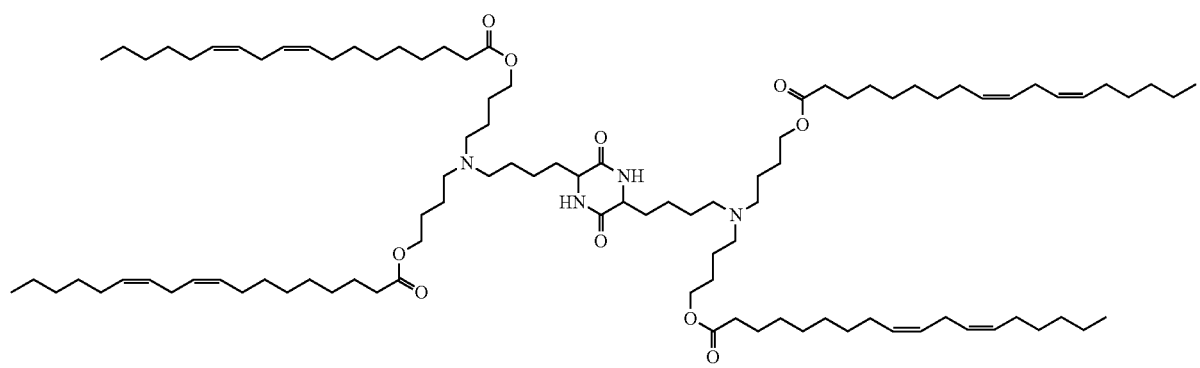

;

or a salt thereof.

9. A particle comprising:
a compound of claim 1, or a salt thereof; and
an agent.

10. A composition comprising a compound of claim 1, or a salt thereof, and optionally an excipient.

11. A composition comprising a particle of claim 9, and optionally an excipient.

12. A method of delivering an agent to a subject, the method comprising administering to the subject a composition of claim 10, wherein the composition further comprises an agent.

13. A method of delivering an agent to a cell, the method comprising contacting the cell with a composition of claim 10, wherein the composition further comprises an agent.

14. The compound of claim 1, wherein X is of the formula:

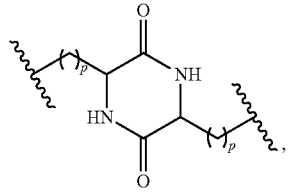

or a salt thereof.

15. The compound of claim 1, wherein the compound is of Formula (I-C):

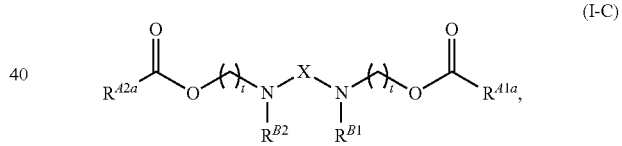

or a salt thereof, wherein each instance of t is 2, 3, 4, 5, or 6.

16. The compound of claim 1, wherein the compound is of the formula:

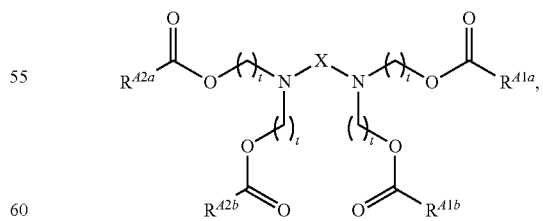

or a salt thereof, wherein each instance of t is 2, 3, 4, 5, or 6.

17. The compound of claim 2, wherein each of $R^{A1a}$, $R^{A2a}$, $R^{A1b}$, and $R^{A2b}$ is independently unsubstituted $C_{7-24}$ alkyl or unsubstituted $C_{7-24}$ alkenyl; or a salt thereof.

18. The compound of claim 2, wherein each of $R^{A1a}$, $R^{A2a}$, $R^{A1b}$, and $R^{A2b}$ is independently:
  $C_{7-24}$ alkyl substituted with one or more instances of halogen; or
  $C_{7-24}$ alkenyl substituted with one or more instances of halogen;
or a salt thereof.

19. The compound of claim 1, wherein the compound is of Formula (I-A):

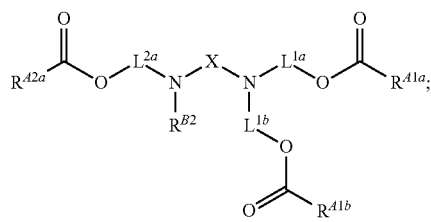

or a salt thereof.

20. The compound of claim 19, wherein each of $L^{1a}$, $L^{2a}$, and $L^{1b}$ is independently substituted or unsubstituted alkylene; or a salt thereof.

21. The compound of claim 1, wherein the compound is of Formula (I-H):

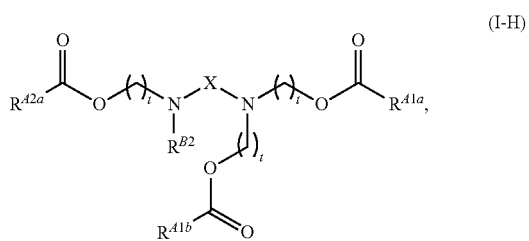

or a salt thereof, wherein each instance of t is 2, 3, 4, 5, or 6.

22. The compound of claim 19, wherein each one of $R^{A1a}$, $R^{A2a}$, and $R^{A1b}$ is independently unsubstituted $C_{7-24}$ alkyl or unsubstituted $C_{7-24}$ alkenyl; or a salt thereof.

23. The compound of claim 19, wherein each one of $R^{A1a}$, $R^{A2a}$, and $R^{A1b}$ is independently:
  $C_{7-24}$ alkyl substituted with one or more instances of halogen; or
  $C_{7-24}$ alkenyl substituted with one or more instances of halogen;
or a salt thereof.

24. The compound of claim 1, wherein the compound is of the formula:

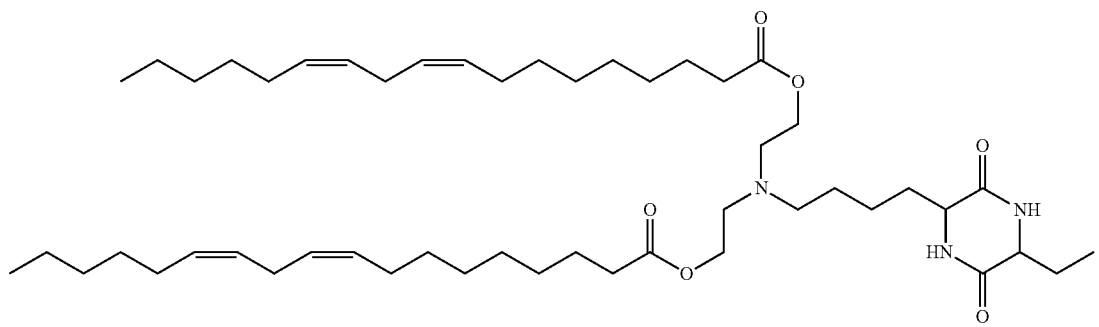

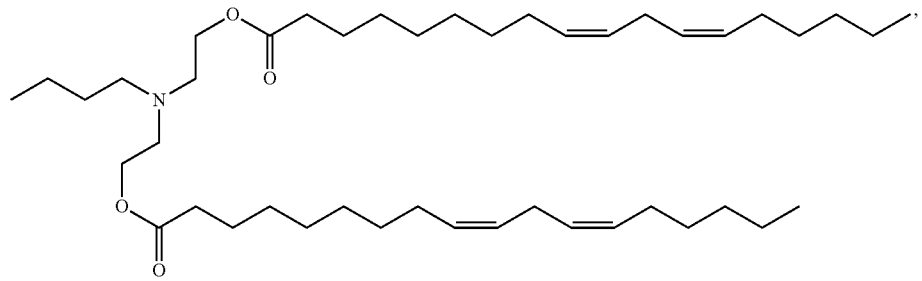

or a salt thereof.

25. The composition of claim 10 further comprising an agent.

26. The composition of claim 25, wherein the agent is a small molecule, protein, peptide, or polynucleotide.

27. The composition of claim 25, wherein the agent is a DNA or RNA.

28. The composition of claim 25, wherein the agent is a small interfering RNA (siRNA) or messenger RNA (mRNA).

29. The composition of claim 25, wherein the agent is a single-stranded RNA (ssRNA), double-stranded RNA (dsRNA), small interfering RNA (siRNA), precursor messenger RNA (pre-mRNA), small hairpin RNA or short hairpin RNA (shRNA), microRNA (miRNA), guide RNA (gRNA), transfer RNA (tRNA), antisense RNA (asRNA), heterogeneous nuclear RNA (hnRNA), coding RNA, non-coding RNA (ncRNA), long non-coding RNA (long ncRNA or lncRNA), satellite RNA, viral satellite RNA, signal recognition particle RNA, small cytoplasmic RNA, small nuclear RNA (snRNA), ribosomal RNA (rRNA), Piwi-interacting RNA (piRNA), polyinosinic acid, ribozyme, flexizyme, small nucleolar RNA (snoRNA), spliced leader RNA, viral RNA, or viral satellite RNA.

\* \* \* \* \*